US011873405B2

(12) United States Patent
Parker et al.

(10) Patent No.: US 11,873,405 B2
(45) Date of Patent: Jan. 16, 2024

(54) HIGH OLEIC OIL COMPOSITIONS AND USES THEREOF

(71) Applicant: Checkerspot, Inc., Alameda, CA (US)

(72) Inventors: Leon Parker, San Francisco, CA (US); Kevin Ward, Emeryville, CA (US); Scott Franklin, Woodside, CA (US); Mona Correa, Hercules, CA (US); Veronica Benites, San Francisco, CA (US)

(73) Assignee: CHECKERSPOT, INC., Alameda, CA (US)

(*) Notice: Subject to any disclaimer, the term of this patent is extended or adjusted under 35 U.S.C. 154(b) by 0 days.

(21) Appl. No.: 18/156,929

(22) Filed: Jan. 19, 2023

(65) Prior Publication Data

US 2023/0303841 A1    Sep. 28, 2023

Related U.S. Application Data

(63) Continuation of application No. PCT/US2022/043695, filed on Sep. 15, 2022.

(60) Provisional application No. 63/245,734, filed on Sep. 17, 2021, provisional application No. 63/245,736, filed on Sep. 17, 2021, provisional application No. 63/245,737, filed on Sep. 17, 2021, provisional application No. 63/245,740, filed on Sep. 17, 2021.

(51) Int. Cl.
| C08L 91/00 | (2006.01) |
| C12P 7/6463 | (2022.01) |
| A23D 9/02 | (2006.01) |

(52) U.S. Cl.
CPC ............ *C08L 91/00* (2013.01); *A23D 9/02* (2013.01); *C12P 7/6463* (2013.01)

(58) Field of Classification Search
CPC . C08L 91/00; C07C 55/22; A23D 9/02; C12P 7/6463
See application file for complete search history.

(56) References Cited

U.S. PATENT DOCUMENTS

| 2,059,052 | A | 10/1936 | Sperr, Jr. |
| 4,349,904 | A | 9/1982 | Janssen et al. |
| 4,545,941 | A | 10/1985 | Rosenburg |
| 5,130,404 | A | 7/1992 | Freeland |
| 6,107,433 | A | 8/2000 | Petrovic et al. |
| 6,414,172 | B1 | 7/2002 | Garces et al. |

(Continued)

FOREIGN PATENT DOCUMENTS

| CN | 106995519 B | 9/2019 |
| DE | 202006018792 U1 | 4/2008 |

(Continued)

OTHER PUBLICATIONS

Co-pending U.S. Appl. No. 17/396,876, inventor Franklin; Scott, filed Aug. 9, 2021.

(Continued)

*Primary Examiner* — Yate' K Cutliff
(74) *Attorney, Agent, or Firm* — Wilson Sonsini Goodrich & Rosati

(57) ABSTRACT

Provided herein are high oleic oil compositions. Further provided herein are methods of producing high oleic oil compositions from microorganisms and applications thereof in end products, including, for example, polyols, polyurethane products, personal care products, and food products.

111 Claims, 10 Drawing Sheets

Specification includes a Sequence Listing.

(56) References Cited

U.S. PATENT DOCUMENTS

| | | | |
|---|---|---|---|
| 6,562,933 B2 | 5/2003 | Ohmori et al. | |
| 6,630,534 B1 | 10/2003 | Tanaka et al. | |
| 7,883,882 B2 | 2/2011 | Franklin et al. | |
| 7,935,515 B2 | 5/2011 | Franklin et al. | |
| 8,187,860 B2 | 5/2012 | Franklin et al. | |
| 8,222,010 B2 | 7/2012 | Franklin et al. | |
| 8,268,610 B2 | 9/2012 | Franklin et al. | |
| 8,435,767 B2 | 5/2013 | Franklin et al. | |
| 8,450,083 B2 | 5/2013 | Day et al. | |
| 8,476,059 B2 | 7/2013 | Trimbur et al. | |
| 8,497,116 B2 | 7/2013 | Trimbur et al. | |
| 8,512,999 B2 | 8/2013 | Trimbur et al. | |
| 8,518,689 B2 | 8/2013 | Trimbur et al. | |
| 8,557,249 B2 | 10/2013 | Brooks et al. | |
| 8,592,188 B2 | 11/2013 | Franklin et al. | |
| 8,633,012 B2 | 1/2014 | Franklin et al. | |
| 8,647,397 B2 | 2/2014 | Trimbur et al. | |
| 8,674,180 B2 | 3/2014 | Franklin et al. | |
| 8,697,402 B2 | 4/2014 | Trimbur et al. | |
| 8,697,427 B2 | 4/2014 | Franklin et al. | |
| 8,765,424 B2 | 7/2014 | Franklin et al. | |
| 8,772,575 B2 | 7/2014 | Franklin et al. | |
| 8,790,914 B2 | 7/2014 | Trimbur et al. | |
| 8,802,422 B2 | 8/2014 | Trimbur et al. | |
| 8,822,176 B2 | 9/2014 | Day et al. | |
| 8,822,177 B2 | 9/2014 | Day et al. | |
| 8,846,375 B2 | 9/2014 | Franklin et al. | |
| 8,852,885 B2 | 10/2014 | Franklin et al. | |
| 8,871,985 B2 | 10/2014 | Van Vliet et al. | |
| 8,889,401 B2 | 11/2014 | Trimbur et al. | |
| 8,889,402 B2 | 11/2014 | Trimbur et al. | |
| 8,945,908 B2 | 2/2015 | Franklin et al. | |
| 8,951,777 B2 | 2/2015 | Franklin et al. | |
| 9,062,294 B2 | 6/2015 | Franklin et al. | |
| 9,066,527 B2 | 6/2015 | Franklin et al. | |
| 9,068,213 B2 | 6/2015 | Franklin et al. | |
| 9,102,973 B2 | 8/2015 | Franklin et al. | |
| 9,109,239 B2 | 8/2015 | Franklin et al. | |
| 9,200,307 B2 | 12/2015 | Franklin et al. | |
| 9,249,252 B2 | 2/2016 | Ngantung et al. | |
| 9,249,436 B2 | 2/2016 | Franklin et al. | |
| 9,249,441 B2 | 2/2016 | Franklin et al. | |
| 9,255,282 B2 | 2/2016 | Franklin et al. | |
| 9,279,136 B2 | 3/2016 | Franklin et al. | |
| 9,328,351 B2 | 5/2016 | Franklin et al. | |
| 9,353,389 B2 | 5/2016 | Franklin et al. | |
| 9,375,703 B2 | 6/2016 | Harlin et al. | |
| 9,388,435 B2 | 7/2016 | Franklin et al. | |
| 9,493,640 B2 | 11/2016 | Cernohous et al. | |
| 9,499,652 B2 | 11/2016 | Spies et al. | |
| 9,518,277 B2 | 12/2016 | Franklin et al. | |
| 9,551,017 B2 | 1/2017 | Franklin et al. | |
| 9,567,615 B2 | 2/2017 | Davis | |
| 9,593,351 B2 | 3/2017 | Franklin et al. | |
| 9,649,368 B2 | 5/2017 | Franklin et al. | |
| 9,657,299 B2 | 5/2017 | Franklin et al. | |
| 9,758,757 B2 | 9/2017 | Harlin et al. | |
| 9,796,949 B2 | 10/2017 | Dummer et al. | |
| 9,909,155 B2 | 3/2018 | Franklin et al. | |
| 10,006,034 B2 | 6/2018 | Franklin et al. | |
| 10,053,646 B2 * | 8/2018 | Schiff-Deb | C10M 169/04 |
| 10,053,715 B2 | 8/2018 | Franklin et al. | |
| 10,100,341 B2 | 10/2018 | Franklin et al. | |
| 10,125,382 B2 | 11/2018 | Casolari et al. | |
| 10,138,435 B2 | 11/2018 | Trimbur et al. | |
| 10,167,489 B2 | 1/2019 | Franklin et al. | |
| 10,260,076 B2 | 4/2019 | Franklin et al. | |
| 10,287,613 B2 | 5/2019 | Franklin et al. | |
| 10,316,299 B2 | 6/2019 | Davis et al. | |
| 10,344,305 B2 | 7/2019 | Franklin et al. | |
| 10,442,922 B2 | 10/2019 | Fudemoto et al. | |
| 10,557,114 B2 | 2/2020 | Rudenko et al. | |
| 10,683,522 B2 | 6/2020 | Franklin et al. | |
| 11,118,134 B2 | 9/2021 | Franklin | |
| 11,208,369 B2 | 12/2021 | Petrovic et al. | |
| 11,352,602 B2 | 6/2022 | Wee et al. | |
| 11,667,870 B2 | 6/2023 | Franklin | |
| 11,673,850 B2 | 6/2023 | Petrovic et al. | |
| 11,691,382 B2 | 7/2023 | Sterbenz et al. | |
| 2004/0241392 A1 | 12/2004 | Sorrentino | |
| 2005/0143508 A1 | 6/2005 | Tyagi et al. | |
| 2006/0264568 A1 | 11/2006 | Pajerski | |
| 2007/0117947 A1 | 5/2007 | Wehner | |
| 2008/0118992 A1 | 5/2008 | Bellini et al. | |
| 2009/0260754 A1 | 10/2009 | Te | |
| 2010/0267925 A1 | 10/2010 | Abraham et al. | |
| 2010/0311992 A1 | 12/2010 | Petrovic et al. | |
| 2011/0113679 A1 | 5/2011 | Cohen et al. | |
| 2011/0256282 A1 | 10/2011 | Piechocki et al. | |
| 2012/0073186 A1 | 3/2012 | Knuth et al. | |
| 2012/0130039 A1 | 5/2012 | Millero, Jr. et al. | |
| 2012/0135479 A1 * | 5/2012 | Dillon | C11B 1/106 554/20 |
| 2012/0196079 A1 | 8/2012 | Brauers et al. | |
| 2013/0053463 A1 | 2/2013 | Gramellini et al. | |
| 2013/0131222 A1 | 5/2013 | Gross | |
| 2013/0323382 A1 | 12/2013 | Franklin et al. | |
| 2013/0338385 A1 | 12/2013 | Franklin et al. | |
| 2014/0145374 A1 | 5/2014 | Altonen et al. | |
| 2014/0178950 A1 * | 6/2014 | Franklin | C12N 15/52 435/320.1 |
| 2014/0256600 A1 | 9/2014 | Dillon et al. | |
| 2014/0288636 A1 | 9/2014 | Headley, Jr. et al. | |
| 2016/0002566 A1 | 1/2016 | Vanhercke et al. | |
| 2016/0009852 A1 | 1/2016 | Yu et al. | |
| 2016/0176800 A1 | 6/2016 | Schiff-Deb et al. | |
| 2016/0193793 A1 | 7/2016 | Filippini | |
| 2016/0194584 A1 | 7/2016 | Ngantung et al. | |
| 2016/0242371 A1 | 8/2016 | Prissok | |
| 2016/0312151 A1 | 10/2016 | Narine et al. | |
| 2016/0348119 A1 | 12/2016 | Franklin et al. | |
| 2017/0066893 A1 | 3/2017 | Falken | |
| 2017/0240253 A1 | 8/2017 | Woo | |
| 2017/0335057 A1 | 11/2017 | Tabor et al. | |
| 2018/0127350 A1 | 5/2018 | Hapiot et al. | |
| 2018/0163170 A1 * | 6/2018 | Wee | C12P 7/64 |
| 2018/0237811 A1 | 8/2018 | Franklin et al. | |
| 2021/0130858 A1 | 5/2021 | Franklin et al. | |
| 2021/0244064 A1 | 8/2021 | Brooks et al. | |
| 2021/0246434 A1 | 8/2021 | Ko et al. | |
| 2022/0119735 A1 | 4/2022 | Franklin | |
| 2022/0144735 A1 | 5/2022 | Petrovic et al. | |
| 2022/0324198 A1 | 10/2022 | Sterbenz et al. | |
| 2022/0356292 A1 | 11/2022 | Sterbenz et al. | |

FOREIGN PATENT DOCUMENTS

| | | |
|---|---|---|
| JP | 2009114247 A | 5/2009 |
| JP | 2011516634 A | 5/2011 |
| JP | 2014500349 A | 1/2014 |
| JP | 2015521033 A | 7/2015 |
| JP | 2018509516 A | 4/2018 |
| KR | 101296172 B1 | 8/2013 |
| WO | WO-0238375 A2 | 5/2002 |
| WO | WO-2006116456 A1 | 11/2006 |
| WO | WO-2008151149 A2 | 12/2008 |
| WO | WO-2009117665 A2 | 9/2009 |
| WO | WO-2010045368 A2 | 4/2010 |
| WO | WO-2010063031 A2 | 6/2010 |
| WO | WO-2010063032 A2 | 6/2010 |
| WO | WO-2010120923 A1 | 10/2010 |
| WO | WO-2010120939 A2 | 10/2010 |
| WO | WO-2011150410 A2 | 12/2011 |
| WO | WO-2011150411 A1 | 12/2011 |
| WO | WO-2012061647 A2 | 5/2012 |
| WO | WO-2012106560 A1 | 8/2012 |
| WO | WO-2013082186 A2 | 6/2013 |
| WO | WO-2013138161 A1 | 9/2013 |
| WO | WO-2013158938 A1 | 10/2013 |
| WO | WO-2014124967 A1 | 8/2014 |
| WO | WO-2014176515 A2 | 10/2014 |
| WO | WO-2014186395 A1 | 11/2014 |
| WO | WO-2015051319 A2 | 4/2015 |
| WO | WO-2020047216 A1 | 3/2020 |

(56) References Cited

FOREIGN PATENT DOCUMENTS

| WO | WO-2020167745 A1 | 8/2020 |
| WO | WO-2021127181 A1 | 6/2021 |
| WO | WO-2021150923 A1 | 7/2021 |
| WO | WO-2021247368 A1 | 12/2021 |
| WO | WO-2022221402 A1 | 10/2022 |
| WO | WO-2023043945 A1 | 3/2023 |
| WO | WO-2023091669 A1 | 5/2023 |
| WO | WO-2023102069 A1 | 6/2023 |

OTHER PUBLICATIONS

Co-pending U.S. Appl. No. 18/072,224, inventors Franklin; Scott et al., filed Nov. 30, 2022.

Neff et al. Soybean oil triacylglycerol analysis by reversed-phase high-performance liquid chromatography coupled with atmospheric pressure chemical ionization mass spectrometry. JAOCS, vol. 72, No. 10, pp. 1185-1191 (1995).

Patel et al. High conversion and productive catalyst turnovers in cross-metathesis reactions of natural oils with 2-butene. Green Chemistry, vol. 8, No. 5, pp. 450-454 (2006). First published online Mar. 22, 2006. DOI: https://doi.org/10.1039/B600956E.

Petrović et al. Polyols and Polyurethanes from Crude Algal Oil. Journal of the American Oil Chemists' Society, vol. 90, Issue 7, pp. 1073-1078 (Jul. 2013). First published Apr. 18, 2013. doi: https://doi.org/10.1007/s11746-013-2245-9.

Petrović. Polyurethanes from Vegetable Oils. Polymer Reviews 48:109-155 (2008).

Uprety et al. Utilization of microbial oil obtained from crude glycerol for the production of polyol and its subsequent conversion to polyurethane foams. Bioresour Technol. Jul. 2017;235:309-315. doi: 10.1016/j.biortech.2017.03.126. Epub Mar. 24, 2017.

Co-pending U.S. Appl. No. 18/304,085, inventor Franklin; Scott, filed Apr. 20, 2023.

PCT/US2022/043695 International Search Report and Written Opinion dated Mar. 28, 2023.

EP22843992.3 Supplementary European Search Report dated Sep. 8, 2023.

Szabo et al. Safety evaluation of oleic-rich triglyceride oil produced by a heterotrophic microalgal fermentation process. Food and Chemical Toxicology 65 (2014) 301-311. Available online Jan. 3, 2014.

Co-pending U.S. Appl. No. 18/241,561, inventors Franklin; Scott et al., filed Sep. 1, 2023.

Co-pending U.S. Appl. No. 18/310,329, inventors Petrovic; Zoran et al., filed May 1, 2023.

Co-pending U.S. Appl. No. 18/317,748, inventors Sterbenz; Matthew et al., filed May 15, 2023.

Co-pending U.S. Appl. No. 18/345,568, inventors Witmer; Garrett et al., filed Jun. 30, 2023.

Co-pending U.S. Appl. No. 18/345,591, inventors Witmer; Garrett et al., filed Jun. 30, 2023.

Co-pending U.S. Appl. No. 18/366,323, inventor Franklin; Scott, filed Aug. 7, 2023.

Co-pending U.S. Appl. No. 18/450,573, inventors Petrovic; Zoran et al., filed Aug. 16, 2023.

\* cited by examiner

|              | 1         10        20        30        40        50        60        70        80 |
|---|---|

Consensus Identity
SEQ ID NO:30
TGTTGAAGAATGAGCCGGCGACTTAAAATAAATGGCAGGCTAAGAGAATTAATAACTCGAAACCTAAGCGAAAGCAAGTCTTAATAGG 1. UTEX1533 rRNA sequence
2. P. moriformis UTEX1435 (KM396205)
SEQ ID NO:31

TGTTGAAGAATGAGCCGGCGACTTAAAATAAATGGCAGGCTAAGAGAATTAATAACTCGAAACCTAAGCGAAAGCAAGTCTTAATAGG
TTAAAATAAATGGCAGGCTAAGAGAATTAATAACTCGAAACCTAAGCGAAAGCAAGTCTTAATAGG 90        100       110       120       130       140       150       160       170

Consensus Identity
GCGCTAATTTAACAAAACATTAAATAAAATCTAAAGTCATTTATTTTAGACCCGAACCTGAGTGATCTAACCATGGTCAGGATGAAAC 1. UTEX1533 rRNA sequence
2. P. moriformis UTEX1435 (KM396205)

GCGCTAATTTAACAAAACATTAAATAAAATCTAAAGTCATTTATTTTAGACCCGAACCTGAGTGATCTAACCATGGTCAGGATGAAAC
GCGCTAATTTAACAAAACATTAAATAAAATCTAAAGTCATTTATTTTAGACCCGAACCTGAGTGATCTAACCATGGTCAGGATGAAAC 180       190       200       210       220       230       240       250       260

Consensus Identity
TTGGGTGACACCAAGTGGAAGTCCGAACCGACCGATGTTGAAAAATCGGCGGATGAACTGTGGTTAGTGGTGAAATACCAGTCGAACT 1. UTEX1533 rRNA sequence
2. P. moriformis UTEX1435 (KM396205)

TTGGGTGACACCAAGTGGAAGTCCGAACCGACCGATGTTGAAAAATCGGCGGATGAACTGTGGTTAGTGGTGAAATACCAGTCGAACT
TTGGGTGACACCAAGTGGAAGTCCGAACCGACCGATGTTGAAAAATCGGCGGATGAACTGTGGTTAGTGGTGAAATACCAGTCGAACT 270       280       290       300       310       320       330       340       350

Consensus Identity
CAGAGCTAGCTGGTTCTCCCCGAAATGCGTTGAGGCGCAGCAATATATCTCGTCTATCTAGGGGTAAAGCACTGTTTCGGTGCGGGCT 1. UTEX1533 rRNA sequence
2. P. moriformis UTEX1435 (KM396205)

CAGAGCTAGCTGGTTCTCCCCGAAATGCGTTGAGGCGCAGCAATATATCTCGTCTATCTAGGGGTAAAGCACTGTTTCGGTGCGGGCT
CAGAGCTAGCTGGTTCTCCCCGAAATGCGTTGAGGCGCAGCAATATATCTCGTCTATCTAGGGGTAAAGCACTGTTTCGGTGCGGGCT 360       370       380       390       400       410       420       430       440

Consensus Identity
ATGAAAATGGTACCAAATCGTGGCAAACTCTGAATACTAGAAATGACGATATATTAGTGAGACTATGGGGGATAAGCTCCATAGTCGA 1. UTEX1533 rRNA sequence
2. P. moriformis UTEX1435 (KM396205)

ATGAAAATGGTACCAAATCGTGGCAAACTCTGAATACTAGAAATGACGATATATTAGTGAGACTATGGGGGATAAGCTCCATAGTCGA
ATGAAAATGGTACCAAATCGTGGCAAACTCTGAATACTAGAAATGACGATATATTAGTGAGACTATGGGGGATAAGCTCCATAGTCGA 450       460       470       480       490       500       510       520

Consensus Identity
GAGGGAAACAGCCCAGACCACCAGTTAAGGCCCCAAAATGATAATGAAGTGGTAAAGGAGGTGAAAATGCAAATACAACCAGGAGGTT 1. UTEX1533 rRNA sequence
2. P. moriformis UTEX1435 (KM396205)

GAGGGAAACAGCCCAGACCACCAGTTAAGGCCCCAAAATGATAATGAAGTGGTAAAGGAGGTGAAAATGCAAATACAACCAGGAGGTT
GAGGGAAACAGCCCAGACCACCAGTTAAGGCCCCAAAATGATAATGAAGTGGTAAAGGAGGTGAAAATGCAAATACAACCAGGAGGTT 530       540       550       560       570 573

Consensus Identity
GGCTTAGAAGCAGCCATCCTTTAAAGAGTGCGTAATAGCTCACTG

1. UTEX1533 rRNA sequence
2. P. moriformis UTEX1435 (KM396205)

GGCTTAGAAGCAGCCATCCTTTAAAGAGTGCGTAATAGCTCACTG
GGCTTAGAAGCAGCCATCCTTTAAA

FIG. 1

Cycle 2 / Round#3

|  | Average Relative Values |  |  | Temp: 28°C |  | pH 6.0 | MEDIA:M20+5%GLU+25mM Citrate+1xVitamix |  |  |  |  |
|---|---|---|---|---|---|---|---|---|---|---|---|
|  | ctrl(-) | 1.9 | 2.5 | 3.3 | 4.4 | 5.9 | 7.9 | 10.5 | 14.1 | 18.8 | 25.0 | μM
| Mock | 1.00 | 1.09 | 0.98 | 0.96 | 0.97 | 0.91 | 0.88 | 0.77 | 0.75 | 0.64 | 0.59 |
| 20KuJ UV + 20μg/mL ICR-191 | 1.00 | 1.08 | 0.99 | 0.95 | 1.00 | 0.89 | 0.86 | 0.77 | 0.71 | 0.65 | 0.57 |
| 20KuJ UV | 1.00 | 0.95 | 0.94 | 0.90 | 0.91 | 0.84 | 0.81 | 0.72 | 0.66 | 0.60 | 0.58 |

Cycle 4 / Round#4

|  | Average Relative Values |  | Temp: 28°C |  |  |  | pH 6.0 | MEDIA:M20+5%GLU+25mM Citrate+1xVitamix |  |  |  |
|---|---|---|---|---|---|---|---|---|---|---|---|
|  | ctrl (-) | 7.5 | 10.0 | 13.3 | 17.8 | 23.7 | 31.6 | 42.2 | 56.3 | 75.0 | 100.0 | μM
| Mock | 1.00 | 0.86 | 0.83 | 0.71 | 0.69 | 0.54 | 0.57 | 0.53 | 0.44 | 0.37 | 0.29 |
| 20KuJ UV + 20μg/mL ICR-191 | 1.00 | 0.89 | 0.83 | 0.77 | 0.72 | 0.76 | 0.63 | 0.60 | 0.54 | 0.45 | 0.35 |
| 20KuJ UV | 1.00 | 0.90 | 0.88 | 0.68 | 0.71 | 0.71 | 0.65 | 0.61 | 0.59 | 0.56 | 0.48 |

C

| Compound (common name) | Structure | Presumed Mode of Action | Expected Lipid Phenotype |
|---|---|---|---|
| Triparanol | 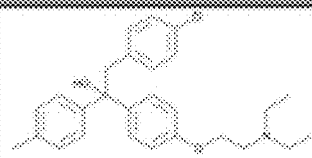 | sterol biosynthesis (e.g., shown to block second alkylation step, removal of 14α-methyl, Δ7 and/or Δ14-reductase, and introduction of Δ22 in Chlorella sp.) | growth inhibition (presumably by interfering w/ sterol production) |
| BASF 13-338 | 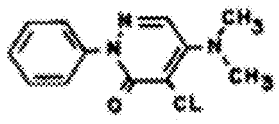 | Δ15 fatty acid desaturase in plants | >C18:1 |
| Cafenstrole | 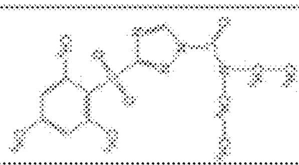 | fatty acid elongases | <lipid titer; >C18:2, <C20:0, <C22:0 |
| PF-04620110 | 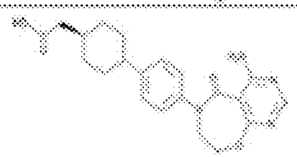 | human diacylglycerol O-acyltransferase 1 | < lipid titer |
| Clomiphene (citrate) | 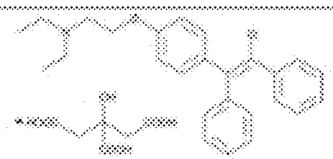 | Originally developed as a selective estrogen receptor agonist (ERα and ERβ) for use in stimulating ovulation. Increases sterol production in S. cerevisiae and in Chlorella kessleri | growth inhibition (presumably by interfering w/ sterol production) |
| Tioconazole | 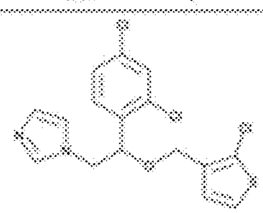 | Originally developed as an antifungal agent to inhibit the growth of various fungi, including C. albicans, C. neoformans, A. fumigatus, and T. rubrum. Inhibits C-14 demethylation of sterols in a cell-free C. albicans homogenate. | growth inhibition (presumably by interfering w/ sterol production) |

FIG. 8

HIGH OLEIC OIL COMPOSITIONS AND USES THEREOF

CROSS-REFERENCE

This application is a continuation of International Application No. PCT/US2022/43695 filed on Sep. 15, 2022, which claims the benefit of U.S. Provisional Application No. 63/245,734, U.S. Provisional Application No. 63/245,736, U.S. Provisional Application No. 63/245,737, and U.S. Provisional Application No. 63/245,740, each filed on Sep. 17, 2021, each of which is incorporated herein by reference in its entirety.

SEQUENCE LISTING

The instant application contains a Sequence Listing which has been submitted electronically in XML file format and is hereby incorporated by reference in its entirety. Said XML, copy, created on Jan. 19, 2023, is named 50727_719_301_SL.xml, and is 148,831 bytes in size.

BACKGROUND

Oleaginous microorganisms have the ability to convert carbon substrates into oils, including triacylglycerides (TAGs) or lipids, and accumulate these oils intracellularly. Some microorganisms can have capacity to accumulate lipids in amounts of up to 80% dry weight. Thus, oleaginous microorganisms, including microalgae, bacteria, fungi, and yeasts, can serve as an ideal source for biobased oil production. Genetic and non-genetic modification techniques can allow for the production of non-naturally occurring oils having particular fatty acid profiles.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

In some aspects, the present disclosure provides a non-naturally occurring oil comprising a triacylglyceride (TAG) component and ergosterol, wherein the TAG component has a fatty acid content comprising 80% or more C18:1 fatty acids.

In some aspects, the present disclosure provides a non-naturally occurring oil, obtained through non-genetic engineering means, comprising a triacylglyceride (TAG) component and ergosterol, wherein the TAG component has a fatty acid content comprising 80% or more C18:1 fatty acids.

In some aspects, the present disclosure provides a formulation comprising a non-naturally occurring oil described herein.

In some aspects, the present disclosure provides an oleaginous, non-naturally occurring microorganism that produces a non-naturally occurring oil described herein.

In some aspects, the present disclosure provides a bioreactor comprising an oleaginous, non-naturally occurring microorganism described herein.

In some aspects, the present disclosure provides a method for producing a non-naturally occurring oil described herein, the method comprising: culturing in a bioreactor an oleaginous, non-naturally occurring microorganism described herein, thereby producing the non-naturally occurring oil.

In some aspects, the present disclosure provides an oil comprising a TAG component and at least 100 mg of ergosterol per 100 g of the oil, wherein the TAG component has a fatty acid content comprising 80% or more C18:1 fatty acids.

In some aspects, the present disclosure provides a microbial cell that produces a TAG oil comprising 80% or more C18:1 fatty acids, wherein the cell does not comprise an exogenous gene or exogenous nucleotides.

In some aspects, the present disclosure provides a method of producing an oil described herein, the method comprising: culturing a cell described herein, in a medium in a bioreactor.

In some aspects, the present disclosure provides a bioreactor comprising an oil described herein.

In some aspects, the present disclosure provides a bioreactor comprising a cell described herein.

In some aspects, the present disclosure provides a method of producing a cell, the method comprising: obtaining a microbial base strain; and subjecting the base strain to a classical strain improvement method to induce random or semi-random mutagenesis, wherein the cell produces a TAG oil comprising 80% or more C18:1 fatty acids, wherein the cell does not comprise an exogenous gene or exogenous nucleotides.

In some aspects, the present disclosure provides a cell produced by a method described herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows a sequence alignment of a region of the plastidic 23 S rDNA between a *Prototheca wickerhamii* strain (UTEX 1533; SEQ ID NO:30) and a *Prototheca moriformis* strain (UTEX 1435; SEQ ID NO:31).

FIG. 8, Panel A shows growth results from the selection strategies described herein. FIG. 8, Panel B shows components of mixture 12 and 14 used in selection strategies described herein. FIG. 8, Panel C describes the various compounds used in selection strategies described herein.

DETAILED DESCRIPTION

Figure 2:
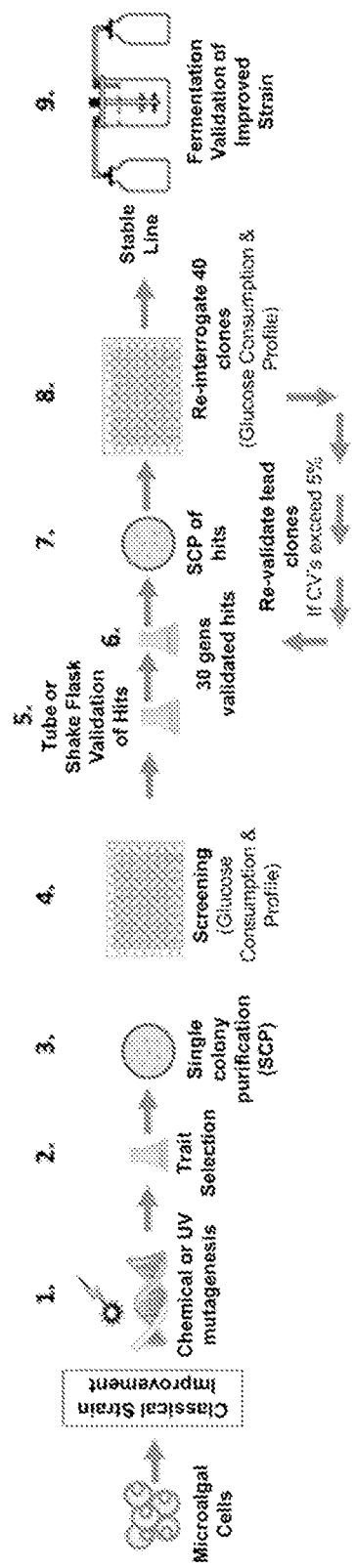
FIG. 2 shows an outline of the mutagenesis, trait selection, high-throughput, and automated screening steps of the improvement process described herein.

Provided herein are oil compositions having high oleic acid content, methods of making thereof, and formulations and applications thereof. Oil compositions provided herein can be produced by a microorganism that is genetically modified or non-genetically modified. Non-genetically modified microorganisms can be produced by classical strain improvement strategies such as those described herein. In turn, these non-naturally occurring microorganism can produce non-naturally occurring oils provided herein.

Genetic and non-genetic modification techniques can allow for the production of non-naturally occurring oils having particular phenotypes. While genetic engineering techniques can tend to be more targeted to phenotypes elicited in a host oleaginous microbe, classical strain improvement or other non-genetic engineering techniques can also be employed to enhance phenotypes. Enhancement of phenotypes can include elaboration of a particular fatty acid profile (e.g., high oleic acid content), yield on carbon, volumetric oil accumulation (e.g., g oil/L culture), oil productivity (e.g., g oil/L culture day), and oil as a percent dry cell weight (DCW) as a measure of strain performance.

A further benefit of classical strain improvement techniques, when used as the sole means to alter or improve strain phenotype and performance, can be realized from both a regulatory and business/marketing perspective. From a regulatory perspective, non-genetically engineered microbes may be exempt from regulatory oversight by entities such as U.S. EPA's Toxic Substances Control Act (TSCA) and the requirement to file a Microbial Commercial Activity Notice (MCAN) when the material is to be used in chemical (non-food) applications. Such dispensation extends to other geographies as well, such as Brazil, for example, where such microbes are exempt from filing a Strain Dossier with the Brazilian regulatory body (the National Technical Commission of Biosafety, Ministry of Science, Technology, Innovation, and Communications or CTNBio) that oversees industrial microbes. The avoidance of such regulatory oversight can save millions of dollars in development costs. From a marketing and consumer branding perspective, the raw materials produced by such non-genetically engineered means can meet GMO-free and organic labeling standards, as well as brands' and consumers' desires for "clean labeling".

As used herein, the term "classical strain improvement" refers to methods of random or semi-random mutagenesis of microbes to create non-naturally occurring strains with improved properties. These methods include, but not limited to, mutagenesis of a population to create genetic variants, random selection or screening of a surviving population to identify an improved strain, and identification of improved strains by assaying fermentation broth for products. Classical strain improvement methods include exposure to UV radiation, chemical mutagens, and/or selective or enrichment agents. Classical strain improvement methods do not include recombinant genetic engineering methods targeted to one or more genomic regions, e.g., via homologous recombination.

As used herein, the term "microbial oil" refers to an oil produced or extracted from a microorganism (microbe), e.g., an oleaginous, single-celled, eukaryotic, or prokaryotic microorganism, including but not limited to, microalgae, yeast, bacteria, and fungi.

As used herein, the term "triacylglycerol", "triglyceride", or "TAG" refers to esters between glycerol and three saturated and/or unsaturated fatty acids. Generally, fatty acids of TAGs have chain lengths of 6 carbon atoms or more.

As used herein, the term "TAG purity", "molecular purity", or "oil purity" refers to the number of molecular species that make up an oil composition, on an absolute basis or present in amounts above a certain threshold. The fewer the number of TAG species in an oil, the greater the "purity" of the oil.

As used herein, the term "fatty acid profile" refers to a fatty acid composition of an oil, e.g., an oil produced by a cell provided herein or a derivative thereof. Derivatives of an oil produced by a cell provided herein include a refined, bleached, and deodorized oil. Fatty acid profiles can be determined by subjecting an oil to transesterification to generate fatty acid methyl esters (FAMEs) and subsequently quantitating fatty acid type by Gas Chromatography equipped with a Flame Ionization Detector (GC/FID).

As used herein, the term "sterol profile" refers to a sterol composition of an oil, e.g., an oil produced by a cell provided herein or a derivative thereof. Derivatives of an oil produced by a cell provided herein include a refined, bleached, and deodorized oil.

As used herein, the term "polyol" refers to triglycerols or fatty acid alcohols comprising hydroxyl functional groups. As used herein, the term "polyol derived from a TAG oil" generally refers to a polyol obtained from chemical conversion of a TAG oil, e.g., via epoxidation and ring opening, ozonolysis and reduction, or hydroformylation and reduction.

As used herein, the term "polyurethane", "PU", or "urethane" refers to a class of polymers comprised of carbamate (urethane) linkages formed between a polyol and an isocyanate moiety.

As used herein, the term "oleic content", "oleic acid content", "oleate content", or "olein content" refers the percentage amount of oleic acid in the fatty acid profile of a substance (e.g., a TAG oil). As used herein, the term "C18:1 content" refers the percentage amount of a C18:1 fatty acid (e.g., oleic acid) in the fatty acid profile of a substance (e.g., a microbial oil).

As used herein, the term "high oleic" can refer to greater than 60% oleic acid, greater than 65% oleic acid, greater than 70% oleic acid, greater than 75% oleic acid, greater than 80% oleic acid, greater than 85% oleic acid, or greater than 90% oleic acid.

As used herein, "sequence identity" refers to a percentage of identical amino acid residues between two sequences being compared after an optimal alignment of sequences. An optimal alignment of sequences may be produced manually or by means of computer programs that use a sequence alignment algorithm (e.g., ClustalW, T-coffee, COBALT, BestFit, FASTA, BLASTP, BLASTN, and TFastA). Sequence identity can be calculated by determining the number of identical positions between the two sequences being compared, dividing this number by the number of positions compared, and multiplying the result obtained by 100 to obtain the sequence identity between the two sequences.

As used herein, the term "about" refers to ±10% from the value provided.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are described herein.

Microbial Cells and Oils Produced Therefrom.

An oil provided herein is obtained from a non-genetically modified microorganism (microbe), for example, oleaginous microalgae, yeast, or bacteria. In some embodiments, the non-genetically modified microorganism is a microalgal cell. In some embodiments, the microalgal cell is a non-genetically modified *Prototheca* sp. strain. The non-genetically modified *Prototheca* sp. strain can be produced by one or more classical strain improvement strategies described herein.

In some embodiments, a cell provided herein does not comprise an exogenous gene or exogenous nucleotides that encodes for an exogenous protein or gene. For example, a cell provided herein does not comprise an exogenous gene in a lipid biosynthetic pathway. In some embodiments, a cell provided herein does not comprise a genetic disruption of one or more alleles of an endogenous gene in a lipid biosynthetic pathway. In some embodiments, a cell provided herein does not comprise a heterologous insertion within a genomic region that encodes for an endogenous gene in a lipid biosynthetic pathway. Non-limiting examples of genes involved in lipid biosynthesis include acyl-ACP thioesterase (FAT), delta-12 fatty acid desaturase (FAD), ketoacyl-ACP synthase (KAS), stearoyl-ACP desaturase (SAD), lysophosphatidic acid acyltransferase (LPAAT), ketoacyl-CoA reductase (KCR), hydroxyacyl-CoA dehydratase (HACD), and enoyl-CoA reductase (ECR).

In some embodiments, a cell provided herein does not comprise an exogenous acyl-ACP thioesterase gene. In some embodiments, a cell provided herein does not comprise a genetic disruption of one or more alleles of an endogenous acyl-ACP thioesterase gene. In some embodiments, a cell provided herein does not comprise a heterologous insertion within a genomic region that encodes for an endogenous acyl-ACP thioesterase gene. In some embodiments, the endogenous acyl-ACP thioesterase gene is FATA.

In some embodiments, a cell provided herein does not comprise an exogenous fatty acid desaturase gene. In some embodiments, a cell provided herein does not comprise a genetic disruption of one or more alleles of an endogenous fatty acid desaturase gene. In some embodiments, a cell provided herein does not comprise a heterologous insertion within a genomic region that encodes for an endogenous fatty acid desaturase gene. In some embodiments, the endogenous fatty acid desaturase gene is a delta-12 fatty acid desaturase. In some embodiments, the endogenous fatty acid desaturase gene is FAD2.

In some embodiments, a cell provided herein does not comprise an exogenous ketoacyl-ACP synthase gene. In some embodiments, a cell provided herein does not comprise a genetic disruption of one or more alleles of an endogenous ketoacyl-ACP synthase gene. In some embodiments, a cell provided herein does not comprise a heterologous insertion within a genomic region that encodes for an endogenous ketoacyl-ACP synthase gene. In some embodiments, the endogenous ketoacyl-ACP synthase gene is KASI, KASII, or KASIII.

In some embodiments, a cell provided herein does not comprise an exogenous stearoyl-ACP desaturase gene. In some embodiments, a cell provided herein does not comprise a genetic disruption of one or more alleles of an endogenous stearoyl-ACP desaturase gene. In some embodiments, a cell provided herein does not comprise a heterologous insertion within a genomic region that encodes for an endogenous stearoyl-ACP desaturase gene. In some embodiments, the endogenous stearoyl-ACP desaturase gene is SAD2.

In some embodiments, a cell provided herein does not comprise an exogenous lysophosphatidic acid acyltransferase gene. In some embodiments, a cell provided herein does not comprise a genetic disruption of one or more alleles of an endogenous lysophosphatidic acid acyltransferase gene. In some embodiments, a cell provided herein does not comprise a heterologous insertion within a genomic region that encodes for an endogenous lysophosphatidic acid acyltransferase gene.

In some embodiments, a cell provided herein does not comprise a genetic disruption of one or more alleles within 1.5 kb of an endogenous V-type proton ATPase catalytic subunit A isoform 1 gene or 6S genomic region. In some embodiments, a cell provided herein does not comprise a heterologous insertion within 1.5 kb of an endogenous V-type proton ATPase catalytic subunit A isoform 1 gene or 6S genomic region.

In some embodiments, a cell provided herein does not comprise a genetic disruption of one or more alleles within 1.5 kb of an endogenous DAO1B gene. In some embodiments, a cell provided herein does not comprise a heterologous insertion within 1.5 kb of an endogenous DAO1B gene.

In some embodiments, a cell provided herein does not comprise a genetic disruption of one or more alleles within 1.5 kb of an endogenous Thi4 gene. In some embodiments, a cell provided herein does not comprise a heterologous insertion within 1.5 kb of an endogenous Thi4 gene.

Accordingly, a cell provided herein comprises uninterrupted sequences of endogenous genes or genomic regions, including FAD2, FATA1, KASII, SAD2, V-type proton ATPase catalytic subunit A isoform 1 (6S), DAO1B, and Thi4 described herein.

In some embodiments, a cell provided herein comprises at least 80%, at least 85%, at least 90%, at least 95%, or at least 99% sequence identity to any one of SEQ ID NO:1-26. In some embodiments, a cell provided herein comprises any one of SEQ ID NO:1-26 (genomic regions of CHK22 and CHK80). In some embodiments, a cell provided herein comprises SEQ ID NO:1-26 (genomic regions of CHK22 and CHK80).

In some embodiments, a cell provided herein comprises at least 80%, at least 85%, at least 90%, at least 95%, or at least 99% sequence identity to any one of SEQ ID NO:1, 3, 5, 7, 9, 11, 13, 15, 18, 19, 21, 23, and 25 (genomic regions of CHK80). In some embodiments, a cell provided herein comprises any one of SEQ ID NO:1, 3, 5, 7, 9, 11, 13, 15, 18, 19, 21, 23, and 25 (genomic regions of CHK80). In some embodiments, a cell provided herein comprises SEQ ID NO:1, 3, 5, 7, 9, 11, 13, 15, 18, 19, 21, 23, and 25 (genomic regions of CHK80).

In some embodiments, an oil provided herein is produced by microalgae. In some embodiments, the microalgae is a species of a genus selected from the group consisting of: *Chlorella* sp., *Pseudochlorella* sp., *Heterochlorella* sp., *Prototheca* sp., *Arthrospira* sp., *Euglena* sp., *Nannochloropsis* sp., *Phaeodactylum* sp., *Chlamydomonas* sp., *Scenedesmus* sp., *Ostreococcus* sp., *Selenastrum* sp., *Haematococcus* sp., *Nitzschia, Dunaliella, Navicula* sp., *Trebouxia* sp., *Pseudotrebouxia* sp., *Vavicula* sp., *Bracteococcus* sp., *Gomphonema* sp., *Watanabea*, sp., *Botryococcus* sp., *Tetraselmis* sp., and *Isochrysis* sp. In some embodiments, the microalgae is

*Prototheca* sp. In some embodiments, the microalgae is *P. moriformis*. In some embodiments, the microalgae is *P. wickerhamii*. In some embodiments, a cell provided herein is derived from a UTEX 1435 base strain. In some embodiments, a cell provided herein is derived from a UTEX 1533 base strain. In some embodiments, a cell provided herein is derived from a base strain having a 23S ribosomal DNA sequence that is at least 80%, at least 85%, at least 90%, at least 95%, or 100% identity to SEQ ID NO:30 or SEQ ID NO:31. In some embodiments, a cell provided herein has a 23S ribosomal DNA sequence that is at least 80%, at least 85%, at least 90%, at least 95%, or 100% identity to SEQ ID NO:30 or SEQ ID NO:31.

In some embodiments, an oil provided herein is produced by oleaginous yeast. In some embodiments, the oleaginous yeast is a species of a genus selected from the group consisting of: *Candida* sp., *Cryptococcus* sp., *Debaromyces* sp., *Endomycopsis* sp., *Geotrichum* sp., *Hyphopichia* sp., *Lipomyces* sp., *Pichia*, sp., *Rodosporidium* sp., *Rhodotorula* sp., *Sporobolomyces* sp., *Starmerella* sp., *Torulaspora* sp., *Trichosporon* sp., *Wickerhamomyces* sp., *Yarrowia* sp., and *Zygoascus* sp.

In some embodiments, an oil provided herein is obtained from or produced by oleaginous bacteria. In some embodiments, the oleaginous bacteria is a species selected from the group consisting of: *Flavimonas oryzihabitans, Pseudomonas aeruginosa, Morococcus* sp., *Rhodobacter sphaeroides, Rhodococcus opacus, Rhodococcus erythropolis, Streptomyces jeddahensis, Ochrobactrum* sp., *Arthrobacter* sp., *Nocardia* sp., *Mycobacteria* sp., *Gordonia* sp., *Catenisphaera* sp., and *Dietzia* sp.

Further provided herein are bioreactors comprising a non-naturally occurring microorganism provided herein. For example, these bioreactors comprise an oleaginous, non-naturally occurring microorganism and an oil produced by the microorganism.

While in many embodiments, an oil provided herein is obtained from a non-genetically modified microorganism or a classically-improved microorganism, in other embodiments, an oil provided herein is obtained from a genetically modified microorganism, for example, oleaginous microalgae, yeast, or bacteria. In some embodiments, an oil provided herein is obtained from a classically-improved microorganism that is then genetically modified to produce a genetically modified microorganism. In some embodiments, the genetically modified microorganism is a genetically modified *Prototheca* sp. strain.

Classical Strain Improvement.

Classical strain improvement strategies can be used to select for organisms having desired phenotypes, e.g., high oleic oil production. Classical strain improvement (also called "mutation breeding") involves exposing organisms to chemicals or radiation to generate mutants with desirable traits. These classical strain improvement methods introduce random or semi-random mutations, which can thereby allow selection of strains exhibiting desirable traits as a result of random mutagenesis. Several iterations of mutagenesis and selection can be performed with one or more mutagens to arrive to a strain having desirable phenotypes. Ultraviolet (UV) light can be used to introduce random mutations within a microorganism's nuclear genome. Chemical mutagens include compounds which inhibit or disrupt biosynthetic processes of a microorganism, e.g., antibiotics, antifungals, or carcinogens. Non-limiting examples of chemical mutagens include ICR-191, ethyl methanesulfonate (EMS), and 4-nitroquinoline-1-oxide (4-NQO). Non-limiting examples of chemical mutagens also include acridine mutagens, amino acid analogs, fatty acid biosynthesis inhibitors, cholesterol biosynthetic inhibitors, mTOR inhibitors, and membrane solubilizing agents. Combinations of chemical mutagens can also be used simultaneously to induce mutagenesis. Following mutagenesis, selective or enrichment agents can be used to select or enrich for strains of interest. Non-limiting examples of enrichment agents include L-canavanine, cerulenin, triparanol, clomiphene, clomiphene citrate, clotrimazole, terfenadine, fluphenazine, AZD8055, BASF 13-338, cafenstrole, clomiphene, PF-042110, and phenethyl alcohol.

Methods provided herein include classical strain improvement methods to improve strain productivity, carbon yield, and oleic acid content. Glucose consumption rate can be highly predictive indicator of lipid titer. As such, glucose consumption rate can be used as an enrichment tool in the mutant selection process. The methods provided herein can further include one or more of determining a total lipid titer of the cell, determining a fatty acid profile of the oil, or determining a C18:1 (e.g., oleic acid) content of the oil. Further, the methods provided herein can include assaying cell media to determine glucose consumption rate, total lipid titer, a fatty acid profile, and/or a C18:1 (e.g., oleic acid) content.

High Oleic Oils of the Disclosure.

The complexity and physical properties of an oil can be evaluated by the fatty acid profile and the TAG profile of the TAG component of an oil. The fatty acid profile is a measure of fatty acid composition, and can be determined by subjecting an oil to transesterification to generate fatty acid methyl esters (FAMEs) and subsequently quantitating fatty acid type by Gas Chromatography equipped with a Flame Ionization Detector (GC/FID). Accordingly, fatty acid content can be determined by GC/FID. Since TAGs comprise of three fatty acids arrayed along the glycerol backbone in the triglyceride molecule, the number of possible distinct regioisomers of TAGs can be defined by the number of fatty acid species in the oil raised to the third power. The TAG profile provides relative amounts of various TAG species in an oil, which can be determined by subjecting the oil to TAG fractionation using Liquid Chromatography/Time of Flight-Mass Spectrometry (LC/TOF-MS) equipped with an Atmospheric Pressure Chemical Ionization (APCI) source.

In some embodiments, an oil provided herein has a high oleic acid content and low saturated fatty acid content. For example, the fatty acid content of the TAG component of an oil provided herein can be high in oleic acid and low in saturated fatty acids.

Non-limiting examples of monounsaturated fatty acids include C10:1, C12:1, C14:1, C16:1, C17:1, C18:1, C18:1-OH, C20:1, C22:1, and C24:1. In some embodiments, an oil provided herein comprises one or more of C10:1, C12:1, C14:1, C16:1, C17:1, C18:1, C18:1-OH, C20:1, C22:1, or C24:1 fatty acids. In some embodiments, an oil provided herein has a monounsaturated fatty acid content of at least 60%, at least 70%, at least 80%, or at least 90%. For example, an oil provided herein has a C18:1 content of at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

In some embodiments, an oil provided herein has a fatty acid content comprising 60% or more, 70% or more, 80% or more, or 90% or more of C18:1 fatty acids. In some embodiments, the C18:1 fatty acids comprise oleic acid. In some embodiments, the C18:1 fatty acids comprise at least 90% oleic acid. In some embodiments, the C18:1 fatty acids comprise at least 95% oleic acid. In some embodiments, the C18:1 fatty acids comprise at least 99% oleic acid.

An oil provided herein has a C18:1 content of from 60-100%, 60-70%, 70-80%, 80-90%, 85-90%, or 80-100%. In some embodiments, an oil provided herein has a C18:1 content of at least 60%, at least 70%, at least 80%, or at least 90%. For example, an oil provided herein has a C18:1 content of at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

An oil provided herein has an oleic content of from 60-100%, 60-70%, 70-80%, 80-90%, 85-90%, or 80-100%. In some embodiments, an oil provided herein has an oleic content of at least 60%, at least 70%, at least 80%, or at least 90%. For example, an oil provided herein has an oleic content of at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

An oil provided herein has a triolein (OOO) content of from 50-100%, 60-100%, 60-90%, 60-80%, 60-70%, 50-70%, or 60-65%. In some embodiments, an oil provided herein has a triolein content of at least 30%, at least 40%, at least 50%, at least 60%, at least 70%, at least 80%, or at least 90%. For example, an oil provided herein has a triolein content of at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, or more.

An oil provided herein has a C16:1 content of from 0.1-5%, 0.1-2%, 0.1-1%, 0.1-0.5% or 0.1-0.2%. In some embodiments, an oil provided herein has a C16:1 content of greater than 0.1%, greater than 0.2%, greater than 0.3%, greater than 0.4%, or greater than In some embodiments, an oil provided herein has a C16:1 content of less than 0.5%, less than 0.4%, less than 0.3%, less than 0.2%, or less than 0.1%. In some embodiments, this oil has a C16:1 content of greater than 0%. In some embodiments, an oil provided herein has a C16:1 content of about 0.1% or about 0.2%.

An oil provided herein has a C20:1 content of from 0.1-5%, 0.1-2%, 0.1-1%, 0.5-2%, or 1-2%. In some embodiments, an oil provided herein has a C20:1 content of greater than 0.1%, greater than 0.2%, greater than 0.3%, greater than 0.4%, greater than 0.5%, greater than 0.6%, greater than 0.7%, greater than 0.8%, greater than 0.9%, or greater than 1%. In some embodiments, an oil provided herein has a C20:1 content of less than 5%, less than 4%, less than 3%, less than 2%, less than 1%, less than 0.9%, less than 0.8%, less than less than 0.6%, less than 0.5%, less than 0.4%, less than 0.3%, less than 0.2%, or less than 0.1%. In some embodiments, this oil has a C20:1 content of greater than 0%. In some embodiments, an oil provided herein has a C20:1 content of about 1% or about 1.5%.

Non-limiting examples of saturated fatty acids include C10:0, C12:0, C14:0, C16:0, C17:0, C18:0, C20:0, C22:0, and C24:0. In some embodiments, an oil provided herein comprises one or more of C10:0, C12:0, C14:0, C16:0, C17:0, C18:0, C20:0, C22:0, or C24:0 fatty acids. In some embodiments, an oil provided herein has a saturated fatty acid content of less than 30%, less than 20%, less than 10%, less than 9%, less than 8%, less than 7%, less than 6%, less than 5%, less than 4%, less than 3%, less than 2%, or less than 1%. For example, an oil provided herein has a saturated fatty acid content of less than about 30%, less than about 29%, less than about 28%, less than about 27%, less than about 26%, less than about 25%, less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, or less. In some embodiments, this oil has a saturated fatty acid content of greater than 0%. In some embodiments, an oil provided herein has a saturated fatty acid content of about 0%.

An oil provided herein has a C14:0 content of from 0.1-1%, 0.1-0.5%, 0.1-0.2%, or In some embodiments, an oil provided herein has a C14:0 content of less than 1%, less than 0.9%, less than 0.8%, less than 0.7%, less than 0.6%, less than 0.5%, less than 0.4%, less than 0.3%, less than 0.2%, or less than 0.1%. In some embodiments, this oil has a C14:0 content of greater than 0%. In some embodiments, an oil provided herein has a C14:0 content of about 0%.

An oil provided herein has a C16:0 content of from 1-10%, 1-5%, 3-5%, or 3-4%. In some embodiments, an oil provided herein has a C16:0 content of less than 10%, less than 9%, less than 8%, less than 7%, less than 6%, less than 5%, less than 4%, less than 3%, less than 2%, or less than 1%. In some embodiments, this oil has a C16:0 content of greater than 0%. In some embodiments, an oil provided herein has a C16:0 content of greater than 3%. In some embodiments, an oil provided herein has a C16:0 content of about 0%.

An oil provided herein has a C18:0 content of from 1-10%, 1-5%, 2-5%, or 2-3%. In some embodiments, an oil provided herein has a C18:0 content of less than 5%, less than 4%, less than 3%, less than 2%, or less than 1%. In some embodiments, this oil has a C18:0 content of greater than 0%. In some embodiments, an oil provided herein has a C18:0 content of about 0%.

An oil provided herein has a C20:0 content of from 1-10%, 1-5%, 1-3%, 1-2%, or 2-3%. In some embodiments, an oil provided herein has a C20:0 content of less than 5%, less than 4%, less than 3%, less than 2%, or less than 1%. In some embodiments, this oil has a C20:0 content of greater than 0%. In some embodiments, an oil provided herein has a C20:0 content of about 0%.

Non-limiting examples of polyunsaturated fatty acids include C18:2, C18:3, C18:3 alpha, C18:3 gamma, and C22:2. In some embodiments, an oil provided herein comprises one or more of C18:2, C18:3, C18:3 alpha, C18:3 gamma, or C22:2 fatty acids. In some embodiments, an oil provided herein has a polyunsaturated fatty acid content of less than 30%, less than 20%, less than 10%, less than 9%, less than 8%, less than 7%, less than 6%, less than 5%, less than 4%, less than 3%, less than 2%, or less than 1%. For example, an oil provided herein has a polyunsaturated fatty acid content of less than about 30%, less than about 29%, less than about 28%, less than about 27%, less than about 26%, less than about 25%, less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, or less. In some embodiments, this oil has a polyunsaturated fatty acid content of greater than 0%. In some embodiments, an oil provided herein has a polyunsaturated fatty acid content of about 0%.

An oil provided herein has a C18:2 content of from 1-10% or 5-10%. In some embodiments, an oil provided herein has a C18:2 content of less than 10%, less than 9%, less than 8%, less than 7%, less than 6%, less than 5%, less than 4%, less than 3%, less than 2%, or less than 1%. In some embodiments, this oil has a C18:2 content of greater than 0%. In some embodiments, an oil provided herein has a C18:2 content of about 0%.

In some embodiments, the fatty acid content of a TAG component comprises one or more of C14:0, C16:0, C16:1, C18:0, C18:1, C18:2, C18:3 alpha, C20:0, or C20:1 fatty acids. In some embodiments, the fatty acid content of the TAG component comprises C16:0, C18:0, C18:1, and C18:2 fatty acids.

The fatty acid content of the TAG component can comprise 1-10%, 1-5%, or 3-5% of C16:0 fatty acids. In some embodiments, the fatty acid content of a TAG component comprises 3% or more of C16:0 fatty acids. In some embodiments, the fatty acid content of a TAG component comprises more than 3% of C16:0 fatty acids.

The fatty acid content of the TAG component can comprise 1-5%, 2-5%, or 2-3% of C18:0 fatty acids. In some embodiments, the fatty acid content of the TAG component comprises 2% or more of C18:0 fatty acids. In some embodiments, the fatty acid content of the TAG component comprises more than 2% of C18:0 fatty acids. In some embodiments, the fatty acid content of the TAG component comprises less than 3% of C18:0 fatty acids.

The fatty acid content of the TAG component can comprise 1-10%, 1-5%, or 5-10% of C18:2 fatty acids. In some embodiments, the fatty acid content of the TAG component comprises 5% or more of C18:2 fatty acids. In some embodiments, the fatty acid content of the TAG component comprises more than 5% of C18:2 fatty acids.

In addition to the fatty acid profile, an oil can be further evaluated by the sterol profile or composition. Sterol composition can be determined by mass spectrometry, for example, gas chromatography-mass spectrometry (GC-MS); liquid chromatography-mass spectrometry (LC-MS); tandem mass spectrometry (MS/MS), and coupled liquid and gas chromatography with subsequent flame ionization detection (LC-GC-FID). Concentration of the different sterols present in an oil can be expressed as mg sterol/100 g of oil. Non-limiting examples of sterols include brassicasterol; campesterol; stigmasterol; beta-sitosterol (β-sitosterol); ergosterol; ergosta-5,7,9(11),22-tetraen-3-ol,(3β,22E), ergosta-7,22-dien-3-ol, (3β,22E); ergost-8(14)-en-3-ol, (3β); ergosta-5,8-dien-3-ol, (3β); 5.xi.-ergost-7-en-3β-ol; 9,19-cyclolanost-24-en-3-ol, (3(3); and 9,19-cyclolanostan-3-ol, 24-methylene-, (3β).

In some embodiments, an oil provided herein comprises one or more of ergosterol; ergosta-5,8-dien-3-ol, (3β); 5.xi.-ergost-7-en-3β-ol; 9,19-cyclolanost-24-en-3-ol, (3β); and 9,19-cyclolanostan-3-ol, 24-methylene-, (3β).

An oil provided herein comprises 50-200 mg, 100-200 mg, 100-150 mg, 100-130 mg, 150-200 mg, 160-180 mg, or 160-170 mg of ergosterol per 100 g of the oil. In some embodiments, an oil provided herein comprises more than 50 mg, more than 100 mg, more than 150 mg, or more than 160 mg of ergosterol per 100 g of the oil. In some embodiments, an oil provided herein comprises no more than 170 mg of ergosterol per 100 g of the oil. In some embodiments, the sterol content (as a percentage of total sterols) of an oil provided herein comprises 40-80%, 40-70%, 50-70%, 50-60%, 40-50%, at least 40%, at least 50%, or at least 60% ergosterol on a weight-by-weight basis.

An oil provided herein comprises 0-10 mg, 0-5 mg, 0-2 mg, or 0-1 mg of campesterol per 100 g of the oil. In some embodiments, an oil provided herein comprises no more than 10 mg, no more than 9 mg, no more than 8 mg, no more than 7 mg, no more than 6 mg, no more than 5 mg, no more than 4 mg, no more than 3 mg, no more than 2 mg, or no more than 1 mg of campesterol per 100 g of the oil. In some embodiments, an oil provided herein does not comprise campesterol. In some embodiments, an oil provided herein does not contain a detectable level of campesterol. In some embodiments, the sterol content (as a percentage of total sterols) of an oil provided herein comprises about 0% campesterol on a weight-by-weight basis.

An oil provided herein can comprise 0-10 mg, 0-5 mg, 0-2 mg, or 0-1 mg of brassicasterol per 100 g of the oil. In some embodiments, an oil provided herein does not contain brassicasterol. In some embodiments, an oil provided herein does not contain a detectable level of brassicasterol. In some embodiments, the sterol content (as a percentage of total sterols) of an oil provided herein comprises about 0% brassicasterol on a weight-by-weight basis.

An oil provided herein comprises 0-10 mg, 0-5 mg, 0-2 mg, or 0-1 mg of stigmasterol per 100 g of the oil. In some embodiments, an oil provided herein comprises no more than 10 mg, no more than 9 mg, no more than 8 mg, no more than 7 mg, no more than 6 mg, no more than 5 mg, no more than 4 mg, no more than 3 mg, no more than 2 mg, or no more than 1 mg of stigmasterol per 100 g of the oil. In some embodiments, an oil provided herein does not contain stigmasterol. In some embodiments, an oil provided herein does not contain a detectable level of stigmasterol. In some embodiments, the sterol content (as a percentage of total sterols) of an oil provided herein comprises about 0% stigmasterol on a weight-by-weight basis.

An oil provided herein can comprise 0-10 mg, 0-5 mg, 0-2 mg, or 0-1 mg of β-sitosterol per 100 g of the oil. In some embodiments, an oil provided herein comprises no more than 20 mg, no more than 15 mg, no more than 10 mg, no more than 9 mg, no more than 8 mg, no more than 7 mg, no more than 6 mg, no more than 5 mg, no more than 4 mg, no more than 3 mg, no more than 2 mg, or no more than 1 mg of β-sitosterol per 100 g of the oil. In some embodiments, an oil provided herein does not contain β-sitosterol. In some embodiments, an oil provided herein does not contain a detectable level of β-sitosterol. In some embodiments, the sterol content (as a percentage of total sterols) of an oil provided herein comprises about 0% β-sitosterol on a weight-by-weight basis.

An oil provided herein can comprise 0.1-100 mg, 0.1-50 mg, 1-20 mg, 1-50 mg, 10-mg, 10-30 mg, or 10-20 mg of ergosta-5,8-dien-3-ol, (3β)-per 100 g of the oil. In some embodiments, an oil provided herein comprises more than 1 mg, more than 5 mg, more than mg, more than 15 mg, more than 20 mg, more than 25 mg, more than 30 mg, more than 35 mg, more than 40 mg, more than 45 mg, or more than 50 mg of ergosta-5,8-dien-3-ol, (3β)-per 100 g of the oil. In some embodiments, the sterol content (as a percentage of total sterols) of an oil provided herein comprises 1-10%, 5-10%, at least 1%, at least 2%, at least 3%, at least 4%, at least 5%, at least 6%, or at least 7% ergosta-5,8-dien-3-ol, (3β)-on a weight-by-weight basis.

An oil provided herein can comprise 0.1-100 mg, 0.1-50 mg, 1-50 mg, 10-50 mg, 20-mg, 30-50 mg, or 30-40 mg of 5.xi.-ergost-7-en-3β-ol, (3β) per 100 g of the oil. In some embodiments, an oil provided herein comprises more than 1 mg, more than 5 mg, more than mg, more than 15 mg, more than 20 mg, more than 25 mg, or more than 30 mg of 5.xi.-ergost-7-en-3β-ol, (3β) per 100 g of the oil. In some embodiments, the sterol content (as a percentage of total sterols) of an oil provided herein comprises 1-20%, 1-10%, 10-20%, at least 1%, at least 2%, at least 3%, at least 4%, at least 5%, at least 6%, at least 7%, at least 8%, at least 9%, at least 10%, at least 11%, or at least 12% 5.xi.-ergost-7-en-3β-ol, (3(3) on a weight-by-weight basis.

An oil provided herein can comprise 0.1-100 mg, 0.1-50 mg, 1-100 mg, 1-50 mg, 50-100 mg, 50-70 mg, 60-70 mg, 30-50 mg, or 30-40 mg of 9,19-cyclolanost-24-en-3-ol, (3β) per 100 g of the oil. In some embodiments, an oil provided herein comprises more than 20 mg, more than 30 mg, more than 40 mg, more than 50 mg, or more than 60 mg of 9,19-cyclolanost-24-en-3-ol, (3β) per 100 g of the oil. In some embodiments, the sterol content (as a percentage of total sterols) of an oil provided herein comprises 1-50%, 10-40%, 10-30%, 20-30%, at least 5%, at least 10%, at least 11%, at least 12%, at least 13%, at least 14%, at least 15%, at least 16%, at least 17%, at least 18%, at least 19%, or at least 20% 9,19-cyclolanost-24-en-3-ol, (3β) on a weight-by-weight basis.

An oil provided herein can comprise 0.1-100 mg, 0.1-50 mg, 1-100 mg, 1-50 mg, 1-mg, or 10-20 mg of 9,19-cyclolanostan-3-ol, 24-methylene-, (3β) per 100 g of the oil. In some embodiments, an oil provided herein comprises more than 1 mg, more than 2 mg, more than 3 mg, more than 4 mg, more than 5 mg, more than 6 mg more than 7 mg, more than 8 mg, more than 9 mg, more than 10 mg, or more than 11 mg of 9,19-cyclolanostan-3-ol, 24-methylene-, (3β) per 100 g of the oil. In some embodiments, the sterol content (as a percentage of total sterols) of an oil provided herein comprises 1-10%, 1-5%, 5-10%, at least 1%, at least 2%, at least 3%, at least 4%, or at least 5% 9,19-cyclolanostan-3-ol, 24-methylene-, (3β) on a weight-by-weight basis.

Polyol Applications and End Products.

The oils described herein can be used or formulated with one or more excipients for a variety of applications, including but not limited to, process oils (e.g., for tires), waxes, lubricants, polyols, macrodiols, polyesterdiols, and polyurethane products, e.g., hard foams, soft foams, cast polyurethanes, thermoplastic polyurethanes (TPUs), elastomers, adhesives, coatings, laminates, films, and dispersions. Polyurethane products can be used to construct aerospace, automotive, medical, electronic, building and construction goods; sporting goods or recreational equipment, e.g., skis, snowboards, sidewalls, boating equipment, kayaks; and other consumer goods, e.g., industrial containers, coolers, mattresses, leather goods, apparel, footwear, mannequins, and phone cases. These polyurethane applications can serve as sustainable alternatives to petroleum-based, non-renewable materials, such as acrylonitrile butadiene styrene (ABS), ultra-high molecular weight polyethylene (UHMWPE), or high density polyethylene (HDPE).

Oil provided herein can have improved production efficiency and a TAG composition that is enhanced for improved control of hydroformylation chemistry for generating polyols. These characteristics of microbial oil result in a greater degree of hydroxyl group (—OH) functionality relative to oils with greater TAG heterogeneity (hence, lower purity) and/or diversity (e.g., oilseed or plant derived oils). Thus, polyols produced from hydroformylation of high oleic oils can be preferable in generating polymers, including in instances where physical properties of a polymer can be compromised by molecular impurities, such as non-hydroxylated fatty acids that may be present in oils having a more diverse or heterogeneous TAG profile.

Polyols derived from hydroformylation of a high oleic oil can be particularly useful for producing polyurethane materials. For example, oils provided herein can have relatively low TAG diversity, low fatty acid diversity, and the majority of fatty acids present in the oils may be unsaturated fatty acids. A higher ratio of unsaturated fatty acid to saturated fatty acid can allow for increased chemical reactivity at the double bonds. Oils having low TAG diversity and a high proportion of unsaturated fatty acids can be especially desirable in production of polyurethanes because hydroformylation of such a mixture yields a greater percentage of fatty acids that can participate in crosslinking reactions with isocyanates. Unlike unsaturated fatty acids, saturated fatty acids do not contain carbon-carbon double bounds and cannot participate in crosslinking reactions with isocyanates. Thus, polyols generated from hydroformylation of unsaturated fatty acids from high oleic oil can yield polyurethane materials having superior properties.

The hydroxyl functionality can be introduced into oils provided herein via a chemical conversion of the TAG component. This conversion requires the presence of a double bond on the acyl moiety of the fatty acid, e.g., an olefinic group, which can be accomplished using several different chemistries including, for example:

i) Epoxidation in the presence of hydrogen peroxide and acid catalyst, followed by ring opening with reagents, such as water, hydrogen, methanol, ethanol, or other polyols. These chemistries result in secondary hydroxyl moieties, and are therefore less reactive, for example, with isocyanate or methyl esters.

ii) Ozonolysis by molecular oxygen results in the formation of ozonides, which upon further oxidation results in scission at the double bond and formation of di-acids, carboxylic acids, and, upon reduction with hydrogen, aldehydes. Ozonolysis and reduction of oleic acid, for example, produces azaleic acid, pelargonic acid, and pelargonaldehyde, respectively.

iii) Hydroformylation with synthesis gas (syngas), using rhodium or cobalt catalysts to form the aldehyde at the olefinic group, followed by reduction of the aldehyde to alcohol in the presence of hydrogen.

While typically carried out in organic solvent, processes that utilize aqueous systems have been developed to improve sustainability of these chemistries. Of the chemistries described above, only hydroformylation results in the preservation of fatty acid length and formation of primary hydroxyl moieties. Primary hydroxyl functionalities are highly desirable due to increased reactivity compared to secondary hydroxyl moieties. Furthermore, only olefinic fatty acids with a double bond that is converted into a site possessing hydroxyl functionality, through epoxidation and ring opening, ozonolysis, or hydroformylation/reduction, can participate in subsequent downstream chemistries, i.e., reaction with an isocyanate moiety to form a urethane linkage or reaction with methyl esters to form polyesters. All other fatty acids, namely, fully saturated fatty acids that do not contain carbon-carbon double bonds, cannot participate in crosslinking reactions with isocyanates. Hence, saturated fatty acids can compromise the structural integrity and degrade performance of the polymer produced therefrom.

Personal Care Product Applications.

The oils described herein can be used or formulated with one or more excipients for a variety of personal care product applications, including but not limited to, cosmetics, creams, face creams, hand creams, balms, lip balms, serums, face serums, body oils, hair oils, soaps, shampoos, conditioners.

Food Applications.

The oils described herein can be used or formulated with one or more excipients for a variety of food applications, including but not limited to, food products, e.g., food-grade oils, cooking oil, frying oils, coatings, salad dressings, spreads, frozen desserts, pharmaceuticals, nutritional supplements, nutraceuticals, meal replacements, infant formulas, beverages, flavoring agents, and food additives.

EXAMPLES

Example 1. Generation of a Classically Improved Microalgal Strain Capable of Producing a Triglyceride Oil that is Highly Enriched in Oleic Acid Strain Acquisition, Isolation, and Characterization.

A *Prototheca wickerhamii* strain (UTEX 1533) was obtained from the University of Texas at Austin Culture Collection of Algae (UTEX). Analysis of the 23S ribosomal DNA (rDNA) sequence of UTEX 1533 (SEQ ID NO:30) suggests that UTEX 1533 is very closely related to a *Prototheca moriformis* strain, UTEX 1435 (SEQ ID NO:31). The 23S rDNA sequence of UTEX 1533 has 100% sequence identity with the published 23S rDNA sequence from UTEX 1435 (FIG. 1). The UTEX 1533 strain acquired from UTEX was verified as axenic through repeated passages on solid media containing various antibiotic and antifungal agents, followed by passage on antibiotic-free solid media to confirm a single cell type and a homogeneous morphology. This parent strain was given the designation "Strain 0" and also known as CHK22.

First Round of Mutagenesis.

Classical strain improvement of Strain 0 was undertaken in an effort to improve strain productivity, carbon yield, and oleic acid content. First, Strain 0 was exposed to UV light to introduce a diverse collection of random mutations within the nuclear genome. To accomplish this, Strain 0 cells were grown to mid-log phase in 50 mL of vegetative growth media (M21 seed media) in a 250-mL baffle flask at 28° C./200 rpm. The cells were then washed in seed media and $3 \times 10^7$ cells were spread on a 150-mm solid tryptone soy agar (TSA)+5 g/L glucose plate+1.5% agar and allowed to dry. The cells on the plate were then exposed to 25,000 µJoules of UV radiation (approximately 8.02 sec) using a Stratalinker ° 1800 UV Crosslinker system. Following UV exposure, the cells were scraped off of the solid media surface with a sterile cell scraper and into M21 seed media lacking both sugar and nitrogen. These cells were then washed extensively in the same nitrogen-free and sugar-free media, and then collected in a sterile 0.2-micron filter sterilization unit by vacuum filtration. Light exposure was kept to a minimum during this process to reduce the frequency of light-dependent repair of UV damage. The cells were washed off of the sterile filter and re-suspended in M20+5 g/L glucose pre-seed media formulated with 10 mM L-serine as a nitrogen source, in lieu of the typical ammonium sulfate. Half of the mutagenized cell population was exposed to the acridine mutagen ICR-191 in M20+5 g/L glucose pre-seed media for 24 h at 28° C. with 200 rpm agitation. ICR-191 can introduce both double strand breaks and frame-shift mutations when used as a single agent, and significant chromosomal rearrangements when used in conjunction with other mutagens, including UV radiation.

The culture of Strain 0 in M22 pre-seed media formulated with 10 mM L-serine as a nitrogen source was previously shown to have little impact or no impact growth. Nonetheless, amino acid uptake studies in related microalgae have suggested that culture under such conditions stimulates the uptake of L-arginine. After 16-24 h of incubation at 28° C./200 rpm agitation, a portion of the mutagenized and mock-mutagenized cultures were independently plated to M20+5 g/L glucose+10 mM L-serine+100 µg/mL L-canavanine+0.8% agarose solid media. L-canavanine is a toxic analog of L-arginine that disrupts protein synthesis and leads to growth arrest. It is possible, albeit exceedingly rare, (i.e., approximately 1 in $10^8$ to 1 in $10^9$) to spontaneously obtain L-canavanine-resistant (L-can$^R$) colonies when plating otherwise wild-type populations of cells onto L-canavanine-containing media in the presence of L-arginine. Based on this possibility, the frequency of L-can$^R$ individuals observed in UV-mutagenized versus mock-mutagenized cell populations can serve as a rough measure of the efficiency of a given mutagenesis at increasing the rate of mutation over background. In the case of this UV-mutagenesis campaign, L-can$^R$ colonies were obtained at a rate >10,000 times more frequently in the UV-mutagenized population than in the mock-mutagenized population, indicating a significant mutagenic load.

The mutagenesis, trait selection, high-throughput, and automated screening steps of the improvement process are outlined in FIG. 2. Briefly, algal cells in log phase of growth were subjected to mutagenesis by means of chemicals or UV light (1). Cells were then sub-cultured into lipid production medium where the cells were subjected to selection/enrichment strategies (2). A non-mutagenized strain was run in parallel with the mutagenized strain until the growth in lipid production medium (as determined by an increase in A750) of the mutant strain exceeded that of the non-mutagenized control, as determined by a statistical analysis. Strains were then plated to solid medium to obtain clonal isolates (3), followed by the interrogation of these isolates in lipid production medium in a 96-well plate format (4). Using glucose consumption as a surrogate for oil production, high glucose consuming strains were validated in lipid production medium in a tube or shake flask format (5). Isolates that were successfully validated were sub-cultured for multiple generations to stabilize mutations (6), followed by purification of clonal isolates (7) and subsequent re-interrogation in lipid production medium (8). Clones deemed to be phenotypically stable were then ready for validation in fermentation (9), while clones that still show variability in (8) are passaged once more (6) to generate stable lines.

Enrichment for changes in fatty acid profiles using cerulenin, an inhibitor of KASI/KASII.

Cerulenin is an antifungal antibiotic reported to inhibit fatty acid and sterol biosynthesis. Data from a number of studies suggest that cerulenin can specifically inhibit both the β-ketoacyl-ACP synthase I (KASI) and the β-ketoacyl-ACP synthase II (KASII) enzymes in plants, bacteria, and fungi. KASI catalyzes the two carbon at a time condensation reaction that generates 6-16 carbon long fatty acids. KASII functions in the condensation of palmitoyl-ACP with malonyl-ACP to yield stearoyl-ACP, which is rapidly desaturated to oleate. UV-induced mutants of Strain 0 that show resistance to cerulenin could achieve this resistance through mutations that increase KASI/KASII activity, a phenotype that could be highly beneficial for oleate production. In order to isolate cerulenin-resistant Strain 0 mutants, the approach illustrated in FIG. 2 was utilized. Briefly, the UV-mutagenized and mock mutagenized populations described previously were allowed to incubate in 5 mL M20 pre-seed media at 28° C./200 rpm for an additional 48 hours after sampling for the L-canavanine resistance test (72 h total). An 8% (v/v) inoculum from each culture was used to initiate a 10 mL seed culture in standard M21 seed media in a 50-mL bioreactor tube. These seed cultures were incubated for 24-26 h hour to mid-log phase, after which the cultures were divided and used to perform a 0.8% inoculation of different wells of a 96-well block containing 0.5 mL of M22 lipid production media and varying amounts of cerulenin or DMSO as a vehicle control. These lipid cultures were incubated for approximately 72 hours. Growth was then assessed by measuring optical density at 750 nm wavelength (OD750) in a Molecular Devices Spectramax M5 plate reader.

While growth of the vast majority of the cells can be negatively impacted by cerulenin, a very small subset of cells with beneficial mutations within the mutant population can be resistant to the antibiotic. To increase the likelihood of isolating these resistant cells, wells in which inhibition of growth was >50% of the growth observed in DMSO-treated controls were collected onto sterile filters, extensively washed in M20 pre-seed media, and then used to initiate another round of M20 pre-seed culture. These cells were then subjected to another round of seed and then lipid culture in the presence of differing amounts of cerulenin or DMSO, as was performed in the first round of enrichment for cerulenin resistance. This cycle was repeated until a "differentiation event" was observed in which the MIC50 of the mutant population is higher than that of the mock mutagenized population. Wells in which statistically significant differences were observed were pooled, collected on sterile filters, washed extensively, and then diluted and plated for single colonies on 10-cm M20+5 g/L glucose+1.5% agar plates. Clonally isolated mutants from the cerulenin-resistant population constituted a cerulenin-resistant "mutant library".

Figure 3:
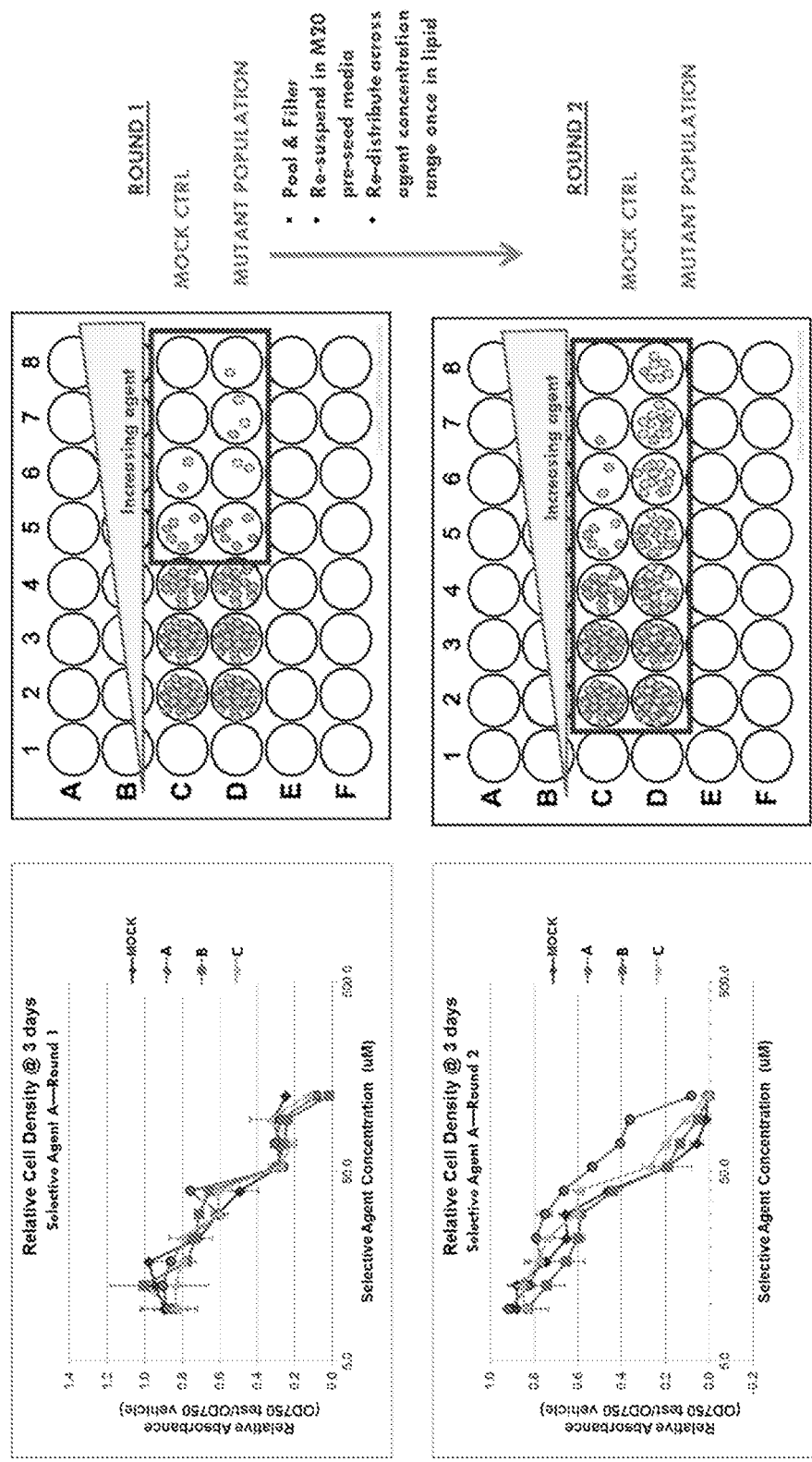
FIG. 3 shows a theoretical example of the enrichment strategy used to isolate cerulenin-resistant microalgae.

Using the UV-mutagenized and UV+ICR-191-mutagenized library of Strain 0, four cycles of enrichment were conducted as described at which time a very small but statistically significant increase in the MIC50 was observed only in the UV-mutagenized mutant population when compared to the mock-mutagenized controls (FIG. 3). Cells in these wells were pooled, collected with 0.2-1 μm filter sterilization units, washed with media, and then re-suspended in media and counted. These cells were then spread onto M20+glucose+1.5% agar solid media to clonally isolate individual mutants.

FIG. 3 shows a prophetic example of the enrichment strategy used to isolate cerulenin-resistant microalgae. As illustrated in FIG. 3, a portion of a 96-deep well block shows wells containing microalgae, with grey circles representing wild type, cerulenin-sensitive a portion of a 96-deep well blocks with wells containing microalgae, with grey circles representing wild type, cerulenin-sensitive cells, and yellow circles representing cerulenin-resistant cells. When resistant cells are collected in the first round of enrichment and then redistributed across the cerulenin concentration gradient in a second round of enrichment, cells with a high tolerance for the cerulenin are present in concentrations that easily outcompete the sensitive cells in the population. These wells should thus have higher levels of growth than the mock-mutagenized populations of cells that have undergone a similar treatment. This "differentiation event" indicates the outgrowth of cerulenin resistance.

Figure 4:
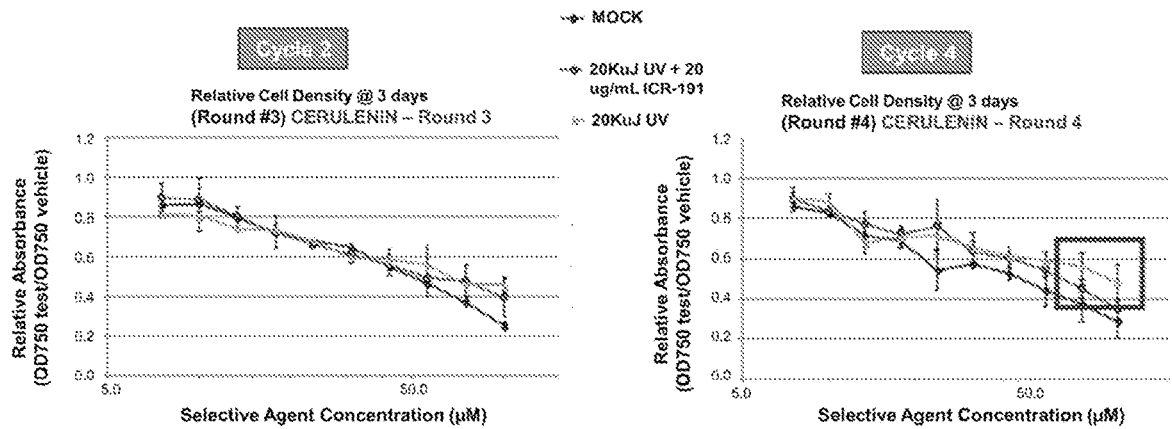
FIG. 4 illustrates an actual enrichment strategy used to isolate cerulenin-resistant microalgae.

FIG. 4 illustrates an actual enrichment strategy used to isolate cerulenin-resistant microalgae. After the first round of exposure to cerulenin, very little difference is observed between the UV-mutagenized and UV+ICR-191-mutagenized populations and the mock-mutagenized controls (left panel). After two additional round of drug exposure, the UV-mutagenized population shows slightly higher growth even at the highest cerulenin concentration then the mock mutagenized controls (right panel; red box). Wells containing these more cerulenin resistant cells were pooled, collected, and washed on sterile filters, and diluted and spread on solid media to isolate single colonies.

Figure 5:
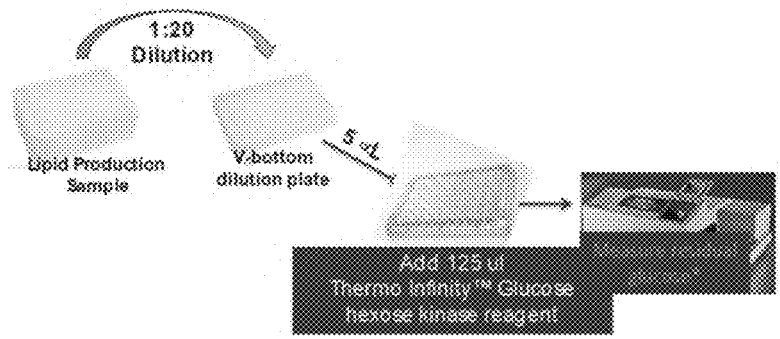
FIG. 5 describes an automated glucose assay used to measure residual glucose during mutant screening.

Colonies arising from individual mutant clones were picked from the solid media plates for screening using a Picolo™ automated colony picking inoculation tool integrated into a TECAN Freedom EVO® 200 automated liquid handling system. Each selected colony was used to inoculate both a single well of an archival 96-well solid media M20+5 g/L glucose+0.8% agarose storage plate, as well as the corresponding well of a 96-well deep well block containing 0.5 mL of M20 pre-seed media. Pre-seed cultures were incubated at 28° C./900 rpm/80% humidity for 72 h. An 8% (v/v) inoculum from each culture was then used to initiate a seed culture in 0.5 mL of standard M21 seed media in corresponding wells of 96-deep well block. These seed cultures were incubated at 28° C./200 rpm/80% humidity for 24-26 h to mid-log phase, and then the cultures were used to perform a 0.8% inoculation of corresponding wells of a 96-deep well block containing 0.5 mL of M22 lipid production media. Lipid cultures were incubated for 72 h and then samples from each culture were assessed for rate of glucose consumption using an automated glucose assay described in FIG. 5 to measure residual glucose in each well. Individual clones with glucose consumption rates greater than or equal to the average consumption rate of the Strain 0 controls were selected for further analysis. Approximately 125 µL of broth from each of the selected lipid cultures were frozen at −80° C. for approximately 1 hour and lyophilized overnight and then submitted for quantitative FAME analysis of fatty acid composition by GC-FID. A number of clones were identified with significant increases in oleate levels and glucose consumption rates equal to or greater than Strain 0 (TABLE 1). These primary hits were re-screened in a tube assay to assess oleate production and lipid titer following 5-days in lipid culture (TABLE 2). Three mutants, Strain 0_G07, Strain 0_E05, and Strain 0_E06, had lipid titers that were comparable to the Strain 0 parental strain while manifesting 9-10% more oleate content.

TABLE 1

| Strain | % Oleate in Block |
|---|---|
| Strain 0_H07 | 60.14 |
| Strain 0_G07 | 69.38 |
| Strain 0_E05 | 68.96 |
| Strain 0_H05 | 71.96 |
| Strain 0_E06 | 69.92 |
| Strain 0_G08 | 71.84 |
| Strain 0 | 59.34 |

TABLE 1 summarizes oleate content of select mutant strains exhibiting higher glucose consumption in a 96-well block lipid assay. Mutant strains (approximately 2,200 isolates) were grown in lipid production medium (0.5 mL) with shaking (900 rpm) for 72 hours at 28° C. at which point glucose consumption was measured. Isolates with high glucose consumption levels were further interrogated for fatty acid composition with lead strains shown here.

TABLE 2

| Strain | Avg DCW | Avg Oil | Oil % CV | Avg NLB | Avg PCP | Avg % Oleate |
|---|---|---|---|---|---|---|
| Strain 0_H07 | 15.5 | 10.8 | 4.5 | 4.7 | 2.3 | 58.82 |
| Strain 0_G07 | 15.1 | 10.1 | 2.6 | 5.0 | 2.0 | 67.60 |
| Strain 0_E05 | 15.2 | 10.3 | 1.1 | 4.9 | 2.1 | 67.87 |
| Strain 0_H05 | 8.2 | 5.1 | 10.7 | 3.0 | 1.7 | 69.16 |
| Strain 0_E06 | 15.1 | 10.2 | 2.3 | 4.8 | 2.1 | 69.24 |
| Strain 0_G08 | 9.1 | 5.6 | 4.2 | 3.5 | 1.6 | 68.89 |
| Strain 0 | 15.0 | 10.3 | 2.6 | 4.7 | 2.2 | 58.45 |

TABLE 2 summarizes the performance of select mutant strains in a tube-based assay based on average dry cell weight (Avg DCW), average oil titer (g/L) (Avg Oil), oil titer g/L, % coefficient of variance (Oil % CV), average non lipid biomass (Avg NLB), average per cell production (oil titer/NLB-Avg PCP), and average % oleate content (Avg % Oleate). Mutants described in TABLE 1 were re-interrogated in a larger tube-based format in which isolates were grown in duplicate in 10 mL of lipid production medium in a 50-mL bioreactor with shaking (200 rpm) for 120 hours at 28° C. at which point 1 mL of biomass was removed, applied to a polycarbonate filter, washed with an equal volume of Milli Q water, and placed in tared glass vial at −80° C. for 30 minutes. Vials containing filters and frozen biomass were lyophilized to dryness overnight, weights were recorded, and filters with dried biomass were subjected to direct transesterification followed by GC/FID to quantitate FAMES. Mutants highlighted in bold showed both high productivity and high oleate levels.

The phenotypic stability of each of the most promising mutants (highlighted in bold in TABLE 2) was evaluated by repeated sub-culturing in vegetative growth media (M21+40 g/L glucose seed media) until 30 or more population doublings had occurred. Cultures were then plated to M20+5 g/L glucose+0.8% agarose solid media. Six colonies were picked to a solid media archival storage plate and were subsequently analyzed in duplicate 10-mL lipid production assays conducted in 50-mL bioreactor tubes at 28° C./200 rpm. One of the strains showed a coefficient of variance (% CV) of less than 3% for oil titer and less than 1% in oleate levels across all six sub-clones. This strain was deemed phenotypically stable and cryo-preserved as strain "Strain 1". The other mutant clones were not phenotypically stable and were reserved for additional rounds of sub-culturing and phenotypic evaluation or subject to additional round of classical strain improvement.

TABLE 3 summarizes the results of tube-based assays assessing stability of classically improved high oleic strains. Tube-based assays in which six isolates from each strain were grown in duplicate in 10 mL of lipid production medium. Cultures were grown with shaking (200 rpm) for 120 hours at 28° C. at which point 1 mL of biomass was removed, applied to a polycarbonate filter, washed with an equal volume of Milli Q water, and placed in tared glass vial at −80° C. for 30 minutes. Vials containing filters and frozen biomass were lyophilized to dryness overnight, their weights recorded and filters with dried biomass were subjected to direct transesterification followed by GC/FID to quantitate FAMES. Strain 0_G07 was determined to be stable and was cryo-preserved as "Strain 1".

TABLE 3

| Strains in Duplicate | Strain | Avg DCW | Avg Oil | Avg PCP | Avg NLB | Avg C18:1 | Avg C16:1 | Avg C18:2 | |
|---|---|---|---|---|---|---|---|---|---|
| 6 | Strain 0_G07_A1-5, B1 | 14.3 | 9.8 | 2.2 | 4.5 | 68.3 | 18.5 | 7.6 | Stable; |
|  | STDEV | 0.2 | 0.2 | 0.2 | 0.1 | 0.1 | 0.1 | 0.1 | banked |
|  | % cv | 1.4 | 1.8 | 3 | 2.2 | 0.2 | 0.7 | 1.1 | as "Strain 1" |
| 6 | Strain 0_E05_A7-11, B8 | 14.5 | 9.9 | 2.2 | 4.6 | 68.6 | 18.2 | 7.5 | Unstable |
|  | STDEV | 0.5 | 0.4 | 0.2 | 0.3 | 0.2 | 0.2 | 0.1 |  |
|  | % cv | 3.7 | 3.5 | 6.9 | 7.0 | 0.3 | 0.9 | 1.0 |  |
| 6 | Strain 0_E06_A1-5, B1 | 14.5 | 10.0 | 2.2 | 4.8 | 70.2 | 16.4 | 7.6 | Unstable |
|  | STDEV | 0.9 | 0.6 | 0.1 | 4.5 | 0.2 | 0.1 | 0.1 |  |
|  | % cv | 6.2 | 5.8 | 3.8 | 0.4 | 0.2 | 0.4 | 0.8 |  |

TABLE 3-continued

| Strains in Duplicate | Strain | Avg DCW | Avg Oil | Avg PCP | Avg NLB | Avg C18:1 | Avg C16:1 | Avg C18:2 |
|---|---|---|---|---|---|---|---|---|
| 1 | Strain 0 | 14.8 | 10.3 | 2.3 | 4.4 | 59.0 | 27.1 | 7.0 |
|   | STDEV | 0.21 | 0.07 | 0.07 | 0.15 | 0.36 | 0.32 | 0.01 |
|   | % cv | 1.4 | 0.6 | 2.7 | 3.3 | 0.6 | 1.2 | 0.2 |

Following the cryo-preservation of Strain 1, a series of fermentation development runs were conducted to ascertain which process conditions would yield the highest oleic acid content compared to the parental base strain, Strain 0, which elaborates ca. 58% oleic acid in low cell density fermentations, and ca. 69% oleic acid under an optimized high cell density, high oleic process in a 0.5-L bioreactor. As illustrated in TABLE 4, feeding a macronutrient bolus ($Mg^{++}$ and $PO_4^{---}$) or administering a complete media replacement bolus, had little impact on oleic accumulation. In contrast, increasing the dissolved oxygen (DO) from 30 to 50%, further elevated the oleic acid content by roughly 3%. Additional attempts at stressing Strain 1 by reducing the run temperature after the base transition from 28° C. to 25° C. showed no additional impact on oleic acid levels.

Example 2. Generation of a Classically Improved Microalgal Strain Capable of Producing a Triglyceride Oil that is Highly Enriched in Oleic Acid Challenging membrane integrity to enrich for mutants with increased oleate levels.

The mutant strain, Strain 0_E06 (Strain E06), while not phenotypically stable, consistently achieved higher oleate levels than the mutant lineage that gave rise to Strain 1 (TABLE 3). As such, this mutant lineage was selected for further rounds of classical strain improvement, and designated as "Strain K". Following overnight growth in M21+40 g/L glucose seed media to mid-log phase, the E06 mutant was exposed to 270 mM ethyl methanesulfonate (EMS) in

TABLE 4

| Strain | Run No. | Nitrogen (mM) | DO set point (%) | Bolus | C18:1 | DCW (g/L) | Oil (g/L) | Peak oil production (g/Ld) | Final oil production (g/Ld) | Final yield (g/g) |
|---|---|---|---|---|---|---|---|---|---|---|
| Strain 0 | 19003 | 220 | 30 | $Mg^{++}, PO_4^{---}$ | 69.54 | 142.9 | 83.5 | 17.97 | 14.52 | .209 |
| Strain 0 | 19004 | 220 | 30 | $Mg^{++}, PO_4^{---}$ | 68.86 | 142.8 | 84.1 | 17.15 | 14.62 | .219 |
| Strain 1 | 19009 | 220 | 30 | $Mg^{++}, PO_4^{---}$ | 73.41 | 140.8 | 81.8 | 15.10 | 13.77 | .218 |
| Strain 1 | 19010 | 220 | 30 | $Mg^{++}, PO_4^{---}$ | 73.68 | 149.6 | 85.9 | 16.29 | 14.47 | .223 |
| Strain 1 | 19013 | 170 | 30 | Complete media replacement | 73.16 | 170.2 | 103.1 | 21.9 | 17.86 | .222 |
| Strain 1 | 19014 | 170 | 30 | Complete media replacement | 73.25 | 167.8 | 103.8 | 21.4 | 18.1 | .232 |
| Strain 1 | 19019 | 220 | 50 | $Mg^{++}, PO_4^{---}$ 25° C. | 75.31 | 132.1 | 68.7 | 12.77 | 12 | .186 |
| Strain 1 | 19020 | 220 | 50 | $Mg^{++}, PO_4^{---}$ 25° C. | 75.38 | 125.5 | 61.9 | 12.89 | 10.87 | .182 |

TABLE 4 shows fermentation development runs for Strain 1 in comparison with the highest oleic content observed in runs of Strain 0 (all at 0.5 L scale). All runs were carried out at 0.5-L scale. Nitrogen refers to the total nitrogen used in the process (batched+fed ammonia). DO refers to dissolved oxygen. $Mg^{++}$ and $PO_4^{---}$ bolus refers to a bolus (equivalent to the amount of each macronutrient that is batched in the initial vessel seed medium) that is administered just after base transition. Complete media replacement refers to administering a bolus (just after base transition) containing all batched media components with the exception of nitrogen. All broth samples for analysis were applied to a polycarbonate filter, washed with an equal volume of Milli Q water, and placed in a tared glass vial at −80° C. for 30 minutes. Vials containing filters and frozen biomass were lyophilized to dryness overnight, weights were recorded, and filters with dried biomass were subjected to direct transesterification followed by GC/FID to quantitate FAMES.

0.1 M potassium phosphate buffer (pH 7.0) for 45 min at room temperature in dark and with periodic gentle agitation. Mutagenesis was terminated with the addition of a sodium thiosulfate solution to final concentration of 3% (w/v). In parallel, a mock-mutagenized control cell population was taken through all the same manipulations, except for exposure to EMS. Cells were collected using 0.2-micron filter sterilization units, washed extensively with water, and then washed with and into 5 mL M20+5 g/L glucose pre-seed media. Pre-seed cultures were incubated at 28° C./900 rpm/80% humidity for 72 h. An 8% (v/v) inoculum from each culture was then used to initiate a seed culture in 10 mL of standard M21+5 g/L glucose seed media in 50-mL bioreactor tubes. These seed cultures were incubated at 28° C./900 rpm/80% humidity for 24-26 h to mid-log phase, and then the cultures were used to perform a 0.8% inoculation of replicate wells in a 96-deep well block containing 0.5 mL of M22 lipid production media formulated with 1.6 μM triparanol and varying concentrations of the membrane fluidizing chemical, phenethyl alcohol, in a range from 2-20 mM. Triparanol is a 24-dehydroreductase inhibitor that disrupts production of cholesterol in mammalian cells. Triparanol can inhibit phytosterol biosynthesis in some microalgae. These lipid cultures were incubated for approximately 72 hours at 28° C./900 rpm/80% humidity. Growth was then assessed by measuring optical density at 750 nm wavelength (OD750) in a Molecular Devices Spectramax M5 plate reader. Cells from lipid cultures with 50% or greater inhibition of growth relative to vehicle (DMSO)-treated controls as measured by optical density (FIG. 6) were pooled in sterile 0.2-micron filter sterilization units, washed extensively with fresh M20+5 g/L glucose pre-seed media, and used to initiate a 10 mL M20+5 g/L glucose pre-seed cultures in 50-mL bioreactor tubes. The surviving population was then subjected to a second round of exposure to a combination of 5 µM triparanol and a range of phenethyl alcohol concentrations, ranging from 4-8 mM, again under lipid production culture conditions. Surviving cells were collected, washed, and recovered into M21+5 g/L glucose seed media, allowed to grow overnight to mid-log phase and then cryopreserved with the addition of dimethyl sulfoxide to 5% (v/v) and flash freezing. This expanded population of rare, surviving mutants was subsequently interrogated for the ability to survive under lipid production conditions in the presence of increasing levels of triparanol.

Figure 7:
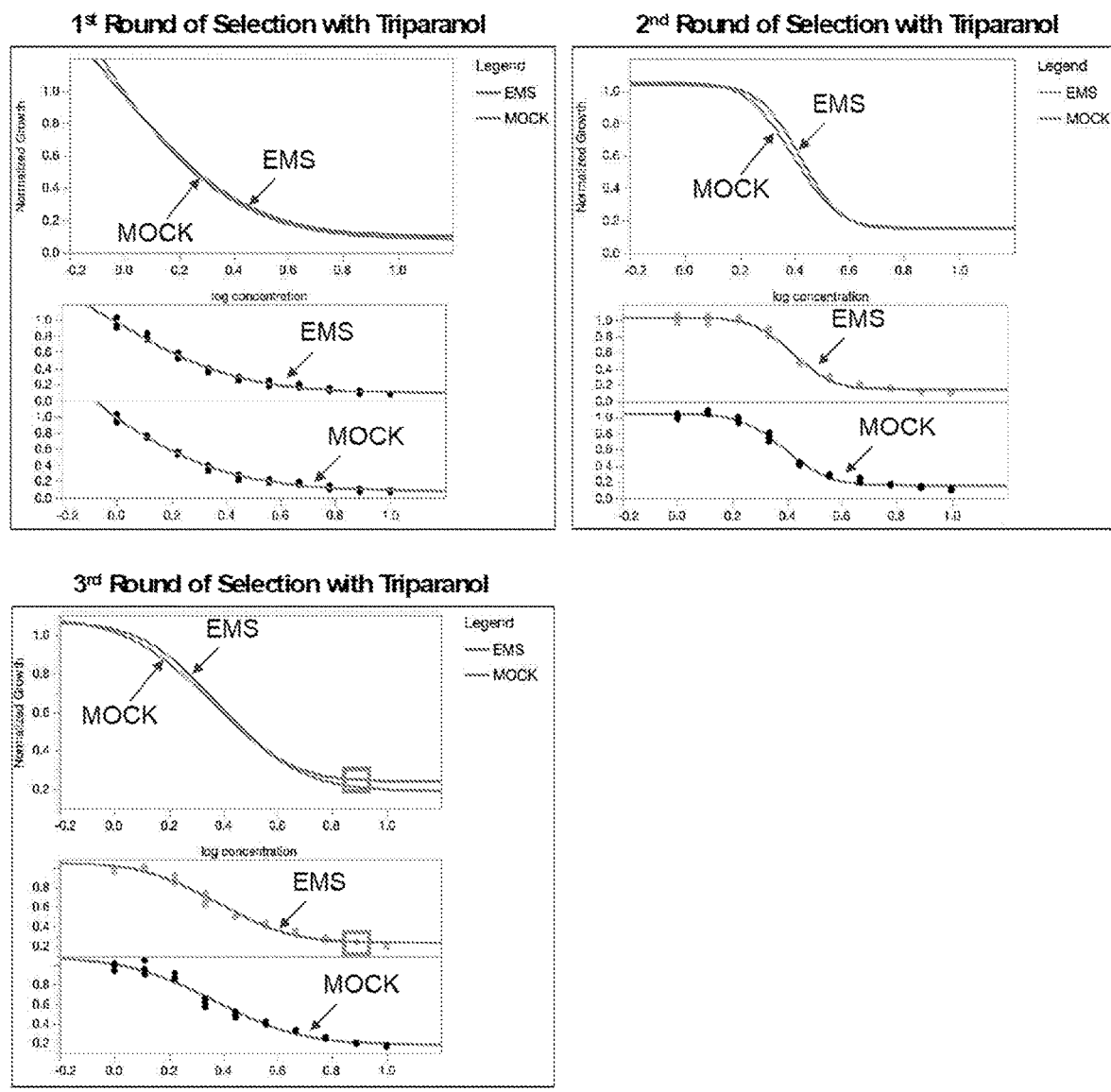
FIG. 7 shows growth curves for selection for mutants with greater tolerance to the triparanol.

The cryo-vials were thawed and used to initiate a 10 mL pre-seed culture in bioreactor tube, which was incubated for 72 h at 28° C./200 rpm. Two rounds of selection and enrichment with increasing amounts of triparanol were conducted following the strategy outlined in FIG. 3. Following the third cycle of selection and enrichment, the mutant population began to significantly differentiate from the mock-mutagenized population when growth was measured during lipid production (FIG. 7). This population was collected on sterile filters, diluted, and spread on solid media. The resulting clonal isolates were screened in our automated 96-well block-based lipid production and glucose consumption assay. A number of strains with increased oleate levels were identified among the mutant clones (TABLE 5). Strains validated in repeat assays were then assessed for phenotypic stability. Stable strains were cryopreserved.

TABLE 5

| Strain | % Oleate in Block |
| --- | --- |
| Strain K_C08 | 72.8 |
| Strain K _B01 | 72.2 |
| Strain K _C01 | 72.4 |
| Strain K _D03 | 72.3 |
| Strain K _D09 | 74.5 |
| Strain K _D11 | 72.6 |
| Strain 0 (average) | 58.2 |

TABLE 5 summarizes the oleate content of select mutant strains exhibiting higher glucose consumption in a 96-well block lipid assay. Mutant strains (approximately 2,200 isolates) were grown in lipid production medium (0.5 mL) with shaking (900 rpm) for 72 hours at 28° C. at which point glucose consumption was measured. Isolates with high glucose consumption levels were further interrogated for fatty acid composition with lead strains shown here.

Figure 6:
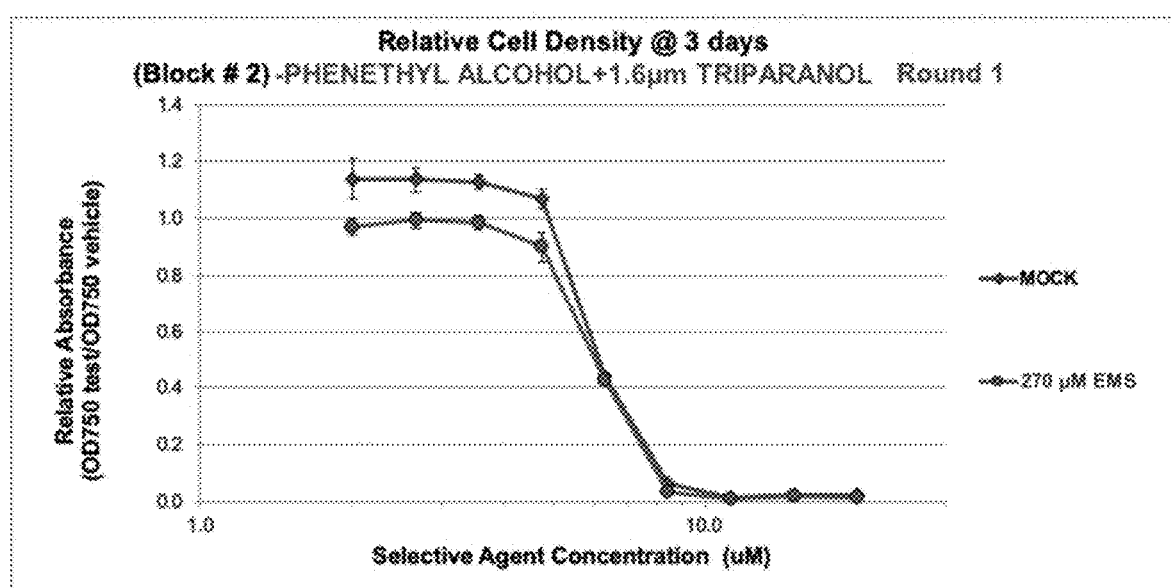
FIG. 6 shows growth curves for selection for mutants with greater tolerance to membrane stress.

FIG. 6 shows growth curves for selection for mutants with greater tolerance to membrane stress. Cells were exposed to a fixed concentration (1.6 µM) of triparanol and increasing concentrations of the membrane fluidizer phenethyl alcohol during a 3-day lipid production culture in a 96-deep well block. Significant inhibition of growth occurred at phenethyl alcohol concentrations >3.6 mM. Rare surviving cells were recovered by sterile filtration from wells treated with ≥6.3 mM phenethyl alcohol, washed with and collected from the filter in M20+glucose pre-seed media and the cultures used to initiate another round of selection for mutants with greater tolerance of membrane stress.

FIG. 7 shows growth curves for selection for mutants with greater tolerance to the triparanol. Cells were exposed to increasing amounts of triparanol during a 3-day lipid production culture in a 96-deep well block. Significant inhibition of growth occurred at phenethyl alcohol concentrations >2 µM. Rare surviving cells presumed to be in wells where 50% inhibition was observed were recovered by sterile filtration, washed with and collected from the filter in M20+glucose pre-seed media. The cultures were then used to initiate another round of selection. By the third round of selection (right panels), a subtle difference in the growth of the mutant population compared to the mock-mutagenized controls was observed. Cells were collected from the replicated wells treated with 7.7 µM triparanol (green boxes) and were plated to non-selective media to generate a mutant library for screening.

Lead strains where subsequently evaluated side-by-side in 10 mL lipid production cultures experiment conducted in 50-mL bioreactor tubes. As shown in TABLE 6, the best performing strain, designated as "Strain 2", manifested >26% more oleate than Strain 1. Strain 2 also achieved a 15% higher lipid titer than Strain 1. Based on its performance in low cell density lipid assays in tubes, the performance of Strain 2 was then evaluated under high cell density fermentation conditions.

TABLE 6

| Strain | Avg DCW (g/L) | Avg Oil Titer (g/L) | Avg NLB (g/L) | Avg PCP | % C18:1 |
| --- | --- | --- | --- | --- | --- |
| Strain 0 | 15.0 | 10.4 | 4.6 | 2.2 | 58.98 |
| Strain 1 | 14.8 | 10.3 | 4.5 | 2.3 | 67.67 |
| Strain K_stbE06 | 16.60 | 12.0 | 4.6 | 2.6 | 72.16 |
| Strain K_stbE07 | 16.63 | 11.9 | 4.7 | 2.5 | 72.65 |
| Strain 2 (Strain K_ stbA02) | 17.3 | 11.7 | 5.6 | 2.1 | 74.59 |
| Strain K_stbC04 | 16.1 | 11.4 | 4.7 | 2.4 | 74.59 |

TABLE 6 summarizes results of tube based assays on classically improved derivatives of Strain 1 showing increased C18:1 content. All strains were run under standard lipid production conditions in which strains were grown in duplicate in 10 mL of lipid production medium. Cultures were grown with shaking (200 rpm) for 120 hours at 28° C. at which point 1 mL of biomass was removed, applied to a polycarbonate filter, washed with an equal volume of Milli Q water, and placed in a tared glass vial at −80° C. for 30 minutes. Vials containing filters and frozen biomass were lyophilized to dryness overnight, weights were recorded, and filters with dried biomass were subjected to direct transesterification followed by GC/FID to quantitate FAMEs.

A series of development runs utilizing Strain 2 were conducted in an effort to explore whether process conditions could further elevate C18:1 levels relative to the ca. 73-74% oleic obtained in tube and block based assays as described above. The results of these efforts are illustrated in TABLE 7 below. Reference runs showing Strain 0 and Strain 1 are also displayed, illustrating the best high oleic processes for these two strains as well. As shown in the data, the 220 mM nitrogen process that incorporated a $Mg^{++}$ and $PO_4^{---}$ bolus post base transition, delivered the highest oleic content. At approximately 81% oleic content, a 5% increase in oleate over the previous high oleic strain, Strain 1, was achieved.

TABLE 7

| Strain | Run No. | Nitrogen (mM) | DO set point (%) | Bolus | C18:1 | DCW (g/L) | Oil (g/L) | Peak oil production (g/Ld) | Final oil production (g/Ld) | Final yield (g/g) |
|---|---|---|---|---|---|---|---|---|---|---|
| Strain 0 | 19003 | 220 | 30 | $Mg^{++}$, $PO_4^{---}$ | 69.54 | 142.9 | 83.5 | 17.97 | 14.52 | .209 |
| Strain 0 | 19004 | 220 | 30 | $Mg^{++}$, $PO_4^{---}$ | 68.86 | 142.8 | 84.1 | 17.15 | 14.62 | .219 |
| Strain 2 | 19021 | 220 | 50 | $Mg^{++}$, $PO_4^{---}$ 2 min. starve | 80.56 | 135.2 | 71.3 | 15.88 | 12.39 | .191 |
| Strain 2 | 19022 | 220 | 50 | $Mg^{++}$, $PO_4^{---}$ 2 min. starve | 80.80 | 144.9 | 76.1 | 17.52 | 13.23 | .201 |
| Strain 2 | 19023 | 220 | 50 | $Mg^{++}$, $PO_4^{---}$ 4 min. starve | 72.15 | 61.4 | 20.5 | 5.2 | 4.50 | .100 |
| Strain 2 | 19024 | 220 | 50 | $Mg^{++}$, $PO_4^{---}$ 4 min. starve | 65.2 | 49.4 | 13.9 | 3.0 | 3.10 | .080 |
| Strain 2 | 19025 | 220 | 50 | $Mg^{++}$, $PO_4^{---}$ | 80.63 | 138.3 | 80.7 | 17.57 | 14.00 | .200 |
| Strain 2 | 19026 | 220 | 50 | $Mg^{++}$, $PO_4^{---}$ | 80.85 | 136.1 | 78.1 | 17.58 | 13.53 | .205 |
| Strain 2 | 19027 | 220 | 50 | $Mg^{++}$, $PO_4^{---}$ $2^{nd}$ $Mg^{++}$ | 80.86 | 141.2 | 80.2 | 16.25 | 13.75 | .192 |
| Strain 2 | 19028 | 220 | 50 | $Mg^{++}$, $PO_4^{---}$ $2^{nd}$ $Mg^{++}$ | 81.29 | 137.8 | 78.8 | 16.68 | 13.51 | .207 |
| Strain 2 | 19029 | 170 | 50 | Complete media replacement | 78.30 | 169.0 | 109.0 | 26.58 | 19.74 | .234 |
| Strain 2 | 19030 | 170 | 50 | Complete media replacement | 78.25 | 168.0 | 112.2 | 25.58 | 17.18 | .245 |

TABLE 7 summarizes results of fermentation development runs for Strain 2 in comparison with the highest oleic content observed for Strain 0 and Strain 1 (all at 0.5-L scale). All runs were carried out at 0.5-L scale. Nitrogen refers to the total nitrogen used in the process (batched+fed ammonia). DO refers to dissolved oxygen. $Mg^{++}$ and $PO_4^{---}$ bolus refers to a bolus (equivalent to the amount of each macronutrient that is batched in the initial vessel seed medium) that is administered just after base transition. Complete media replacement refers to administering a bolus (just after base transition) containing all batched media components with the exception of nitrogen. All broth samples for analysis were applied to a polycarbonate filter, washed with an equal volume of Milli Q water, and placed in a pre-weighed glass vial at −80° C. for 30 minutes. Vials containing filters and frozen biomass were lyophilized to dryness overnight, weights were recorded, and filters with dried biomass were subjected to direct transesterification followed by GC/FID to quantitate FAMES.

Example 3. Generation of a Classically Improved Microalgal Strain Capable of Producing a Triglyceride Oil that is Highly Enriched in Oleic Acid To further increase the oleate levels achieved in Strain 2 by classical strain improvement methods, a number of different cocktails of metabolic inhibitors and herbicides were tested with the goal of increasing genetic diversity in mutant libraries and biasing mutant populations toward higher oleate and/or increased lipid production. To generate a diverse library of mutants, Strain 2 was exposed to 360 mM ethyl methane sulfonate for 1 hour at room temperature, followed by inactivation of the mutagen and recovery of the cells after culture for 24 h. The resulting mutant population was subjected to a single round of enrichment with different cocktails of selective agents (FIG. 8, Panel A) that impact disparate aspects of fatty acid, triacylglycerol, or sterol production. Two selective agent cocktail-treated mutant cultures exposed to inhibitor mixtures 12 and 14 (FIG. 8, Panels A and B) grew ≥1.5-fold more than their paired, mock-treated control populations and were thus considered to have differentiated phenotypically. The mutant libraries derived from these cultures were plated on solid media to isolate individual mutant clones. These clones were initially screened for glucose consumption rates and those showing a statistically significant increase in glucose consumption compared to controls were analyzed for fatty acid profile. One isolate, M05_H03, showed a significant increase in oleate compared to the Strain 2 parental strain and was evaluated for phenotypic stability (TABLE 8). In initial stability evaluations, some instability in both profile and glucose consumption was observed. As such, the sub-clone manifesting the highest oleate level, M05_H03.D02, was selected for additional multi-generational sub-culture, and subsequently a re-evaluation of phenotypic stability. However, the sub-clone was shown to be unstable and was designated as "Strain 3".

TABLE 8

| Strain | C14:0 | C16:0 | C18:0 | C18:1 | C18:2 | C18:3 | Glucose consumption (g/L * D) |
|---|---|---|---|---|---|---|---|
| Strain 0* | 1.43 ± 0.02 | 27.56 ± 0.09 | 3.48 ± 0.05 | 58.29 ± 0.21 | 7.32 ± 0.07 | 0.52 ± 0.01 | 6.4 ± 0.2 |
| Strain 2 ** | 1.01 ± 0.02 | 13.91 ± 0.22 | 3.13 ± 0.06 | 72.84 ± 0.31 | 7.53 ± 0.12 | 0.39 ± 0.01 | 7.4 ± 0.2 |
| Strain 3 (M05_H03.D02) | 0.64 | 8.22 | 2.79 | 78.89 | 8.21 | 0.31 | 6.0 |
| M05_H03.D03 | 0.65 | 8.22 | 3.01 | 78.62 | 8.32 | 0.40 | 6.8 |

TABLE 8-continued

| Strain | C14:0 | C16:0 | C18:0 | C18:1 | C18:2 | C18:3 | Glucose consumption (g/L * D) |
|---|---|---|---|---|---|---|---|
| M05_H03.H04 | 0.68 | 8.33 | 2.84 | 78.56 | 8.19 | 0.37 | 6.0 |
| M05_H03.C05 | *0.86* | *10.99* | *3.41* | *75.48* | *7.88* | *0.40* | *6.0* |
| M05_H03.C04 | 0.66 | 8.13 | 2.97 | 78.45 | 8.30 | 0.42 | 7.2 |

*N = 8; α = 0.05
**N = 40; α = 0.05

TABLE 8 shows representative fatty acid profiles for sub-clones of a promising Strain 2 mutant generated through an additional round of classical strain improvement. All strains were run under standard lipid production conditions in a 96-well block format in which cells are grown in 0.5 mL of lipid production media. Cultures were grown with shaking (900 rpm) for 72 hours at 28° C., at which point 125 µL of biomass was removed, transferred to glass micro-vials, and frozen −80° C. for 30-60 minutes. The micro-vials containing frozen biomass were lyophilized to dryness overnight and then subjected to direct transesterification followed by GC/FID to quantitate FAMES. The sub-clone, M05_H03.005 (highlighted in bold italics), showed a significant deviation in fatty acid profile from the other sub-clones of the original mutant that was identified. Note that the glucose consumption rate in grams/liter*day (g/L*D) correlated linearly with lipid titer in this assay and also showed significant variability in this mutant clone. Given this phenotypic instability, one of the sub-clones that produced the highest level of oleate, M05_H03.D02 (also highlighted in bold), was selected for additional sub-culture stability re-evaluation.

Figure 8:
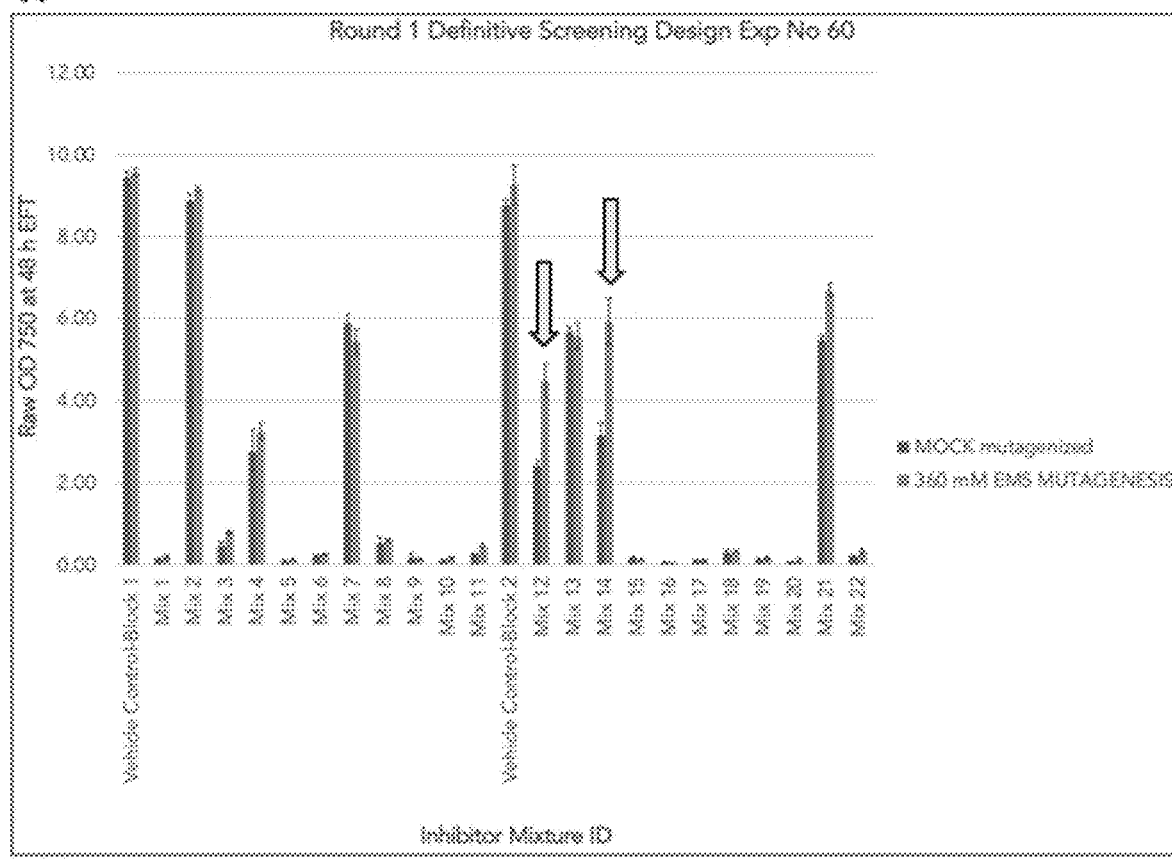
FIG. 8 summarizes the classical strain improvement of Strain 2 by generation of diverse mutant libraries through exposure to different mixtures of metabolic inhibitors and herbicides.

FIG. 8 summarizes the classical strain improvement of Strain 2 by generation of diverse mutant libraries through exposure to different mixtures of metabolic inhibitors and herbicides. Following mutagenesis with ethyl methane sulfonate (EMS) and recovery, the resulting mutated cell populations were cultured under standard 96-well block lipid production conditions in 0.5 mL of lipid production media containing different combinations of inhibitors and/or herbicides. Mock-mutagenized cultures taken through all the same manipulations except for exposure to EMS were exposed to the same mixtures of inhibitors and herbicides in parallel. Cultures were grown with shaking (900 rpm) for 72 hours at 28° C. after which samples were removed from each well and diluted. Growth was assessed through optical density measurement at 750 nm in a 96-well plate reader (FIG. 8, Panel A). Error bars in the bar plot for each inhibitor mixture show the standard error derived from 4 replicate wells subjected to the same treatment. Cultures treated with inhibitor mixtures that showed a ≥1.5-fold higher level of growth compared to the mock-mutagenized control (yellow arrows; student t-test assuming unequal variances, α=0.05) were plated to solid media to generate clonal mutant libraries and screened. Mixtures 12 and 14 contained different combinations and concentrations of metabolic inhibitors (FIG. 8, Panel B) whose reported target activity and hypothesized mechanism of action in the lipid assay are described in the table in FIG. 8, Panel C.

Example 4. Generation of a Classically Improved Microalgal Strain Capable of Producing a Triglyceride Oil that is Highly Enriched in Oleic Acid As an alternative to stabilizing Strain 3, a new round of mutagenesis was pursued for Strain 2 utilizing treatment of cells with the mutagen 4-nitroquinoline-1-oxide (4-NQO) for 5 minutes at 28° C. Mutagenized cells were enriched by growing under conditions of limited glucose (14 g/L) for three days, then the cells were subjected to fraction over a 60% Percoll/0.15 M NaCl density gradient. Cells recovered from a density zone of 1.06 g/mL were plated and assessed for glucose consumption and fatty acid profile. One of these clones was subsequently stabilized and given the strain designation "Strain 4".

Example 5. Generation of a Classically Improved Microalgal Strain Capable of Producing a Triglyceride Oil that is Highly Enriched in Oleic Acid A subpopulation of the Strain 4 lineage was concurrently subjected to an enrichment strategy employing one round of enrichment in an inhibitor cocktail (Inhibitor Cocktail 2 in FIG. 8, Panel B) comprised of 0.115 µM clomiphene citrate, 12.35 µM terfenadine, 18.582 fluphenazine, and 1.654 µM triparanol. Cells recovered from the enrichment were plated and subsequently assessed for glucose consumption and fatty acid profile in a 72-hour, 96-well block based format. One of these clones was subsequently stabilized and given the strain designation "Strain 5".

Example 6. Generation of a Classically Improved Microalgal Strain Capable of Producing a Triglyceride Oil that is Highly Enriched in Oleic Acid Strain 5 was subjected to another round of mutagenesis with increasing concentrations and exposure time to 4-NQO (37 µM for 30 minutes at 28° C.). This population of cells was subsequently subdivided and grown in standard lipid production medium supplemented with a range of cerulenin concentrations (7-50 µM). Cells from all concentrations were pooled and fractionated over a 60% Percoll/0.15 M NaCl density gradient. Oil laden cells recovered from a density zone of 1.02 g/mL were plated and assessed for glucose consumption and fatty acid profile. One of these clones was subsequently stabilized and given the strain designation "Strain 6".

Example 7. Generation of a Classically Improved Microalgal Strain Capable of Producing a Triglyceride Oil that is Highly Enriched in Oleic Acid Strain 6 was subsequently mutagenized with 8,000 µJoules of UV radiation. The resulting population of cells were subdivided and grown in standard lipid production medium supplemented with a range of concentrations (26-75 µM) of the mTOR (mammalian target of rapamycin) ATP-competitive inhibitor, AZD8055. Cells from all concentrations were pooled and fractionated over a 60% Percoll/0.15 M NaCl density gradient. Oil laden cells recovered from a density zone of 1.02-1.04 g/mL were plated and assessed for glucose consumption and fatty acid profile. One of these clones was subsequently stabilized and given the strain designation "Strain 7". TABLE 9 shows the fatty acid profiles of strains depicted in FIG. 9 from a 3-day, 96-well block lipid assay.

TABLE 9

| Sample Name | C14:0 | C16:0 | C16:1 | C18:0 | C18:1 | C18:2 | C18:3 alpha | C20:0 | C20:1 |
|---|---|---|---|---|---|---|---|---|---|
| Strain 0 | 1.38 | 27.40 | 0.85 | 3.33 | 58.32 | 6.70 | 0.51 | 0.40 | 0.20 |
| Strain K | 0.76 | 15.21 | 0.61 | 3.53 | 70.62 | 7.23 | 0.51 | 0.42 | 0.16 |
| Strain 2 | 1.00 | 13.84 | 0.59 | 2.89 | 73.21 | 7.48 | 0.36 | 0.15 | 0.12 |
| Strain 3 | 0.87 | 9.76 | 0.51 | 2.43 | 74.83 | 10.30 | 0.48 | 0.21 | 0.33 |
| Strain 4 | 0.52 | 11.09 | 0.58 | 2.38 | 77.53 | 6.98 | 0.29 | 0.14 | 0.29 |
| Strain 5 | 0.51 | 8.45 | 0.42 | 2.77 | 78.78 | 7.90 | 0.38 | 0.12 | 0.37 |
| Strain 6 | 0.31 | 5.75 | 0.30 | 2.67 | 81.45 | 7.83 | 0.34 | 0.13 | 0.66 |
| Strain 7 | 0.28 | 5.29 | 0.27 | 2.45 | 82.58 | 7.78 | 0.34 | 0.11 | 0.63 |

Figure 9:
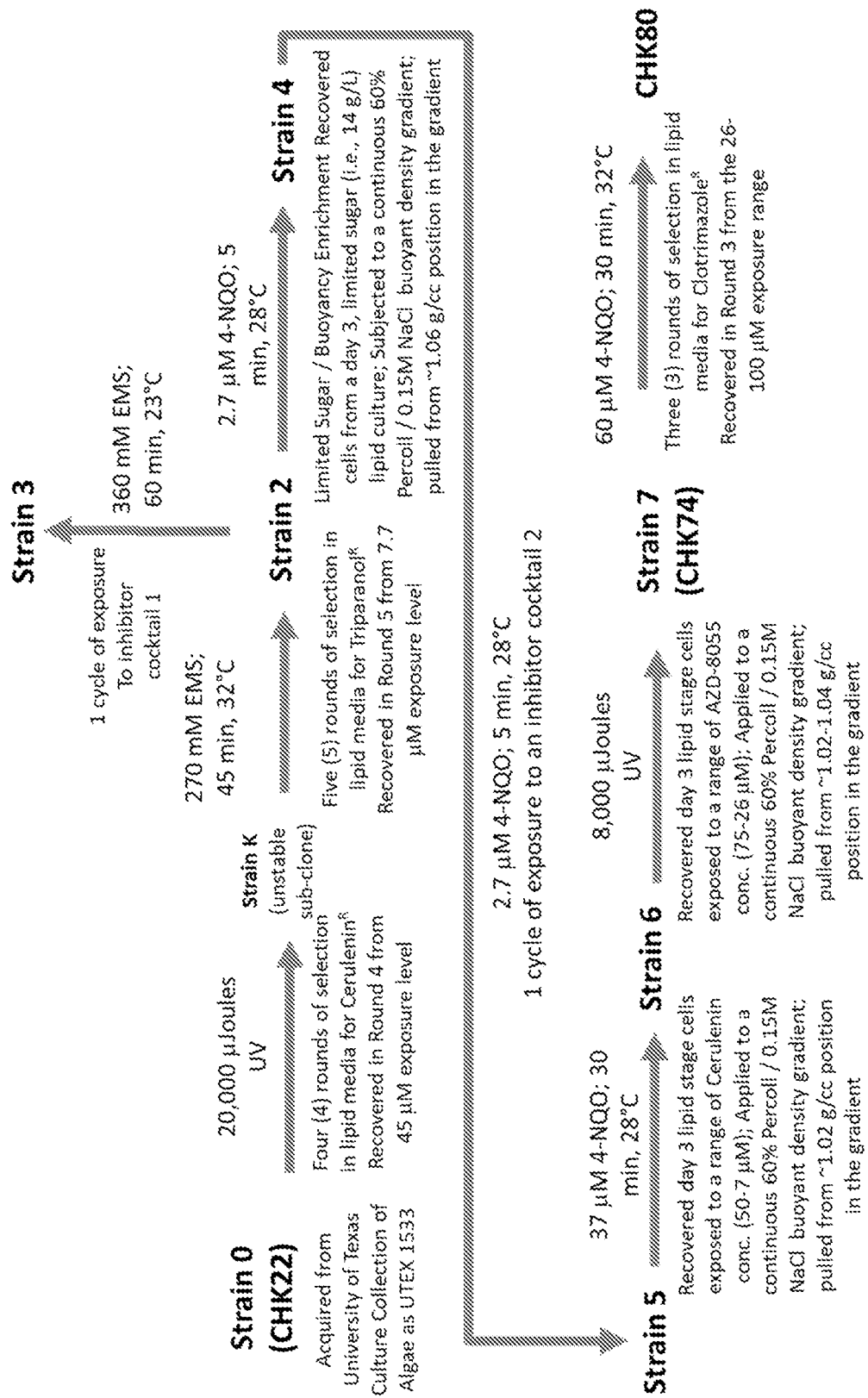
FIG. 9 shows an overview of an example classical strain improvement strategy for generation of mutants derived from UTEX 1533.

FIG. 9 shows an overview of classical strain improvement and provenance of Strain 7 by generation of mutants derived from UTEX 1533 using mutagens and a series of selective agents and enrichment strategies. Inhibitor cocktail 1 (Strain 2 to Strain 3) comprised of 131.2 µM BASF 13-338, 1.1 µM cafenstrole, 0.4 µM clomiphene, 9.1 µM PF-042110, and 1.5 µM triparanol. Inhibitor cocktail 2 (Strain 4 to Strain 5) comprised of 0.115 clomiphene citrate, 12.35 µM terfenadine, 18.582 µM fluphenazine, and 1.654 µM triparanol. TABLE 10 shows the fatty acid profiles of various strains described herein.

C. with 40 µM or 60 µM 4-NQO or subjected to sham mutagenesis with the addition of only the mutagen solvent, 0.06% DMSO. The two mutagenized and the mock-mutagenized populations were each independently cultured in lipid production media supplemented with different concentrations of the inhibitor, clomiphene, along with 2.44 g/L Tween-40, 2.49 g/L Tween-60, & 0.2 g/L linoleic acid. The Tween-emulsified linoleic acid was added to enrich for mutants that inherently produce lower levels of C18:2. After the first cycle of exposure, mutant cells exposed to concentrations of clomiphene where growth was reduced >50% based on OD750 measurements were collected, pooled, washed free of the inhibitor, and subjected to another round of clomiphene exposure for 72 h in lipid media with linoleic supplementation, each time increasing the range of clomiphene exposures. By the third cycle of exposure, a resistant population arose from the 60 µM 4-NQO mutant library compared to both the 40 µM 4-NQO mutant population or

TABLE 10

| Strain | Mutagen | Enrichment | Scale | Process | % Oleic | Titer (g/L) |
|---|---|---|---|---|---|---|
| Strain 0 | NA | NA | 10 mL | Low Cell Density | 59.61 (±0.30) | 9.2 (±0.3) |
| Strain 0 | | | 1 L | High Productivity | 62.08 | 105.4 |
| Strain 0 | | | 1 L | High Oleic | 69.07 | 86.1 |
| Strain 2 | EMS | Triparanol | 10 mL | Low Cell Density | 74.22 (±0.23) | 10.1 (±0.4) |
| Strain 2 | | | 1 L | High Productivity | 74.21 | 123.4 |
| Strain 2 | | | 1 L | High Oleic | 80.22 | 98.4 |
| Strain 2 | | | 300 L | High Oleic | 83.75 | 77.5 |
| Strain 4 | Strain 2 treated with 4-NQO (Nitroquinoline 4-oxide) | LSBE (Limited Sugar Buoyancy Enrichment) | 10 mL | Low Cell Density | 77.75 (±0.14) | 10.1 (±0.5) |
| Strain 4 | | | 1 L | High Productivity | 76.32 | 118.1 |
| Strain 4 | | | 1 L | High Oleic | 79.89 | 79.7 |
| Strain 5 | Strain 4 treated with 2.7 NQO | DOE mix (1.654 µM Triparanol 0.115 µM Clomiphene 12.35 µM Terfenadine 18.582 µM Fluphenazine) | 10 mL | Low Cell Density | 81.87 (±0.11) | 10.3 (±0.4) |
| Strain 5 | | | 1 L | High Productivity | 80.24 | 135.2 |
| Strain 5 | | | 1 L | High Oleic | 82.86 | 85.4 |

Example 8. Generation of a Classically Improved Microalgal Strain (CHK80) Capable of Producing a Triglyceride Oil that is Highly Enriched in Oleic Acid Strain 7 (CHK74) described in Example 7 was further subjected to classical strain improvement to produce the strain "CHK80". CHK74 was mutagenized for 30 min at 32° C. with 40 µM or 60 µM 4-NQO or subjected to sham mutagenesis with the addition of only the mutagen solvent, 0.06% DMSO. The two mutagenized and the mock-mutagenized populations were each independently cultured in lipid production media supplemented with different concentrations of the inhibitor, clomiphene, along with 2.44 g/L Tween-40, 2.49 g/L Tween-60, & 0.2 g/L linoleic acid. The mock-mutagenized controls (FIG. 9). This population was collected, washed free of inhibitor, expanded in pre-seed media for 3 days and plated for single colonies. Mutant clones were then picked and assessed for glucose consumption and fatty acid profile in a 72 h, 96-well block-based lipid production assay. A mutant identified in the screen was subsequently stabilized and given the strain designation "CHK80".

TABLE 11 shows sequence alignments of genes involved in fatty acid biosynthesis in CHK80 and CHK22 (Strain 0; original progenitor strain): FAD2-1, FAD2-2, FATA1-1, FATA1-2, KASII-1, KASII-2, SAD2-1, and SAD2-2.

TABLE 11

```
FAD2-1_CHK80  cggcgcgctgcttcgcgtgccgggtgcagcaatcagatccaagtctgacgacttgcgcgc
(SEQ ID NO: 1)
FAD2-1_CHK22  cggcgcgctgcttcgcgtgccgggtgcagcaatcagatccaagtctgacgacttgcgcgc
(SEQ ID NO: 2)

FAD2-1_CHK80  acgcgccggatccttcaattccaaagtgtcgtccgcgtgcgcttcttcgccttcgtcctc
FAD2-1_CHK22  acgcgccggatccttcaattccaaagtgtcgtccgcgtgcgcttcttcgccttcgtcctc FAD2-1_CHK80  ttgaacatccagcgacgcaagcgcagggcgctgggcggctggcgtcccgaaccggcctcg
FAD2-1_CHK22  ttgaacatccagcgacgcaagcgcagggcgctgggcggctggcgtcccgaaccggcctcg FAD2-1_CHK80  gcgcacgcggctgaaattgccgatgtcggcaatgtagtgccgctccgcccacctctcaat
FAD2-1_CHK22  gcgcacgcggctgaaattgccgatgtcggcaatgtagtgccgctccgcccacctctcaat FAD2-1_CHK80  taagttttcagcgcgtggtttgggaatgatctgcgctcatggggcgaaagaaggggttca
FAD2-1_CHK22  taagttttcagcgcgtggtttgggaatgatctgcgctcatggggcgaaagaaggggttca FAD2-1_CHK80  gaggtgctttattgttactcgactgggcgtaccagcattcgtgcatgactgattatacat
FAD2-1_CHK22  gaggtgctttattgttactcgactgggcgtaccagcattcgtgcatgactgattatacat FAD2-1_CHK80  acaaaagtacagctcgcttcaatgccctgcgattcctactcccgagcgagcactcctctc
FAD2-1_CHK22  acaaaagtacagctcgcttcaatgccctgcgattcctactcccgagcgagcactcctctc FAD2-1_CHK80  accgtcgggttgcttcccacgaccacgccggtaagagggtctgtggcctcgcgcccctcg
FAD2-1_CHK22  accgtcgggttgcttcccacgaccacgccggtaagagggtctgtggcctcgcgcccctcg FAD2-1_CHK80  cgagcgcatctttccagccacgtctgtatgattttgcgctcatacgtctggcccgtcgac
FAD2-1_CHK22  cgagcgcatctttccagccacgtctgtatgattttgcgctcatacgtctggcccgtcgac FAD2-1_CHK80  cccaaaatgacgggatcctgcataatatcgcccgaaatgggatccaggcattcgtcagga
FAD2-1_CHK22  cccaaaatgacgggatcctgcataatatcgcccgaaatgggatccaggcattcgtcagga FAD2-1_CHK80  ggcgtcagccccgcgggagatgccggtcccgccgcattggaaaggtgtagaggggggtgaa
FAD2-1_CHK22  ggcgtcagccccgcgggagatgccggtcccgccgcattggaaaggtgtagaggggggtgaa FAD2-1_CHK80  tcccccatttcatgaaatgcttggtcaacgatggtgcgcattcgtgcaaagtgaatatgg
FAD2-1_CHK22  tcccccatttcatgaaatgcttggtcaacgatggtgcgcattcgtgcaaagtgaatatgg FAD2-1_CHK80  ggtcacgcggtggacgaacgcggaggggcatgaccgaatctaggctcgcattcctcaga
FAD2-1_CHK22  ggtcacgcggtggacgaacgcggaggggcatgaccgaatctaggctcgcattcctcaga FAD2-1_CHK80  tcacttcatgccggcggtccggggtttgcgcgtcgcgcaaggctacgtctccctagccgc
FAD2-1_CHK22  tcacttcatgccggcggtccggggtttgcgcgtcgcgcaaggctacgtctccctagccgc FAD2-1_CHK80  tgcgcaccacgcgtgcgacgcggaggccatcttccggagcaacgaccatggattgtctta
FAD2-1_CHK22  tgcgcaccacgcgtgcgacgcggaggccatcttccggagcaacgaccatggattgtctta FAD2-1_CHK80  gcgatcgcacgaatgagtgctagtgagtcgtacgctcgacccagtcgctcgcaggagaag
FAD2-1_CHK22  gcgatcgcacgaatgagtgctagtgagtcgtacgctcgacccagtcgctcgcaggagaag FAD2-1_CHK80  gcggcagctgccgagcttcggcttaccagtcgtgactcgtatgtgatcaggaatcattgg
FAD2-1_CHK22  gcggcagctgccgagcttcggcttaccagtcgtgactcgtatgtgatcaggaatcattgg FAD2-1_CHK80  cattggtagcattataattcggcttccgcgctgcgtatgggcatggcaatgtctcatgca
FAD2-1_CHK22  cattggtagcattataattcggcttccgcgctgcgtatgggcatggcaatgtctcatgca FAD2-1_CHK80  gtcgatcttagtcaaccaattttgggtggccaggtccgggcgaccgggctccgtgtcgcc
FAD2-1_CHK22  gtcgatcttagtcaaccaattttgggtggccaggtccgggcgaccgggctccgtgtcgcc FAD2-1_CHK80  gggcaccacctcctgccaggagtagcagggccgccctctcgtcccgacgttggcccactg
FAD2-1_CHK22  gggcaccacctcctgccaggagtagcagggccgccctctcgtcccgacgttggcccactg FAD2-1_CHK80  aataccgtggcttcgagccctacatgatgggctgcctagtcgggcgggacgcgcaactgc
FAD2-1_CHK22  aataccgtggcttcgagccctacatgatgggctgcctagtcgggcgggacgcgcaactgc FAD2-1_CHK80  ccgcgcgatctgggggctggtctgaatccttcaggcgggtgttacccgagaaagaaaggg
FAD2-1_CHK22  ccgcgcgatctgggggctggtctgaatccttcaggcgggtgttacccgagaaagaaaggg FAD2-1_CHK80  tgccgatttcaaagcagacccatgtgccgggccctgtggcctgtgttggcgcctatgtag
FAD2-1_CHK22  tgccgatttcaaagcagacccatgtgccgggccctgtggcctgtgttggcgcctatgtag FAD2-1_CHK80  tcacccccccctcacccaattgtcgccagtttgcgcactccataaactcaaaacagcagct
FAD2-1_CHK22  tcacccccccctcacccaattgtcgccagtttgcgcactccataaactcaaaacagcagct
```

TABLE 11-continued

```
FAD2-1_CHK80  tctgagctgcgctgttcaagaacacctctggggtttgctcacccgcgaggtcgacgccca
FAD2-1_CHK22  tctgagctgcgctgttcaagaacacctctggggtttgctcacccgcgaggtcgacgccca FAD2-1_CHK80  gcATGGCTATCAAGACGAACAGGCAGCCTGTGGAGAAGCCTCCGTTCACGATCGGGACGC
FAD2-1_CHK22  gcATGGCTATCAAGACGAACAGGCAGCCTGTGGAGAAGCCTCCGTTCACGATCGGGACGC FAD2-1_CHK80  TGCGCAAGGCCATCCCCGCGCACTGTTTCGAGCGCTCGGCGCTTCGTAGCAGCATGTACC
FAD2-1_CHK22  TGCGCAAGGCCATCCCCGCGCACTGTTTCGAGCGCTCGGCGCTTCGTAGCAGCATGTACC FAD2-1_CHK80  TGGCCTTTGACATCGCGGTCATGTCCCTGCTCTACGTCGCGTCGACGTACATCGACCCTG
FAD2-1_CHK22  TGGCCTTTGACATCGCGGTCATGTCCCTGCTCTACGTCGCGTCGACGTACATCGACCCTG FAD2-1_CHK80  CACCGGTGCCTACGTGGGTCAAGTACGGCATCATGTGGCCGCTCTACTGGTTCTTCCAGG
FAD2-1_CHK22  CACCGGTGCCTACGTGGGTCAAGTACGGCATCATGTGGCCGCTCTACTGGTTCTTCCAGG FAD2-1_CHK80  TGTGTTTGAGGGTTTTGGTTGCCCGTATTGAGGTCCTGGTGGCGCGCATGGAGGAGAAGG
FAD2-1_CHK22  TGTGTTTGAGGGTTTTGGTTGCCCGTATTGAGGTCCTGGTGGCGCGCATGGAGGAGAAGG FAD2-1_CHK80  CGCCTGTCCCGCTGACCCCCCCGCCGACCCTCCCCCCACCTTCCAGGGCGCCTTCGGCAC
FAD2-1_CHK22  CGCCTGTCCCGCTGACCCCCCCGCCGACCCTCCCCC-ACCTTCCAGGGCGCCTTCGGCAC FAD2-1_CHK80  GGGTGTCTGGGTGTGCGCGCACGAGTGCGGTCACCAGGCCTTTTCCTCCAGCCAGGCCAT
FAD2-1_CHK22  GGGTGTCTGGGTGTGCGCGCACGAGTGCGGTCACCAGGCCTTTTCCTCCAGCCAGGCCAT FAD2-1_CHK80  CAACGACGGCGTGGGCCTGGTGTTCCACAGCCTGCTGCTGGTGCCCTACTACTCCTGGAA
FAD2-1_CHK22  CAACGACGGCGTGGGCCTGGTGTTCCACAGCCTGCTGCTGGTGCCCTACTACTCCTGGAA FAD2-1_CHK80  GCACTCGCACCGCCGCCACCACTCCAACACGGGGTGCCTGGACAAGGACGAGGTGTTTGT
FAD2-1_CHK22  GCACTCGCACCGCCGCCACCACTCCAACACGGGGTGCCTGGACAAGGACGAGGTGTTTGT FAD2-1_CHK80  GCCGCCGCACCGTGCGGTGGCGCACGAGGGCCTGGAGTGGGAGGAGTGGCTGCCCATCCG
FAD2-1_CHK22  GCCGCCGCACCGTGCGGTGGCGCACGAGGGCCTGGAGTGGGAGGAGTGGCTGCCCATCCG FAD2-1_CHK80  CATGGGCAAGGTGCTGGTCACCTTGACCCTGGGCTGGCCGCTGTACCTCATGTTCAACGT
FAD2-1_CHK22  CATGGGCAAGGTGCTGGTCACCTTGACCCTGGGCTGGCCGCTGTACCTCATGTTCAACGT FAD2-1_CHK80  CGCCTCCCGCCCTTACCCGCGCTTCGCCAACCACTTTGACCCGTGGTCGCCCATCTTCAG
FAD2-1_CHK22  CGCCTCCCGCCCTTACCCGCGCTTCGCCAACCACTTTGACCCGTGGTCGCCCATCTTCAG FAD2-1_CHK80  CAAGCGCGAGCGCATCGAGGTGGTCATCTCCGACCTCGCGTTGGTGGCGGTGCTCAGCGG
FAD2-1_CHK22  CAAGCGCGAGCGCATCGAGGTGGTCATCTCCGACCTCGCGTTGGTGGCGGTGCTCAGCGG FAD2-1_CHK80  GCTCAGCGTGCTGGGCCGCACCATGGGCTGGGCCTGGCTGGTCAAGACCTACGTGGTGCC
FAD2-1_CHK22  GCTCAGCGTGCTGGGCCGCACCATGGGCTGGGCCTGGCTGGTCAAGACCTACGTGGTGCC FAD2-1_CHK80  CTACATGATCGTGAACATGTGGCTGGTGCTCATCACGCTGCTCCAGCACACGCACCCGGC
FAD2-1_CHK22  CTACATGATCGTGAACATGTGGCTGGTGCTCATCACGCTGCTCCAGCACACGCACCCGGC FAD2-1_CHK80  CCTGCCGCACTACTTCGAGAAGGACTGGGACTGGCTACGCGGCGCCATGGCCACCGTCGA
FAD2-1_CHK80  CCTGCCGCACTACTTCGAGAAGGACTGGGACTGGCTACGCGGCGCCATGGCCACCGTCGA FAD2-1_CHK80  CCGCTCCATGGGCCCGCCCTTCATGGACAGCATCCTGCACCACATCTCCGACACCCACGT
FAD2-1_CHK22  CCGCTCCATGGGCCCGCCCTTCATGGACAGCATCCTGCACCACATCTCCGACACCCACGT FAD2-1_CHK80  GCTGCACCACCTCTTCAGCACCATCCCGCACTACCACGCCGAGGAGGCCTCCGCCGCCAT
FAD2-1_CHK22  GCTGCACCACCTCTTCAGCACCATCCCGCACTACCACGCCGAGGAGGCCTCCGCCGCCAT FAD2-1_CHK80  CCGGCCCATCCTGGGCAAGTACTACCAATCCGACAGCCGCTGGGTCGGCCGCGCCCTGTG
FAD2-1_CHK22  CCGGCCCATCCTGGGCAAGTACTACCAATCCGACAGCCGCTGGGTCGGCCGCGCCCTGTG FAD2-1_CHK80  GGAGGACTGGCGCGACTGCCGCTACGTCGTCCCCGACGCGCCCGAGGACGACTCCGCGCT
FAD2-1_CHK22  GGAGGACTGGCGCGACTGCCGCTACGTCGTCCCCGACGCGCCCGAGGACGACTCCGCGCT FAD2-1_CHK80  CTGGTTCCACAAGTGAgcgcgcctgcgcgaggacgcagaacaacgctgccgccgtgtctt
FAD2-1_CHK22  CTGGTTCCACAAGTGAgcgcgcctgcgcgaggacgcagaacaacgctgccgccgtgtctt FAD2-1_CHK80  ttgcacgcgcgactccggcgcttcgctggtggcaccccataaagaaaccctcaattctg
FAD2-1_CHK22  ttgcacgcgcgactccggcgcttcgctggtggcaccccataaagaaaccctcaattctg FAD2-1_CHK80  tttgtggaagacacggtgtaccccacccacccacctgcacctctattattggtattatt
FAD2-1_CHK22  tttgtggaagacacggtgtaccccacccacccacctgcacctctattattggtattatt FAD2-1_CHK80  gacgcgggagtgggcgttgtaccctacaacgtagcttctctagttttcagctggctccca
FAD2-1_CHK22  gacgcgggagtgggcgttgtaccctacaacgtagcttctctagttttcagctggctccca FAD2-1_CHK80  ccattgtaaattcatgctagaatagtgcgtggttatgtgagaggtatagtgtgtctgagc
FAD2-1_CHK22  ccattgtaaattcatgctagaatagtgcgtggttatgtgagaggtatagtgtgtctgagc FAD2-1_CHK80  agacggggcgggatgcatgtcgtggtggtgatctttggctcaaggcgtcgtcgacgtgac
FAD2-1_CHK22  agacggggcgggatgcatgtcgtggtggtgatctttggctcaaggcgtcgtcgacgtgac
```

TABLE 11-continued

```
FAD2-1_CHK80  gtgcccgatcatgagagcaataccgcgctcaaagccgacgcatagcctttactccgcaat
FAD2-1_CHK22  gtgcccgatcatgagagcaataccgcgctcaaagccgacgcatagcctttactccgcaat FAD2-1_CHK80  ccaaacgactgtcgctcgtatttttttggatatctattttaaagagcgagcacagcgccgg
FAD2-1_CHK22  ccaaacgactgtcgctcgtatttttttggatatctattttaaagagcgagcacagcgccgg FAD2-1_CHK80  gcatgggcctgaaaggcctcgcggccgtgctcgtggtgggggccgcgagcgcgtggggca
FAD2-1_CHK22  gcatgggcctgaaaggcctcgcggccgtgctcgtggtgggggccgcgagcgcgtggggca FAD2-1_CHK80  tcgcggcagtgcaccaggcgcagacggaggaacgcatggtgcgtgcgcaatataagatac
FAD2-1_CHK22  tcgcggcagtgcaccaggcgcagacggaggaacgcatggtgcgtgcgcaatataagatac FAD2-1_CHK80  atgtattgttgtctgtactataatgctagagcatcaccaggggcttagtcatcgcacctg
FAD2-1_CHK22  atgtattgttgtctgtactataatgctagagcatcaccaggggcttagtcatcgcacctg FAD2-1_CHK80  ctttggtcattacagaaattgcacaagggcgtcctccgggatgaggagatgtaccagctc
FAD2-1_CHK22  ctttggtcattacagaaattgcacaagggcgtcctccgggatgaggagatgtaccagctc FAD2-1_CHK80  aagctggagcggcttcgagccaagcaggagcgcggcgcatgacgacctatccacatgtga
FAD2-1_CHK22  aagctggagcggcttcgagccaagcaggagcgcggcgcatgacgacctatccacatgtga FAD2-1_CHK80  caaaggggtctgggtcgtacgaatcgacaaaccagtcaggagacagcggggtccatgagt
FAD2-1_CHK22  caaaggggtctgggtcgtacgaatcgacaaaccagtcaggagacagcggggtccatgagt FAD2-1_CHK80  tggcccgctcgcagcttcagcgctttgagcatcgcggcattgtccacgatccaaggctcc
FAD2-1_CHK22  tggcccgctcgcagcttcagcgctttgagcatcgcggcattgtccacgatccaaggctcc FAD2-1_CHK80  cgcagcgcctccttgggaccccgtgcggagaagcgtgtgccgagagggctgtgagggcg
FAD2-1_CHK22  cgcagcgcctccttgggaccccgtgcggagaagcgtgtgccgagagggctgtgagggcg FAD2-1_CHK80  gaggctggaggagaggctgcgaatcattgcgctgcctaggcgtctgccgagtagtagcac
FAD2-1_CHK22  gaggctggaggagaggctgcgaatcattgcgctgcctaggcgtctgccgagtagtagcac FAD2-1_CHK80  accacgcgccggtgctttcatttcattgtgtccgttgctgtaatgcatgcgagcaatcct
FAD2-1_CHK22  accacgcgccggtgctttcatttcattgtgtccgttgctgtaatgcatgcgagcaatcct FAD2-1_CHK80  gcactaaaagctgcgatcaccacctcggcgttgttggtctctagtaccgctcacctgacc
FAD2-1_CHK22  gcactaaaagctgcgatcaccacctcggcgttgttggtctctagtaccgctcacctgacc FAD2-1_CHK80  acgcgcacggaagtatggcggtcggcgacggcctgctgcacgtggcagtgcagatccacg
FAD2-1_CHK22  acgcgcacggaagtatggcggtcggcgacggcctgctgcacgtggcagtgcagatccacg FAD2-1_CHK80  tggcccaggagcaggtctcgcagctgcaacaccgcgccctcgtgctcgccggggtccatc
FAD2-1_CHK22  tggcccaggagcaggtctcgcagctgcaacaccgcgccctcgtgctcgccggggtccatc FAD2-1_CHK80  cagtccatacccccgcgccgggccctcgagccggacggccagcagccagggccgggggtcc
FAD2-1_CHK22  cagtccatacccccgcgccgggccctcgagccggacggccagcagccagggccgggggtcc FAD2-1_CHK80  gcgccgacgcccggcggccccgccgcgcagctggggtcggccaggaagagccactggacg
FAD2-1_CHK22  gcgccgacgcccggcggccccgccgcgcagctggggtcggccaggaagagccactggacg FAD2-1_CHK80  gccggcccgggcgagccccgcgccggcgtgggacccacccgcagcaccaccgcctgctcc
FAD2-1_CHK22  gccggcccgggcgagccccgcgccggcgtgggacccacccgcagcaccaccgcctgctcc FAD2-1_CHK80  aggtccacgtcgctcggcggcaggcccgcgtgcggcgcctgcgccagcgtccagggcagg
FAD2-1_CHK22  aggtccacgtcgctcggcggcaggcccgcgtgcggcgcctgcgccagcgtccagggcagg FAD2-1_CHK80  cggggccgggcgtgcatg
FAD2-1_CHK22  cggggccgggcgtgcatg FAD2-2_CHK80  cggctcgctgctttgcgtgccgggtgcagcgatcagatccaagtctgacgacttgtgctg
(SEQ ID NO: 3)
FAD2-2_CHK22  cggctcgctgctttgcgtgccgggtgcagcgatcagatccaagtctgacgacttgtgctg
(SEQ ID NO: 4)

FAD2-2_CHK80  atgtactgtgtcctttgagtccagagcgccggccgcacgcgcttcttcccccttcttcttc
FAD2-2_CHK22  atgtactgtgtcctttgagtccagagcgccggccgcacgcgcttcttcccccttcttcttc FAD2-2_CHK80  ctctcgaacatccagcgatgcaagtgcagggcgctgggcggctggcgtcccgaaccggcc
FAD2-2_CHK22  ctctcgaacatccagcgatgcaagtgcagggcgctgggcggctggcgtcccgaaccggcc FAD2-2_CHK80  tcggcgcacgcggctgaaattgccaatgtcggcaatgtagtgccgctcggcccatccctc
FAD2-2_CHK22  tcggcgcacgcggctgaaattgccaatgtcggcaatgtagtgccgctcggcccatccctc FAD2-2_CHK80  gatcaagttttttcagcgcgtggttggggatgatctgcgctcatgggaagataaaagggt
FAD2-2_CHK22  gatcaagttttttcagcgcgtggttggggatgatctgcgctcatgggaagataaaagggt FAD2-2_CHK80  tctgaggtggttgattggtactttaccggaagtactcatattcatacatgactgatccca
FAD2-2_CHK22  tctgaggtggttgattggtactttaccggaagtactcatattcatacatgactgatccca
```

TABLE 11-continued

```
FAD2-2_CHK80  cacaaaaacaaagctcacttcaaagaaccgcgcatgtctactccccagcaatcacttcgc
FAD2-2_CHK22  cacaaaaacaaagctcacttcaaagaaccgcgcatgtctactccccagcaatcacttcgc FAD2-2_CHK80  tcaccgtcgggttgcttcccacgacaacgccggtgagagggtcggtggcctcgcgacctt
FAD2-2_CHK22  tcaccgtcgggttgcttcccacgacaacgccggtgagagggtcggtggcctcgcgacctt FAD2-2_CHK80  cgcgggcacatctttccagccatgtctgtataatctcacgctcatacgtctggcccgtcg
FAD2-2_CHK22  cgcgggcacatctttccagccatgtctgtataatctcacgctcatacgtctggcccgtcg FAD2-2_CHK80  accccaaaatgacgggatcctgcatgatatcgcccgagatggggtccaggcattcctctg
FAD2-2_CHK22  accccaaaatgacgggatcctgcatgatatcgcccgagatggggtccaggcattcctctg FAD2-2_CHK80  gaggcgtcagccctgcgggagatgccggtcccaccgcattggaaaggcacaaaggggtg
FAD2-2_CHK22  gaggcgtcagccctgcgggagatgccggtcccaccgcattggaaaggcacaaaggggtg FAD2-2_CHK80  aatcccccatttcatgaaattgttggtcagcgatggtgcgcactcgtgcgcaatgaatat
FAD2-2_CHK22  aatcccccatttcatgaaattgttggtcagcgatggtgcgcactcgtgcgcaatgaatat FAD2-2_CHK80  ggggtcacgcggtggacgaacgcggagggggcctggccgaatctaggcttgcattcctca
FAD2-2_CHK22  ggggtcacgcggtggacgaacgcggagggggcctggccgaatctaggcttgcattcctca FAD2-2_CHK80  gatcactttctgccggcggtccggggtttgcgcgtcgcgcaacgctccgtctccctagcc
FAD2-2_CHK22  gatcactttctgccggcggtccggggtttgcgcgtcgcgcaacgctccgtctccctagcc FAD2-2_CHK80  *gctgcgcaccgcgcgtgcgacgcgaaggtcattttccagaacaacgaccatggcttgtct*
FAD2-2_CHK22  *gctgcgcaccgcgcgtgcgacgcgaaggtcattttccagaacaacgaccatggcttgtct*

FAD2-2_CHK80  *tagcgatcgctcgaatgactgctagtgagtcgtacgctcgacccagtcgctcgcaggaga*
FAD2-2_CHK22  *tagcgatcgctcgaatgactgctagtgagtcgtacgctcgacccagtcgctcgcaggaga*

FAD2-2_CHK80  *acgcggcaactgccgagcttcggcttgccagtcgtgactcgtatgtgatcaggaatcatt*
FAD2-2_CHK22  *acgcggcaactgccgagcttcggcttgccagtcgtgactcgtatgtgatcaggaatcatt*

FAD2-2_CHK80  *ggcattggtagcattataattcggcttccgcgctgtttatgggcatggcaatgtctcatg*
FAD2-2_CHK22  *ggcattggtagcattataattcggcttccgcgctgtttatgggcatggcaatgtctcatg*

FAD2-2_CHK80  *cagtcgaccttagtcaaccaattctgggtggccagctccgggcgaccgggctccgtgtcg*
FAD2-2_CHK22  *cagtcgaccttagtcaaccaattctgggtggccagctccgggcgaccgggctccgtgtcg*

FAD2-2_CHK80  *ccgggcaccacctcctgccatgagtaacagggccgccctctcctcccgacgttggcccac*
FAD2-2_CHK22  *ccgggcaccacctcctgccatgagtaacagggccgccctctcctcccgacgttggcccac*

FAD2-2_CHK80  *tgaataccgtgtcttggggccctacatgatgggctgcctagtcggcggggacgcgcaact*
FAD2-2_CHK22  *tgaataccgtgtcttggggccctacatgatgggctgcctagtcggcggggacgcgcaact*

FAD2-2_CHK80  *gcccgcgcaatctgggacgtggtctgaatcctccaggcgggtttccccgagaaagaaagg*
FAD2-2_CHK22  *gcccgcgcaatctgggacgtggtctgaatcctccaggcgggtttccccgagaaagaaagg*

FAD2-2_CHK80  *gtgccgatttcaaagcagagccatgtgccgggccctgtggcctgtgttggcgcctatgta*
FAD2-2_CHK22  *gtgccgatttcaaagcagagccatgtgccgggccctgtggcctgtgttggcgcctatgta*

FAD2-2_CHK80  *gtcaccccccctcacccaattgtcgccagtttgcgcaatccataaactcaaaactgcagc*
FAD2-2_CHK22  *gtcaccccccctcacccaattgtcgccagtttgcgcaatccataaactcaaaactgcagc*

FAD2-2_CHK80  *ttctgagctgcgctgttcaagaacacctctggggtttgctcacccgcgaggtcgacgccc*
FAD2-2_CHK22  *ttctgagctgcgctgttcaagaacacctctggggtttgctcacccgcgaggtcgacgccc*

FAD2-2_CHK80  *agc*ATGGCTATCAAGACGAACAGGCAGCCTGTGGAGAAGCCTCCGTTCACGATCGGGACG
FAD2-2_CHK22  *agc*ATGGCTATCAAGACGAACAGGCAGCCTGTGGAGAAGCCTCCGTTCACGATCGGGACG FAD2-2_CHK80  CTGCGCAAGGCCATCCCCGCGCACTGTTTCGAGCGCTCGGCGCTTCGTAGCAGCATGTAC
FAD2-2_CHK22  CTGCGCAAGGCCATCCCCGCGCACTGTTTCGAGCGCTCGGCGCTTCGTAGCAGCATGTAC

FAD2-2_CHK80  CTGGCCTTTGACATCGCGGTCATGTCCCTGCTCTACGTCGCGTCGACGTACATCGACCCT
FAD2-2_CHK22  CTGGCCTTTGACATCGCGGTCATGTCCCTGCTCTACGTCGCGTCGACGTACATCGACCCT

FAD2-2_CHK80  GCGCCGGTGCCTACGTGGGTCAAGTATGGCGTCATGTGGCCGCTCTACTGGTTCTTCCAG
FAD2-2_CHK22  GCGCCGGTGCCTACGTGGGTCAAGTATGGCGTCATGTGGCCGCTCTACTGGTTCTTCCAG

FAD2-2_CHK80  GTGTGTGTGAGGGTTGTGGTTGCCCGTATCGAGGTCCTGGTGGCGCGCATGGGGGAGAAG
FAD2-2_CHK22  GTGTGTGTGAGGGTTGTGGTTGCCCGTATCGAGGTCCTGGTGGCGCGCATGGGGGAGAAG

FAD2-2_CHK80  GCGCCTGTCCCGCTGACCCCCCCGGCTACCCTCCCGGCACCTTCCAGGGCGCCTTCGGCA
FAD2-2_CHK22  GCGCCTGTCCCGCTGACCCCCCCGGCTACCCTCCCGGCACCTTCCAGGGCGCCTTCGGCA

FAD2-2_CHK80  CGGGTGTCTGGGTGTGCGCGCACGAGTGCGGCCACCAGGCCTTTTCCTCCAGCCAGGCCA
FAD2-2_CHK22  CGGGTGTCTGGGTGTGCGCGCACGAGTGCGGCCACCAGGCCTTTTCCTCCAGCCAGGCCA
```

TABLE 11-continued

```
FAD2-2_CHK80  TCAACGACGGCGTGGGCCTGGTGTTCCACAGCCTGCTGCTGGTGCCCTACTACTCCTGGA
FAD2-2_CHK22  TCAACGACGGCGTGGGCCTGGTGTTCCACAGCCTGCTGCTGGTGCCCTACTACTCCTGGA

FAD2-2_CHK80  AGCACTCGCACCGCCGCCACCACTCCAACACGGGGTGCCTGGACAAGGACGAGGTGTTTG
FAD2-2_CHK22  AGCACTCGCACCGCCGCCACCACTCCAACACGGGGTGCCTGGACAAGGACGAGGTGTTTG

FAD2-2_CHK80  TGCCGCCGCACCGCGCAGTGGCGCACGAGGGCCTGGAGTGGGAGGAGTGGCTGCCCATCC
FAD2-2_CHK22  TGCCGCCGCACCGCGCAGTGGCGCACGAGGGCCTGGAGTGGGAGGAGTGGCTGCCCATCC

FAD2-2_CHK80  GCATGGGCAAGGTGCTGGTCACCCTGACCCTGGGCTGGCCGCTGTACCTCATGTTCAACG
FAD2-2_CHK22  GCATGGGCAAGGTGCTGGTCACCCTGACCCTGGGCTGGCCGCTGTACCTCATGTTCAACG

FAD2-2_CHK80  TCGCCTCGCGGCCGTACCCGCGCTTCGCCAACCACTTTGACCCGTGGTCGCCCATCTTCA
FAD2-2_CHK22  TCGCCTCGCGGCCGTACCCGCGCTTCGCCAACCACTTTGACCCGTGGTCGCCCATCTTCA

FAD2-2_CHK80  GCAAGCGCGAGCGCATCGAGGTGGTCATCTCCGACCTGGCGCTGGTGGCGGTGCTCAGCG
FAD2-2_CHK22  GCAAGCGCGAGCGCATCGAGGTGGTCATCTCCGACCTGGCGCTGGTGGCGGTGCTCAGCG

FAD2-2_CHK80  GGCTCAGCGTGCTGGGCCGCACCATGGGCTGGGCCTGGCTGGTCAAGACCTACGTGGTGC
FAD2-2_CHK22  GGCTCAGCGTGCTGGGCCGCACCATGGGCTGGGCCTGGCTGGTCAAGACCTACGTGGTGC

FAD2-2_CHK80  CCTACCTGATCGTGAACATGTGGCTCGTGCTCATCACGCTGCTCCAGCACACGCACCCGG
FAD2-2_CHK22  CCTACCTGATCGTGAACATGTGGCTCGTGCTCATCACGCTGCTCCAGCACACGCACCCGG

FAD2-2_CHK80  CGCTGCCGCACTACTTCGAGAAGGACTGGGACTGGCTGCGCGGCGCCATGGCCACCGTGG
FAD2-2_CHK22  CGCTGCCGCACTACTTCGAGAAGGACTGGGACTGGCTGCGCGGCGCCATGGCCACCGTGG

FAD2-2_CHK80  ACCGCTCCATGGGCCCGCCCTTCATGGACAACATCCTGCACCACATCTCCGACACCCACG
FAD2-2_CHK22  ACCGCTCCATGGGCCCGCCCTTCATGGACAACATCCTGCACCACATCTCCGACACCCACG

FAD2-2_CHK80  TGCTGCACCACCTCTTCAGCACCATCCCGCACTACCACGCCGAGGAGGCCTCCGCCGCCA
FAD2-2_CHK22  TGCTGCACCACCTCTTCAGCACCATCCCGCACTACCACGCCGAGGAGGCCTCCGCCGCCA

FAD2-2_CHK80  TCAGGCCCATCCTGGGCAAGTACTACCAGTCCGACAGCCGCTGGGTCGGCCGCGCCCTGT
FAD2-2_CHK22  TCAGGCCCATCCTGGGCAAGTACTACCAGTCCGACAGCCGCTGGGTCGGCCGCGCCCTGT

FAD2-2_CHK80  GGGAGGACTGGCGCGACTGCCGCTACGTCGTCCCGGACGCGCCCGAGGACGACTCCGCGC
FAD2-2_CHK22  GGGAGGACTGGCGCGACTGCCGCTACGTCGTCCCGGACGCGCCCGAGGACGACTCCGCGC

FAD2-2_CHK80  TCTGGTTCCACAAGTGAgtgagtgagtcgctcactcagcgcgcctgcgcggggatgcgga
FAD2-2_CHK22  TCTGGTTCCACAAGTGAgtgagtgagtcgctcactcagcgcgcctgcgcggggatgcgga FAD2-2_CHK80  acgccgccgccgccttgtcttttgcacgcgcgactccgtcgcttcgcgggtggcacccccc
FAD2-2_CHK22  acgccgccgccgccttgtcttttgcacgcgcgactccgtcgcttcgcgggtggcacccccc FAD2-2_CHK80  attgaaaaaaacctcaattctgtttgtggaagacacggtgtaccccaaccacccacctg
FAD2-2_CHK22  attgaaaaaaacctcaattctgtttgtggaagacacggtgtaccccaaccacccacctg FAD2-2_CHK80  cacctctattattggtattattgacgcgggagcgggcgttgtactctacaacgtagcgtc
FAD2-2_CHK22  cacctctattattggtattattgacgcgggagcgggcgttgtactctacaacgtagcgtc FAD2-2_CHK80  tctggttttcagctggctcccaccattgtaaattcttgctaaaatagtgcgtggttatgt
FAD2-2_CHK22  tctggttttcagctggctcccaccattgtaaattcttgctaaaatagtgcgtggttatgt FAD2-2_CHK80  gagaggtatggtgtaacagggcgtcagtcatgttggttttcgtgctgatctcgggcacaa
FAD2-2_CHK22  gagaggtatggtgtaacagggcgtcagtcatgttggttttcgtgctgatctcgggcacaa FAD2-2_CHK80  ggcgtcgtcgacgtgacgtgcccgtgatgagagcaataccgcgctcaaagccgacgcatg
FAD2-2_CHK22  ggcgtcgtcgacgtgacgtgcccgtgatgagagcaataccgcgctcaaagccgacgcatg FAD2-2_CHK80  gcctttactccgcactccaaacgactgtcgctcgtattttcggatatctatttttttaag
FAD2-2_CHK22  gcctttactccgcactccaaacgactgtcgctcgtattttcggatatctatttttttaag FAD2-2_CHK80  agcgagcacagcgccgggcatgggcctgaaaggcctcgcggccgtgctcgtggtgggggc
FAD2-2_CHK22  agcgagcacagcgccgggcatgggcctgaaaggcctcgcggccgtgctcgtggtgggggc FAD2-2_CHK80  cgcgagcgcgtggggcatcgcggcagtgcaccaggcgcagacggaggaacgcatggtgag
FAD2-2_CHK22  cgcgagcgcgtggggcatcgcggcagtgcaccaggcgcagacggaggaacgcatggtgag FAD2-2_CHK80  tgcgcatcacaagatgcatgtcttgttgtctgtactataatgctagagcatcaccagggg
FAD2-2_CHK22  tgcgcatcacaagatgcatgtcttgttgtctgtactataatgctagagcatcaccagggg FAD2-2_CHK80  cttagtcatcgcacctgctttggtcattacagaaattgcacaagggcgtcctccgggatg
FAD2-2_CHK22  cttagtcatcgcacctgctttggtcattacagaaattgcacaagggcgtcctccgggatg FAD2-2_CHK80  aggagatgtaccagctcaagctggagcggcttcgagccaagcaggagcgcggcgcatgac
FAD2-2_CHK22  aggagatgtaccagctcaagctggagcggcttcgagccaagcaggagcgcggcgcatgac
```

TABLE 11-continued

```
FAD2-2_CHK80   gacctacccacatgcgacaaaggggtctgggtcgtacgacaaaccagtcaggaggcggcg
FAD2-2_CHK22   gacctacccacatgcgacaaaggggtctgggtcgtacgacaaaccagtcaggaggcggcg FAD2-2_CHK80   gggtccatgagctggcccgctcgcagcttcagcgcttcgagcatcgcggcgttgtccgcg
FAD2-2_CHK22   gggtccatgagctggcccgctcgcagcttcagcgcttcgagcatcgcggcgttgtccgcg FAD2-2_CHK80   atccaagcctcccgcagcgcctccttggggcccctgtgcggagaggcgggtgccgagagg
FAD2-2_CHK22   atccaagcctcccgcagcgcctccttgggccccctgtgcggagaggcgggtgccgagagg FAD2-2_CHK80   gctgtgagggcggaggctggaggacaggctgcgaatcgtcgcgctgcctaggcgtctgcc
FAD2-2_CHK22   gctgtgagggcggaggctggaggacaggctgcgaatcgtcgcgctgcctaggcgtctgcc FAD2-2_CHK80   gaggagaagcacaccacgcgccgccgcttcatttcattgtgcccgttgctgtaatgcat
FAD2-2_CHK22   gaggagaagcacaccacgcgccgccgcttcatttcattgtgcccgttgctgtaatgcat FAD2-2_CHK80   gcgagcgatcctgcactaaagctgcgatcgccacctcagcgttgttcgtctctagcaccg
FAD2-2_CHK22   gcgagcgatcctgcactaaagctgcgatcgccacctcagcgttgttcgtctctagcaccg FAD2-2_CHK80   ctcacctgaccacgcgcacggaagagtggcggtcggcgacggcctgctgcacgtggcagt
FAD2-2_CHK22   ctcacctgaccacgcgcacggaagagtggcggtcggcgacggcctgctgcacgtggcagt FAD2-2_CHK80   gcaggtccacgtggccgaggagcaggtctcgcagctgcagcaccgcgcccctcgtgctcgc
FAD2-2_CHK22   gcaggtccacgtggccgaggagcaggtctcgcagctgcagcaccgcgcccctcgtgctcgc FAD2-2_CHK80   cggggtccatccagtccatgcccgcgccgggcctcgagccggacggccagcagccagg
FAD2-2_CHK22   cggggtccatccagtccatgcccgcgccgggcctcgagccggacggccagcagccagg FAD2-2_CHK80   gccggggggtccgcgccgacgcccggcggccccgccgcgcagctggggtcggccaggaaga
FAD2-2_CHK22   gccggggggtccgcgccgacgcccggcggccccgccgcgcagctggggtcggccaggaaga FAD2-2_CHK80   gccactgggcggccggcccgggcgagccccgcgccggcgcgggacccacccgcagcacca
FAD2-2_CHK22   gccactgggcggccggcccgggcgagccccgcgccggcgcgggacccacccgcagcacca FAD2-2_CHK80   ccgcctggtccaggtcgacgtcgctcggcggcaggcccgcgtgcggcgcctgcgccagcg
FAD2-2_CHK22   ccgcctggtccaggtcgacgtcgctcggcggcaggcccgcgtgcggcgcctgcgccagcg FAD2-2_CHK80   tccagggcaggcggggcgcgcgtgca
FAD2-2_CHK22   tccagggcaggcggggcgcgcgtgca FATA1-1_CHK80   gcaatggcgctcggtacagggtctgcgtccgtgctgggctccctctcctacgatgcacaa
(SEQ ID NO: 5)
FATA1-1_CHK22   gcaatggcgctcggtacagggtctgcgtccgtgctgggctccctctcctacgatgcacaa
(SEQ ID NO: 6)

FATA1-1_CHK80   gggagcgccccggccagctcagcgcgtccacaacctcccctcgtcacacacacacctgcg
FATA1-1_CHK22   gggagcgccccggccagctcagcgcgtccacaacctcccctcgtcacacacacacctgcg FATA1-1_CHK80   gaaccaggccgcccatttgctgcttgagcatgccttgcatcatgtccgggtttcccatca
FATA1-1_CHK22   gaaccaggccgcccatttgctgcttgagcatgccttgcatcatgtccgggtttcccatca FATA1-1_CHK80   tatcgttgaggttcttgggctccagcttctgctccagcacaccatcctgtcgatcgaaga
FATA1-1_CHK22   tatcgttgaggttcttgggctccagcttctgctccagcacaccatcctgtcgatcgaaga FATA1-1_CHK80   gaaggagacatgtgtacattattggtgtgagggcgctgaatcggccatttttta-aatga
FATA1-1_CHK22   gaaggagacatgtgtacattattggtgtgagggcgctgaatcggccatttttta aaatga FATA1-1_CHK80   tcacgctcatgccaatagacgcggcacataacgacgttcaaaccccgccaaagccgcgg
FATA1-1_CHK22   tcacgctcatgccaatagacgcggcacataacgacgttcaaaccccgccaaagccgcgg FATA1-1_CHK80   acaacccatccctccacaccccccacacaaagaacccgccaccgcttaccttgcccacg
FATA1-1_CHK22   acaacccatccctccacaccccccacacaaagaacccgccaccgcttaccttgcccacg FATA1-1_CHK80   aggtaggcctttcgttgcgcaaaaccggcctcggtgatgaatgcatgcccgttcctgacg
FATA1-1_CHK22   aggtaggcctttcgttgcgcaaaaccggcctcggtgatgaatgcatgcccgttcctgacg FATA1-1_CHK80   agcgctgcccggccaacacgctcttttgctgcgtctcctcaggcttgggggcctccttg
FATA1-1_CHK22   agcgctgcccggccaacacgctcttttgctgcgtctcctcaggcttgggggcctccttg FATA1-1_CHK80   ggcttgggtgccgccatgatctgcgcgcatcagagaaacgttgctggt-aaaaggagcgc
FATA1-1_CHK22   ggcttgggtgccgccatgatctgcgcgcatcagagaaacgttgctggtaaaaaggagcgc FATA1-1_CHK80   ccggctgcgcaatatatatataggcatgccaacacagcccaacctcactcgggagcccgt
FATA1-1_CHK22   ccggctgcgcaatatatatataggcatgccaacacagcccaacctcactcgggagcccgt FATA1-1_CHK80   cccaccaccccccaagtcgcgtgccttgacggcatactgctgcagaagcttcatgagaatg
FATA1-1_CHK22   cccaccaccccccaagtcgcgtgccttgacggcatactgctgcagaagcttcatgagaatg FATA1-1_CHK80   atgccgaacaagaggggcacgaggacccaat*cccggacatccttgtcgataatgatctcg*
FATA1-1_CHK22   atgccgaacaagaggggcacgaggacccaat*cccggacatccttgtcgataatgatctcg*
```

TABLE 11-continued

```
FATA1-1_CHK80  tgagtccccatcgtccgcccgacgctccggggagcccgccgatgctcaagacgagagggc
FATA1-1_CHK22  tgagtccccatcgtccgcccgacgctccggggagcccgccgatgctcaagacgagagggc FATA1-1_CHK80  cctcgaccaggaggggctggcccggggcgggcactggcgtcgaaggtgcgcccgtcgttcg
FATA1-1_CHK22  cctcgaccaggaggggctggcccggggcgggcactggcgtcgaaggtgcgcccgtcgttcg FATA1-1_CHK80  cctgcagtcctatgccacaaaacaagtcttctgacggggtgcgtttgctcccgtgcgggc
FATA1-1_CHK22  cctgcagtcctatgccacaaaacaagtcttctgacggggtgcgtttgctcccgtgcgggc FATA1-1_CHK80  aggcaacagaggtattcaccctggtcatggggagatcggcgatcgagctgggataagaga
FATA1-1_CHK22  aggcaacagaggtattcaccctggtcatggggagatcggcgatcgagctgggataagaga FATA1-1_CHK80  tacggtcccgcgcaaggatcgctcatcctggtctgagccggacagtcattctggcaagca
FATA1-1_CHK22  tacggtcccgcgcaaggatcgctcatcctggtctgagccggacagtcattctggcaagca FATA1-1_CHK80  atgacaacttgtcaggaccggaccgtgccatatatttctcacctagcgccgcaaaaccta
FATA1-1_CHK22  atgacaacttgtcaggaccggaccgtgccatatatttctcacctagcgccgcaaaaccta FATA1-1_CHK80  acaatttgggagtcactgtgccactgagttcgactggtagctgaatggagtcgctgctcc
FATA1-1_CHK22  acaatttgggagtcactgtgccactgagttcgactggtagctgaatggagtcgctgctcc FATA1-1_CHK80  actaaacgaattgtcagcaccgccagccggccgaggacccgagtcatagcgagggtagta
FATA1-1_CHK22  actaaacgaattgtcagcaccgccagccggccgaggacccgagtcatagcgagggtagta FATA1-1_CHK80  gcgcgccatggcaccgaccagcctgcttgccagtactggcgtctcttccgcttctctgtg
FATA1-1_CHK22  gcgcgccatggcaccgaccagcctgcttgccagtactggcgtctcttccgcttctctgtg FATA1-1_CHK80  gtcctctgcgcgctccagcgcgtgcgcttttccggtggatcatgcggtccgtggcgcacc
FATA1-1_CHK22  gtcctctgcgcgctccagcgcgtgcgcttttccggtggatcatgcggtccgtggcgcacc FATA1-1_CHK80  gcagcggccgctgcccatgcagcgccgctgcttccgaacagtggcggtcagggccgcacc
FATA1-1_CHK22  gcagcggccgctgcccatgcagcgccgctgcttccgaacagtggcggtcagggccgcacc FATA1-1_CHK80  cgcggtagccgtccgtccggaacccgcccaagagttttgggagcagcttgagctctgcaa
FATA1-1_CHK22  cgcggtagccgtccgtccggaacccgcccaagagttttgggagcagcttgagccctgcaa FATA1-1_CHK80  gATGGCGGAGGACAAGCGCATCTTCCTGGAGGAGCACCGGTGCGTGGAGGTCCGGGGCTG
FATA1-1_CHK22  gATGGCGGAGGACAAGCGCATCTTCCTGGAGGAGCACCGGTGCGTGGAGGTCCGGGGCTG FATA1-1_CHK80  ACCGGCCGTCGCATTCAACGTAATCAATCGCATGATGATCAGAGGACACGAAGTCTTGGT
FATA1-1_CHK22  ACCGGCCGTCGCATTCAACGTAATCAATCGCATGATGATCAGAGGACACGAAGTCTTGGT FATA1-1_CHK80  GGCGGTGGCCAGAAACACTGTCCATTGCAAGGGCATAGGGATGCGTTCCTTCACCTCTCA
FATA1-1_CHK22  GGCGGTGGCCAGAAACACTGTCCATTGCAAGGGCATAGGGATGCGTTCCTTCACCTCTCA FATA1-1_CHK80  TTTCTCATTTCTGAATCCCTCCCTGCTCACTCTTTCTCCTCCTCCTTCCCGTTCACGCAG
FATA1-1_CHK22  TTTCTCATTTCTGAATCCCTCCCTGCTCACTCTTTCTCCTCCTCCTTCCCGTTCACGCAG FATA1-1_CHK80  CATTCGGGGCAACGAGGTGGGCCCCTCGCAGCGGCTGACGATCACGGCGGTGGCCAACAT
FATA1-1_CHK22  CATTCGGGGCAACGAGGTGGGCCCCTCGCAGCGGCTGACGATCACGGCGGTGGCCAACAT FATA1-1_CHK80  CCTGCAGGAGGCGGCGGGCAACCACGCGGTGGCCATGTGGGGCCGGAGCTCGGAGGGTTT
FATA1-1_CHK22  CCTGCAGGAGGCGGCGGGCAACCACGCGGTGGCCATGTGGGGCCGGAGCTCGGAGGGTTT FATA1-1_CHK80  CGCGACGGACCCGGAGCTGCAGGAGGCGGGTCTCATCTTTGTGATGACGCGCATGCAGAT
FATA1-1_CHK22  CGCGACGGACCCGGAGCTGCAGGAGGCGGGTCTCATCTTTGTGATGACGCGCATGCAGAT FATA1-1_CHK80  CCAGATGTACCGCTACCCGCGCTGGGGCGACCTGATGCAGGTGGAGACCTGGTTCCAGAC
FATA1-1_CHK22  CCAGATGTACCGCTACCCGCGCTGGGGCGACCTGATGCAGGTGGAGACCTGGTTCCAGAC FATA1-1_CHK80  GGCGGGCAAGCTGGGCGCGCAGCGCGAGTGGGTGCTGCGCGACAAGCTGACCGGCGAGGC
FATA1-1_CHK22  GGCGGGCAAGCTGGGCGCGCAGCGCGAGTGGGTGCTGCGCGACAAGCTGACCGGCGAGGC FATA1-1_CHK80  GCTGGGCGCGGCCACCTCGAGCTGGGTCATGATCAACATCCGCACGCGCCGGCCGTGCCG
FATA1-1_CHK22  GCTGGGCGCGGCCACCTCGAGCTGGGTCATGATCAACATCCGCACGCGCCGGCCGTGCCG FATA1-1_CHK80  CATGCCGGAGCTCGTCCGCGTCAAGTCGGCCTTCTTCGCGCGCGAGCCGCCGCGCCTGGC
FATA1-1_CHK22  CATGCCGGAGCTCGTCCGCGTCAAGTCGGCCTTCTTCGCGCGCGAGCCGCCGCGCCTGGC FATA1-1_CHK80  GCTGCCGCCCGCGGTCACGCGTGCCAAGCTGCCCAACATCGCGACGCCGGCGCCGCTGCG
FATA1-1_CHK22  GCTGCCGCCCGCGGTCACGCGTGCCAAGCTGCCCAACATCGCGACGCCGGCGCCGCTGCG FATA1-1_CHK80  CGGGCACCGCCAGGTCGCGCGCCGCACCGACATGGACATGAACGGGCACGTGAACAACGT
FATA1-1_CHK22  CGGGCACCGCCAGGTCGCGCGCCGCACCGACATGGACATGAACGGGCACGTGAACAACGT FATA1-1_CHK80  GGCCTACCTGGCCTGGTGCCTGGAGGCCGTGCCCGAGCACGTCTTCAGCGACTACCACCT
FATA1-1_CHK22  GGCCTACCTGGCCTGGTGCCTGGAGGCCGTGCCCGAGCACGTCTTCAGCGACTACCACCT
```

TABLE 11-continued

```
FATA1-1_CHK80  CTACCAGATGGAGATCGACTTCAAGGCCGAGTGCCACGCGGGCGACGTCATCTCCTCCCA
FATA1-1_CHK22  CTACCAGATGGAGATCGACTTCAAGGCCGAGTGCCACGCGGGCGACGTCATCTCCTCCCA

FATA1-1_CHK80  GGCCGAGCAGATCCCGCCCCAGGAGGCGCTCACGCACAACGGCGCCGGCCGCAACCCCTC
FATA1-1_CHK22  GGCCGAGCAGATCCCGCCCCAGGAGGCGCTCACGCACAACGGCGCCGGCCGCAACCCCTC

FATA1-1_CHK80  CTGCTTCGTCCATAGCATTCTGCGCGCCGAGACCGAGCTCGTCCGCGCGCGAACCACATG
FATA1-1_CHK22  CTGCTTCGTCCATAGCATTCTGCGCGCCGAGACCGAGCTCGTCCGCGCGCGAACCACATG

FATA1-1_CHK80  GTCGGCCCCATCGACGCGCCCGCCGCCAAGCCGCCCAAGGCGAGCCACTGAggacaggg
FATA1-1_CHK22  GTCGGCCCCATCGACGCGCCCGCCGCCAAGCCGCCCAAGGCGAGCCACTGAggacaggg FATA1-1_CHK80  tggttggctggatggggaaacgctggtcgcgggattcgatcctgctgcttatatcctccc
FATA1-1_CHK22  tggttggctggatggggaaacgctggtcgcgggattcgatcctgctgcttatatcctccc FATA1-1_CHK80  tggaagcacacccacgactctgaagaagaaaacgtgcacacacacaacccaaccggccga
FATA1-1_CHK22  tggaagcacacccacgactctgaagaagaaaacgtgcacacacacaacccaaccggccga FATA1-1_CHK80  atatttgcttccttatcccgggtccaagagagactgcgatgcccccctcaatcagcatcc
FATA1-1_CHK22  atatttgcttccttatcccgggtccaagagagactgcgatgcccccctcaatcagcatcc FATA1-1_CHK80  tcctccctgccgcttcaatcttccctgcttgcctgcgcccgcggtgcgccgtctgcccgc
FATA1-1_CHK22  tcctccctgccgcttcaatcttccctgcttgcctgcgcccgcggtgcgccgtctgcccgc FATA1-1_CHK80  ccagtcagtcactcctgcacaggccccttgtgcgcagtgctcctgtaccctttaccgctc
FATA1-1_CHK22  ccagtcagtcactcctgcacaggccccttgtgcgcagtgctcctgtaccctttaccgctc FATA1-1_CHK80  cttccattctgcgaggcccccctattgaatgtattcgttgcctgtgtggccaagcgggctg
FATA1-1_CHK22  cttccattctgcgaggcccccctattgaatgtattcgttgcctgtgtggccaagcgggctg FATA1-1_CHK80  ctgggcgcgccgccgtcgggcagtgctcggcgactttggcggaagccgattgttcttctg
FATA1-1_CHK22  ctgggcgcgccgccgtcgggcagtgctcggcgactttggcggaagccgattgttcttctg FATA1-1_CHK80  taagccacgcgcttgctgctttgggaagagaagggggggggtactgaatggatgaggagga
FATA1-1_CHK22  taagccacgcgcttgctgctttgggaagagaagggggggggtactgaatggatgaggagga FATA1-1_CHK80  gaaggaggggtattggtattatctgagttggggaggcagggagagttggaaaatgtaagt
FATA1-1_CHK22  gaaggaggggtattggtattatctgagttggggaggcagggagagttggaaaatgtaagt FATA1-1_CHK80  ggcacgacgggcaaggagaatggtgagcatgtgcatggtgatgtcgttggtcgaggacga
FATA1-1_CHK22  ggcacgacgggcaaggagaatggtgagcatgtgcatggtgatgtcgttggtcgaggacga FATA1-1_CHK80  tcctgcacgcgtgtatctgatgtagaatacggcaatcaccctagtctacatctataccttt
FATA1-1_CHK22  tcctgcacgcgtgtatctgatgtagaatacggcaatcaccctagtctacatctataccttt FATA1-1_CHK80  ctccgtataacgccctttccaaatgccctcccgtttctctcctattcttgatccacatga
FATA1-1_CHK22  ctccgtataacgccctttccaaatgccctcccgtttctctcctattcttgatccacatga FATA1-1_CHK80  tgaccctggcactatttcaagggctggacatttcaagaaggtttgcgtatctgaagaagg
FATA1-1_CHK22  tgaccctggcactatttcaagggctggacatttcaagaaggtttgcgtatctgaagaagg FATA1-1_CHK80  attggtttggagaggtggccgatgaaagtggggtcaagctgcgtggagcccctctgcacgg
FATA1-1_CHK22  attggtttggagaggtggccgatgaaagtggggtcaagctgcgtggagcccctctgcacgg FATA1-1_CHK80  atttctatggtaatctgcgtccacgtcatcagtagccgtacgcctctgcggcgtcgccgt
FATA1-1_CHK22  atttctatggtaatctgcgtccacgtcatcagtagccgtacgcctctgcggcgtcgccgt FATA1-1_CHK80  gctcctcagccgccgcttcaccaccagccaggagcccccatacgcacgcgctcccagacgg
FATA1-1_CHK22  gctcctcagccgccgcttcaccaccagccaggagcccccatacgcacgcgctcccagacgg FATA1-1_CHK80  cgcgcgcgacggggacgatcatgagcagcgcgatctggggcgtgtcgtgcgagctgagcc
FATA1-1_CHK22  cgcgcgcgacggggacgatcatgagcagcgcgatctggggcgtgtcgtgcgagctgagcc FATA1-1_CHK80  gcacaaccacgttgccctggccgcgcgtggtgtactggcagttggtcgagaccatggtgt
FATA1-1_CHK22  gcacaaccacgttgccctggccgcgcgtggtgtactggcagttggtcgagaccatggtgt FATA1-1_CHK80  cggacttgaagtaggagccgtcaaagcgcgggaggcgcgtctcggccgagacgttgccgc
FATA1-1_CHK22  cggacttgaagtaggagccgtcaaagcgcgggaggcgcgtctcggccgagacgttgccgc FATA1-1_CHK80  cgatgaccaggctctggcgcttctggcgcgggtcgcggccctgccactgcgcggagccgc
FATA1-1_CHK22  cgatgaccaggctctggcgcttctggcgcgggtcgcggccctgccactgcgcggagccgc FATA1-1_CHK80  ccaggagcaggcgcgactcgtcacggccgcgcagcttgacgtcggccgccagcgccgtgc
FATA1-1_CHK22  ccaggagcaggcgcgactcgtcacggccgcgcagcttgacgtcggccgccagcgccgtgc FATA1-1_CHK80  ccggctcgtaggccgaccccatcttgacgaagaggcggccgatcgctgcgcggaccttga
FATA1-1_CHK22  ccggctcgtaggccgaccccatcttgacgaagaggcggccgatcgctgcgcggaccttga
```

TABLE 11-continued

```
FATA1-1_CHK80  ccgcgtcggacaggcgcaggcgctcgtccagcttgaccccgagcgccgcgttgccgggct
FATA1-1_CHK22  ccgcgtcggacaggcgcaggcgctcgtccagcttgaccccgagcgccgcgttgccgggct FATA1-1_CHK80  tgaacggcagcgagaactcctcgcccagcttggagccgagcaggcccagcgccagcttct
FATA1-1_CHK22  tgaacggcagcgagaactcctcgcccagcttggagccgagcagcccagcgccagcttct FATA1-1_CHK80  gccgcttgccgcgcgcgcgcaggcgcgagtcgacgcgcagcgtgtagag
FATA1-1_CHK22  gccgcttgccgcgcgcgcgcaggcgcgagtcgacgcgcagcgtgtagag FATA1-2_CHK80  gcaatggcgctctgtgcagggtctgtgtccggtctccctctcctacgatgcacaaggcaa
(SEQ ID NO: 7)
FATA1-2_CHK22  gcaatggcgctctgtgcagggtctgtgtccggtctccctctcctacgatgcacaaggcaa
(SEQ ID NO: 8)

FATA1-2_CHK80  cgcctttgctgactcagcgcgtccacaacctcccctcgtcacacacacctgcggaaccag
FATA1-2_CHK22  cgcctttgctgactcagcgcgtccacaacctcccctcgtcacacacacctgcggaaccag FATA1-2_CHK80  gccgcccatttgctgcttgagcatgccttgcatcatgtccgggttgcccatcatatcgtt
FATA1-2_CHK22  gccgcccatttgctgcttgagcatgccttgcatcatgtccgggttgcccatcatatcgtt FATA1-2_CHK80  gaggttcttgggctccagtttctgctccagcacgccatcctgtcggtcgaagaggaggag
FATA1-2_CHK22  gaggttcttgggctccagtttctgctccagcacgccatcctgtcggtcgaagaggaggag FATA1-2_CHK80  acatgtaagcgttgttgggatgagggttgctaaattggccattattttaatgatcacgc
FATA1-2_CHK22  acatgtaagcgttgttgggatgagggttgctaaattggccattattttaatgatcacgc FATA1-2_CHK80  tcgtgccaatagacgcggcacattgcgatgttcaaactcccgtcaaagccgcggacaacc
FATA1-2_CHK22  tcgtgccaatagacgcggcacattgcgatgttcaaactcccgtcaaagccgcggacaacc FATA1-2_CHK80  acatccctccacaccccacacacaaagaacccgccaccgctcaccttgcccacgaggtag
FATA1-2_CHK22  acatccctccacaccccacacacaaagaacccgccaccgctcaccttgcccacgaggtag FATA1-2_CHK80  gcctttcgttgcgcaaacccggcctcggtgatgaatgcgtgcccgttcctgacgagcgct
FATA1-2_CHK22  gcctttcgttgcgcaaacccggcctcggtgatgaatgcgtgcccgttcctgacgagcgct FATA1-2_CHK80  gcccgggccaacacgctcttttgctgcgtctcctcaggcttgggggcctccttgggcttg
FATA1-2_CHK22  gcccgggccaacacgctcttttgctgcgtctcctcaggcttgggggcctccttgggcttg FATA1-2_CHK80  ggggccgccatgatctgcgcgcaccagagagaagtcattggtgaaaaggagcgcccggct
FATA1-2_CHK22  ggggccgccatgatctgcgcgcaccagagagaagtcattggtgaaaaggagcgcccggct FATA1-2_CHK80  gcgctatatatatatatatatgctcaggccaataaagtccaacctcactggggagccccg
FATA1-2_CHK22  gcgctatatatatatatatatgctcaggccaataaagtccaacctcactggggagccccg FATA1-2_CHK80  tcccaccaccccaagtcgcgtaccttgacggcatactgctgcagaagcttcatgaggat
FATA1-2_CHK22  tcccaccaccccaagtcgcgtaccttgacggcatactgctgcagaagcttcatgaggat FATA1-2_CHK80  gatgccgaacaagaggggcacaaggacccaatcccggacatccttgtcgataatgatctc
FATA1-2_CHK22  gatgccgaacaagaggggcacaaggacccaatcccggacatccttgtcgataatgatctc FATA1-2_CHK80  gtgagtcccatcgtccgcccgacgctgcggggagcccgccgatgctcaagacgagaggg
FATA1-2_CHK22  gtgagtcccatcgtccgcccgacgctgcggggagcccgccgatgctcaagacgagaggg FATA1-2_CHK80  ccctcgaccaggaggggctggcccgggcgggcactggcgtcgaaggtgcgcccgtcgttc
FATA1-2_CHK22  ccctcgaccaggaggggctggcccgggcgggcactggcgtcgaaggtgcgcccgtcgttc FATA1-2_CHK80  gcctgcagtccgatgacacaaaacaagtcttctgacggggtgcgtttgctcccgtgcggg
FATA1-2_CHK22  gcctgcagtccgatgacacaaaacaagtcttctgacggggtgcgtttgctcccgtgcggg FATA1-2_CHK80  caggcaacagaggtattcaacctggtcatggcgagatcggcgatcgagctgggataagag
FATA1-2_CHK22  caggcaacagaggtattcaacctggtcatggcgagatcggcgatcgagctgggataagag FATA1-2_CHK80  atacggtcccgcgcgaggatcgctcatcctggtctgagccggacagtcattctggcaagc
FATA1-2_CHK22  atacggtcccgcgcgaggatcgctcatcctggtctgagccggacagtcattctggcaagc FATA1-2_CHK80  aatgacaacttgccaggaccggaccgtgccatatatttctcacctagcgcggcaaaacct
FATA1-2_CHK22  aatgacaacttgccaggaccggaccgtgccatatatttctcacctagcgcggcaaaacct FATA1-2_CHK80  aacaatttggaagtcactgtgccactgagctcgactggtagctgaatggagtcgctgctc
FATA1-2_CHK22  aacaatttggaagtcactgtgccactgagctcgactggtagctgaatggagtcgctgctc FATA1-2_CHK80  cactaatcgaattgtcagcaccgccagccggccgaggacccgagtcatagcgagggtagt
FATA1-2_CHK22  cactaatcgaattgtcagcaccgccagccggccgaggacccgagtcatagcgagggtagt FATA1-2_CHK80  agcgcgccatggcaccgaccagcctgcttgcccgtactggcgtctcttccgcttctctgt
FATA1-2_CHK22  agcgcgccatggcaccgaccagcctgcttgcccgtactggcgtctcttccgcttctctgt FATA1-2_CHK80  gctcctctacgcgctccggcgcgtgcgcttttccggtggatcatgcggtccgtggcgcac
FATA1-2_CHK22  gctcctctacgcgctccggcgcgtgcgcttttccggtggatcatgcggtccgtggcgcac
```

TABLE 11-continued

```
FATA1-2_CHK80  cgcagcggccgctgcccatgcagcgccgctgcttccgaacagtggctgtcagggccgcac
FATA1-2_CHK22  cgcagcggccgctgcccatgcagcgccgctgcttccgaacagtggctgtcagggccgcac FATA1-2_CHK80  ccgcagtagccgtccgtccggaacccgcccaagagttttgggagcagcttgagccctgca
FATA1-2_CHK22  ccgcagtagccgtccgtccggaacccgcccaagagttttgggagcagcttgagccctgca FATA1-2_CHK80  agATGGCGGAGGACAAGCGCATCTTCCTGTAGGAGCACCGGTGCGCGGAGGTCCGGGGCT
FATA1-2_CHK22  agATGGCGGAGGACAAGCGCATCTTCCTGGAGGAGCACCGGTGCGCGGAGGTCCGGGGCT FATA1-2_CHK80  GACCGGCCGTCGCATTCAACGTAATCAATCGCATGATGATCACAGGACGCGACGTCTTGG
FATA1-2_CHK22  GACCGGCCGTCGCATTCAACGTAATCAATCGCATGATGATCACAGGACGCGACGTCTTGG FATA1-2_CHK80  TGGCGGTGGCCAGGGACACTGCCCATTGCACAGGCATAGGAATGCGTTCCTTCTCATTTC
FATA1-2_CHK22  TGGCGGTGGCCAGGGACACTGCCCATTGCACAGGCATAGGAATGCGTTCCTTCTCATTTC FATA1-2_CHK80  TCAGTTTTCTGAGCCCCTCCCTCTTCACTCTTTCTCCTCCTCCTCCCCTCTCACGCAGCA
FATA1-2_CHK22  TCAGTTTTCTGAGCCCCTCCCTCTTCACTCTTTCTCCTCCTCCTCCCCTCTCACGCAGCA FATA1-2_CHK80  TTCGTGGCAACGAGGTGGGCCCCTCGCAGCGGCTGACGATCACGGCGGTGGCCAACATCC
FATA1-2_CHK22  TTCGTGGCAACGAGGTGGGCCCCTCGCAGCGGCTGACGATCACGGCGGTGGCCAACATCC FATA1-2_CHK80  TGCAGGAGGCGGCGGGCAACCACGCGGTGGCCATGTGGGGTCGGAGCTCGGAGGGTTTCG
FATA1-2_CHK22  TGCAGGAGGCGGCGGGCAACCACGCGGTGGCCATGTGGGGTCGGAGCTCGGAGGGTTTCG FATA1-2_CHK80  CGACGGACCCGGAGCTGCAGGAGGCGGGCCTCATCTTTGTGATGACGCGCATGCAGATCC
FATA1-2_CHK22  CGACGGACCCGGAGCTGCAGGAGGCGGGCCTCATCTTTGTGATGACGCGCATGCAGATCC FATA1-2_CHK80  AAATGTACCGCTACCCGCGCTGGGGCGACCTGATGCAGGTGGAGACCTGGTTCCAGACGG
FATA1-2_CHK22  AAATGTACCGCTACCCGCGCTGGGGCGACCTGATGCAGGTGGAGACCTGGTTCCAGACGG FATA1-2_CHK80  CGGGCAAGCTAGGCGCGCAGCGCGAGTGGGTGCTGCGCGACAAGCTGACCGGCGAGGCGC
FATA1-2_CHK22  CGGGCAAGCTAGGCGCGCAGCGCGAGTGGGTGCTGCGCGACAAGCTGACCGGCGAGGCGC FATA1-2_CHK80  TGGGCGCGGCCACCTCCAGCTGGGTCATGATCAACATCCGCACGCGCCGGCCGTGCCGCA
FATA1-2_CHK22  TGGGCGCGGCCACCTCCAGCTGGGTCATGATCAACATCCGCACGCGCCGGCCGTGCCGCA FATA1-2_CHK80  TGCCCGAGCTCGTCCGCGTCAAGTCGGCCTTCTTCGCGCGCGAGCCGCCGCGCCTGGCGC
FATA1-2_CHK22  TGCCCGAGCTCGTCCGCGTCAAGTCGGCCTTCTTCGCGCGCGAGCCGCCGCGCCTGGCGC FATA1-2_CHK80  TGCCGCCCACGGTCACGCGCGCCAAGCTGCCCAACATCGCGACGCCGGCGCCGCTGCGCG
FATA1-2_CHK22  TGCCGCCCACGGTCACGCGCGCCAAGCTGCCCAACATCGCGACGCCGGCGCCGCTGCGCG FATA1-2_CHK80  GGCACCGCCAGGTCGCGCGCCGCACCGACATGGACATGAACGGCCACGTGAACAACGTTG
FATA1-2_CHK22  GGCACCGCCAGGTCGCGCGCCGCACCGACATGGACATGAACGGCCACGTGAACAACGTTG FATA1-2_CHK80  CCTACCTGGCCTGGTGCCTGGAGGCCGTGCCCGAGCACGTCTTCAGCGACTACCACCTCT
FATA1-2_CHK22  CCTACCTGGCCTGGTGCCTGGAGGCCGTGCCCGAGCACGTCTTCAGCGACTACCACCTCT FATA1-2_CHK80  ACCAGATGGAGATCGACTTCAAGGCCGAGTGCCACGCGGGCGACGTCATCTCCTCCCAGG
FATA1-2_CHK22  ACCAGATGGAGATCGACTTCAAGGCCGAGTGCCACGCGGGCGACGTCATCTCCTCCCAGG FATA1-2_CHK80  CCGAGCAGATCCCGCCCCAGGAGGCGCTCACGCACAACGGCGCCGGCCGCAACCCCTCCT
FATA1-2_CHK22  CCGAGCAGATCCCGCCCCAGGAGGCGCTCACGCACAACGGCGCCGGCCGCAACCCCTCCT FATA1-2_CHK80  GCTTCGTCCACAGCATTCTGCGCGCCGAGACCGAGCTCGTCCGCGCGCGCACCACCTGGT
FATA1-2_CHK22  GCTTCGTCCACAGCATTCTGCGCGCCGAGACCGAGCTCGTCCGCGCGCGCACCACCTGGT FATA1-2_CHK80  CGGCCCCCGTCGACGCGCCCGCCGCCAAGCCGCCCAAGGCGAGCCACTGAgcagaggaga
FATA1-2_CHK22  CGGCCCCCGTCGACGCGCCCGCCGCCAAGCCGCCCAAGGCGAGCCACTGAgcagaggaga FATA1-2_CHK80  gggtggctggtagttgcgggatggctggtcgcccgtcgatcctgctgctgctattgtctc
FATA1-2_CHK22  gggtggctggtagttgcgggatggctggtcgcccgtcgatcctgctgctgctattgtctc FATA1-2_CHK80  ctcctgcacaagcccacccacgactccgaagaagaagaagaaaacgcgcacacacacaac
FATA1-2_CHK22  ctcctgcacaagcccacccacgactccgaagaagaagaagaaaacgcgcacacacacaac FATA1-2_CHK80  ccaaccggccgaatatttgcttccttatcccgggtccaagagagacggcgatgccccct
FATA1-2_CHK22  ccaaccggccgaatatttgcttccttatcccgggtccaagagagacggcgatgccccct FATA1-2_CHK80  caatcagcctcctcctccctgccgctccaatcttccctgcttgcatgcgcccgcgagagg
FATA1-2_CHK22  caatcagcctcctcctccctgccgctccaatcttccctgcttgcatgcgcccgcgagagg FATA1-2_CHK80  ctgtctgcgcgccccgtcagtcactcccgtgcagacgcctcgtgctcggtgctcctgta
FATA1-2_CHK22  ctgtctgcgcgccccgtcagtcactcccgtgcagacgcctcgtgctcggtgctcctgta FATA1-2_CHK80  tcctttaccgctcctttcattctgcgaggcccctgttgaatgtattcgttgcctgtgtg
FATA1-2_CHK22  tcctttaccgctcctttcattctgcgaggcccctgttgaatgtattcgttgcctgtgtg
```

TABLE 11-continued

```
FATA1-2_CHK80  gccaagcgcgctgctgggcgcgccgccgtcggcggtgctcggcgactctggcggaagcc
FATA1-2_CHK22  gccaagcgcgctgctgggcgcgccgccgtcggcggtgctcggcgactctggcggaagcc FATA1-2_CHK80  ggttgttcttctgtaagccacgcgcttgctgcttttggaaaagagggggtttactgaat
FATA1-2_CHK22  ggttgttcttctgtaagccacgcgcttgctgcttttggaaaagagggggtttactgaat FATA1-2_CHK80  ggaggaggagcaggataattggtagtatctgagttgttggggaggcaggaagagttggga
FATA1-2_CHK22  ggaggaggagcaggataattggtagtatctgagttgttggggaggcaggaagagttggga FATA1-2_CHK80  aatggaagtggcacgatgggcaaggagaatggtgagcatgcgcagggtgatgtcgttggc
FATA1-2_CHK22  aatggaagtggcacgatgggcaaggagaatggtgagcatgcgcagggtgatgtcgttggc FATA1-2_CHK80  cgagaacgatcctgcactcccgtaagtagaatacggcaatcacgttgatctacatctcta
FATA1-2_CHK22  cgagaacgatcctgcactcccgtaagtagaatacggcaatcacgttgatctacatctcta FATA1-2_CHK80  acttctccatttaaagcccctttccacatgccctcgcgtttgcatcctacaccctttgatc
FATA1-2_CHK22  acttctccatttaaagcccctttccacatgccctcgcgtttgcatcctacaccctttgatc FATA1-2_CHK80  cacatgattgatgaccctggcactatcttaagggctggacatttcaagaaggtttgcgta
FATA1-2_CHK22  cacatgattgatgaccctggcactatcttaagggctggacatttcaagaaggtttgcgta FATA1-2_CHK80  tctgaagaagggctggtttgaaggggtcgccgatgagagtgggaacaagctgcgaggatg
FATA1-2_CHK22  tctgaagaagggctggtttgaaggggtcgccgatgagagtgggaacaagctgcgaggatg FATA1-2_CHK80  cctctgcgcgaattcctaaaggagtaatctgcgtccacgtcatcagtagccgtaggcctc
FATA1-2_CHK22  cctctgcgcgaattcctaaaggagtaatctgcgtccacgtcatcagtagccgtaggcctc FATA1-2_CHK80  tgcgacgtcgccgtgctcctcggccgccgcttcgccgccgcccagcagccccagacgcac
FATA1-2_CHK22  tgcgacgtcgccgtgctcctcggccgccgcttcgccgccgcccagcagccccagacgcac FATA1-2_CHK80  gcgctcccagacggcgcgcgcgacgggacgatcatgagcagcgcgatctggggcgtgtc
FATA1-2_CHK22  gcgctcccagacggcgcgcgcgacgggacgatcatgagcagcgcgatctggggcgtgtc FATA1-2_CHK80  gtgcgagctgagccggacgaccacgttgccctggccgcgcgtggtgtactggcagtttgc
FATA1-2_CHK22  gtgcgagctgagccggacgaccacgttgccctggccgcgcgtggtgtactggcagtttgc FATA1-2_CHK80  cgagaccatggtgtctgacttgaagtaggagccgtcaaagcgcgggaggcgcgtctcggc
FATA1-2_CHK22  cgagaccatggtgtctgacttgaagtaggagccgtcaaagcgcgggaggcgcgtctcggc FATA1-2_CHK80  cgagacgttgccgccgacgaccaggctctggcgcttctgacgcgggtcgcggccctgcca
FATA1-2_CHK22  cgagacgttgccgccgacgaccaggctctggcgcttctgacgcgggtcgcggccctgcca FATA1-2_CHK80  ctgcgcggagcctcccaggagcaggcgcgcctcgtcgcggctgcgcagcttgaggtcggc
FATA1-2_CHK22  ctgcgcggagcctcccaggagcaggcgcgcctcgtcgcggctgcgcagcttgaggtcggc FATA1-2_CHK80  cgccagcgccgtgcccggctcgtaggccgaccccatcttgacgaagaggcggccgaccgc
FATA1-2_CHK22  cgccagcgccgtgcccggctcgtaggccgaccccatcttgacgaagaggcggccgaccgc FATA1-2_CHK80  cgcgcggagcttgaccgcgtcggacaggcgcaggcgctcgtccagcttgaccccgagcgc
FATA1-2_CHK22  cgcgcggagcttgaccgcgtcggacaggcgcaggcgctcgtccagcttgaccccgagcgc FATA1-2_CHK80  cgcgttgccgggcttgaacggcagcgagaactcctcgcccagcttggagccgagcaggcc
FATA1-2_CHK22  cgcgttgccgggcttgaacggcagcgagaactcctcgcccagcttggagccgagcaggcc FATA1-2_CHK80  cagcgccagcttctgccgcttgccgcgcgcgcgcaggcgcgagtcgacgcgcagcgtgta
FATA1-2_CHK22  cagcgccagcttctgccgcttgccgcgcgcgcgcaggcgcgagtcgacgcgcagcgtgta FATA1-2_CHK80  gag
FATA1-2_CHK22  gag KASII-1_CHK80  gcctgcctcgccaactgcgagttctgcgcgcgcggcgggcgcgagggccgcgacggcgcg
(SEQ ID NO: 9)
KASII-1_CHK22  gcctgcctcgccaactgcgagttctgcgcgcgcggcgggcgcgagggccgcgacggcgcg
(SEQ ID NO: 10)

KASII-1_CHK80  ccggggttcaccgcctcggtcgaggagctctgggagcggcggcgaacagagtttgtgcac
KASII-1_CHK22  ccggggttcaccgcctcggtcgaggagctctgggagcggcggcgaacagagtttgtgcac KASII-1_CHK80  ctcccggagcaggagtttgccggcatcatgctcgtcatcatgccctgccgctctgacaag
KASII-1_CHK22  ctcccggagcaggagtttgccggcatcatgctcgtcatcatgccctgccgctctgacaag KASII-1_CHK80  tcgaaaaaaggcgtcgccaagtacgcaagcgggggtggggtgggttggggggtggtggcga
KASII-1_CHK22  tcgaaaaaaggcgtcgccaagtacgcaagcgggggtggggtgggttggggggtggtggcga KASII-1_CHK80  tgcgatgaaaatggtggtgttggtggttccgattggcgtgtcggaattttgtgaactgag
KASII-1_CHK22  tgcgatgaaaatggtggtgttggtggttccgattggcgtgtcggaattttgtgaactgag KASII-1_CHK80  cggcactctgcggctctgccggcgcatgcctagtccagttttcgatgtgcgctatcatgt
KASII-1_CHK22  cggcactctgcggctctgccggcgcatgcctagtccagttttcgatgtgcgctatcatgt
```

TABLE 11-continued

```
KASII-1_CHK80  accacgccgcatgcgaatctcacccttcttctccgccccaggtatggtcacctgagcga
KASII-1_CHK22  accacgccgcatgcgaatctcacccttcttctccgccccaggtatggtcacctgagcga KASII-1_CHK80  cggcctgttgcacctggtgctcatcaggcggtgcagccgcctccagtacctcaagtttct
KASII-1_CHK22  cggcctgttgcacctggtgctcatcaggcggtgcagccgcctccagtacctcaagtttct KASII-1_CHK80  gctcaggatgtcgcacatcggccttgaggcgggcgggcagcacgggtcctacatccaggt
KASII-1_CHK22  gctcaggatgtcgcacatcggccttgaggcgggcgggcagcacgggtcctacatccaggt KASII-1_CHK80  cttgcctgcccacgcggtgcacatcgaagcggtacgagcgtggatcgggaggcacttgac
KASII-1_CHK22  cttgcctgcccacgcggtgcacatcgaagcggtacgagcgtggatcgggaggcacttgac KASII-1_CHK80  agtcgcgtcgccgaacaagggacgggtaccctgaggagcttgttggaccgctgattcact
KASII-1_CHK22  agtcgcgtcgccgaacaagggacgggtaccctgaggagcttgttggaccgctgattcact KASII-1_CHK80  ccctgacctccctttctctttccaaaacaggttggccaggagagccactggaacgtcga
KASII-1_CHK22  ccctgacctccctttctctttccaaaacaggttggccaggagagccactggaacgtcga KASII-1_CHK80  tggggagctcattcaaagccgcacgataaacgcgcagctccaccgcggagtgatcgatgt
KASII-1_CHK22  tggggagctcattcaaagccgcacgataaacgcgcagctccaccgcggagtgatcgatgt KASII-1_CHK80  gtttgcccgaggcgtggagggctgacgtgcgcgaaactagctgggggcccccattcccgc
KASII-1_CHK22  gtttgcccgaggcgtggagggctgacgtgcgcgaaactagctgggggcccccattcccgc KASII-1_CHK80  cctttaaacgcctgcctcctggtccccgaccggtgctggcggccctgatcaattcgtcca
KASII-1_CHK22  cctttaaacgcctgcctcctggtccccgaccggtgctggcggccctgatcaattcgtcca KASII-1_CHK80  ttccgttttattctttgacaatgagcgcctcatcccagtgccaccgcccatccccaaatt
KASII-1_CHK22  ttccgttttattctttgacaatgagcgcctcatcccagtgccaccgcccatccccaaatt KASII-1_CHK80  gttcctctcaaacctctcagatacctcccttcaaactgctcccaagagtgcacgagtact
KASII-1_CHK22  gttcctctcaaacctctcagatacctcccttcaaactgctcccaagagtgcacgagtact KASII-1_CHK80  tgtaatgttatgcgaccgctgttcacaatgtagtcggcatgcttgtgtgagcgcgttcga
KASII-1_CHK22  tgtaatgttatgcgaccgctgttcacaatgtagtcggcatgcttgtgtgagcgcgttcga KASII-1_CHK80  aactcgctcagcccgtcggcctgcccatggacgtcccctgatcgctttatgcccaccgca
KASII-1_CHK22  aactcgctcagcccgtcggcctgcccatggacgtcccctgatcgctttatgcccaccgca KASII-1_CHK80  tggaccgcgacacgccagttttcggattcaatagcaacgaatacgcatcgataattctgt
KASII-1_CHK22  tggaccgcgacacgccagttttcggattcaatagcaacgaatacgcatcgataattctgt KASII-1_CHK80  gacattgcatgcctcaccgcgtgaattgctgtcccaaacgtaagcattatcatggctcgg
KASII-1_CHK22  gacattgcatgcctcaccgcgtgaattgctgtcccaaacgtaagcattatcatggctcgg KASII-1_CHK80  tcacgcgatcctggatccggggatcctggaccgctggtggagagcgctgccgtcggattg
KASII-1_CHK22  tcacgcgatcctggatccggggatcctggaccgctggtggagagcgctgccgtcggattg KASII-1_CHK80  gtggcaagcaagattgcgcaggttggcgaagggagagaccaaaaccggaggctggaagcg
KASII-1_CHK22  gtggcaagcaagattgcgcaggttggcgaagggagagaccaaaaccggaggctggaagcg KASII-1_CHK80  ggcacaacatcgtattattgcgtatagtagagcagtggcagtcgcatttcgaggtccgca
KASII-1_CHK22  ggcacaacatcgtattattgcgtatagtagagcagtggcagtcgcatttcgaggtccgca KASII-1_CHK80  acggatctcgcaagctcgctacgctcacagtaggagatagggaccactgcccctgccag
KASII-1_CHK22  acggatctcgcaagctcgctacgctcacagtaggagatagggaccactgcccctgccag KASII-1_CHK80  aATGGTCGCGACCCTGTCCCTCGCCGGCCCCGCCTGCAACACGCAGTGCGTATCCAGCAA
KASII-1_CHK22  aATGGTCGCGACCCTGTCCCTCGCCGGCCCCGCCTGCAACACGCAGTGCGTATCCAGCAA KASII-1_CHK80  GCGGGTTGTCGCCTTCAACCGCCCCCATGTTGGCGTCCGGGCTCGATCAGGTGCGCTGAG
KASII-1_CHK22  GCGGGTTGTCGCCTTCAACCGCCCCCATGTTGGCGTCCGGGCTCGATCAGGTGCGCTGAG KASII-1_CHK80  GGGGGTTTGGTGGGCCCGCGCCTCTGGGCCCGTGTCGGCCGTGCGGACGTGGGGCCCGGG
KASII-1_CHK22  GGGGGTTTGGTGGGCCCGCGCCTCTGGGCCCGTGTCGGCCGTGCGGACGTGGGGCCCGGG KASII-1_CHK80  GTAGTGGATCAGCAGGGGTTGCATGCAAATGCCTATACCGGCGATTGAATAGCGATGAAC
KASII-1_CHK22  GTAGTGGATCAGCAGGGGTTGCATGCAAATGCCTATACCGGCGATTGAATAGCGATGAAC KASII-1_CHK80  GGGATACGGTTGCGCTCACTCCATGCCCATGCGACCCCGTTTCTGTCCGCCAGCCGTGGT
KASII-1_CHK22  GGGATACGGTTGCGCTCACTCCATGCCCATGCGACCCCGTTTCTGTCCGCCAGCCGTGGT KASII-1_CHK80  CGCCCGAGCTGCGAAGCGGGACCCCACCCAGCGCATTGTGATCACCGGAATGGGCGTGGC
KASII-1_CHK22  CGCCCGAGCTGCGAAGCGGGACCCCACCCAGCGCATTGTGATCACCGGAATGGGCGTGGC KASII-1_CHK80  CTCCGTGTTTGGCAACGATGTCGAGACCTTTTACGACAAGCTTCTGGAAGGAACGAGCGG
KASII-1_CHK22  CTCCGTGTTTGGCAACGATGTCGAGACCTTTTACGACAAGCTTCTGGAAGGAACGAGCGG
```

TABLE 11-continued

```
KASII-1_CHK80  CGTGGACCTGATTTCCAGGTGCGTAGGTCCTTGGATGAATGCGTCTAGGTTGCGAGGTGA
KASII-1_CHK22  CGTGGACCTGATTTCCAGGTGCGTAGGTCCTTGGATGAATGCGTCTAGGTTGCGAGGTGA

KASII-1_CHK80  CTGGCCAGGAAGCAGCAGGCTTGGGGTTTGGTGTTCTGATTTCTGGTAATTTGAGGTTTC
KASII-1_CHK22  CTGGCCAGGAAGCAGCAGGCTTGGGGTTTGGTGTTCTGATTTCTGGTAATTTGAGGTTTC

KASII-1_CHK80  ATTATAAGATTCTGTACGGTCTTGTTTCGAAAACATGCAACAACTCCACACACACACACT
KASII-1_CHK22  ATTATAAGATTCTGTACGGTCTTGTTTCGAAAACATGCAACAACTCCACACACACACACT

KASII-1_CHK80  CCTCTCAACTGAGTCTGCAGGTTTGACATCTCCGAGTTCCCGACCAAGTTTGCGGCGCAG
KASII-1_CHK22  CCTCTCAACTGAGTCTGCAGGTTTGACATCTCCGAGTTCCCGACCAAGTTTGCGGCGCAG

KASII-1_CHK80  ATCACCGGCTTCTCCGTGGAGGACTGCGTGGACAAGAAGAACGCGCGGCGGTACGACGAC
KASII-1_CHK22  ATCACCGGCTTCTCCGTGGAGGACTGCGTGGACAAGAAGAACGCGCGGCGGTACGACGAC

KASII-1_CHK80  GCGCTGTCGTACGCGATGGTGGCCTCCAAGAAGGCCCTGCGCCAGGCAGGCCTGGAGAAG
KASII-1_CHK22  GCGCTGTCGTACGCGATGGTGGCCTCCAAGAAGGCCCTGCGCCAGGCAGGCCTGGAGAAG

KASII-1_CHK80  GACAAGTGCCCCGAGGGCTACGGGGCGCTGGACAAGACGCGCACGGGCGTGCTGGTCGGC
KASII-1_CHK22  GACAAGTGCCCCGAGGGCTACGGGGCGCTGGACAAGACGCGCACGGGCGTGCTGGTCGGC

KASII-1_CHK80  TCGGGCATGGGCGGGCTGACGGTCTTCCAGGACGGCGTCAAGGCGCTGGTGGAGAAGGGC
KASII-1_CHK22  TCGGGCATGGGCGGGCTGACGGTCTTCCAGGACGGCGTCAAGGCGCTGGTGGAGAAGGGC

KASII-1_CHK80  TACAAGAAGATGAGCCCCTTCTTCATCCCCTACGCCATCACCAACATGGGCTCCGCGCTG
KASII-1_CHK22  TACAAGAAGATGAGCCCCTTCTTCATCCCCTACGCCATCACCAACATGGGCTCCGCGCTG

KASII-1_CHK80  GTGGGCATCGACCAGGGCTTCATGGGCCCCAACTACTCCGTCTCCACAGCCTGCGCGACG
KASII-1_CHK22  GTGGGCATCGACCAGGGCTTCATGGGCCCCAACTACTCCGTCTCCACAGCCTGCGCGACG

KASII-1_CHK80  TCCAACTACGCATTTGTGAACGCGGCCAACCACATCCGCAAGGGCGACGCGGACGTCATG
KASII-1_CHK22  TCCAACTACGCATTTGTGAACGCGGCCAACCACATCCGCAAGGGCGACGCGGACGTCATG

KASII-1_CHK80  GTCGTCGGCGGCACCGAGGCCTCCATCGTGCCCGTGGGCCTGGGCGGCTTTGTGGCCTGC
KASII-1_CHK22  GTCGTCGGCGGCACCGAGGCCTCCATCGTGCCCGTGGGCCTGGGCGGCTTTGTGGCCTGC

KASII-1_CHK80  CGCGCGCTGTCCACGCGCAACGACGAGCCCAAGCGCGCGAGCCGGCCGTGGGACGAGGGC
KASII-1_CHK22  CGCGCGCTGTCCACGCGCAACGACGAGCCCAAGCGCGCGAGCCGGCCGTGGGACGAGGGC

KASII-1_CHK80  CGCGACGGCTTTGTGATGGGCGAGGGCGCGGCCGTGCTGGTCATGGAGTCGCTGGAGCAC
KASII-1_CHK22  CGCGACGGCTTTGTGATGGGCGAGGGCGCGGCCGTGCTGGTCATGGAGTCGCTGGAGCAC

KASII-1_CHK80  GCGCAGAAGCGTGGCGCGACCATCCTGGGCGAGTACCTGGGCGGCGCCATGACCTGCGAC
KASII-1_CHK22  GCGCAGAAGCGTGGCGCGACCATCCTGGGCGAGTACCTGGGCGGCGCCATGACCTGCGAC

KASII-1_CHK80  GCGCACCACATGACGGACCCGCACCCCGAGGGCCTGGGCGTGAGCACCTGCATCCGCCTG
KASII-1_CHK22  GCGCACCACATGACGGACCCGCACCCCGAGGGCCTGGGCGTGAGCACCTGCATCCGCCTG

KASII-1_CHK80  GCGCTCGAGGACGCCGGCGTCTCGCCCGACGAGGTCAACTACGTCAACGCGCACGCCACC
KASII-1_CHK22  GCGCTCGAGGACGCCGGCGTCTCGCCCGACGAGGTCAACTACGTCAACGCGCACGCCACC

KASII-1_CHK80  TCCACCCTGGTGGGCGACAAGGCCGAGGTGCGCGCGGTCAAGTCGGTCTTTGGCGACATG
KASII-1_CHK22  TCCACCCTGGTGGGCGACAAGGCCGAGGTGCGCGCGGTCAAGTCGGTCTTTGGCGACATG

KASII-1_CHK80  AAGGGTATCAAGATGAACGCCACCAAGAGTATGATCGGGCACTGCCTGGGCGCCGCCGGC
KASII-1_CHK22  AAGGGTATCAAGATGAACGCCACCAAGAGTATGATCGGGCACTGCCTGGGCGCCGCCGGC

KASII-1_CHK80  GGCATGGAGGCCGTCGCGACGCTCATGGCCATCCGCACCGGCTGGGTGCACCCCACCATC
KASII-1_CHK22  GGCATGGAGGCCGTCGCGACGCTCATGGCCATCCGCACCGGCTGGGTGCACCCCACCATC

KASII-1_CHK80  AACCACGACAACCCCATCGCCGAGGTCGATGGCCTGGACGTCGTCGCCAACGCCAAGGCC
KASII-1_CHK22  AACCACGACAACCCCATCGCCGAGGTCGATGGCCTGGACGTCGTCGCCAACGCCAAGGCC

KASII-1_CHK80  CAGCACGACATCAACGTCGCCATCTCCAACTCCTTCGGCTTTGGCGGGCACAACTCCGTC
KASII-1_CHK22  CAGCACGACATCAACGTCGCCATCTCCAACTCCTTCGGCTTTGGCGGGCACAACTCCGTC

KASII-1_CHK80  GTCGCCTTTGCGCCCTTCCGCGAGTAGgtgaagcgagcgtgctttgctgaggagggaggc
KASII-1_CHK22  GTCGCCTTTGCGCCCTTCCGCGAGTAGgtgaagcgagcgtgctttgctgaggagggaggc KASII-1_CHK80  ggggtgcgagcgctctggccgtgcgcgcgatactctccccgcatgagcagactcctcgtg
KASII-1_CHK22  ggggtgcgagcgctctggccgtgcgcgcgatactctccccgcatgagcagactcctcgtg KASII-1_CHK80  ccacgcccgaatctacttgtcaacgagcaactgtgtgttttgtccgtggccaatcttatt
KASII-1_CHK22  ccacgcccgaatctacttgtcaacgagcaactgtgtgttttgtccgtggccaatcttatt KASII-1_CHK80  atttctccgactgtggccgtactctgtttggctgtgcaagcaccccaggaactcttttgt
KASII-1_CHK22  atttctccgactgtggccgtactctgtttggctgtgcaagcaccccaggaactcttttgt
```

TABLE 11-continued

```
KASII-1_CHK80  tgagcgggggttatcgtagagagggtttgcgaaatgggcaccgatcggaaggccttgca
KASII-1_CHK22  tgagcgggggttatcgtagagagggtttgcgaaatgggcaccgatcggaaggccttgca KASII-1_CHK80  aacgtggcggtcattggccgacatgatttccgtggattcactgatgcggcattgcttacc
KASII-1_CHK22  aacgtggcggtcattggccgacatgatttccgtggattcactgatgcggcattgcttacc KASII-1_CHK80  attcatattgaaaagacagccttgcaacctacaatttgatggagcaaatacatatatata
KASII-1_CHK22  attcatattgaaaagacagccttgcaacctacaatttgatggagcaaatacatatatata KASII-1_CHK80  cggggccgacgtgtcagatggccgttgcgctcttgagctccacggcccgacacagctgct
KASII-1_CHK22  cggggccgacgtgtcagatggccgttgcgctcttgagctccacggcccgacacagctgct KASII-1_CHK80  cgatagcttcctccagcggcaggcagccgcgctggccgtcagcgtacgtgcgcaccgcca
KASII-1_CHK22  cgatagcttcctccagcggcaggcagccgcgctggccgtcagcgtacgtgcgcaccgcca KASII-1_CHK80  gggtcgagctcccggcctcttccgggccgatgaccgccatgacggggactttggccctct
KASII-1_CHK22  gggtcgagctcccggcctcttccgggccgatgaccgccatgacggggactttggccctct KASII-1_CHK80  cggcgttgcgaacgagcttgcccatggaggcgccgccgggcgcgagctccacgcgcaggc
KASII-1_CHK22  cggcgttgcgaacgagcttgcccatggaggcgccgccgggcgcgagctccacgcgcaggc KASII-1_CHK80  cgcgcgcgcgcatggcggctgccaccgtctccatgtacggccgcaccgcgtccgtcgtgg
KASII-1_CHK22  cgcgcgcgcgcatggcggctgccaccgtctccatgtacggccgcaccgcgtccgtcgtgg KASII-1_CHK80  gcagcagtcgcacctgctccggggccagccagagcgggaaggcgcccgcgtagtgctcga
KASII-1_CHK22  gcagcagtcgcacctgctccggggccagccagagcgggaaggcgcccgcgtagtgctcga KASII-1_CHK80  tcaggatgccgaagaagcgctccagcgagccgagcagggcgcggtgcaccatgatgggcc
KASII-1_CHK22  tcaggatgccgaagaagcgctccagcgagccgagcagggcgcggtgcaccatgatgggcc KASII-1_CHK80  gctggcggctgccgtcggccgccgcgtactcgagcccgaaccgctcgggcaggttgaagt
KASII-1_CHK22  gctggcggctgccgtcggccgccgcgtactcgagcccgaaccgctcgggcaggttgaagt KASII-1_CHK80  ccagctgcaccgtggagcactgccacttgcgcccgagcgcgtcctggatcttgacgtcga
KASII-1_CHK22  ccagctgcaccgtggagcactgccacttgcgcccgagcgcgtcctggatcttgacgtcga KASII-1_CHK80  tcttcgggccgtaaaaggcgccgccgccgacgtccaccgtgaaggcccagccctgtcgat
KASII-1_CHK22  tcttcgggccgtaaaaggcgccgccgccgacgtccaccgtgaaggcccagccctgtcgat KASII-1_CHK80  gaatgattgttgggaggggggggtttcgaggttggatgacaccacaataatatagtcagcg
KASII-1_CHK22  gaatgattgttgggaggggggggtttcgaggttggatgacaccacaataatatagtcagcg KASII-1_CHK80  acacgcgtgctgcacgataattaccagtacagactcggcgatgataacaccacccttttc
KASII-1_CHK22  acacgcgtgctgcacgataattaccagtacagactcggcgatgataacaccacccttttc KASII-1_CHK80  atcaaccgaaatgagccgttccctgttgacaaacacacacgcacacacaccttgtcgttg
KASII-1_CHK22  atcaaccgaaatgagccgttccctgttgacaaacacacacgcacacacaccttgtcgttg KASII-1_CHK80  agcgcttcagcgagcgccgcctcggccctggcccagtcctcgtcggacccgaccgactcg
KASII-1_CHK22  agcgcttcagcgagcgccgcctcggccctggcccagtcctcgtcggacccgaccgactcg KASII-1_CHK80  tccggccgcgtggagaggttgacctcgaaccggcacgcgtcgaagccaaaggcgcggaag
KASII-1_CHK22  tccggccgcgtggagaggttgacctcgaaccggcacgcgtcgaagccaaaggcgcggaag KASII-1_CHK80  acgcgctccgtgaggtccagcacggcccggatctcggccgcgatctgctccggcaggcag
KASII-1_CHK22  acgcgctccgtgaggtccagcacggcccggatctcggccgcgatctgctccggcaggcag KASII-1_CHK80  aagatgtgggcgtcgtcctgcgtgaagccgcgcacgcggaagaggccgtgcatggtgccg
KASII-1_CHK22  aagatgtgggcgtcgtcctgcgtgaagccgcgcacgcggaagaggccgtgcatggtgccg KASII-1_CHK80  gagcgctcgtagcggtagacagtgcccagctccgcccagcgcagcggcaggtcgcggtag
KASII-1_CHK22  gagcgctcgtagcggtagacagtgcccagctccgcccagcgcagcggcaggtcgcggtag KASII-1_CHK80  ctgacgggcctggccgcgtagacgctga
KASII-1_CHK22  ctgacgggcctggccgcgtagacgctga KASII-2_CHK80  gcctgcctcgccaactgcgagttctgcgcgcgcggcgggcgcgagggccgcgacggcgcg
(SEQ ID NO: 11)
KASII-2_CHK22  gcctgcctcgccaactgcgagttctgcgcgcgcggcgggcgcgagggccgcgacggcgcg
(SEQ ID NO: 12)

KASII-2_CHK80  gcggggttcaccgcctcggccgaggagctctgggagcggcggcgagcagagtttgtgcac
KASII-2_CHK22  gcggggttcaccgcctcggccgaggagctctgggagcggcggcgagcagagtttgtgcac KASII-2_CHK80  ctcccggagcaggagtttgcaggcatcatgctcgtcatcatgccctgccgctctgacaag
KASII-2_CHK22  ctcccggagcaggagtttgcaggcatcatgctcgtcatcatgccctgccgctctgacaag KASII-2_CHK80  tcgaaaaagggcgtcgccaagtacgcaagcacaggggtggggtggggtggggtggtgg
KASII-2_CHK22  tcgaaaaagggcgtcgccaagtacgcaagcacaggggtggggtggggtggggtggtgg
```

TABLE 11-continued

```
KASII-2_CHK80  cggtgcgatgaaaatggtggtgtttggtggttcacattggcgtgtcggagttttgtgaag
KASII-2_CHK22  cggtgcgatgaaaatggtggtgtttggtggttcacattggcgtgtcggagttttgtgaag KASII-2_CHK80  tgagcttcactctgcggctctccccggcgcatgcctagtccagttttcgatgtgcgctatc
KASII-2_CHK22  tgagcttcactctgcggctctccccggcgcatgcctagtccagttttcgatgtgcgctatc KASII-2_CHK80  gtgtaccacgccgcgtgcgaatcccacccttttcttctccgccccaggtatggtcacctga
KASII-2_CHK22  gtgtaccacgccgcgtgcgaatcccacccttttcttctccgccccaggtatggtcacctga KASII-2_CHK80  gcgacggcctgctgcacctggtgctcatcaggcggtgcagccgcctccagtacctcaagt
KASII-2_CHK22  gcgacggcctgctgcacctggtgctcatcaggcggtgcagccgcctccagtacctcaagt KASII-2_CHK80  ttctgctcaggatgtcgcacatcggcctcgaggcgggcgggcagcacgggtcctacatcc
KASII-2_CHK22  ttctgctcaggatgtcgcacatcggcctcgaggcgggcgggcagcacgggtcctacatcc KASII-2_CHK80  aggtcctgcccgcccacgcggtgcacatcgaagcggtacgagcgtggatcgggaggcact
KASII-2_CHK22  aggtcctgcccgcccacgcggtgcacatcgaagcggtacgagcgtggatcgggaggcact KASII-2_CHK80  tgacagtcgcgtcgcccgacaaggcacgggcgccctgaggagcttgttgggccgctgatt
KASII-2_CHK22  tgacagtcgcgtcgcccgacaaggcacgggcgccctgaggagcttgttgggccgctgatt KASII-2_CHK80  cacttccctggcctcccctttctctttccaaaccaggttggccaggagagccactggaac
KASII-2_CHK22  cacttccctggcctcccctttctctttccaaaccaggttggccaggagagccactggaac KASII-2_CHK80  gtcgatggggagctcattcaaagccgcacgatcaacgcgcagctccaccgcggagtgatc
KASII-2_CHK22  gtcgatggggagctcattcaaagccgcacgatcaacgcgcagctccaccgcggagtgatc KASII-2_CHK80  gacgtgtttgccagaggcgtggagggctgacgagcgcgaaactagctgggggcccattc
KASII-2_CHK22  gacgtgtttgccagaggcgtggagggctgacgagcgcgaaactagctgggggcccattc KASII-2_CHK80  ccgcccttgaaacgcctgcctcctgggccctggccggtgctggcggccctgaccgattcg
KASII-2_CHK22  ccgcccttgaaacgcctgcctcctgggccctggccggtgctggcggccctgaccgattcg KASII-2_CHK80  tccattccgtttattctttgacaatgagcgcctcatcccagtgcctcatcccagtgcca
KASII-2_CHK22  tccattccgtttattctttgacaatgagcgcctcatcccagtgcctcatcccagtgcca KASII-2_CHK80  ccgcccatccccaaattgttcctctcaaacctctcagata-ccccttcaaactgctccc
KASII-2_CHK22  ccgcccatccccaaattgttcctctcaaacctctcagatacccccttcaaactgctccc KASII-2_CHK80  aagagtgcacgagtatttgtaatgttatacgaccgctgttcacaatgtagtcggcatgct
KASII-2_CHK22  aagagtgcacgagtatttgtaatgttatacgaccgctgttcacaatgtagtcggcatgct KASII-2_CHK80  tgtatgagcctgttcgaaactcgctcagcccgtcggcctgcccatggacctccccctgatc
KASII-2_CHK22  tgtatgagcctgttcgaaactcgctcagcccgtcggcctgcccatggacctccccctgatc KASII-2_CHK80  gcttcacgcccaccgcatggactgcgacacgccagttttgggattcaatatcaaaaaata
KASII-2_CHK22  gcttcacgcccaccgcatggactgcgacacgccagttttgggattcaatatcaaaaaata KASII-2_CHK80  cgcttcggtaattctgtaacgttgcatgcctcaccgcgtgaattgctgtcccaaacgtaa
KASII-2_CHK22  cgcttcggtaattctgtaacgttgcatgcctcaccgcgtgaattgctgtcccaaacgtaa KASII-2_CHK80  gcatcatcgtggctcggtcacgcgatcctggatccggggatcctagaccgctggtggaga
KASII-2_CHK22  gcatcatcgtggctcggtcacgcgatcctggatccggggatcctagaccgctggtggaga KASII-2_CHK80  gcgctgccgtcggattggtggcaagtaagattgcgcaggttggcgaagggagagaccaaa
KASII-2_CHK22  gcgctgccgtcggattggtggcaagtaagattgcgcaggttggcgaagggagagaccaaa KASII-2_CHK80  accggaggctggaagcgggcacaacatcgtattattgcgtatagtagagcagtggcagtc
KASII-2_CHK22  accggaggctggaagcgggcacaacatcgtattattgcgtatagtagagcagtggcagtc KASII-2_CHK80  gcatttcgaggtccgcaacggatctcgcaagctcgctacgctcacagtaggagaaagggg
KASII-2_CHK22  gcatttcgaggtccgcaacggatctcgcaagctcgctacgctcacagtaggagaaagggg KASII-2_CHK80  accactgcccctgccagaATGGTCGCGACCCTCTCCCTCGCCGGCCCCGCCTGCAACACG
KASII-2_CHK22  accactgcccctgccagaATGGTCGCGACCCTCTCCCTCGCCGGCCCCGCCTGCAACACG KASII-2_CHK80  CAGTGCGTATCCGGCAAGCGGGCTGTCGCCTTCAACCGCCCCCATGTTGGCGTCCGGGCT
KASII-2_CHK22  CAGTGCGTATCCGGCAAGCGGGCTGTCGCCTTCAACCGCCCCCATGTTGGCGTCCGGGCT KASII-2_CHK80  CGATCAGGTGCGCTGAGGGGGGTTTGGTGTGCCCGCGCCTCTGGGCCCGTGTCGGCCGTG
KASII-2_CHK22  CGATCAGGTGCGCTGAGGGGGGTTTGGTGTGCCCGCGCCTCTGGGCCCGTGTCGGCCGTG KASII-2_CHK80  CGGACGTGGGGCCCTGGGCAGTGGATCAGCAGGGTTTGCGTGCAAATGCCTATACCGGCG
KASII-2_CHK22  CGGACGTGGGGCCCTGGGCAGTGGATCAGCAGGGTTTGCGTGCAAATGCCTATACCGGCG KASII-2_CHK80  ATTGAATAGCGATGAACGGGATACGGTTGCGCTCACTCCATGCCCATGCGACCCCGTTTC
KASII-2_CHK22  ATTGAATAGCGATGAACGGGATACGGTTGCGCTCACTCCATGCCCATGCGACCCCGTTTC
```

TABLE 11-continued

```
KASII-2_CHK80  TGTCCGCCAGCCGTGGTCGCCCGGGCTGCGAAGCGGGACCCCACCCAGCGCATTGTGATC
KASII-2_CHK22  TGTCCGCCAGCCGTGGTCGCCCGGGCTGCGAAGCGGGACCCCACCCAGCGCATTGTGATC

KASII-2_CHK80  ACCGGAATGGGCGTGGCCTCCGTGTTTGGCAACGATGTCGAGACCTTTTACAACAAGCTT
KASII-2_CHK22  ACCGGAATGGGCGTGGCCTCCGTGTTTGGCAACGATGTCGAGACCTTTTACAACAAGCTT

KASII-2_CHK80  CTGGAAGGAACGAGCGGCGTGGACCTGATTTCCAGGTGCGTAGGTCCTTGGATGCATGCG
KASII-2_CHK22  CTGGAAGGAACGAGCGGCGTGGACCTGATTTCCAGGTGCGTAGGTCCTTGGATGCATGCG

KASII-2_CHK80  TCTAGGTTGGGAGGCGGCTGGCGAGGAAGCAGCAGGCTTGGGGTTTGGTGTTCCGATTTC
KASII-2_CHK22  TCTAGGTTGGGAGGCGGCTGGCGAGGAAGCAGCAGGCTTGGGGTTTGGTGTTCCGATTTC

KASII-2_CHK80  TGGCAATTTGAGGTTTCATTGTGAGATTCTATGCGGTCTTGTTTCGAAAACATGCAACAA
KASII-2_CHK22  TGGCAATTTGAGGTTTCATTGTGAGATTCTATGCGGTCTTGTTTCGAAAACATGCAACAA

KASII-2_CHK80  CTCCACACACACACACTCCTCTCCACCAACTCTGCAGGTTTGACATCTCCGAGTTCCCGA
KASII-2_CHK22  CTCCACACACACACACTCCTCTCCACCAACTCTGCAGGTTTGACATCTCCGAGTTCCCGA

KASII-2_CHK80  CCAAGTTTGCGGCGCAGATCACCGGCTTCTCCGTGGAGGACTGCGTGGACAAGAAGAACG
KASII-2_CHK22  CCAAGTTTGCGGCGCAGATCACCGGCTTCTCCGTGGAGGACTGCGTGGACAAGAAGAACG

KASII-2_CHK80  CGCGGCGGTACGACGACGCGCTGTCGTACGCGATGGTGGCCTCCAAGAAGGCCCTGCGCC
KASII-2_CHK22  CGCGGCGGTACGACGACGCGCTGTCGTACGCGATGGTGGCCTCCAAGAAGGCCCTGCGCC

KASII-2_CHK80  AGGCGGGACTGGAGAAGGACAAGTGCCCCGAGGGCTACGGAGCGCTGGATAAGACGCGCG
KASII-2_CHK22  AGGCGGGACTGGAGAAGGACAAGTGCCCCGAGGGCTACGGAGCGCTGGATAAGACGCGCG

KASII-2_CHK80  CGGGCGTGCTGGTCGGCTCGGGCATGGGCGGGCTGACGGTCTTCCAGGACGGCGTCAAGG
KASII-2_CHK22  CGGGCGTGCTGGTCGGCTCGGGCATGGGCGGGCTGACGGTCTTCCAGGACGGCGTCAAGG

KASII-2_CHK80  CGCTGGTGGAGAAGGGCTACAAGAAGATGAGCCCCTTCTTCATCCCCTACGCCATCACCA
KASII-2_CHK22  CGCTGGTGGAGAAGGGCTACAAGAAGATGAGCCCCTTCTTCATCCCCTACGCCATCACCA

KASII-2_CHK80  ACATGGGCTCCGCGCTGGTGGGCATCGACCAGGGCTTCATGGGGCCCAACTACTCCGTCT
KASII-2_CHK22  ACATGGGCTCCGCGCTGGTGGGCATCGACCAGGGCTTCATGGGGCCCAACTACTCCGTCT

KASII-2_CHK80  CCACGGCCTGCGCGACCTCCAACTACGCCTTTGTGAACGCGGCCAACCACATCCGCAAGG
KASII-2_CHK22  CCACGGCCTGCGCGACCTCCAACTACGCCTTTGTGAACGCGGCCAACCACATCCGCAAGG

KASII-2_CHK80  GCGACGCGGACGTCATGGTCGTGGGCGGCACCGAGGCCTCCATCGTGCCCGTGGGCCTGG
KASII-2_CHK22  GCGACGCGGACGTCATGGTCGTGGGCGGCACCGAGGCCTCCATCGTGCCCGTGGGCCTGG

KASII-2_CHK80  GCGGCTTTGTGGCCTGCCGCGCGCTGTCCACGCGCAACGACGAGCCCAAGCGCGCGAGCC
KASII-2_CHK22  GCGGCTTTGTGGCCTGCCGCGCGCTGTCCACGCGCAACGACGAGCCCAAGCGCGCGAGCC

KASII-2_CHK80  GGCCGTGGGACGAGGGCCGCGACGGCTTCGTGATGGGCGAGGGCGCGGCCGTGCTGGTCA
KASII-2_CHK22  GGCCGTGGGACGAGGGCCGCGACGGCTTCGTGATGGGCGAGGGCGCGGCCGTGCTGGTCA

KASII-2_CHK80  TGGAGTCGCTGGAGCACGCGCAGAAGCGCGGCGCGACCATCCTGGGCGAGTACCTGGGGG
KASII-2_CHK22  TGGAGTCGCTGGAGCACGCGCAGAAGCGCGGCGCGACCATCCTGGGCGAGTACCTGGGGG

KASII-2_CHK80  GCGCCATGACCTGCGACGCGCACCACATGACGGACCCGCACCCCGAGGGCCTGGGCGTGA
KASII-2_CHK22  GCGCCATGACCTGCGACGCGCACCACATGACGGACCCGCACCCCGAGGGCCTGGGCGTGA

KASII-2_CHK80  GCACCTGCATCCGCCTGGCGCTCGAGGACGCCGGCGTCTCGCCCGACGAGGTCAACTACG
KASII-2_CHK22  GCACCTGCATCCGCCTGGCGCTCGAGGACGCCGGCGTCTCGCCCGACGAGGTCAACTACG

KASII-2_CHK80  TCAACGCGCACGCCACCTCCACCCTGGTGGGCGACAAGGCCGAGGTGCGCGCGGTCAAGT
KASII-2_CHK22  TCAACGCGCACGCCACCTCCACCCTGGTGGGCGACAAGGCCGAGGTGCGCGCGGTCAAGT

KASII-2_CHK80  CGGTCTTTGGCGACATGAAGGGCATCAAGATGAACGCCACCAAGTCCATGATCGGGCACT
KASII-2_CHK22  CGGTCTTTGGCGACATGAAGGGCATCAAGATGAACGCCACCAAGTCCATGATCGGGCACT

KASII-2_CHK80  GCCTGGGCGCCGCCGGCGGCATGGAGGCCGTCGCCACGCTCATGGCCATCCGCACCGGCT
KASII-2_CHK22  GCCTGGGCGCCGCCGGCGGCATGGAGGCCGTCGCCACGCTCATGGCCATCCGCACCGGCT

KASII-2_CHK80  GGGTGCACCCCACCATCAACCACGACAACCCCATCGCCGAGGTCGACGGCCTGGACGTCG
KASII-2_CHK22  GGGTGCACCCCACCATCAACCACGACAACCCCATCGCCGAGGTCGACGGCCTGGACGTCG

KASII-2_CHK80  TCGCCAACGCGCAAGGCCCAGCACAAAATCAACGTCGCCATCTCCAACTCCTTCGGCTTCG
KASII-2_CHK22  TCGCCAACGCGCAAGGCCCAGCACAAAATCAACGTCGCCATCTCCAACTCCTTCGGCTTCG

KASII-2_CHK80  GCGGGCACAACTCCGTCGTCGCCTTTGCGCCCTTCCGCGAGTAGgcggagcgagcgcgct
KASII-2_CHK22  GCGGGCACAACTCCGTCGTCGCCTTTGCGCCCTTCCGCGAGTAGgcggagcgagcgcgct KASII-2_CHK80  tggctgaggagggaggcggggtgcgagcccttggctgcgcgcgatactctccccgcacg
KASII-2_CHK22  tggctgaggagggaggcggggtgcgagcccttggctgcgcgcgatactctccccgcacg
```

TABLE 11-continued

```
KASII-2_CHK80  agcagactccacgcgcctgaatctacttgtcaacgagcaaccgtgtgttttgtccgtggc
KASII-2_CHK22  agcagactccacgcgcctgaatctacttgtcaacgagcaaccgtgtgttttgtccgtggc KASII-2_CHK80  cattcttattatttctccgactgtggccgtactctgtttggctgtgcaagcaccccagga
KASII-2_CHK22  cattcttattatttctccgactgtggccgtactctgtttggctgtgcaagcaccccagga KASII-2_CHK80  actcttttgtcgagcgggggtgtcgtagagagggtccgcgaaacaggcaccgatcgcga
KASII-2_CHK22  actcttttgtcgagcgggggtgtcgtagagagggtccgcgaaacaggcaccgatcgcga KASII-2_CHK80  gcctcgtggtggtcattgttcgacatgattcccggagattcactgatgcggcattgctta
KASII-2_CHK22  gcctcgtggtggtcattgttcgacatgattcccggagattcactgatgcggcattgctta KASII-2_CHK80  ccattcatttgaaaagacagcttgcaacctacaattcgaaggagcgaatacatatatata
KASII-2_CHK22  ccattcatttgaaaagacagcttgcaacctacaattcgaaggagcgaatacatatatata KASII-2_CHK80  cggggccggcgtgtcagatcgccgtttcgctcttgagctccacggcccgacacagctgct
KASII-2_CHK22  cggggccggcgtgtcagatcgccgtttcgctcttgagctccacggcccgacacagctgct KASII-2_CHK80  cgatgacttcctccagcggcaggcagccgcgctggccgtcggcgtacgtgcgcaccgcca
KASII-2_CHK22  cgatgacttcctccagcggcaggcagccgcgctggccgtcggcgtacgtgcgcaccgcca KASII-2_CHK80  gggtcgagctcccggcctcttccgggccgatgaccgccatgacggggaccttggccctct
KASII-2_CHK22  gggtcgagctcccggcctcttccgggccgatgaccgccatgacggggaccttggccctct KASII-2_CHK80  cggcgttgcggatgagcttgcccatggaggccccgccgggcgcgagctccacgcgcaggc
KASII-2_CHK22  cggcgttgcggatgagcttgcccatggaggccccgccgggcgcgagctccacgcgcaggc KASII-2_CHK80  cgcgcgcgcgcatggcgtctgccaccgtctccatgtagggccgcaccgcgtccgtcgtgg
KASII-2_CHK22  cgcgcgcgcgcatggcgtctgccaccgtctccatgtagggccgcaccgcgtccgtcgtgg KASII-2_CHK80  gcagcaggcgcacctgctccggggccagccagagcgggaaggcgcccgcgtagtgctcga
KASII-2_CHK22  gcagcaggcgcacctgctccggggccagccagagcgggaaggcgcccgcgtagtgctcga KASII-2_CHK80  tcaggatgccgaagaagcgctccagcgagccgagcagggcgcggtgaatcatgatgggcc
KASII-2_CHK22  tcaggatgccgaagaagcgctccagcgagccgagcagggcgcggtgaatcatgatgggcc KASII-2_CHK80  gctggcggctgccgtcggcggccgcgtactcgagcccaaaccgctcgggcaaattgaagt
KASII-2_CHK22  gctggcggctgccgtcggcggccgcgtactcgagcccaaaccgctcgggcaaattgaagt KASII-2_CHK80  ccagctgcaccgtggagcactgccacttgcgcccgagcgcgtcctggatcttgacgtcga
KASII-2_CHK22  ccagctgcaccgtggagcactgccacttgcgcccgagcgcgtcctggatcttgacgtcga KASII-2_CHK80  tcttcgggccgtaaaaggcgccgccgccggcgtccaccgtgaaggcccagccctgtcgat
KASII-2_CHK22  tcttcgggccgtaaaaggcgccgccgccggcgtccaccgtgaaggcccagccctgtcgat KASII-2_CHK80  gaatgattcgtggttgagagggcggattttttcgaggtctggatgatgatacggtatgcgc
KASII-2_CHK22  gaatgattcgtggttgagagggcggattttttcgaggtctggatgatgatacggtatgcgc KASII-2_CHK80  cacaataatactacactcgcgccagtcagcgacacgcgtgctgcacaatgcctactacta
KASII-2_CHK22  cacaataatactacactcgcgccagtcagcgacacgcgtgctgcacaatgcctactacta KASII-2_CHK80  tagactcggtgatgatgataccaccctttcatcgaacgagatgggccattccctactga
KASII-2_CHK22  tagactcggtgatgatgataccaccctttcatcgaacgagatgggccattccctactga KASII-2_CHK80  caaacacacacgcaccttgtcgttcagcgcttcggcgagcgccgcctcggccctggccca
KASII-2_CHK22  caaacacacacgcaccttgtcgttcagcgcttcggcgagcgccgcctcggccctggccca KASII-2_CHK80  gtcctcgtcggacccgaccgactcgtccggccgcgtggagaggttgacctcgaaccggcg
KASII-2_CHK22  gtcctcgtcggacccgaccgactcgtccggccgcgtggagaggttgacctcgaaccggcg KASII-2_CHK80  cgcgtcgaagccaaaggcgcggaagacgcgctccgtgaggtccagcacggcccggatctc
KASII-2_CHK22  cgcgtcgaagccaaaggcgcggaagacgcgctccgtgaggtccagcacggcccggatctc KASII-2_CHK80  ggccgcgatctgctccggcaggcagaagacgtgggcgtcgtcctgcgtgaagccgcgcac
KASII-2_CHK22  ggccgcgatctgctccggcaggcagaagacgtgggcgtcgtcctgcgtgaagccgcgcac KASII-2_CHK80  gcggaagaggccgtgcatggtgccggagcgctcgtagcggtagaccgtgcccagctccgc
KASII-2_CHK22  gcggaagaggccgtgcatggtgccggagcgctcgtagcggtagaccgtgcccagctccgc KASII-2_CHK80  ccagcgcagcggcaggtcgcggtagctgacgggccgggccgcgtagacgctga
KASII-2_CHK22  ccagcgcagcggcaggtcgcggtagctgacgggccgggccgcgtagacgctga SAD2-1_CHK80   aaacccgatgatgcccagcgcggagctcagcatgtcgccgagcatcgctggataggacga
(SEQ ID NO: 13)
SAD2-1_CHK22   aaacccgatgatgcccagcgcggagctcagcatgtcgccgagcatcgctggataggacga
(SEQ ID NO: 14)

SAD2-1_CHK80   attggcagggtaccacctgaagaatgggaggcaggtgctgctgattacgagtgtggaaaa
SAD2-1_CHK22   attggcagggtaccacctgaagaatgggaggcaggtgctgctgattacgagtgtggaaaa
```

TABLE 11-continued

```
SAD2-1_CHK80  gaaaggggcagagagccgtcctcagatccgaccactatgcaggtagccgctcgcccgtg
SAD2-1_CHK22  gaaaggggcagagagccgtcctcagatccgaccactatgcaggtagccgctcgcccgtg SAD2-1_CHK80  cccgcctggctgaatattgacacatgcccatcaaggcaggcaggcatttctgtgcatgca
SAD2-1_CHK22  cccgcctggctgaatattgacacatgcccatcaaggcaggcaggcatttctgtgcatgca SAD2-1_CHK80  ccaaacccataatcttcgaaaacacacagcatgtaccaacgcacgcgtaaaagtttgggt
SAD2-1_CHK22  ccaaacccataatcttcgaaaacacacagcatgtaccaacgcacgcgtaaaagtttgggt SAD2-1_CHK80  gctgccagtgcgtcatgccaggcatgatgtgctcctgcacatcggccatgatctcctcca
SAD2-1_CHK22  gctgccagtgcgtcatgccaggcatgatgtgctcctgcacatcggccatgatctcctcca SAD2-1_CHK80  tcgtctcgggcgtctccggcgcctggtccgggagccgttccgccagatacccagacgcca
SAD2-1_CHK22  tcgtctcgggcgtctccggcgcctggtccgggagccgttccgccagatacccagacgcca SAD2-1_CHK80  cctccgacctcacggggtacttttcgagcgactgtcggtagtcgacgatcgcgtccacca
SAD2-1_CHK22  cctccgacctcacggggtacttttcgagcgactgtcggtagtcgacgatcgcgtccacca SAD2-1_CHK80  tggagtagccgaggcgccggaactggcgtgacggagggagaacagggggggttgatgatc
SAD2-1_CHK22  tggagtagccgaggcgccggaactggcgtgacggagggagaacagggggggttgatgatc SAD2-1_CHK80  acacgccagtctcacaacgcatgtaagacccgttggattatgagtataatcatgcattac
SAD2-1_CHK22  acacgccagtctcacaacgcatgtaagacccgttggattatgagtataatcatgcattac SAD2-1_CHK80  tagttgggtgagcgccaggcataaggcacaccgacgtcgatggcacgagcaactcccgca
SAD2-1_CHK22  tagttgggtgagcgccaggcataaggcacaccgacgtcgatggcacgagcaactcccgca SAD2-1_CHK80  tcatatttcctattgtcctaacgccaagccggtcaccacccgcatgctcgtactacagcg
SAD2-1_CHK22  tcatatttcctattgtcctaacgccaagccggtcaccacccgcatgctcgtactacagcg SAD2-1_CHK80  cacgcaccgcttcgtgatccaccgggtgaacgtagtcctcgacggaaacatctggttcgg
SAD2-1_CHK22  cacgcaccgcttcgtgatccaccgggtgaacgtagtcctcgacggaaacatctggttcgg SAD2-1_CHK80  gcctcctgcttgcactcccgcccatgccgacaacctttctgctgttaccacgacccacaa
SAD2-1_CHK22  gcctcctgcttgcactcccgcccatgccgacaacctttctgctgttaccacgacccacaa SAD2-1_CHK80  tgcaacgcgacacgaccgtgtgggactgatcggttcactgcacctgcatgcaattgtcac
SAD2-1_CHK22  tgcaacgcgacacgaccgtgtgggactgatcggttcactgcacctgcatgcaattgtcac SAD2-1_CHK80  aagcgcttactccaattgtattcgtttgttttctgggagcagttgctcgaccgcccgcgt
SAD2-1_CHK22  aagcgcttactccaattgtattcgtttgttttctgggagcagttgctcgaccgcccgcgt SAD2-1_CHK80  cccgcaggcagcgatgacgtgtgcgtggcctgggtgtttcgtcgaaaggccagcaaccct
SAD2-1_CHK22  cccgcaggcagcgatgacgtgtgcgtggcctgggtgtttcgtcgaaaggccagcaaccct SAD2-1_CHK80  aaatcgcaggcgatccggagattgggatctgatccgagtttggaccagatccgccccgat
SAD2-1_CHK22  aaatcgcaggcgatccggagattgggatctgatccgagtttggaccagatccgccccgat SAD2-1_CHK80  gcggcacgggaactgcatcgactcggcgcggaacccagctttcgtaaatgccagattggt
SAD2-1_CHK22  gcggcacgggaactgcatcgactcggcgcggaacccagctttcgtaaatgccagattggt SAD2-1_CHK80  gtccgatacctggatttgccatcagcgaaacaagacttcagcagcgagcgtatttggcgg
SAD2-1_CHK22  gtccgatacctggatttgccatcagcgaaacaagacttcagcagcgagcgtatttggcgg SAD2-1_CHK80  gcgtgctaccagggttgcatacattgcccatttctgtctggaccgctttactggcgcaga
SAD2-1_CHK22  gcgtgctaccagggttgcatacattgcccatttctgtctggaccgctttactggcgcaga SAD2-1_CHK80  gggtgagttgatggggttggcaggcatcgaaacgcgcgtgcatggtgtgcgtgtctgttt
SAD2-1_CHK22  gggtgagttgatggggttggcaggcatcgaaacgcgcgtgcatggtgtgcgtgtctgttt SAD2-1_CHK80  tcggctgcacgaattcaatagtcggatgggcgacggtagaattgggtgtggcgctcgcgt
SAD2-1_CHK22  tcggctgcacgaattcaatagtcggatgggcgacggtagaattgggtgtggcgctcgcgt SAD2-1_CHK80  gcatgcctcgcccgtcgggtgtcatgacccgggactggaatcccccctcgcgaccatctt
SAD2-1_CHK22  gcatgcctcgcccgtcgggtgtcatgacccgggactggaatcccccctcgcgaccatctt SAD2-1_CHK80  gctaacgctcccgactctcccgaccgcgcgcaggatagactcttgttcaaccaatcgaca
SAD2-1_CHK22  gctaacgctcccgactctcccgaccgcgcgcaggatagactcttgttcaaccaatcgaca SAD2-1_CHK80  ATGGCGTCTGCCGTCACCTTTGCGTGCGCCCCTCCCCGCGGCGCGGTCGCCGCGCCGGGT
SAD2-1_CHK22  ATGGCGTCTGCCGTCACCTTTGCGTGCGCCCCTCCCCGCGGCGCGGTCGCCGCGCCGGGT SAD2-1_CHK80  CGCCGCGCTGCCTCGCGTCCCCTGGTGGTGCGCGCGGTCGCCAGCGAGGCCCCGCTGGGC
SAD2-1_CHK22  CGCCGCGCTGCCTCGCGTCCCCTGGTGGTGCGCGCGGTCGCCAGCGAGGCCCCGCTGGGC SAD2-1_CHK80  GTTCCGCCCTCGGTGCAGCGCCCCTCCCCCGTGGTCTACTCCAAGCTGGACAAGCAGCAC
SAD2-1_CHK22  GTTCCGCCCTCGGTGCAGCGCCCCTCCCCCGTGGTCTACTCCAAGCTGGACAAGCAGCAC SAD2-1_CHK80  CGCCTGACGCCCGAGCGCCTGGAGCTGGTGCAGAGCATGGGGCAGTTTGCGGAGGAGAGG
SAD2-1_CHK22  CGCCTGACGCCCGAGCGCCTGGAGCTGGTGCAGAGCATGGGGCAGTTTGCGGAGGAGAGG
```

TABLE 11-continued

```
SAD2-1_CHK80  GTGCTGCCCGTGCTGCACCCCGTGGACAAGCTGTGGCAGCCGCAGGACTTTTTGCCCGAC
SAD2-1_CHK22  GTGCTGCCCGTGCTGCACCCCGTGGACAAGCTGTGGCAGCCGCAGGACTTTTTGCCCGAC

SAD2-1_CHK80  CCCGAGTCGCCCGACTTCGAGGATCAGGTGGCGGAGCTGCGCGCGCGCGCCAAGGACCTG
SAD2-1_CHK22  CCCGAGTCGCCCGACTTCGAGGATCAGGTGGCGGAGCTGCGCGCGCGCGCCAAGGACCTG

SAD2-1_CHK80  CCCGACGAGTACTTTGTGGTGCTGGTGGGGGACATGATCACGGAGGAGGCGCTGCCGACC
SAD2-1_CHK22  CCCGACGAGTACTTTGTGGTGCTGGTGGGGGACATGATCACGGAGGAGGCGCTGCCGACC

SAD2-1_CHK80  TACATGGCCATGCTCAACACGCTGGACGGCGTGCGCGACGACACGGGCGCGGCCGACCAC
SAD2-1_CHK22  TACATGGCCATGCTCAACACGCTGGACGGCGTGCGCGACGACACGGGCGCGGCCGACCAC

SAD2-1_CHK80  CCGTGGGCGCGCTGGACGCGGCAGTGGGTGGCCGAGGAGAACCGGCACGGCGACCTGCTG
SAD2-1_CHK22  CCGTGGGCGCGCTGGACGCGGCAGTGGGTGGCCGAGGAGAACCGGCACGGCGACCTGCTG

SAD2-1_CHK80  AACAAGTACTGCTGGCTGACGGGGCGCGTCAACATGCGGGCCGTGGAGGTGACCATCAAC
SAD2-1_CHK22  AACAAGTACTGCTGGCTGACGGGGCGCGTCAACATGCGGGCCGTGGAGGTGACCATCAAC

SAD2-1_CHK80  AACCTGATCAAGAGCGGCATGAACCCGCAGACGGACAACAACCCTTATTTGGGGTTCGTC
SAD2-1_CHK22  AACCTGATCAAGAGCGGCATGAACCCGCAGACGGACAACAACCCTTATTTGGGGTTCGTC

SAD2-1_CHK80  TACACCTCCTTCCAGGAGCGCGCCACCAAGTACAGCCACGGCAACACCGCGCGCCTTGCG
SAD2-1_CHK22  TACACCTCCTTCCAGGAGCGCGCCACCAAGTACAGCCACGGCAACACCGCGCGCCTTGCG

SAD2-1_CHK80  GCCGAGCACGGCGACAAGAACCTGAGCAAGATCTGCGGGCTGATCGCCAGCGACGAGGGC
SAD2-1_CHK22  GCCGAGCACGGCGACAAGAACCTGAGCAAGATCTGCGGGCTGATCGCCAGCGACGAGGGC

SAD2-1_CHK80  CGGCACGAGATCGCCTACACGCGCATCGTGGACGAGTTCTTCCGCCTCGACCCCGAGGGC
SAD2-1_CHK22  CGGCACGAGATCGCCTACACGCGCATCGTGGACGAGTTCTTCCGCCTCGACCCCGAGGGC

SAD2-1_CHK80  GCCGTCGCCGCCTACGCCAACATGATGCGCAAGCAGATCACCATGCCCGCGCACCTCATG
SAD2-1_CHK22  GCCGTCGCCGCCTACGCCAACATGATGCGCAAGCAGATCACCATGCCCGCGCACCTCATG

SAD2-1_CHK80  GACGACATGGGCCACGGCGAGGCCAACCCGGGCCGCAACCTCTTCGCCGACTTCTCCGCG
SAD2-1_CHK22  GACGACATGGGCCACGGCGAGGCCAACCCGGGCCGCAACCTCTTCGCCGACTTCTCCGCG

SAD2-1_CHK80  GTCGCCGAGAAGATCGACGTCTACGACGCCGAGGACTACTGCCGCATCCTGGAGCACCTC
SAD2-1_CHK22  GTCGCCGAGAAGATCGACGTCTACGACGCCGAGGACTACTGCCGCATCCTGGAGCACCTC

SAD2-1_CHK80  AACGCGCGCTGGAAGGTGGACGAGCGCCAGGTCAGCGGCCAGGCCGCCGCGGACCAGGAG
SAD2-1_CHK22  AACGCGCGCTGGAAGGTGGACGAGCGCCAGGTCAGCGGCCAGGCCGCCGCGGACCAGGAG

SAD2-1_CHK80  TACGTCCTGGGCCTGCCCCAGCGCTTCCGGAAACTCGCCGAGAAGACCGCCGCCAAGCGC
SAD2-1_CHK22  TACGTCCTGGGCCTGCCCCAGCGCTTCCGGAAACTCGCCGAGAAGACCGCCGCCAAGCGC

SAD2-1_CHK80  AAGCGCGTCGCGCGCAGGCCCGTCGCCTTCTCCTGGATCTCCGGGCGCGAGATCATGGTC
SAD2-1_CHK22  AAGCGCGTCGCGCGCAGGCCCGTCGCCTTCTCCTGGATCTCCGGGCGCGAGATCATGGTC

SAD2-1_CHK80  TAGggagcgacgagtgtgcgtgcggggctggcgggagtgggacgccctcctcgctcctct
SAD2-1_CHK22  TAGggagcgacgagtgtgcgtgcggggctggcgggagtgggacgccctcctcgctcctct SAD2-1_CHK80  ctgttctgaacggaacaatcggccaccccgcgctacgcgccacgcatcgagcaacgaaga
SAD2-1_CHK22  ctgttctgaacggaacaatcggccaccccgcgctacgcgccacgcatcgagcaacgaaga SAD2-1_CHK80  aaaccccccgatgataggttgcggtggctgccgggatatagatccggccgcacatcaaag
SAD2-1_CHK22  aaaccccccgatgataggttgcggtggctgccgggatatagatccggccgcacatcaaag SAD2-1_CHK80  ggccccctccgccagagaagaagctcctttcccagcagactccttctgctgccaaaacact
SAD2-1_CHK22  ggccccctccgccagagaagaagctcctttcccagcagactccttctgctgccaaaacact SAD2-1_CHK80  tctctgtccacagcaacaccaaaggatgaacagatcaacttgcgtctccgcgtagcttcc
SAD2-1_CHK22  tctctgtccacagcaacaccaaaggatgaacagatcaacttgcgtctccgcgtagcttcc SAD2-1_CHK80  tcggctagcgtgcttgcaacaggtccctgcactattatcttcctgctttcctctgaatta
SAD2-1_CHK22  tcggctagcgtgcttgcaacaggtccctgcactattatcttcctgctttcctctgaatta SAD2-1_CHK80  tgcggcaggcgagcgctcgctctggcgagcgctccttcgcgccgccctcgctgatcgagt
SAD2-1_CHK22  tgcggcaggcgagcgctcgctctggcgagcgctccttcgcgccgccctcgctgatcgagt SAD2-1_CHK80  gtacagtcaatgaatggtcctgggcgaagaacgagggaatttgtgggtaaaacaagcatc
SAD2-1_CHK22  gtacagtcaatgaatggtcctgggcgaagaacgagggaatttgtgggtaaaacaagcatc SAD2-1_CHK80  gtctctcaggcccggcgcagtggccgttaaagtccaagaccgtgaccaggcagcgcagc
SAD2-1_CHK22  gtctctcaggcccggcgcagtggccgttaaagtccaagaccgtgaccaggcagcgcagc SAD2-1_CHK80  gcgtccgtgtgcgggccctgcctggcggctcggcgtgccaggctcgagagcagctccctc
SAD2-1_CHK22  gcgtccgtgtgcgggccctgcctggcggctcggcgtgccaggctcgagagcagctccctc
```

TABLE 11-continued

```
SAD2-1_CHK80  aggtcgccttggacggcctctgcgaggccggtgagggcctgcaggagcgcctcgagcgtg
SAD2-1_CHK22  aggtcgccttggacggcctctgcgaggccggtgagggcctgcaggagcgcctcgagcgtg SAD2-1_CHK80  gcagtggcggtcgtatccgggtcgccggtcaccgcctgcgactcgccatccgaagagcca
SAD2-1_CHK22  gcagtggcggtcgtatccgggtcgccggtcaccgcctgcgactcgccatccgaagagcca SAD2-1_CHK80  tcgtcgtcgtctcccagactggacgcgctcgccatcggccccgccgatgcagaacacgcc
SAD2-1_CHK22  tcgtcgtcgtctcccagactggacgcgctcgccatcggccccgccgatgcagaacacgcc SAD2-1_CHK80  tctgcgctcgccgtgcgcagcgcggcgcgcagcgctgcgcgcgccagggccgcgtccagc
SAD2-1_CHK22  tctgcgctcgccgtgcgcagcgcggcgcgcagcgctgcgcgcgccagggccgcgtccagc SAD2-1_CHK80  aggcccatcgccagctcccggccgcgagggccggccagcgcctcaaagccgccggcgcgg
SAD2-1_CHK22  aggcccatcgccagctcccggccgcgagggccggccagcgcctcaaagccgccggcgcgg SAD2-1_CHK80  gcggccgccaccaccgaggccagcgcggcgcgcgcgccctccagggtcggcgcccgggtc
SAD2-1_CHK22  gcggccgccaccaccgaggccagcgcggcgcgcgcgccctccagggtcggcgcccgggtc SAD2-1_CHK80  acggcgtcgcgcgcccaggcggccagcgccgccccccgtagaacgcagtgcgcctccatc
SAD2-1_CHK22  acggcgtcgcgcgcccaggcggccagcgccgccccccgtagaacgcagtgcgcctccatc SAD2-1_CHK80  gaccgcacaaagtgggagacccggtggctcgtggggtcgtagggccgcacgcggcggcgc
SAD2-1_CHK22  gaccgcacaaagtgggagacccggtggctcgtggggtcgtagggccgcacgcggcggcgc SAD2-1_CHK80  gcgggcctcgtggttgcgcgcgtgctgctccgcagccccgcaatcgtcacgctcccttgc
SAD2-1_CHK22  gcgggcctcgtggttgcgcgcgtgctgctccgcagccccgcaatcgtcacgctcccttgc SAD2-1_CHK80  cgatccacgctcgcggcggccagcctggcccaggccagctggaggcccaggcgcatgctg
SAD2-1_CHK22  cgatccacgctcgcggcggccagcctggcccaggccagctggaggcccaggcgcatgctg SAD2-1_CHK80  gcgcggacctgctccagaaaggggccgtcgcccagcatgcacagcggccaggggagcgtc
SAD2-1_CHK22  gcgcggacctgctccagaaaggggccgtcgcccagcatgcacagcggccaggggagcgtc SAD2-1_CHK80  aggtcgaaccgcaggcgctccagcgtggcgacgcgcggaggctcgcccgggagcggccag
SAD2-1_CHK22  aggtcgaaccgcaggcgctccagcgtggcgacgcgcggaggctcgcccgggagcggccag SAD2-1_CHK80  ggacgagcgggcgattgggtggccggcggcgaataaccaggtgcactccgtcagcagcc
SAD2-1_CHK22  ggacgagcgggcgattgggtggccggcggcgaataaccaggtgcactccgtcagcagcc SAD2-1_CHK80  tcctccgacctcacaccccctgcctcttgagctggcggcaccgggccgcgatggccgca
SAD2-1_CHK22  tcctccgacctcacaccccctgcctcttgagctggcggcaccgggccgcgatggccgca SAD2-1_CHK80  ccggcgctgtccagcacgcccgcttccacagccacgtgcagctcgatgccggcgacgtcc
SAD2-1_CHK22  ccggcgctgtccagcacgcccgcttccacagccacgtgcagctcgatgccggcgacgtcc SAD2-1_CHK80  gtctc
SAD2-1_CHK22  gtctc SAD2-2_CHK80  ggagctcagcatgtcg-ccagcatcgctggataagacgaattggcagggtaccacctgaa
(SEQ ID NO: 15)
SAD2-2_CHK22  ggagctcagcatgtcgcccagcatcgccggataagacgaattggcagggtaccacctgaa
(SEQ ID NO: 16)

SAD2-2_CHK80  gaatgggaggcaggtgttgctgattacgagtgtgtaaaagaaaggggtagagagccgtcc
SAD2-2_CHK22  gaatgggaggcaggtgttgttgattatgagtgtgtaaaagaaaggggtagagagccgtcc SAD2-2_CHK80  tcagatccgaccactatgcaggtagccgctcgcccatgcccgcctggctgaatattgaca
SAD2-2_CHK22  tcagatccgactactatgcaggtagccgctcgcccatgcccgcctggctgaatattgatg SAD2-2_CHK80  catgcccatcaaggcaggcaggcatttctgtgcatgcaccaagcccacaatcttccacaa
SAD2-2_CHK22  catgcccatcaaggcaggcaggcatttctgtgcacgcaccaagcccacaatcttccacaa SAD2-2_CHK80  cacacagcatgtaccaacgcacgcgtaaaagttggggtgctgccagtgcgtcatgccagg
SAD2-2_CHK22  cacacagcatgtaccaacgcacgcgtaaaagttggggtgctgccagtgcgtcatgccagg SAD2-2_CHK80  catgatgtgctcctgcacatcggccatgatctcctccatcgtctcgggtgtctccggcgc
SAD2-2_CHK22  catgatgtgctcctgcacatccgccatgatctcctccatcgtctcgggtgtttccggcgc SAD2-2_CHK80  ctggtccgggagccgttccgccagatacccagacgccacctccgacctcacggggtactt
SAD2-2_CHK22  ctggtccgggagccgttccgccagatacccagacgccacctccgacctcacggggtactt SAD2-2_CHK80  ttcgagcgactgtcggtagtcgacgatcgcgtccaccatggagtagccgaggcgccggaa
SAD2-2_CHK22  ttcgagcgtctgccggtagtcgacgatcgcgtccaccatggagtagccgaggcgccggaa SAD2-2_CHK80  ctggcgtgacggagggaggagagggaggagagag----------gggggggggatgatc
SAD2-2_CHK22  ctggcgtgacggagggaggagagggaggagagagaggggggggggggggggggatgatt
```

TABLE 11-continued

```
SAD2-2_CHK80  acacgccagtctcacaacgcatgtaagacccgtttgattatgagtacaatcatgcactac
SAD2-2_CHK22  acacgccagtctcacaacgcatgcaagacccgtttgattatgagtacaatcatgcactac SAD2-2_CHK80  tagttggatgagcgccaggcataaggcacaccgacgtcgatggcacgagcaactcccgca
SAD2-2_CHK22  tagatggatgagcgccaggcataaggcacaccgacgttgatggcatgagcaactcccgca SAD2-2_CHK80  tcatatttcctattgtcctcacgccaagccggtcaccatccgcatgctcgtattacagcg
SAD2-2_CHK22  tcatatttcctattgtcctcacgccaagccggtcaccatccgcatgctcatattacagcg SAD2-2_CHK80  cacgcaccgcttcgtgatccaccgggtgaacgtagtcctcgacggaaacatctggttcgg
SAD2-2_CHK22  cacgcaccgcttcgtgatccaccgggtgaacgtagtcctcgacggaaacatctggctcgg SAD2-2_CHK80  gcctcgtgctggcactccctcccatgccgacaaccttctgctgtcaccacgacccacga
SAD2-2_CHK22  gcctcgtgctggcactccctcccatgccgacaaccttctgctgtcaccacgacccacga SAD2-2_CHK80  tgcaacgcgacacga-ccggtgggactgatcggttcactgcacctgcatgcaattgtcac
SAD2-2_CHK22  tgcaacgcgacacgacccggtgggactgatcggttcactgcacctgcatgcaattgtcac SAD2-2_CHK80  aagcgcatactccaatcgtatccgtttgatttctgtgaaaactcgctcgaccgcccgcgt
SAD2-2_CHK22  aagcgcatactccaatcgtatccgtttgatttctgtgaaaactcgctcgaccgcccgcgt SAD2-2_CHK80  cccgcaggcagcgatgacgtgtgcgtggcctgggtgtttcgtcgaaaggccagcaacccc
SAD2-2_CHK22  cccgcaggcagcgatgacgtgtgcgtgacctgggtgtttcgtcgaaaggccagcaacccc SAD2-2_CHK80  aaatcgcaggcgatccggagattgggatctgatccgag-ttggaccagatccccc-cgat
SAD2-2_CHK22  aaatcgcaggcgatccggagattgggatctgatccgagcttggaccagatcccccacgat SAD2-2_CHK80  gcggcacgggaactgcatcgactcggcgcggaacccagctttcgtaaatgccagattggt
SAD2-2_CHK22  gcggcacgggaactgcatcgactcggcgcggaacccagctttcgtaaatgccagattggt SAD2-2_CHK80  gtccgataccttgatttgccatcagcgaaacaagacttcagcagcgagcgtatttggcgg
SAD2-2_CHK22  gtccgataccttgatttgccatcagcgaaacaagacttcagcagcgagcgtatttggcgg SAD2-2_CHK80  gcgtgctaccagggttgcatacattgcccatttctgtctggaccgctttactggcgcaga
SAD2-2_CHK22  gcgtgctaccagggttgcatacattgcccatttctgtctggaccgctttaccggcgcaga SAD2-2_CHK80  gggtgagttgatggggttggcaggcatcgaaacgcgcgtgcatggtgtgtgtgtctgttt
SAD2-2_CHK22  gggtgagttgatggggttggcaggcatcgaaacgcgcgtgcatggtgtgtgtgtctgttt SAD2-2_CHK80  tcggctgcacaat-tcaatagtcggatgggcgacggtagaattgggtgttgcgctcgcgt
SAD2-2_CHK22  tcggctgcacaatttcaatagtcggatgggcgacggtagaattgggtgttgcgctcgcgt SAD2-2_CHK80  gcatgcctcgcccgtcgggtgtcatgaccgggactggaatccccctcgcgaccctctt
SAD2-2_CHK22  gcatgcctcgcccgtcgggtgtcatgaccgggactggaatccccctcgcgaccctct SAD2-2_CHK80  gctaacgctcccgactctcccgcccgcgcgcaggatagactctagttcaaccaatcgaca
SAD2-2_CHK22  gctaacgctcccgactctcccgcccgcgcgcaggatagactctagttcaaccaatcgaca SAD2-2_CHK80  ATGGCGTCTGCCGTCACCTTTGCGTGCGCCCCTCCCCGCGGCGCGGTCGCCGCGCCGGGT
SAD2-2_CHK22  ATGGCGTCTGCCGTCACCTTTGCGTGCGCCCCTCCCCGCGGCGCGGTCGCCGCGCCGGGT SAD2-2_CHK80  CGCCGCGCTGCCTCGCGTCCCCTGGTGGTGCGCGCCGTCGCCAGCGAGGCCCCGCTGGGC
SAD2-2_CHK22  CGCCGCGCTGCCTCGCGTCCCCTGGTGGTGCACGCCGTCGCCAGCGAGGCCCCGCTGGGC SAD2-2_CHK80  GTGCCGCCCTCGGTGCAGCGCCCCTCCCCCGTGGTCTACTCCAAGCTGGACAAGCAACAC
SAD2-2_CHK22  GTGCCGCCCTCGGTGCAGCGCCCCTCCCCCGTGGTCTACTCCAAGCTGGACAAGCAACAC SAD2-2_CHK80  CGCCTGACGCCCGAGCGCCTGGAGCTGGTGCAGAGCATGGGTCAGTTTGCGGAGGAGAGG
SAD2-2_CHK22  CGCCTGACGCCCGAGCGCCTGGAGCTGGTGCAGAGCATGGGTCAGTTTGCGGAGGAGAGG SAD2-2_CHK80  GTGCTCCCCGTGCTGCACCCCGTGGACAAGCTGTGGCAGCCGCAGGACTTTTTGCCCGAC
SAD2-2_CHK22  GTGCTCCCCGTGCTGCACCCCGTGGACAAGCTGTGGCAGCCGCAGGACTTTCCTGCCCGAC SAD2-2_CHK80  CCCGAGTCGCCCGACTTCGAGGACCAGGTGGCGGAGCTGCGCGCGCGCGCCAAGGACCTG
SAD2-2_CHK22  CCCGAGTCGCCCGACTTCGAGGACCAGGTGGCGGAGCTGCGCGCGCGCGCCAAGGACCTG SAD2-2_CHK80  CCCGACGAGTACTTTGTGGTGCTGGTGGGCGACATGATCACGGAGGAGGCGCTGCCGACC
SAD2-2_CHK22  CCCGACGAGTACTTTGTGGTGCTGGTGGGCGACATGATCACGGAGGAGGCGCTGCCGACC SAD2-2_CHK80  TACATGGCCATGCTCAACACCTTGGACGGTGTGCGCGACGACACGGGCGCGGCTGACCAC
SAD2-2_CHK22  TACATGGCCATGCTCAACACCTTGGACGGTGTGCGCGACGACACGGGCGCGGCTGACCAC SAD2-2_CHK80  CCGTGGGCGCGCTGGACGCGGCAGTGGGTGGCCGAGGAGAACCGGCACGGCGACCTGCTG
SAD2-2_CHK22  CCGTGGGCGCGCTGGACGCGGCAGTGGGTGGCCGAGGAGAACCGGCACGGCGACCTGCTG SAD2-2_CHK80  AACAAGTACTGTTGGCTGACGGGGCGCGTCAACATGCGGGCCGTGGAGGTGACCATCAAC
SAD2-2_CHK22  AACAAGTACTGTTGGCTGACGGGGCGCGTCAACATGCGGGCCGTGGAGGTGACCATCAAC
```

TABLE 11-continued

```
SAD2-2_CHK80  AACCTGATCAAGAGCGGCATGAACCCGCAGACGGACAACAACCCTTACTTGGGCTTCGTC
SAD2-2_CHK22  AACCTGATCAAGAGCGGCATGAACCCGCAGACGGACAACAACCCTTACTTGGGCTTCGTC

SAD2-2_CHK80  TACACCTCCTTCCAGGAGCGCGCGACCAAGTACAGCCACGGCAACACCGCGCGCCTGGCG
SAD2-2_CHK22  TACACCTCCTTCCAGGAGCGCGCGACCAAGTACAGCCACGGCAACACCGCGCGCCTGGCG

SAD2-2_CHK80  GCCGAGCACGGCGACAAGGGCCTGAGCAAGATCTGCGGGCTGATCGCCAGCGACGAGGGC
SAD2-2_CHK22  GCCGAGCACGGCGACAAGGGCCTGAGCAAGATCTGCGGGCTGATCGCCAGCGACGAGGGC

SAD2-2_CHK80  CGGCACGAGATCGCCTACACGCGCATCGTGGACGAGTTCTTCCGCCTCGACCCCGAGGGC
SAD2-2_CHK22  CGGCACGAGATCGCCTACACGCGCATCGTGGACGAGTTCTTCCGCCTCGACCCCGAGGGC

SAD2-2_CHK80  GCCGTCGCCGCCTACGCCAACATGATGCGCAAGCAGATCACCATGCCCGCGCACCTCATG
SAD2-2_CHK22  GCCGTCGCCGCCTACGCCAACATGATGCGCAAGCAGATCACCATGCCCGCGCACCTCATG

SAD2-2_CHK80  GACGACATGGGCCACGGCGAGGCCAACCCGGGCCGCAACCTCTTCGCCGACTTCTCCGCC
SAD2-2_CHK22  GACGACATGGGCCACGGCGAGGCCAACCCGGGCCGCAACCTCTTCGCCGACTTCTCCGCC

SAD2-2_CHK80  GTCGCCGAGAAGATCGACGTCTACGACGCCGAGGACTACTGCCGCATCCTGGAGCACCTC
SAD2-2_CHK22  GTCGCCGAGAAGATCGACGTCTACGACGCCGAGGACTACTGCCGCATCCTGGAGCACCTC

SAD2-2_CHK80  AACGCGCGCTGGAAGGTGGACGAGCGCCAGGTCAGCGGCCAGGCCGCCGCGGACCAGGAG
SAD2-2_CHK22  AACGCGCGCTGGAAGGTGGACGAGCGCCAGGTCAGCGGCCAGGCCGCCGCGGACCAGGAG

SAD2-2_CHK80  TACGTTCTGGGCCTGCCCCAGCGCTTCCGGAAACTCGCCGAGAAGACCGCCGCCAAGCGC
SAD2-2_CHK22  TACGTTCTGGGCCTGCCCCAGCGCTTCCGGAAACTCGCCGAGAAGACCGCCGCCAAGCGC

SAD2-2_CHK80  AAGCGCGTCGCGCGCAGGCCCGTCGCCTTCTCCTGGATCTCCGGACGCGAGATTATGGTC
SAD2-2_CHK22  AAGCGCGTCGCGCGCAGGCCCGTCGCCTTCTCCTGGATCTCCGGACGCGAGATTATGGTC

SAD2-2_CHK80  TAGggaggtacgagcgcgcgcgagggattggtgggagtgggacgcgctcgtcgctcctttt
SAD2-2_CHK22  TAGggaggtacgagcgcgcgcgagggattggtgggagtgggacgcgctcgtcgctcctttt SAD2-2_CHK80  ctattctgaagggaagattggccaccccgctccacgcgccacgcatcgagcaacgaagaa
SAD2-2_CHK22  ctattctgaagggaagattggccaccccgctccacgcgccacgcatcgagcaacgaagaa SAD2-2_CHK80  aaccccccgatgataggttgcagtggctgccgagatatagatccggctgcacgtcaaagg
SAD2-2_CHK22  aaccccccgatgataggttgcagtggctgccgagatatagatccggctgcacgtcaaagg SAD2-2_CHK80  gcccctcggccagagaagaagctctttt-ccagcgaccgcagactccttctgccaaaaac
SAD2-2_CHK22  gcccctcggccagagaagaagctctttt ccagcgaccgcagactccttctgccaaaaac SAD2-2_CHK80  actcttctctgtccacagcaacaccaatggatggacagatcaacttgtgtcttcgcgtag
SAD2-2_CHK22  actcttctctgtccacagcaacaccaatggatggacagatcaacatgtgtcttcgcgtag SAD2-2_CHK80  cttcctcggctagcgtgcttgcaacaggtccctgcactattatcctcctgcttttcctctg
SAD2-2_CHK22  cttcctcggctagcgtgcttgcaacaggtccctgcactattatcctcctgcttttcctctg SAD2-2_CHK80  aattatgcggcaggcgagcgctcgctcttgcgagcgctccttcgcgccgccctcgctgat
SAD2-2_CHK22  aattatgcggcaggcgagcgctcgctcttgcgagcgctccttcgcgccgccctcgctgat SAD2-2_CHK80  cgagtgtacagtcaatgaatggtcctgggcgaagaacgagggaatttgtgggcgagagag
SAD2-2_CHK22  cgagtgtacagtcaatgaatggtcctgggcgaagaacgagggaatttgtgggcgagagag SAD2-2_CHK80  catcgtctctcaggccccagcgcagtggccgttaaagtccaagaccgtgaccaggcagcg
SAD2-2_CHK22  catcgtctctcaggccccagcgcagtggccgttaaagtccaagaccgtgaccaggcagcg SAD2-2_CHK80  catcgcgtccgtgtgcgggccctgcctggcggctcggcgcgccaggctcgagagcagctc
SAD2-2_CHK22  catcgcgtccgtgtgcgggccctgcctggcggctcggcgcgccaggctcgagagcagctc SAD2-2_CHK80  cctcaggtcgcccttggacagcctctgcgaggccggtgagggtctgcaggagcgcctcgag
SAD2-2_CHK22  cctcaggtcgcccttggacagcctctgcgaggccggtgagggtctgcaggagcgcctcgag SAD2-2_CHK80  cgtggcagtggcggttgtatccgggtcgccggtcatcgactgcgactcgccatccgaaga
SAD2-2_CHK22  cgtggcagtggcggttgtatccgggtcgccggtcatcgactgcgactcgccatccgaaga SAD2-2_CHK80  gccatcgtcgtcgtctcccagactggaagcgctcgccatcggccccgccgatacagaaaa
SAD2-2_CHK22  gccatcgtcgtcgtctcccagactggaagcgctcgccatcggccccgccgatacagaaaa SAD2-2_CHK80  cgcctctgcgctcgccgtgcgcagcgcggcgcgcaccagggccgcgtccagcagacccat
SAD2-2_CHK22  cgcctctgcgctcgccgtgcgcagcgcggcgcgcaccagggccgcgtccagcagacccat SAD2-2_CHK80  cgccagctcccggccgcgagggccggccagcgcctcaaagccgccggcgcgggcggccgc
SAD2-2_CHK22  cgccagctcccggccgcgagggccggccagcgcctcaaagccgccggcgcgggcggccgc SAD2-2_CHK80  cgccgccgaggccagcgcggcgcgcgcgccctccagggtcggcgcccgggtcacggcgtc
SAD2-2_CHK22  cgccgccgaggccagcgcggcgcgcgcgccctccagggtcggcgcccgggtcacggcgtc
```

TABLE 11-continued

```
SAD2-2_CHK80  gcgcgcccaggcggccagcgccgcccccccgcaggacgcagtgcgcctccatcgaccgcac
SAD2-2_CHK22  gcgcgcccaggcggccagcgccgcccccccgcaggacgcagtgcgcctccatcgaccgcac SAD2-2_CHK80  aaagtgggagacccggtggctcgtggggtcgtagggccgcacgcggcggcgcgcgggcct
SAD2-2_CHK22  aaagtgggagacccggtggctcgtggggtcgtagggccgcacgcggcggcgcgcgggcct SAD2-2_CHK80  cgtgaacgtgcgtttgccattccgcagccctgcggtcgtcacactcccttgccgatccac
SAD2-2_CHK22  cgtgaacgtgcgtttgccattccgcagccctgcggtcgtcacactcccttgccgatccac SAD2-2_CHK80  gctcgcggcggccagcctggcccaggccagctggaggcccaggagcatgccggcgcggac
SAD2-2_CHK22  gctcgcggcggccagcctggcccaggccagctggaggcccaggagcatgccggcgcggac SAD2-2_CHK80  ctgctccagaaaggggccgttgcccagcatgcacagtggccaggggagcgtcaggtggaa
SAD2-2_CHK22  ctgctccagaaaggggccgttgcccagcatgcacagtggccaggggagcgtcaggtggaa SAD2-2_CHK80  ccgcaggcgctccagcgtggcgacgcgcggaggctcgcccgggagcggccagggacgcgt
SAD2-2_CHK22  ccgcaggcgctccagcgtggcgacgcgcggaggctcgcccgggagcggccagggacgcgt SAD2-2_CHK80  ggacgattgggtggcg-gcatcgaagtgctggagcgcactccgtcagcggcctccgccga
SAD2-2_CHK22  ggacgattgggtggcgggcatcgaagtgctggagcgcactccgtcagcggcctccgccga SAD2-2_CHK80  cgccgcacccccctgcctcttgagctggcggcaccgggccgcgatggccgcaccggcgct
SAD2-2_CHK22  cgccgcacccccctgcctcttgagctggcggcaccgggccgcgatggccgcaccggcgct SAD2-2_CHK80  gtccagcacgcccgcttccacagccacgtgcagctcgatgccggcgacgtctgtctccat
SAD2-2_CHK22  gtccagcacgcccgcttccacagccacgtgcagctcgatgccggcgacgtctgtctccat SAD2-2_CHK80  ca
SAD2-2_CHK22  ca
```

Key:
Non-coding: lowercase, non-italicized, non-bold
Promoter: italicized, non-bold
Coding: CAPITAL, BOLD, NON-ITALICIZED
Intron: CAPITAL, NON-BOLD, NON-ITALICIZED
SNP difference: underlined a c g t TABLE 12 shows sequence alignments of genomic regions of CHK80 and CHK22: 6S, DAO1B, FAD2, FATA1, and Thi4.

TABLE 12

```
6S_CHK22  acgaattgttgctttgaagggtgctgaatggcaccagatactgggtcggtggcatttgct
(SEQ ID NO: 17)
6S_CHK80  acgaattgttgctttgaagggtgctgaatggcaccagatactgggtcggtggcatttgct
(SEQ ID NO: 18)

6S_CHK22  caggcgtcatttgtaggttctgccaataataattccatgaggacagcaagccattgacaa
6S_CHK80  caggcgtcatttgtaggttctgccaataataattccatgaggacagcaagccattgacaa 6S_CHK22  gcccactgactcgaattttagagcaacctacgagaccacaccatccgtgcacgcacctcg
6S_CHK80  gcccactgactcgaattttagagcaacctacgagaccacaccatccgtgcacgcacctcg 6S_CHK22  aggctgtttttggatacgtgcagccgagcgcatggcccgtcgccgtcctcggtagaggga
6S_CHK80  aggctgtttttggatacgtgcagccgagcgcatggcccgtcgccgtcctcggtagaggga 6S_CHK22  gggcagcacagggccctctctttcttttttgactggccaagctggcacgctttcggctgcc
6S_CHK80  gggcagcacagggccctctctttcttttttgactggccaagctggcacgctttcggctgcc 6S_CHK22  gggatcaggtgagctttcgtcggcggggcgagcagggccaccaggtcgaggacctccct
6S_CHK80  gggatcaggtgagctttcgtcggcggggcgagcagggccaccaggtcgaggacctccct 6S_CHK22  ctccaggcagccaatggtgtggagcaggcctctatgctggtgatgagccgcttgctgctc
6S_CHK80  ctccaggcagccaatggtgtggagcaggcctctatgctggtgatgagccgcttgctgctc 6S_CHK22  ctggctgtcggcaccggtcctcctggatggcggaggtggcgcaagaacacccgtgtgtcg
6S_CHK80  ctggctgtcggcaccggtcctcctggatggcggaggtggcgcaagaacacccgtgtgtcg 6S_CHK22  cacgttcatcaacacgtcttgcgcagtgtcgcacaccgcaaggacgcaggtactttaaaa
6S_CHK80  cacgttcatcaacacgtcttgcgcagtgtcgcacaccgcaaggacgcaggtactttaaaa 6S_CHK22  agacacaagcgtgacatgtgcgtgatcattgcaacggctgccgcagaggacttaccccag
6S_CHK80  agacacaagcgtgacatgtgcgtgatcattgcaacggctgccgcagaggacttaccccag 6S_CHK22  ctcagcaagcagtgttgagacggccttggccaccccatcgagctcagcgagcagcttttc
6S_CHK80  ctcagcaagcagtgttgagacggccttggccaccccatcgagctcagcgagcagcttttc
```

TABLE 12-continued

```
6S_CHK22  gtgctggaaggccaggacctcgttttcttgctgggtctccacggctcgccgtcgggattc
6S_CHK80  gtgctggaaggccaggacctcgttttcttgctgggtctccacggctcgccgtcgggattc 6S_CHK22  ctggagggaggagggagcccaggggagagtggtgttgtgatgacgacgcgtgtgcgcaga
6S_CHK80  ctggagggaggagggagcccaggggagagtggtgttgtgatgacgacgcgtgtgcgcaga 6S_CHK22  ggcagtaggatgctcatgagtgcagcctctttgcagccaggtttgcctgtcgcacagact
6S_CHK80  ggcagtaggatgctcatgagtgcagcctctttgcagccaggtttgcctgtcgcacagact 6S_CHK22  tgagaggcaccacccaaagtctactatccaaataatgctcagagcatcagcaatgttgg
6S_CHK80  tgagaggcaccacccaaagtctactatccaaataatgctcagagcatcagcaatgttgg 6S_CHK22  ccaccttcagtaccaacgctcccaccctcgtctgcgcacctgcgctgcccgccccgcgc
6S_CHK80  ccaccttcagtaccaacgctcccaccctcgtctgcgcacctgcgctgcccgccccgcgc 6S_CHK22  ggcctcggcagcgacggacgcgcccgccgcgccctcggcggcctccgcctgcgcctcgag
6S_CHK80  ggcctcggcagcgacggacgcgcccgccgcgccctcggcggcctccgcctgcgcctcgag 6S_CHK22  cgcctcacgttcccttttccagcgccgccagcgaggcctggacgtccaccaggtgcttgaa
6S_CHK80  cgcctcacgttcccttttccagcgccgccagcgaggcctggacgtccaccaggtgcttgaa 6S_CHK22  ccgagcaaagttgcgctcctgcagcccggccaggttggccaccagctcctccatgctgga
6S_CHK80  ccgagcaaagttgcgctcctgcagcccggccaggttggccaccagctcctccatgctgga 6S_CHK22  gtagcctgtggccgtggagatcttctggaaagcgtcggtgatggcctgctcgcgctgcgc
6S_CHK80  gtagcctgtggccgtggagatcttctggaaagcgtcggtgatggcctgctcgcgctgcgc 6S_CHK22  gtgcgacgcaaagtggacgcctggtgaggccgcgccctggccgtcgagggaggaccccc
6S_CHK80  gtgcgacgcaaagtggacgcctggtgaggccgcgccctggccgtcgagggaggaccccc 6S_CHK22  gcccggcccggcctcggcggcgcccgccgcgccgcccagcgccctcgcccccgccggcgc
6S_CHK80  gcccggcccggcctcggcggcgcccgccgcgccgcccagcgccctcgcccccgccggcgc 6S_CHK22  gccgccgtgcgcgtccagccgcacgggcgctgggtagtcctgcgagaagagctgggccat
6S_CHK80  gccgccgtgcgcgtccagccgcacgggcgctgggtagtcctgcgagaagagctgggccat 6S_CHK22  ctcctgctcgcgcgcggcacgctccgcgcggcgatcggcgtcccgggtcgcgcgctcctg
6S_CHK80  ctcctgctcgcgcgcggcacgctccgcgcggcgatcggcgtcccgggtcgcgcgctcctg 6S_CHK22  ctggatgagcgccgccagccgccgccactcctgctcgagcgcgcccgactcgcgctccgc
6S_CHK80  ctggatgagcgccgccagccgccgccactcctgctcgagcgcgcccgactcgcgctccgc 6S_CHK22  ctGCGCCCGCGCGTGCGCCGCCAGCGCCTTGGCCTTTTCGCCGCGCTCGTGCGCGTCGCT
6S_CHK80  ctGCGCCCGCGCGTGCGCCGCCAGCGCCTTGGCCTTTTCGCCGCGCTCGTGCGCGTCGCT 6S_CHK22  GATGTCCATCACCAGGTCCATGAGGTCTGCCTTGCGCCGGCTGAGCCACTGCTTCGTCCG
6S_CHK80  GATGTCCATCACCAGGTCCATGAGGTCTGCCTTGCGCCGGCTGAGCCACTGCTTCGTCCG 6S_CHK22  GGCGGCCAAGAGGAGCATGAGGGAGGACTCCTGGTCCAGGGTCCTGACGTGGTCGCGGCT
6S_CHK80  GGCGGCCAAGAGGAGCATGAGGGAGGACTCCTGGTCCAGGGTCCTGACGTGGTCGCGGCT 6S_CHK22  CTGGGAGCGGGCCAGCATCATCTGGCTCTGCCGCACCGAGGCCGCCTCCAACTGGTCCTC
6S_CHK80  CTGGGAGCGGGCCAGCATCATCTGGCTCTGCCGCACCGAGGCCGCCTCCAACTGGTCCTC 6S_CHK22  CAGCAGCCGCAGTCGCCGCCGACCCTGGCAGAGGAAGACAGGTGAGGGGGGTATGAATTG
6S_CHK80  CAGCAGCCGCAGTCGCCGCCGACCCTGGCAGAGGAAGACAGGTGAGGGGGGTATGAATTG 6S_CHK22  TACAGAACAACCACGAGCCTTGTCTAGGCAGAATCCCTACCAGTCATGGCTTTACCTGGA
6S_CHK80  TACAGAACAACCACGAGCCTTGTCTAGGCAGAATCCCTACCAGTCATGGCTTTACCTGGA 6S_CHK22  TGACGGCCTGCGAACAGCTGTCCAGCGACCCTCGCTGCCGCCGCTTCTCCCGCACGCTTC
6S_CHK80  TGACGGCCTGCGAACAGCTGTCCAGCGACCCTCGCTGCCGCCGCTTCTCCCGCACGCTTC 6S_CHK22  TTTCCAGCACCGTGATGGCGCGAGCCAGCGCCGCACGCTGGCGCTGCGCTTCGCCGATCT
6S_CHK80  TTTCCAGCACCGTGATGGCGCGAGCCAGCGCCGCACGCTGGCGCTGCGCTTCGCCGATCT 6S_CHK22  GAGGACAGTCGGGGAACTCTGATCAGTCTAAACCCCCTTGCGCGTTAGTGTTGCCATCCT
6S_CHK80  GAGGACAGTCGGGGAACTCTGATCAGTCTAAACCCCCTTGCGCGTTAGTGTTGCCATCCT 6S_CHK22  TTGCAGACCGGTGAGAGCCGACTTGTTGTGCGCCACCCCCCACACCACCTCCTCCCAGAC
6S_CHK80  TTGCAGACCGGTGAGAGCCGACTTGTTGTGCGCCACCCCCCACACCACCTCCTCCCAGAC 6S_CHK22  CAATTCTGTCACCTTTTTGGCGAAGGCATCGGCCTCGGCCTGCAGAGAGGACAGCAGTGC
6S_CHK80  CAATTCTGTCACCTTTTTGGCGAAGGCATCGGCCTCGGCCTGCAGAGAGGACAGCAGTGC 6S_CHK22  CCAGCCGCTGGGGGTTGGCGGATGCACGCTCAGCTTGTTTTCCAGAAGGAGTTGCTCCTT
6S_CHK80  CCAGCCGCTGGGGGTTGGCGGATGCACGCTCAGCTTGTTTTCCAGAAGGAGTTGCTCCTT
```

TABLE 12-continued

```
6S_CHK22  GAGCCTTTCATTCTCAGCCTCGATAACCTCCAAAGCCGCTCTAATTGTGGAGGGGGTTCG
6S_CHK80  GAGCCTTTCATTCTCAGCCTCGATAACCTCCAAAGCCGCTCTAATTGTGGAGGGGGTTCG

6S_CHK22  AATTTAAAAGCTTGGAATGTTGGTTCGTGCGTCTGGAACAAGCCCAGACTTGTTGCTCAC
6S_CHK80  AATTTAAAAGCTTGGAATGTTGGTTCGTGCGTCTGGAACAAGCCCAGACTTGTTGCTCAC

6S_CHK22  TGGGAAAAGGACCATCAGCTCCAAAAAACTTGCCGCTCAAACCGCGTACCTCTGCTTTCG
6S_CHK80  TGGGAAAAGGACCATCAGCTCCAAAAAACTTGCCGCTCAAACCGCGTACCTCTGCTTTCG

6S_CHK22  CGCAATCTGCCCTGTTGAAATCGCCACCACATTCATATTGTGACGCTTGAGCAGTCTGTA
6S_CHK80  CGCAATCTGCCCTGTTGAAATCGCCACCACATTCATATTGTGACGCTTGAGCAGTCTGTA

6S_CHK22  ATTGCCTCAGAATGTGGAATCATCTGCCCCCTGTGCGAGCCCATGCCAGGCATGTCGCGG
6S_CHK80  ATTGCCTCAGAATGTGGAATCATCTGCCCCCTGTGCGAGCCCATGCCAGGCATGTCGCGG

6S_CHK22  GCGAGGACACCCGCCACTCGTACAGCAGACCATTATGCTACCTCACAATAGTTCATAACA
6S_CHK80  GCGAGGACACCCGCCACTCGTACAGCAGACCATTATGCTACCTCACAATAGTTCATAACA

6S_CHK22  GTGACCATATTTCTCGAAGCTCCCCAACGAGCACCTCCATGCTCTGAGTGGCCACCCCCC
6S_CHK80  GTGACCATATTTCTCGAAGCTCCCCAACGAGCACCTCCATGCTCTGAGTGGCCACCCCCC

6S_CHK22  GGCCCTGGTGCTTGCGGAGGGCAGGTCAACCGGCATGGGGCTACCGAAATCCCCGACCGG
6S_CHK80  GGCCCTGGTGCTTGCGGAGGGCAGGTCAACCGGCATGGGGCTACCGAAATCCCCGACCGG

6S_CHK22  ATCCCACCACCCCCGCGATGGGAAGAATCTCTCCCCGGGATGTGGGCCCACCACCAGCAC
6S_CHK80  ATCCCACCACCCCCGCGATGGGAAGAATCTCTCCCCGGGATGTGGGCCCACCACCAGCAC

6S_CHK22  AACCTGCTGGCCCAGGCGAGCGTCAAACCATACCACACAAATATCCTTGGCATCGGCCCT
6S_CHK80  AACCTGCTGGCCCAGGCGAGCGTCAAACCATACCACACAAATATCCTTGGCATCGGCCCT

6S_CHK22  GAATTCCTTCTGCCGCTCTGCTACCCGGTGCTTCTGTCCGAAGCAGGGGTTGCTAGGGAT
6S_CHK80  GAATTCCTTCTGCCGCTCTGCTACCCGGTGCTTCTGTCCGAAGCAGGGGTTGCTAGGGAT

6S_CHK22  CGCTCCGAGTCCGCAAACCCTTGTCGCGTGGCGGGGCTTGTTCGAGCtcgcagcatcgct
6S_CHK80  CGCTCCGAGTCCGCAAACCCTTGTCGCGTGGCGGGGCTTGTTCGAGCtcgcagcatcgct 6S_CHK22  tgcacggggctatcttcaagtagtcgggaagcatgggtcgcgacgtcgagacgggcgag
6S_CHK80  tgcacggggctatcttcaagtagtcgggaagcatgggtcgcgacgtcgagacgggcgag 6S_CHK22  cgggcctatgggtgagtcggccgtgcatggggagggctagcgccagggctcgggtcgccc
6S_CHK80  cgggcctatgggtgagtcggccgtgcatggggagggctagcgccagggctcgggtcgccc 6S_CHK22  cgatggccggggtctttgctcggggtgcacgcggccgtgggtgcgagacaggttgcgtga
6S_CHK80  cgatggccggggtctttgctcggggtgcacgcggccgtgggtgcgagacaggttgcgtga 6S_CHK22  cgaatttcttggcaccccccacggatgcctcacgcgggcgccccctccctcgcaggta
6S_CHK80  cgaatttcttggcaccccccacggatgcctcacgcgggcgccccctccctcgcaggta 6S_CHK22  cgtccgcaaggtgtccggcccggtggtggtggccagcagcatgagcgggtctgccatgta
6S_CHK80  cgtccgcaaggtgtccggcccggtggtggtggccagcagcatgagcgggtctgccatgta 6S_CHK22  cgagctggtccgcgtgggcgcggacaagctgattggcgagatcattcgcctcgagggaga
6S_CHK80  cgagctggtccgcgtgggcgcggacaagctgattggcgagatcattcgcctcgagggaga 6S_CHK22  cacggcgaccatccaggtgaggtggcggggaggctgcttgagtggaagtggggcgcaca
6S_CHK80  cacggcgaccatccaggtgaggtggcggggaggctgcttgagtggaagtggggcgcaca 6S_CHK22  accctccattggttggcggccaaggatgcagggaagcgaatgtcgagcattgcgcgcttt
6S_CHK80  accctccattggttggcggccaaggatgcagggaagcgaatgtcgagcattgcgcgcttt 6S_CHK22  tgcttgctgacatatcgttgcttgcaccccatgtattctccaggtgtacgaggatacctc
6S_CHK80  tgcttgctgacatatcgttgcttgcaccccatgtattctccaggtgtacgaggatacctc 6S_CHK22  gggcctgacggtgggcgacacggtcgtccgctccggcaaggtgtggagggtgtgagagtt
6S_CHK80  gggcctgacggtgggcgacacggtcgtccgctccggcaaggtgtggagggtgtgagagtt 6S_CHK22  gatgtatatgctttggtcgcccccttgctctggcacgtcagaggcgcaccttcagtgctc
6S_CHK80  gatgtatatgctttggtcgcccccttgctctggcacgtcagaggcgcaccttcagtgctc 6S_CHK22  acaagtggtgccgttagtgaaactgaacaagtgcttgactgtgtaggatttccgctcgcc
6S_CHK80  acaagtggtgccgttagtgaaactgaacaagtgcttgactgtgtaggatttccgctcgcc 6S_CHK22  cctttcttaccctctcccctttctctctttctccacccctcaaaatctccagccctgtc
6S_CHK80  cctttcttaccctctcccctttctctctttctccacccctcaaaatctccagccctgtc 6S_CHK22  tgtggagctgggccccggcatcatgggcaccatcttttgacggcatccagcgcccgctcaa
6S_CHK80  tgtggagctgggccccggcatcatgggcaccatcttttgacggcatccagcgcccgctcaa
```

TABLE 12-continued

```
6S_CHK22   gtcgatcgcggtggacagcgattcgtgcttcatcccgcgcggcgtggacgtgccggccct
6S_CHK80   gtcgatcgcggtggacagcgattcgtgcttcatcccgcgcggcgtggacgtgccggccct 6S_CHK22   ggaccgcaaggcctcgtgggagtttgacccggtgtcaagcttcaaggtgggcgaccgcat
6S_CHK80   ggaccgcaaggcctcgtgggagtttgacccggtgtcaagcttcaaggtgggcgaccgcat 6S_CHK22   cacgggcggcgacatctacggcgtggtgcacgagaacacgctgatggagcacaaggtgct
6S_CHK80   cacgggcggcgacatctacggcgtggtgcacgagaacacgctgatggagcacaaggtgct 6S_CHK22   gcttccgccgggcgcgcgcggcaccatctcctacatcgcgccggcggggagctacagcat
6S_CHK80   gcttccgccgggcgcgcgcggcaccatctcctacatcgcgccggcggggagctacagcat 6S_CHK22   cacggacaagatcatcgaggtcgagtttggcggcgcgcgcaaggagtactccatgctgca
6S_CHK80   cacggacaagatcatcgaggtcgagtttggcggcgcgcgcaaggagtactccatgctgca 6S_CHK22   gctctggcccgtgcgcgcgccgcgccccgtggcgcagaagctgctggccaacacgccgct
6S_CHK80   gctctggcccgtgcgcgcgccgcgccccgtggcgcagaagctgctggccaacacgccgct 6S_CHK22   gctgacggggcagcgcgtgctggacgcgctcttccccggcgtgctgggcgggacgtgcgc
6S_CHK80   gctgacggggcagcgcgtgctggacgcgctcttccccggcgtgctgggcgggacgtgcgc 6S_CHK22   catcccgggcgcgtttggctgcggcaagacggtcatctcgcaggcgctgtcaaagtacag
6S_CHK80   catcccgggcgcgtttggctgcggcaagacggtcatctcgcaggcgctgtcaaagtacag 6S_CHK22   taactcggagggcatcatctacgtcggctgcggcgagcgcggcaacgagatggccgaggt
6S_CHK80   taactcggagggcatcatctacgtcggctgcggcgagcgcggcaacgagatggccgaggt 6S_CHK22   gctcatggacttccccgcgctgaccatgaccatgccggacgggcgcgaggagagcatcat
6S_CHK80   gctcatggacttccccgcgctgaccatgaccatgccggacgggcgcgaggagagcatcat 6S_CHK22   gcagcgcaccacgctcgtggccaacacctccaacatgcccgtcgccgcgcgcgaggccag
6S_CHK80   gcagcgcaccacgctcgtggccaacacctccaacatgcccgtcgccgcgcgcgaggccag 6S_CHK22   catctaca
6S_CHK80   catctaca DAO1B_CHK80  gcaatctcccgcccaacctccaccagccggcgcaggacctggagcgcgaaagaggatttc
(SEQ ID NO: 19)
DAO1B_CHK22  gcaatctcccgcccaacctccaccagccggcgcaggacctggagcgcgaaagaggatttc
(SEQ ID NO: 20)

DAO1B_CHK80  gggggtgtggggagagtgagcgcgatggaagacactgatttgcataaacaacctttggc
DAO1B_CHK22  ggg_gtgtggggagagtgagcgcgatggaagacactgatttgcataaacaacctttggc DAO1B_CHK80  cgctttcaaagcaccacctcaccaccataaaaccctccctcccatgcataccttgatgcc
DAO1B_CHK22  cgctttcaaagcaccacctcaccaccataaaaccctccctcccatgcataccttgatgcc DAO1B_CHK80  tgccgagatggcctgggcttggtggaccatggccatgtagtccggcgtggtcgcgatgga
DAO1B_CHK22  tgccgagatggcctgggcttggtggaccatggccatgtagtccggcgtggtcgcgatgga DAO1B_CHK80  cgccgcacgttgtgcgatgagcgccttgccccgtcctcgtgcccgagcccgcgtccggg
DAO1B_CHK22  cgccgcacgttgtgcgatgagcgccttgccccgtcctcgtgcccgagcccgcgtccggg DAO1B_CHK80  cggctcggccagccccgccagcagccccgggtccagctcggcgttgagggagcgctttgc
DAO1B_CHK22  cggctcggccagccccgccagcagccccgggtccagctcggcgttgagggagcgctttgc DAO1B_CHK80  cagcgcacggatggactcgtacggcagcgtgatgaggtggagcaggctgtcgagcaggcc
DAO1B_CHK22  cagcgcacggatggactcgtacggcagcgtgatgaggtggagcaggctgtcgagcaggcc DAO1B_CHK80  cggctgcgaccagagcatggtgaggatgcgcgccgccgcgggcgtgccgggctgcaccgc
DAO1B_CHK22  cggctgcgaccagagcatggtgaggatgcgcgccgccgcgggcgtgccgggctgcaccgc DAO1B_CHK80  cagcagcaacgcggcgaccgtctcggccgcaaacaccgccaggaagcagccctccgaggt
DAO1B_CHK22  cagcagcaacgcggcgaccgtctcggccgcaaacaccgccaggaagcagccctccgaggt DAO1B_CHK80  cgggccgggctccagcaggggaccgcaggcgtgcactatgtccaggcgctccgtgatgat
DAO1B_CHK22  cgggccgggctccagcaggggaccgcaggcgtgcactatgtccaggcgctccgtgatgat DAO1B_CHK80  gtgcatggccagcggcagcagcgagcgcagcacgctgctggccaggtgcgtgagcgtgct
DAO1B_CHK22  gtgcatggccagcggcagcagcgagcgcagcacgctgctggccaggtgcgtgagcgtgct DAO1B_CHK80  cgtgccggccgagtccgaggtctcgtccgtggccaggtccatgggcggcagcgtgcgctc
DAO1B_CHK22  cgtgccggccgagtccgaggtctcgtccgtggccaggtccatgggcggcagcgtgcgctc DAO1B_CHK80  gctcgcctggtgcgccgtccagctgcgccggtggcacagcagccgcagcaccgcgtggaa
DAO1B_CHK22  gctcgcctggtgcgccgtccagctgcgccggtggcacagcagccgcagcaccgcgtggaa DAO1B_CHK80  gagcggcaggcagcccgcctccaccgccgcggcggcggccggggcgccgccctcctgcag
DAO1B_CHK22  gagcggcaggcagcccgcctccaccgccgcggcggcggccggggcgccgccctcctgcag
```

TABLE 12-continued

```
DAO1B_CHK80  gctggcgcgcaggatggccgccgactgccgcgccgccgacagctgctgcctgtgtctcaa
DAO1B_CHK22  gctggcgcgcaggatggccgccgactgccgcgccgccgacagctgctgcctgtgtctcaa DAO1B_CHK80  aagctgcgacagcgtcggagagatgtcctgcggctccggctccgggatgtgctggatgcc
DAO1B_CHK22  aagctgcgacagcgtcggagagatgtcctgcggctccggctccgggatgtgctggatgcc DAO1B_CHK80  acgcacaccggtcgcaatcacctgttggataatgggtggcaggatggttggttaggttct
DAO1B_CHK22  acgcacaccggtcgcaatcacctgttggataatgggtggcaggatggttggttaggttct DAO1B_CHK80  gatgcggtcggggaggcggataaggtcacagccgcgtgatcttgctgaccaaacactgct
DAO1B_CHK22  gatgcggtcggggaggcggataaggtcacagccgcgtgatcttgctgaccaaacactgct DAO1B_CHK80  ggccacccaacaaaagtcgattgccaccgatgcacacggcatggcgcccagacagaagct
DAO1B_CHK22  ggccacccaacaaaagtcgattgccaccgatgcacacggcatggcgcccagacagaagct DAO1B_CHK80  cagcatacccctcaggagggccagggccaggccaggccacatgtgcagctggaagccggc
DAO1B_CHK22  cagcatacccctcaggagggccagggccaggccaggccacatgtgcagctggaagccggc DAO1B_CHK80  tgggctgaagcatgggccagcacgctcagggcatggttttgaaaggcaggaacgtggctt
DAO1B_CHK22  tgggctgaagcatgggccagcacgctcagggcatggttttgaaaggcaggaacgtggctt DAO1B_CHK80  gtcacgtcaacaaccagggaagaggcctgcgacatcaaggggcaaagttggaatgttcag
DAO1B_CHK22  gtcacgtcaacaaccagggaagaggcctgcgacatcaaggggcaaagttggaatgttcag DAO1B_CHK80  catcatcagcctgggaccaatactctgctcacggttcagggcagaaaggtggcatagtca
DAO1B_CHK22  catcatcagcctgggaccaatactctgctcacggttcagggcagaaaggtggcatagtca DAO1B_CHK80  gggcctcgttcagaatttcaagtcccagtttaaacttcgtacctccgcgaggctgatccc
DAO1B_CHK22  gggcctcgttcagaatttcaagtcccagtttaaacttcgtacctccgcgaggctgatccc DAO1B_CHK80  ctcgccctgagcggactggggccggggagccggggtgggaccggtggtcacctgcgccat
DAO1B_CHK22  ctcgccctgagcggactggggccggggagccggggtgggaccggtggtcacctgcgccat DAO1B_CHK80  gGCTAGCCCGCACCCTCGTTGATCTGGGAGCCCTGCGCAGCCCCTTAAATCATCTCAGTC
DAO1B_CHK22  gGCTAGCCCGCACCCTCGTTGATCTGGGAGCCCTGCGCAGCCCCTTAAATCATCTCAGTC DAO1B_CHK80  AGGTTTCTGTGTTCAACTGAGCCTAAAGGGCTTTCGTCATGCGCACGAGCACACGTATAT
DAO1B_CHK22  AGGTTTCTGTGTTCAACTGAGCCTAAAGGGCTTTCGTCATGCGCACGAGCACACGTATAT DAO1B_CHK80  CGGCCACGCAGTTTCTCAAAAGCGGTAGAACAGTTCGCGAGCCCTCGTAGGTCGAAAACT
DAO1B_CHK22  CGGCCACGCAGTTTCTCAAAAGCGGTAGAACAGTTCGCGAGCCCTCGTAGGTCGAAAACT DAO1B_CHK80  TGCGCCAGTACTATTAAATTAAATTAATTGATCGAACGAGACGCGAAACTTTTGCAGAAT
DAO1B_CHK22  TGCGCCAGTACTATTAAATTAAATTAATTGATCGAACGAGACGCGAAACTTTTGCAGAAT DAO1B_CHK80  GCCACCGAGTTTGCCCAGAGAATGGGAGTGGCGCCATTCACCATCCGCCTGTGCCCGGCT
DAO1B_CHK22  GCCACCGAGTTTGCCCAGAGAATGGGAGTGGCGCCATTCACCATCCGCCTGTGCCCGGCT DAO1B_CHK80  TGATTCGCCGAGACGATGGACGGCGAGACCAGGGAGCGGCTTGCGAGCCCCGAGCCGGTA
DAO1B_CHK22  TGATTCGCCGAGACGATGGACGGCGAGACCAGGGAGCGGCTTGCGAGCCCCGAGCCGGTA DAO1B_CHK80  GCAGGAACAATGATCGACAATCTTCCTGTCCAATTACTGGCAACCATTAGAAAGAGCCGG
DAO1B_CHK22  GCAGGAACAATGATCGACAATCTTCCTGTCCAATTACTGGCAACCATTAGAAAGAGCCGG DAO1B_CHK80  AGCGCGTTGAAAGTCTGCAATCGAGTAATTTTTCGATACGTCGGGCCTGCTGAACCCTAA
DAO1B_CHK22  AGCGCGTTGAAAGTCTGCAATCGAGTAATTTTTCGATACGTCGGGCCTGCTGAACCCTAA DAO1B_CHK80  GGCTCCGGACTTTGTTTAAGGCGATCCAAGATGCACGCGGCCCCAGGCACGTATCTCAAG
DAO1B_CHK22  GGCTCCGGACTTTGTTTAAGGCGATCCAAGATGCACGCGGCCCCAGGCACGTATCTCAAG DAO1B_CHK80  CACAAACCCCAGCCTTAGTTTCGAGACTTTGGGAGATAGCGACCGATATCTAGTTTGGCA
DAO1B_CHK22  CACAAACCCCAGCCTTAGTTTCGAGACTTTGGGAGATAGCGACCGATATCTAGTTTGGCA DAO1B_CHK80  TTTTGTATATTAATTACCTCAAGCAATGGAGCGCTCTGATGCGGTGCAGCGTCGGCTGCA
DAO1B_CHK22  TTTTGTATATTAATTACCTCAAGCAATGGAGCGCTCTGATGCGGTGCAGCGTCGGCTGCA DAO1B_CHK80  GCACCTGGCAGTGGCGCTAGGGTCGCCCTATCGCTCGGAACCTGGTCAGCTGGCTCCCGC
DAO1B_CHK22  GCACCTGGCAGTGGCGCTAGGGTCGCCCTATCGCTCGGAACCTGGTCAGCTGGCTCCCGC DAO1B_CHK80  CTCCTGCTCAGCCTCTTCCAGCCGTAGCGTCTGCGTGTTGGGAGCTGGAGTCGTGGGCTT
DAO1B_CHK22  CTCCTGCTCAGCCTCTTCCAGCCGTAGCGTCTGCGTGTTGGGAGCTGGAGTCGTGGGCTT DAO1B_CHK80  GACGACGGCGCTGCAGCTGTTGCAGGATGTGCCTGGCGTGCGCGTTCACGTCGTGGCTGA
DAO1B_CHK22  GACGACGGCGCTGCAGCTGTTGCAGGATGTGCCTGGCGTGCGCGTTCACGTCGTGGCTGA DAO1B_CHK80  GAAATATGGCGACGAAACGTTGACGGCTGGGGCCGGCGGGCTGTGGATGCCATACGCATT
DAO1B_CHK22  GAAATATGGCGACGAAACGTTGACGGCTGGGGCCGGCGGGCTGTGGATGCCATACGCATT
```

TABLE 12-continued

```
DA01B_CHK80  GGGTACGCGGCCATTGGATGGGATTGATAGGCTTATGGAGGGATAATAGAGTTTTTGCCG
DA01B_CHK22  GGGTACGCGGCCATTGGATGGGATTGATAGGCTTATGGAGGGATAATAGAGTTTTTGCCG

DA01B_CHK80  GATCCAACGCATGTGGATGCGGTATCCCGGTGGGCTGAAAGTGTGGAAGGATAGTGCATT
DA01B_CHK22  GATCCAACGCATGTGGATGCGGTATCCCGGTGGGCTGAAAGTGTGGAAGGATAGTGCATT

DA01B_CHK80  GGCTATTCACATGCACTGCCCACCCCTTTTGGCAGGAAATGTGCCGGCATCGTTGGTGCA
DA01B_CHK22  GGCTATTCACATGCACTGCCCACCCCTTTTGGCAGGAAATGTGCCGGCATCGTTGGTGCA

DA01B_CHK80  CCGATGGGGAAAATCGACGTTCGACCACTACATGAAGATTTATACGTCTGAAGATGCAGC
DA01B_CHK22  CCGATGGGGAAAATCGACGTTCGACCACTACATGAAGATTTATACGTCTGAAGATGCAGC

DA01B_CHK80  GACTGCGGGTGCGAAACGGATGACGGTTTGGTCGTGTATGTCACAGCATGTGCTGGATCT
DA01B_CHK22  GACTGCGGGTGCGAAACGGATGACGGTTTGGTCGTGTATGTCACAGCATGTGCTGGATCT

DA01B_CHK80  TGCGGGCTAACTCCCCCTGCCACGGCCCATTGCAGGTGTCATGTTGACTGGAGGGTACGA
DA01B_CHK22  TGCGGGCTAACTCCCCCTGCCACGGCCCATTGCAGGTGTCATGTTGACTGGAGGGTACGA

DA01B_CHK80  CCTTTCGTCCGTCAAATTCCCAGAGGAGGACCCGCTCTGGGCCGACATTGTGCCCACTtt
DA01B_CHK22  CCTTTCGTCCGTCAAATTCCCAGAGGAGGACCCGCTCTGGGCCGACATTGTGCCCACTtt

DA01B_CHK80  tcgccgcctgggcaaggcagagctcctggcctacgaccccagcggcaagtcgatcgacgg
DA01B_CHK22  tcgccgcctgggcaaggcagagctcctggcctacgaccccagcggcaagtcgatcgacgg DA01B_CHK80  ctacggcttcaccaccatcatcacgtacgatgctcaatgaaaggggagttcattgccttc
DA01B_CHK22  ctacggcttcaccaccatcatcacgtacgatgctcaatgaaaggggagttcattgccttc DA01B_CHK80  actagagaaacatacatgggtctatgtaaacttgatcgatctccgaatttcctcttgttg
DA01B_CHK22  actagagaaacatacatgggtctatgtaaacttgatcgatctccgaatttcctcttgttg DA01B_CHK80  tgtctctggttgtgcagggaaggtcgcctctacctgccctggctgatgcagcagattcaa
DA01B_CHK22  tgtctctggttgtgcagggaaggtcgcctctacctgccctggctgatgcagcagattcaa DA01B_CHK80  ggcttggggggaccttttgaacggcgccgcatctccagcctgtcggagctgaaggagtat
DA01B_CHK22  ggcttggggggaccttttgaacggcgccgcatctccagcctgtcggagctgaaggagtat DA01B_CHK80  gatgccatcgtcaattgcacaggtgggttggagttagtccaggagatgtcgatagaccaa
DA01B_CHK22  gatgccatcgtcaattgcacaggtgggttggagttagtccaggagatgtcgatagaccaa DA01B_CHK80  tgcaaatcgtgtgcaacgcattagacccaatcactgcctccctcgccgctctcaggcctg
DA01B_CHK22  tgcaaatcgtgtgcaacgcattagacccaatcactgcctccctcgccgctctcaggcctg DA01B_CHK80  gaggcgccaaagctggtgcaggacgagtccatgtacccggtgcgcgggcacgttctgcgc
DA01B_CHK22  gaggcgccaaagctggtgcaggacgagtccatgtacccggtgcgcgggcacgttctgcgc DA01B_CHK80  gtacgggcgccctgggtccgccactacatcaaccgcgacgggggcacctacatcatcccc
DA01B_CHK22  gtacgggcgccctgggtccgccactacatcaaccgcgacgggggcacctacatcatcccc DA01B_CHK80  aacacggacacggtggtgctgggcggcatcacgcaaaagggcaactggtccctcgagccg
DA01B_CHK22  aacacggacacggtggtgctgggcggcatcacgcaaaagggcaactggtccctcgagccg DA01B_CHK80  accgaggaggatcggcgcgggatcctggagcgctgctacgagatcctgcccagcctgcgc
DA01B_CHK22  accgaggaggatcggcgcgggatcctggagcgctgctacgagatcctgcccagcctgcgc DA01B_CHK80  aaggcgccgatcctgcgcgagtgggtcgggctccggcccggccgcccagacatccgcctg
DA01B_CHK22  aaggcgccgatcctgcgcgagtgggtcgggctccggcccggccgcccagacatccgcctg DA01B_CHK80  gagcgcgaagatgcgcagctcgacggcaagtccgtacccgtcatccacaactacgggcac
DA01B_CHK22  gagcgcgaagatgcgcagctcgacggcaagtccgtacccgtcatccacaactacgggcac DA01B_CHK80  ggcgggtccgggctcaccctgggctggggctgcgccgcagacgccgtcgcgctcgtgcgc
DA01B_CHK22  ggcgggtccgggctcaccctgggctggggctgcgccgcagacgccgtcgcgctcgtgcgc DA01B_CHK80  agggcgctggccctctgacggtgagagggcctgttgcaggctgtgcggtcccgctcatct
DA01B_CHK22  agggcgctggccctctgacggtgagagggcctgttgcaggctgtgcggtcccgctcatct DA01B_CHK80  caaaggccttggaattggctgggcgaatattctgatgcattgatgtgtatctcttcgctt
DA01B_CHK22  caaaggccttggaattggctgggcgaatattctgatgcattgatgtgtatctcttcgctt DA01B_CHK80  ttcttatgatgcaccactttggagcgagtattctggtgccaattgtgctttgaaatcacg
DA01B_CHK22  ttcttatgatgcaccactttggagcgagtattctggtgccaattgtgctttgaaatcacg DA01B_CHK80  ctgcccacggtggcaaatgcaatgagagccgagtaagtggactggtagttcctaaggcga
DA01B_CHK22  ctgcccacggtggcaaatgcaatgagagccgagtaagtggactggtagttcctaaggcga DA01B_CHK80  cgggcagctcaaggaaagccagcccccgatcccagctcgccacatccttgttgcacgcct
DA01B_CHK22  cgggcagctcaaggaaagccagcccccgatcccagctcgccacatccttgttgcacgcct
```

TABLE 12-continued

```
DAO1B_CHK80  gtatctggcggtttgaatgagactcgcgtccacccaggccggccctcgcgctgcggctcc
DAO1B_CHK22  gtatctggcggtttgaatgagactcgcgtccacccaggccggccctcgcgctgcggctcc DAO1B_CHK80  gcccacaactcgagcagcttgtcctttgcccctggcaacatggtctcgatggtgtcgtac
DAO1B_CHK22  gcccacaactcgagcagcttgtcctttgcccctggcaacatggtctcgatggtgtcgtac DAO1B_CHK80  acgggggcaggaaccaggtgcaggcctggagaagagggatggaagtgcgcacagattcga
DAO1B_CHK22  acgggggcaggaaccaggtgcaggcctggagaagagggatggaagtgcgcacagattcga DAO1B_CHK80  gaaggtgatggccctcttgccgaaatgcacaccctctttccccagcctctgcctccaccc
DAO1B_CHK22  gaaggtgatggccctcttgccgaaatgcacaccctctttccccagcctctgcctccaccc DAO1B_CHK80  accgtctgctcgggaagggatgcggcagtccaggacaacgtccgggttgcgctggtgtcg
DAO1B_CHK22  accgtctgctcgggaagggatgcggcagtccaggacaacgtccgggttgcgctggtgtcg DAO1B_CHK80  gagctccatatcgcggccccgttctgaatggatggggtgggacagttggtgtgaccgg
DAO1B_CHK22  gagctccatatcgcggccccgttctgaatggatggggtgggacagttggtgtgaccgg FAD2-2_CHK80  cggctcgctgctttgcgtgccgggtgcagcgatcagatccaagtctgacgacttgtgctg
(SEQ ID NO: 21)
FAD2-2_CHK22  cggctcgctgctttgcgtgccgggtgcagcgatcagatccaagtctgacgacttgtgctg
(SEQ ID NO: 22)

FAD2-2_CHK80  atgtactgtgtcctttgagtccagagcgccggccgcacgcgcttcttcccccttcttcttc
FAD2-2_CHK22  atgtactgtgtcctttgagtccagagcgccggccgcacgcgcttcttcccccttcttcttc FAD2-2_CHK80  ctctcgaacatccagcgatgcaagtgcagggcgctgggcggctggcgtcccgaaccggcc
FAD2-2_CHK22  ctctcgaacatccagcgatgcaagtgcagggcgctgggcggctggcgtcccgaaccggcc FAD2-2_CHK80  tcggcgcacgcggctgaaattgccaatgtcggcaatgtagtgccgctcggcccatccctc
FAD2-2_CHK22  tcggcgcacgcggctgaaattgccaatgtcggcaatgtagtgccgctcggcccatccctc FAD2-2_CHK80  gatcaagttttttcagcgcgtggttggggatgatctgcgctcatgggaagataaaagggt
FAD2-2_CHK22  gatcaagttttttcagcgcgtggttggggatgatctgcgctcatgggaagataaaagggt FAD2-2_CHK80  tctgaggtggttgattggtactttaccggaagtactcatattcatacatgactgatccca
FAD2-2_CHK22  tctgaggtggttgattggtactttaccggaagtactcatattcatacatgactgatccca FAD2-2_CHK80  cacaaaaacaaagctcacttcaaagaaccgcgcatgtctactccccagcaatcacttcgc
FAD2-2_CHK22  cacaaaaacaaagctcacttcaaagaaccgcgcatgtctactccccagcaatcacttcgc FAD2-2_CHK80  tcaccgtcgggttgcttcccacgacaacgccggtgagagggtcggtggcctcgcgacctt
FAD2-2_CHK22  tcaccgtcgggttgcttcccacgacaacgccggtgagagggtcggtggcctcgcgacctt FAD2-2_CHK80  cgcgggcacatcttttccagccatgtctgtataatctcacgctcatacgtctggcccgtcg
FAD2-2_CHK22  cgcgggcacatcttttccagccatgtctgtataatctcacgctcatacgtctggcccgtcg FAD2-2_CHK80  accccaaaatgacgggatcctgcatgatatcgcccgagatggggtccaggcattcctctg
FAD2-2_CHK22  accccaaaatgacgggatcctgcatgatatcgcccgagatggggtccaggcattcctctg FAD2-2_CHK80  gaggcgtcagccctgcgggagatgccggtcccaccgcattggaaaggcacaaaggggtg
FAD2-2_CHK22  gaggcgtcagccctgcgggagatgccggtcccaccgcattggaaaggcacaaaggggtg FAD2-2_CHK80  aatcccccatttcatgaaattgttggtcagcgatggtgcgcactcgtgcgcaatgaatat
FAD2-2_CHK22  aatcccccatttcatgaaattgttggtcagcgatggtgcgcactcgtgcgcaatgaatat FAD2-2_CHK80  ggggtcacgcggtggacgaacgcggaggggggcctggccgaatctaggcttgcattcctca
FAD2-2_CHK22  ggggtcacgcggtggacgaacgcggaggggggcctggccgaatctaggcttgcattcctca FAD2-2_CHK80  gatcactttctgccggcggtccggggtttgcgcgtcgcgcaacgctccgtctccctagcc
FAD2-2_CHK22  gatcactttctgccggcggtccggggtttgcgcgtcgcgcaacgctccgtctccctagcc FAD2-2_CHK80  gctgcgcaccgcgcgtgcgacgcgaaGGTCATTTTCCAGAACAACGACCATGGCTTGTCT
FAD2-2_CHK22  gctgcgcaccgcgcgtgcgacgcgaaGGTCATTTTCCAGAACAACGACCATGGCTTGTCT FAD2-2_CHK80  TAGCGATCGCTCGAATGACTGCTAGTGAGTCGTACGCTCGACCCAGTCGCTCGCAGGAGA
FAD2-2_CHK22  TAGCGATCGCTCGAATGACTGCTAGTGAGTCGTACGCTCGACCCAGTCGCTCGCAGGAGA FAD2-2_CHK80  ACGCGGCAACTGCCGAGCTTCGGCTTGCCAGTCGTGACTCGTATGTGATCAGGAATCATT
FAD2-2_CHK22  ACGCGGCAACTGCCGAGCTTCGGCTTGCCAGTCGTGACTCGTATGTGATCAGGAATCATT FAD2-2_CHK80  GGCATTGGTAGCATTATAATTCGGCTTCCGCGCTGTTTATGGGCATGGCAATGTCTCATG
FAD2-2_CHK22  GGCATTGGTAGCATTATAATTCGGCTTCCGCGCTGTTTATGGGCATGGCAATGTCTCATG FAD2-2_CHK80  CAGTCGACCTTAGTCAACCAATTCTGGGTGGCCAGCTCCGGGCGACCGGGCTCCGTGTCG
FAD2-2_CHK22  CAGTCGACCTTAGTCAACCAATTCTGGGTGGCCAGCTCCGGGCGACCGGGCTCCGTGTCG FAD2-2_CHK80  CCGGGCACCACCTCCTGCCATGAGTAACAGGGCCGCCCTCTCCTCCCGACGTTGGCCCAC
FAD2-2_CHK22  CCGGGCACCACCTCCTGCCATGAGTAACAGGGCCGCCCTCTCCTCCCGACGTTGGCCCAC
```

TABLE 12-continued

```
FAD2-2_CHK80  TGAATACCGTGTCTTGGGGCCCTACATGATGGGCTGCCTAGTCGGGCGGGACGCGCAACT
FAD2-2_CHK22  TGAATACCGTGTCTTGGGGCCCTACATGATGGGCTGCCTAGTCGGGCGGGACGCGCAACT

FAD2-2_CHK80  GCCCGCGCAATCTGGGACGTGGTCTGAATCCTCCAGGCGGGTTTCCCCGAGAAAGAAAGG
FAD2-2_CHK22  GCCCGCGCAATCTGGGACGTGGTCTGAATCCTCCAGGCGGGTTTCCCCGAGAAAGAAAGG

FAD2-2_CHK80  GTGCCGATTTCAAAGCAGAGCCATGTGCCGGGCCCTGTGGCCTGTGTTGGCGCCTATGTA
FAD2-2_CHK22  GTGCCGATTTCAAAGCAGAGCCATGTGCCGGGCCCTGTGGCCTGTGTTGGCGCCTATGTA

FAD2-2_CHK80  GTCACCCCCCCTCACCCAATTGTCGCCAGTTTGCGCAATCCATAAACTCAAAACTGCAGC
FAD2-2_CHK22  GTCACCCCCCCTCACCCAATTGTCGCCAGTTTGCGCAATCCATAAACTCAAAACTGCAGC

FAD2-2_CHK80  TTCTGAGCTGCGCTGTTCAAGAACACCTCTGGGGTTTGCTCACCCGCGAGGTCGACGCCC
FAD2-2_CHK22  TTCTGAGCTGCGCTGTTCAAGAACACCTCTGGGGTTTGCTCACCCGCGAGGTCGACGCCC

FAD2-2_CHK80  AGCATGGCTATCAAGACGAACAGGCAGCCTGTGGAGAAGCCTCCGTTCACGATCGGGACG
FAD2-2_CHK22  AGCATGGCTATCAAGACGAACAGGCAGCCTGTGGAGAAGCCTCCGTTCACGATCGGGACG

FAD2-2_CHK80  CTGCGCAAGGCCATCCCCGCGCACTGTTTCGAGCGCTCGGCGCTTCGTAGCAGCATGTAC
FAD2-2_CHK22  CTGCGCAAGGCCATCCCCGCGCACTGTTTCGAGCGCTCGGCGCTTCGTAGCAGCATGTAC

FAD2-2_CHK80  CTGGCCTTTGACATCGCGGTCATGTCCCTGCTCTACGTCGCGTCGACGTACATCGACCCT
FAD2-2_CHK22  CTGGCCTTTGACATCGCGGTCATGTCCCTGCTCTACGTCGCGTCGACGTACATCGACCCT

FAD2-2_CHK80  GCGCCGGTGCCTACGTGGGTCAAGTATGGCGTCATGTGGCCGCTCTACTGGTTCTTCCAG
FAD2-2_CHK22  GCGCCGGTGCCTACGTGGGTCAAGTATGGCGTCATGTGGCCGCTCTACTGGTTCTTCCAG

FAD2-2_CHK80  GTGTGTGTGAGGGTTGTGGTTGCCCGTATCGAGGTCCTGGTGGCGCGCATGGGGGAGAAG
FAD2-2_CHK22  GTGTGTGTGAGGGTTGTGGTTGCCCGTATCGAGGTCCTGGTGGCGCGCATGGGGGAGAAG

FAD2-2_CHK80  GCGCCTGTCCCGCTGACCCCCCCGGCTACCCTCCCGGCACCTTCCAGGGCGCCTTCGGCA
FAD2-2_CHK22  GCGCCTGTCCCGCTGACCCCCCCGGCTACCCTCCCGGCACCTTCCAGGGCGCCTTCGGCA

FAD2-2_CHK80  CGGGTGTCTGGGTGTGCGCGCACGAGTGCGGCCACCAGGCCTTTTCCTCCAGCCAGGCCA
FAD2-2_CHK22  CGGGTGTCTGGGTGTGCGCGCACGAGTGCGGCCACCAGGCCTTTTCCTCCAGCCAGGCCA

FAD2-2_CHK80  TCAACGACGGCGTGGGCCTGGTGTTCCACAGCCTGCTGCTGGTGCCCTACTACTCCTGGA
FAD2-2_CHK22  TCAACGACGGCGTGGGCCTGGTGTTCCACAGCCTGCTGCTGGTGCCCTACTACTCCTGGA

FAD2-2_CHK80  AGCACTCGCACCGCCGCCACCACTCCAACACGGGGTGCCTGGACAAGGACGAGGTGTTTG
FAD2-2_CHK22  AGCACTCGCACCGCCGCCACCACTCCAACACGGGGTGCCTGGACAAGGACGAGGTGTTTG

FAD2-2_CHK80  TGCCGCCGCACCGCGCAGTGGCGCACGAGGGCCTGGAGTGGGAGGAGTGGCTGCCCATCC
FAD2-2_CHK22  TGCCGCCGCACCGCGCAGTGGCGCACGAGGGCCTGGAGTGGGAGGAGTGGCTGCCCATCC

FAD2-2_CHK80  GCATGGGCAAGGTGCTGGTCACCCTGACCCTGGGCTGGCCGCTGTACCTCATGTTCAACG
FAD2-2_CHK22  GCATGGGCAAGGTGCTGGTCACCCTGACCCTGGGCTGGCCGCTGTACCTCATGTTCAACG

FAD2-2_CHK80  TCGCCTCGCGGCCGTACCCGCGCTTCGCCAACCACTTTGACCCGTGGTCGCCCATCTTCA
FAD2-2_CHK22  TCGCCTCGCGGCCGTACCCGCGCTTCGCCAACCACTTTGACCCGTGGTCGCCCATCTTCA

FAD2-2_CHK80  GCAAGCGCGAGCGCATCGAGGTGGTCATCTCCGACCTGGCGCTGGTGGCGGTGCTCAGCG
FAD2-2_CHK22  GCAAGCGCGAGCGCATCGAGGTGGTCATCTCCGACCTGGCGCTGGTGGCGGTGCTCAGCG

FAD2-2_CHK80  GGCTCAGCGTGCTGGGCCGCACCATGGGCTGGGCCTGGCTGGTCAAGACCTACGTGGTGC
FAD2-2_CHK22  GGCTCAGCGTGCTGGGCCGCACCATGGGCTGGGCCTGGCTGGTCAAGACCTACGTGGTGC

FAD2-2_CHK80  CCTACCTGATCGTGAACATGTGGCTCGTGCTCATCACGCTGCTCCAGCACACGCACCCGG
FAD2-2_CHK22  CCTACCTGATCGTGAACATGTGGCTCGTGCTCATCACGCTGCTCCAGCACACGCACCCGG

FAD2-2_CHK80  CGCTGCCGCACTACTTCGAGAAGGACTGGGACTGGCTGCGCGGCGCCATGGCCACCGTGG
FAD2-2_CHK22  CGCTGCCGCACTACTTCGAGAAGGACTGGGACTGGCTGCGCGGCGCCATGGCCACCGTGG

FAD2-2_CHK80  ACCGCTCCATGGGCCCGCCCTTCATGGACAACATCCTGCACCACATCTCCGACACCCACG
FAD2-2_CHK22  ACCGCTCCATGGGCCCGCCCTTCATGGACAACATCCTGCACCACATCTCCGACACCCACG

FAD2-2_CHK80  TGCTGCACCACCTCTTCAGCACCATCCCGCACTACCACGCCGAGGAGGCCTCCGCCGCCA
FAD2-2_CHK22  TGCTGCACCACCTCTTCAGCACCATCCCGCACTACCACGCCGAGGAGGCCTCCGCCGCCA

FAD2-2_CHK80  TCAGGCCCATCCTGGGCAAGTACTACCAGTCCGACAGCCGCTGGGTCGGCCGCGCCCTGT
FAD2-2_CHK22  TCAGGCCCATCCTGGGCAAGTACTACCAGTCCGACAGCCGCTGGGTCGGCCGCGCCCTGT

FAD2-2_CHK80  GGGAGGACTGGCGCGACTGCCGCTACGTCGTCCCGGACGCGCCCGAGGACGACTCCGCGC
FAD2-2_CHK22  GGGAGGACTGGCGCGACTGCCGCTACGTCGTCCCGGACGCGCCCGAGGACGACTCCGCGC

FAD2-2_CHK80  TCTGGTTCCACAAGTGAGTGAGTGAGTCGCTCACTCAGCGCGCCTGCGCGGGGATGCGGA
FAD2-2_CHK22  TCTGGTTCCACAAGTGAGTGAGTGAGTCGCTCACTCAGCGCGCCTGCGCGGGGATGCGGA
```

TABLE 12-continued

```
FAD2-2_CHK80  ACGCCGCCGCCGCCTTGTCTTTTGCACGCGCGACTCCGTCGCTTCGCGGGTGGCACCCCC
FAD2-2_CHK22  ACGCCGCCGCCGCCTTGTCTTTTGCACGCGCGACTCCGTCGCTTCGCGGGTGGCACCCCC

FAD2-2_CHK80  ATTGAAAAAAACCTCAATTCTGTTTGTGGAAGACACGGTGTACCCCCAACCACCCACCTG
FAD2-2_CHK22  ATTGAAAAAAACCTCAATTCTGTTTGTGGAAGACACGGTGTACCCCCAACCACCCACCTG

FAD2-2_CHK80  CACCTCTATTATTGGTATTATTGACGCGGGAGCGGGCGTTGTACTCTACAACGTAGCGTC
FAD2-2_CHK22  CACCTCTATTATTGGTATTATTGACGCGGGAGCGGGCGTTGTACTCTACAACGTAGCGTC

FAD2-2_CHK80  TCTGGTTTTCAGCTGGCTCCCACCATTGTAAATTCTTGCTAAAATAGTGCGTGGTTATGT
FAD2-2_CHK22  TCTGGTTTTCAGCTGGCTCCCACCATTGTAAATTCTTGCTAAAATAGTGCGTGGTTATGT

FAD2-2_CHK80  GAGAGGTATGGTGTAACAGGGCGTCAGTCATGTTGGTTTTCGTGCTGATCTCGGGCACAA
FAD2-2_CHK22  GAGAGGTATGGTGTAACAGGGCGTCAGTCATGTTGGTTTTCGTGCTGATCTCGGGCACAA

FAD2-2_CHK80  GGCGTCGTCGACGTGACGTGCCCGTGATGAGAGCAATACCGCGCTCAAAGCCGACGCATG
FAD2-2_CHK22  GGCGTCGTCGACGTGACGTGCCCGTGATGAGAGCAATACCGCGCTCAAAGCCGACGCATG

FAD2-2_CHK80  GCCTTTACTCCGCACTCCAAACGACTGTCGCTCGTATTTTTCGGATATCTATTTTTTAAG
FAD2-2_CHK22  GCCTTTACTCCGCACTCCAAACGACTGTCGCTCGTATTTTTCGGATATCTATTTTTTAAG

FAD2-2_CHK80  AGCGAGCACAGCGCCGGGCATGGGCCTGAAAGGCCTCGCGGCCGTGCTCGTGGTGGGGGC
FAD2-2_CHK22  AGCGAGCACAGCGCCGGGCATGGGCCTGAAAGGCCTCGCGGCCGTGCTCGTGGTGGGGGC

FAD2-2_CHK80  CGCGAGCGCGTGGGGCATCGCGGCAGTGCACCAGGCGCAGACGGAGGAACGCATGGTGAG
FAD2-2_CHK22  CGCGAGCGCGTGGGGCATCGCGGCAGTGCACCAGGCGCAGACGGAGGAACGCATGGTGAG

FAD2-2_CHK80  TGCGCATCACAAGATGCATGTCTTGTTGTCTGTACTATAATGCTAGAGCATCACCAGGGG
FAD2-2_CHK22  TGCGCATCACAAGATGCATGTCTTGTTGTCTGTACTATAATGCTAGAGCATCACCAGGGG

FAD2-2_CHK80  CTTAGTCATCGCACCTGCTTTGGTCATTACAGAAATTGCACAAGGGCGTCCTCCGGGATG
FAD2-2_CHK22  CTTAGTCATCGCACCTGCTTTGGTCATTACAGAAATTGCACAAGGGCGTCCTCCGGGATG

FAD2-2_CHK80  AGGAGATGTACCAGCTCAAGCTGGAGCGGCTTCGAGCCAAGCAGGAGCGCGGCGCATGAC
FAD2-2_CHK22  AGGAGATGTACCAGCTCAAGCTGGAGCGGCTTCGAGCCAAGCAGGAGCGCGGCGCATGAC

FAD2-2_CHK80  GACCTACCCACatgcgacaaaggggtctgggtcgtacgacaaaccagtcaggaggcggcg
FAD2-2_CHK22  GACCTACCCACatgcgacaaaggggtctgggtcgtacgacaaaccagtcaggaggcggcg FAD2-2_CHK80  gggtccatgagctggcccgctcgcagcttcagcgcttcgagcatcgcggcgttgtccgcg
FAD2-2_CHK22  gggtccatgagctggcccgctcgcagcttcagcgcttcgagcatcgcggcgttgtccgcg FAD2-2_CHK80  atccaagcctcccgcagcgcctccttggggccctgtgcggagaggcgggtgccgagagg
FAD2-2_CHK22  atccaagcctcccgcagcgcctccttggggccctgtgcggagaggcgggtgccgagagg FAD2-2_CHK80  gctgtgagggcggaggctggaggacaggctgcgaatcgtcgcgctgcctaggcgtctgcc
FAD2-2_CHK22  gctgtgagggcggaggctggaggacaggctgcgaatcgtcgcgctgcctaggcgtctgcc FAD2-2_CHK80  gaggagaagcacaccacgcgccgccgctttcatttcattgtgcccgttgctgtaatgcat
FAD2-2_CHK22  gaggagaagcacaccacgcgccgccgctttcatttcattgtgcccgttgctgtaatgcat FAD2-2_CHK80  gcgagcgatcctgcactaaagctgcgatcgccacctcagcgttgttcgtctctagcaccg
FAD2-2_CHK22  gcgagcgatcctgcactaaagctgcgatcgccacctcagcgttgttcgtctctagcaccg FAD2-2_CHK80  ctcacctgaccacgcgcacggaagagtggcggtcggcgacggcctgctgcacgtggcagt
FAD2-2_CHK22  ctcacctgaccacgcgcacggaagagtggcggtcggcgacggcctgctgcacgtggcagt FAD2-2_CHK80  gcaggtccacgtggccgaggagcaggtctcgcagctgcagcaccgcgccctcgtgctcgc
FAD2-2_CHK22  gcaggtccacgtggccgaggagcaggtctcgcagctgcagcaccgcgccctcgtgctcgc FAD2-2_CHK80  cggggtccatccagtccatgccccgcgccgggccctcgagccggacggccagcagcagg
FAD2-2_CHK22  cggggtccatccagtccatgccccgcgccgggccctcgagccggacggccagcagcagg FAD2-2_CHK80  gccgggggtccgcgccgacgcccggcggccccgccgcgcagctggggtcggccaggaaga
FAD2-2_CHK22  gccgggggtccgcgccgacgcccggcggccccgccgcgcagctggggtcggccaggaaga FAD2-2_CHK80  gccactgggcggccggcccgggcgagccccgcgccggcgcgggaccccacccgcagcacca
FAD2-2_CHK22  gccactgggcggccggcccgggcgagccccgcgccggcgcgggaccccacccgcagcacca FAD2-2_CHK80  ccgcctggtccaggtcgacgtcgctcggcggcaggcccgcgtgcggcgcctgcgccagcg
FAD2-2_CHK22  ccgcctggtccaggtcgacgtcgctcggcggcaggcccgcgtgcggcgcctgcgccagcg FAD2-2_CHK80  tccagggcaggcgggggcgcgcgtgca
FAD2-2_CHK22  tccagggcaggcgggggcgcgcgtgca FATA1_CHK80   gcaatggcgctcggtacagggtctgcgtccgtgctgggctccctctcctacgatgcacaa
(SEQ ID NO: 23)
FATA1_CHK22   gcaatggcgctcggtacagggtctgcgtccgtgctgggctccctctcctacgatgcacaa
(SEQ ID NO: 24)
```

TABLE 12-continued

```
FATA1_CHK80  gggagcgccccggccagctcagcgcgtccacaacctccoctcgtcacacacacacctgcg
FATA1_CHK22  gggagcgccccggccagctcagcgcgtccacaacctccoctcgtcacacacacacctgcg FATA1_CHK80  gaaccaggccgcccatttgctgcttgagcatgccttgcatcatgtccgggttccccatca
FATA1_CHK22  gaaccaggccgcccatttgctgcttgagcatgccttgcatcatgtccgggttccccatca FATA1_CHK80  tatcgttgaggttcttgggctccagcttctgctccagcacaccatcctgtcgatcgaaga
FATA1_CHK22  tatcgttgaggttcttgggctccagcttctgctccagcacaccatcctgtcgatcgaaga FATA1_CHK80  gaaggagacatgtgtacattattggtgtgagggcgctgaatcggccatttttta-aatga
FATA1_CHK22  gaaggagacatgtgtacattattggtgtgagggcgctgaatcggccatttttttaaaatga FATA1_CHK80  tcacgctcatgccaatagacgcggcacataacgacgttcaaaccccccgccaaagccgcgg
FATA1_CHK22  tcacgctcatgccaatagacgcggcacataacgacgttcaaaccccccgccaaagccgcgg FATA1_CHK80  acaacccccatccctccacaccccccacacaaagaacccgccaccgcttaccttgcccacg
FATA1_CHK22  acaacccccatccctccacaccccccacacaaagaacccgccaccgcttaccttgcccacg FATA1_CHK80  aggtaggcctttcgttgcgcaaaaccggcctcggtgatgaatgcatgcccgttcctgacg
FATA1_CHK22  aggtaggcctttcgttgcgcaaaaccggcctcggtgatgaatgcatgcccgttcctgacg FATA1_CHK80  agcgctgcccgggccaacacgctcttttgctgcgtctcctcaggcttgggggcctccttg
FATA1_CHK22  agcgctgcccgggccaacacgctcttttgctgcgtctcctcaggcttgggggcctccttg FATA1_CHK80  ggcttgggtgccgccatgatctgcgcgcatcagagaaacgttgctggt-aaaaggagcgc
FATA1_CHK22  ggcttgggtgccgccatgatctgcgcgcatcagagaaacgttgctggtaaaaaggagcgc FATA1_CHK80  ccggctgcgcaatatatatataggcatgccaacacagcccaacctcactcgggagcccgt
FATA1_CHK22  ccggctgcgcaatatatatataggcatgccaacacagcccaacctcactcgggagcccgt FATA1_CHK80  cccaccaccccccaagtcgcgtgccttgacggcatactgctgcagaagcttcatgagaatg
FATA1_CHK22  cccaccaccccccaagtcgcgtgccttgacggcatactgctgcagaagcttcatgagaatg FATA1_CHK80  atgccgaacaagagggggcacgaggacccaatcccggacatccttgtcgataatgatctcg
FATA1_CHK22  atgccgaacaagagggggcacgaggacccaatcccggacatccttgtcgataatgatctcg FATA1_CHK80  tgagtccccatcgtccgcccgacgctccggggagcccgccgatgctcaagacgagagggc
FATA1_CHK22  tgagtccccatcgtccgcccgacgctccggggagcccgccgatgctcaagacgagagggc FATA1_CHK80  cctcgaccaggaggggctggcccgggcgggcactggcgtcgaaggtgcgcccgtcgttcg
FATA1_CHK22  cctcgaccaggaggggctggcccgggcgggcactggcgtcgaaggtgcgcccgtcgttcg FATA1_CHK80  cctgcagtcctatgccacaaaacaagtcttctgacggggtgcgtttgctcccgtgcgggc
FATA1_CHK22  cctgcagtcctatgccacaaaacaagtcttctgacggggtgcgtttgctcccgtgcgggc FATA1_CHK80  aggcaacagaggtattcaccctggtcatggggagatcggcgatcgagctgggataagaga
FATA1_CHK22  aggcaacagaggtattcaccctggtcatggggagatcggcgatcgagctgggataagaga FATA1_CHK80  tacggtcccgcgcaaggatcgctcatcctggtctgagccggacagtcattctggcaagca
FATA1_CHK22  tacggtcccgcgcaaggatcgctcatcctggtctgagccggacagtcattctggcaagca FATA1_CHK80  atgacaacttgtcaggaccggaccgtgccatatatttctcacctagcgccgcaaaaccta
FATA1_CHK22  atgacaacttgtcaggaccggaccgtgccatatatttctcacctagcgccgcaaaaccta FATA1_CHK80  aCAATTTGGGAGTCACTGTGCCACTGAGTTCGACTGGTAGCTGAATGGAGTCGCTGCTCC
FATA1_CHK22  aCAATTTGGGAGTCACTGTGCCACTGAGTTCGACTGGTAGCTGAATGGAGTCGCTGCTCC FATA1_CHK80  ACTAAACGAATTGTCAGCACCGCCAGCCGGCCGAGGACCCGAGTCATAGCGAGGGTAGTA
FATA1_CHK22  ACTAAACGAATTGTCAGCACCGCCAGCCGGCCGAGGACCCGAGTCATAGCGAGGGTAGTA FATA1_CHK80  GCGCGCCATGGCACCGACCAGCCTGCTTGCCAGTACTGGCGTCTCTTCCGCTTCTCTGTG
FATA1_CHK22  GCGCGCCATGGCACCGACCAGCCTGCTTGCCAGTACTGGCGTCTCTTCCGCTTCTCTGTG FATA1_CHK80  GTCCTCTGCGCGCTCCAGCGCGTGCGCTTTTCCGGTGGATCATGCGGTCCGTGGCGCACC
FATA1_CHK22  GTCCTCTGCGCGCTCCAGCGCGTGCGCTTTTCCGGTGGATCATGCGGTCCGTGGCGCACC FATA1_CHK80  GCAGCGGCCGCTGCCCATGCAGCGCCGCTGCTTCCGAACAGTGGCGGTCAGGGCCGCACC
FATA1_CHK22  GCAGCGGCCGCTGCCCATGCAGCGCCGCTGCTTCCGAACAGTGGCGGTCAGGGCCGCACC FATA1_CHK80  CGCGGTAGCCGTCCGTCCGGAACCCGCCCAAGAGTTTTGGGAGCAGCTTGAGCTCTGCAA
FATA1_CHK22  CGCGGTAGCCGTCCGTCCGGAACCCGCCCAAGAGTTTTGGGAGCAGCTTGAGCCCTGCAA FATA1_CHK80  GATGCGGAGGACAAGCGCATCTTCCTGGAGGAGCACCGGTGCGTGGAGGTCCGGGGCTG
FATA1_CHK22  GATGCGGAGGACAAGCGCATCTTCCTGGAGGAGCACCGGTGCGTGGAGGTCCGGGGCTG FATA1_CHK80  ACCGGCCGTCGCATTCAACGTAATCAATCGCATGATGATCAGAGGACACGAAGTCTTGGT
FATA1_CHK22  ACCGGCCGTCGCATTCAACGTAATCAATCGCATGATGATCAGAGGACACGAAGTCTTGGT
```

TABLE 12-continued

```
FATA1_CHK80  GGCGGTGGCCAGAAACACTGTCCATTGCAAGGGCATAGGGATGCGTTCCTTCACCTCTCA
FATA1_CHK22  GGCGGTGGCCAGAAACACTGTCCATTGCAAGGGCATAGGGATGCGTTCCTTCACCTCTCA

FATA1_CHK80  TTTCTCATTTCTGAATCCCTCCCTGCTCACTCTTTCTCCTCCTCCTTCCCGTTCACGCAG
FATA1_CHK22  TTTCTCATTTCTGAATCCCTCCCTGCTCACTCTTTCTCCTCCTCCTTCCCGTTCACGCAG

FATA1_CHK80  CATTCGGGGCAACGAGGTGGGCCCCTCGCAGCGGCTGACGATCACGGCGGTGGCCAACAT
FATA1_CHK22  CATTCGGGGCAACGAGGTGGGCCCCTCGCAGCGGCTGACGATCACGGCGGTGGCCAACAT

FATA1_CHK80  CCTGCAGGAGGCGGCGGGCAACCACGCGGTGGCCATGTGGGGCCGGAGCTCGGAGGGTTT
FATA1_CHK22  CCTGCAGGAGGCGGCGGGCAACCACGCGGTGGCCATGTGGGGCCGGAGCTCGGAGGGTTT

FATA1_CHK80  CGCGACGGACCCGGAGCTGCAGGAGGCGGGTCTCATCTTTGTGATGACGCGCATGCAGAT
FATA1_CHK22  CGCGACGGACCCGGAGCTGCAGGAGGCGGGTCTCATCTTTGTGATGACGCGCATGCAGAT

FATA1_CHK80  CCAGATGTACCGCTACCCGCGCTGGGGCGACCTGATGCAGGTGGAGACCTGGTTCCAGAC
FATA1_CHK22  CCAGATGTACCGCTACCCGCGCTGGGGCGACCTGATGCAGGTGGAGACCTGGTTCCAGAC

FATA1_CHK80  GGCGGGCAAGCTGGGCGCGCAGCGCGAGTGGGTGCTGCGCGACAAGCTGACCGGCGAGGC
FATA1_CHK22  GGCGGGCAAGCTGGGCGCGCAGCGCGAGTGGGTGCTGCGCGACAAGCTGACCGGCGAGGC

FATA1_CHK80  GCTGGGCGCGGCCACCTCGAGCTGGGTCATGATCAACATCCGCACGCGCCGGCCGTGCCG
FATA1_CHK22  GCTGGGCGCGGCCACCTCGAGCTGGGTCATGATCAACATCCGCACGCGCCGGCCGTGCCG

FATA1_CHK80  CATGCCGGAGCTCGTCCGCGTCAAGTCGGCCTTCTTCGCGCGCGAGCCGCCGCGCCTGGC
FATA1_CHK22  CATGCCGGAGCTCGTCCGCGTCAAGTCGGCCTTCTTCGCGCGCGAGCCGCCGCGCCTGGC

FATA1_CHK80  GCTGCCGCCCGCGGTCACGCGTGCCAAGCTGCCCAACATCGCGACGCCGGCGCCGCTGCG
FATA1_CHK22  GCTGCCGCCCGCGGTCACGCGTGCCAAGCTGCCCAACATCGCGACGCCGGCGCCGCTGCG

FATA1_CHK80  CGGGCACCGCCAGGTCGCGCGCCGCACCGACATGGACATGAACGGGCACGTGAACAACGT
FATA1_CHK22  CGGGCACCGCCAGGTCGCGCGCCGCACCGACATGGACATGAACGGGCACGTGAACAACGT

FATA1_CHK80  GGCCTACCTGGCCTGGTGCCTGGAGGCCGTGCCCGAGCACGTCTTCAGCGACTACCACCT
FATA1_CHK22  GGCCTACCTGGCCTGGTGCCTGGAGGCCGTGCCCGAGCACGTCTTCAGCGACTACCACCT

FATA1_CHK80  CTACCAGATGGAGATCGACTTCAAGGCCGAGTGCCACGCGGGCGACGTCATCTCCTCCCA
FATA1_CHK22  CTACCAGATGGAGATCGACTTCAAGGCCGAGTGCCACGCGGGCGACGTCATCTCCTCCCA

FATA1_CHK80  GGCCGAGCAGATCCCGCCCCAGGAGGCGCTCACGCACAACGGCGCCGGCCGCAACCCCTC
FATA1_CHK22  GGCCGAGCAGATCCCGCCCCAGGAGGCGCTCACGCACAACGGCGCCGGCCGCAACCCCTC

FATA1_CHK80  CTGCTTCGTCCATAGCATTCTGCGCGCCGAGACCGAGCTCGTCCGCGCGCGAACCACATG
FATA1_CHK22  CTGCTTCGTCCATAGCATTCTGCGCGCCGAGACCGAGCTCGTCCGCGCGCGAACCACATG

FATA1_CHK80  GTCGGCCCCCATCGACGCGCCCGCCGCCAAGCCGCCCAAGGCGAGCCACTGAGGACAGGG
FATA1_CHK22  GTCGGCCCCCATCGACGCGCCCGCCGCCAAGCCGCCCAAGGCGAGCCACTGAGGACAGGG

FATA1_CHK80  TGGTTGGCTGGATGGGGAAACGCTGGTCGCGGGATTCGATCCTGCTGCTTATATCCTCCC
FATA1_CHK22  TGGTTGGCTGGATGGGGAAACGCTGGTCGCGGGATTCGATCCTGCTGCTTATATCCTCCC

FATA1_CHK80  TGGAAGCACACCCACGACTCTGAAGAAGAAAACGTGCACACACACAACCCCAACCGGCCGA
FATA1_CHK22  TGGAAGCACACCCACGACTCTGAAGAAGAAAACGTGCACACACACAACCCCAACCGGCCGA

FATA1_CHK80  ATATTTGCTTCCTTATCCCGGGTCCAAGAGAGACTGCGATGCCCCCCTCAATCAGCATCC
FATA1_CHK22  ATATTTGCTTCCTTATCCCGGGTCCAAGAGAGACTGCGATGCCCCCCTCAATCAGCATCC

FATA1_CHK80  TCCTCCCTGCCGCTTCAATCTTCCCTGCTTGCCTGCGCCCGCGGTGCGCCGTCTGCCCGC
FATA1_CHK22  TCCTCCCTGCCGCTTCAATCTTCCCTGCTTGCCTGCGCCCGCGGTGCGCCGTCTGCCCGC

FATA1_CHK80  CCAGTCAGTCACTCCTGCACAGGCCCCTTGTGCGCAGTGCTCCTGTACCCTTTACCGCTC
FATA1_CHK22  CCAGTCAGTCACTCCTGCACAGGCCCCTTGTGCGCAGTGCTCCTGTACCCTTTACCGCTC

FATA1_CHK80  CTTCCATTCTGCGAGGCCCCCTATTGAATGTATTCGTTGCCTGTGTGGCCAAGCGGGCTG
FATA1_CHK22  CTTCCATTCTGCGAGGCCCCCTATTGAATGTATTCGTTGCCTGTGTGGCCAAGCGGGCTG

FATA1_CHK80  CTGGGCGCGCCGCCGTCGGGCAGTGCTCGGCGACTTTGGCGGAAGCCGATTGTTCTTCTG
FATA1_CHK22  CTGGGCGCGCCGCCGTCGGGCAGTGCTCGGCGACTTTGGCGGAAGCCGATTGTTCTTCTG

FATA1_CHK80  TAAGCCACGCGCTTGCTGCTTTGGGAAGAGAAGGGGGG-GGTACTGAATGGATGAGGAGG
FATA1_CHK22  TAAGCCACGCGCTTGCTGCTTTGGGAAGAGAAGGGGGG-GGTACTGAATGGATGAGGAGG

FATA1_CHK80  AGAAGGAGGGTATTGGTATTATCTGAGTTGGGGAGGCAGggagagttggaaaatgtaag
FATA1_CHK22  AGAAGGAGGGTATTGGTATTATCTGAGTTGGGGAGGCAGggagagttggaaaatgtaag FATA1_CHK80  tggcacgacgggcaaggagaatggtgagcatgtgcatggtgatgtcgttggtcgaggacg
FATA1_CHK22  tggcacgacgggcaaggagaatggtgagcatgtgcatggtgatgtcgttggtcgaggacg
```

TABLE 12-continued

```
FATA1_CHK80  atcctgcacgcgtgtatctgatgtagaatacggcaatcaccctagtctacatctatacct
FATA1_CHK22  atcctgcacgcgtgtatctgatgtagaatacggcaatcaccctagtctacatctatacct

FATA1_CHK80  tctccgtataacgccctttccaaatgccctcccgtttctctcctattcttgatccacatg
FATA1_CHK22  tctccgtataacgccctttccaaatgccctcccgtttctctcctattcttgatccacatg FATA1_CHK80  atgaccctggcactatttcaagggctggacatttcaagaaggtttgcgtatctgaagaag
FATA1_CHK22  atgaccctggcactatttcaagggctggacatttcaagaaggtttgcgtatctgaagaag FATA1_CHK80  gattggtttggagaggtggccgatgaaagtggggtcaagctgcgtggagccctctgcacg
FATA1_CHK22  gattggtttggagaggtggccgatgaaagtggggtcaagctgcgtggagccctctgcacg FATA1_CHK80  gatttctatggtaatctgcgtccacgtcatcagtagccgtacgcctctgcggcgtcgccg
FATA1_CHK22  gatttctatggtaatctgcgtccacgtcatcagtagccgtacgcctctgcggcgtcgccg FATA1_CHK80  tgctcctcagccgccgcttcaccaccagccaggagccccatacgcacgcgctcccagacg
FATA1_CHK22  tgctcctcagccgccgcttcaccaccagccaggagccccatacgcacgcgctcccagacg FATA1_CHK80  gcgcgcgcgacggggacgatcatgagcagcgcgatctgggcgtgtcgtgcgagctgagc
FATA1_CHK22  gcgcgcgcgacggggacgatcatgagcagcgcgatctgggcgtgtcgtgcgagctgagc FATA1_CHK80  cgcacaaccacgttgccctggccgcgcgtggtgtactggcagttggtcgagaccatggtg
FATA1_CHK22  cgcacaaccacgttgccctggccgcgcgtggtgtactggcagttggtcgagaccatggtg FATA1_CHK80  tcggacttgaagtaggagccgtcaaagcgcgggaggcgcgtctcggccgagacgttgccg
FATA1_CHK22  tcggacttgaagtaggagccgtcaaagcgcgggaggcgcgtctcggccgagacgttgccg FATA1_CHK80  ccgatgaccaggctctggcgcttctggcgcgggtcgcggccctgccactgcgcggagccg
FATA1_CHK22  ccgatgaccaggctctggcgcttctggcgcgggtcgcggccctgccactgcgcggagccg FATA1_CHK80  cccaggagcaggcgcgactcgtcacggccgcgcagcttgacgtcggccgccagcgccgtg
FATA1_CHK22  cccaggagcaggcgcgactcgtcacggccgcgcagcttgacgtcggccgccagcgccgtg FATA1_CHK80  cccggctcgtaggccgaccccatcttgacgaagaggcggccgatcgctgcgcggaccttg
FATA1_CHK22  cccggctcgtaggccgaccccatcttgacgaagaggcggccgatcgctgcgcggaccttg FATA1_CHK80  accgcgtcggacaggcgcaggcgctcgtccagcttgaccccgagcgccgcgttgccgggc
FATA1_CHK22  accgcgtcggacaggcgcaggcgctcgtccagcttgaccccgagcgccgcgttgccgggc FATA1_CHK80  ttgaacggcagcgagaactcctcgcccagcttggagccgagcaggcccagcgccagcttc
FATA1_CHK22  ttgaacggcagcgagaactcctcgcccagcttggagccgagcaggcccagcgccagcttc FATA1_CHK80  tgccgcttgccgcgcgcgcgcaggcgcgagtcgacgcgcagcgtgtagag
FATA1_CHK22  tgccgcttgccgcgcgcgcgcaggcgcgagtcgacgcgcagcgtgtagag Thi4_CHK80   ttgcgattcctcttgacccagccacacgcataaattttaacgcaagctggcccaatatgg
(SEQ ID NO: 25)
Thi4_CHK22   ttgcgattcctcttgacccagccacacgcataaattttaacgcaagctggcccaatatgg
(SEQ ID NO: 26)

Thi4_CHK80   tatccgctgtgctcagaacagcaccctcgtgcaccctctggctctgaatctcaccgtcac
Thi4_CHK22   tatccgctgtgctcagaacagcaccctcgtgcaccctctggctctgaatctcaccgtcac Thi4_CHK80   ggtcatcctcctcctagcctgccagcgcttgggcgcagccatcgggcctgcatagagaaa
Thi4_CHK22   ggtcatcctcctcctagcctgccagcgcttgggcgcagccatcgggcctgcatagagaaa Thi4_CHK80   gggtacaaagcaacatatataaatacacgtggtattcataatactcgcgcatgtttgtct
Thi4_CHK22   gggtacaaagcaacatatataaatacacgtggtattcataatactcgcgcatgtttgtct Thi4_CHK80   tgcgcacgcatgcccacgctcgtcgacgcgctcacctctggccaggcagcccccttgcgg
Thi4_CHK22   tgcgcacgcatgcccacgctcgtcgacgcgctcacctctggccaggcagcccccttgcgg Thi4_CHK80   ggtcgcccgcagcgggcaccgcgaggcctgaggcgccaccagcagcatgtttgaattatt
Thi4_CHK22   ggtcgcccgcagcgggcaccgcgaggcctgaggcgccaccagcagcatgtttgaattatt Thi4_CHK80   tatacgcagttgtttgaggtacagagaaaccccttgtcattctcttcttgtgtgggggtgt
Thi4_CHK22   tatacgcagttgtttgaggtacagagaaaccccttgtcattctcttcttgtgtgggggtgt Thi4_CHK80   cgagtgccattgcagtggtctggccaccggcatatcggataagattgcctgcggatgtcg
Thi4_CHK22   cgagtgccattgcagtggtctggccaccggcatatcggataagattgcctgcggatgtcg Thi4_CHK80   ttcgtgccagcgtcatcggggcgagagtttataacgcgtgcccacgccagaagccctcac
Thi4_CHK22   ttcgtgccagcgtcatcggggcgagagtttataacgcgtgcccacgccagaagccctcac Thi4_CHK80   gctttgcacttggcgaggtacaaaaaaataccaaaccgcgtcctgaagcattatggcggcg
Thi4_CHK22   gctttgcacttggcgaggtacaaaaaaataccaaaccgcgtcctgaagcattatggcggcg Thi4_CHK80   aggacgaggctgttcaaggtgcggatcgcgaccttgagtgagagacgctccgatggtcgc
Thi4_CHK22   aggacgaggctgttcaaggtgcggatcgcgaccttgagtgagagacgctccgatggtcgc
```

TABLE 12-continued

```
Thi4_CHK80  ggccagaaccccagcgcccgtcaaaagccggtcctcacgccccagggctgagtgcgcgcc
Thi4_CHK22  ggccagaaccccagcgcccgtcaaaagccggtcctcacgccccagggctgagtgcgcgcc Thi4_CHK80  cgcaaaccccttttgcaggaactcaaggaggtggctcgatccaaggacaacaacggcatc
Thi4_CHK22  cgcaaaccccttttgcaggaactcaaggaggtggctcgatccaaggacaacaacggcatc Thi4_CHK80  gagctcattcccaatgactccaacatcttcctctggcgggcggtgattgaggcaaggggg
Thi4_CHK22  gagctcattcccaatgactccaacatcttcctctggcgggcggtgattgaggcaaggggg Thi4_CHK80  tctgcttcattgggtggagggagatgagttgtgtgcagggcgctcaaaggaggttttggt
Thi4_CHK22  tctgcttcattgggtggagggagatgagttgtgtgcagggcgctcaaaggaggttttggt Thi4_CHK80  cgcctattgcccaaggtcatgcatccgtgtgtatcccgtgcccctcccttcaacagggc
Thi4_CHK22  cgcctattgcccaaggtcatgcatccgtgtgtatcccgtgcccctcccttcaacagggc Thi4_CHK80  cccgcggactcgccctatcaggggggtcactttgaactcagcatccaagtgcctgagcag
Thi4_CHK22  cccgcggactcgccctatcaggggggtcactttgaactcagcatccaagtgcctgagcag Thi4_CHK80  tacccattggtcccgccgcaagtcaagttcaagaccaagctcttccacccgaacgtgcac
Thi4_CHK22  tacccattggtcccgccgcaagtcaagttcaagaccaagctcttccacccgaacgtgcac Thi4_CHK80  ttcaaggtgagctgtttggagacaaaggtggcagggagagtgctagcaagcaggggttga
Thi4_CHK22  ttcaaggtgagctgtttggagacaaaggtggcagggagagtgctagcaagcaggggttga Thi4_CHK80  cgggcgttgctgttgagttttgatgtatagactcggccgggaacttgagtggaagccgac
Thi4_CHK22  cgggcgttgctgttgagttttgatgtatagactcggccgggaacttgagtggaagccgac Thi4_CHK80  agacctttcatctgcctctctgcccatgcagacgggagagatctgcctcgacattctcaa
Thi4_CHK22  agacctttcatctgcctctctgcccatgcagacgggagagatctgcctcgacattctcaa Thi4_CHK80  gaacgcctggagcccagcttggacgctgcaggtacgattgtttggtttaggagaggcggc
Thi4_CHK22  gaacgcctggagcccagcttggacgctgcaggtacgattgtttggtttaggagaggcggc Thi4_CHK80  -cccttggtcgtccctggcactcacgactcttgggaaaatatgccgatctccgcattcc
Thi4_CHK22  ccccttggtcgtccctggcactcacgactcttgggaaaatatgccgatctccgcattcc Thi4_CHK80  tgtctccagacgcctgctctgtgcgcgctgtctcgatgaagcattcttttcctccccaat
Thi4_CHK22  tgtctccagacgcctgctctgtgcgcgctgtctcgatgaagcattcttttcctccccaat Thi4_CHK80  gcccgcagtcggtgtgccaggccatcgtggcgctcttgacagattctgcgccagactccc
Thi4_CHK22  gcccgcagtcggtgtgccaggccatcgtggcgctcttgacagattctgcgccagactccc Thi4_CHK80  CCCTCAACTGCGACGCTGGGAACCTTCTCCGGGCAGGCGATGTGCGTGGGTTTGCCTCCT
Thi4_CHK22  CCCTCAACTGCGACGCTGGGAACCTTCTCCGGGCAGGCGATGTGCGTGGGTTTGCCTCCT Thi4_CHK80  TGGCACGGCTCTACACCGTCGAGTACGCCATGAGGCGGTGATGGCTGTGTCGGTTGCCAC
Thi4_CHK22  TGGCACGGCTCTACACCGTCGAGTACGCCATGAGGCGGTGATGGCTGTGTCGGTTGCCAC Thi4_CHK80  TTCGTCCAGAGACGGCAAGTCGTCCATCCTCTGCGTGTGTGGCGCGACGCTGCAGCAGTC
Thi4_CHK22  TTCGTCCAGAGACGGCAAGTCGTCCATCCTCTGCGTGTGTGGCGCGACGCTGCAGCAGTC Thi4_CHK80  CCTCTGCAGCAGATGAGCGTGACTTTGGCCATTTCACGCACTCGAGTGTACACAATCCAT
Thi4_CHK22  CCTCTGCAGCAGATGAGCGTGACTTTGGCCATTTCACGCACTCGAGTGTACACAATCCAT Thi4_CHK80  TTTTCTTAAAGCAAATGACTGCTGATTGACCAGATACTGTAACGCTGATTTCGCTCCAGA
Thi4_CHK22  TTTTCTTAAAGCAAATGACTGCTGATTGACCAGATACTGTAACGCTGATTTCGCTCCAGA Thi4_CHK80  TCGCACAGATAGCGACCATGTTGCTGCGTCTGAAAATCTGGATTCCGAATTCGACCCTGG
Thi4_CHK22  TCGCACAGATAGCGACCATGTTGCTGCGTCTGAAAATCTGGATTCCGAATTCGACCCTGG Thi4_CHK80  CGCTCCATCCATGCAACAGATGGCGACACTTGTTACAATTCCTGTCACCCATCGGCATGG
Thi4_CHK22  CGCTCCATCCATGCAACAGATGGCGACACTTGTTACAATTCCTGTCACCCATCGGCATGG Thi4_CHK80  AGCAGGTCCACTTAGATTCCCGATCACCCACGCACATCTCGCTAATAGTCATTCGTTCGT
Thi4_CHK22  AGCAGGTCCACTTAGATTCCCGATCACCCACGCACATCTCGCTAATAGTCATTCGTTCGT Thi4_CHK80  GTCTTCGATCAATCTCAAGTGAGTGTGCATGGATCTTGGTTGACGATGCGGTATGGGTTT
Thi4_CHK22  GTCTTCGATCAATCTCAAGTGAGTGTGCATGGATCTTGGTTGACGATGCGGTATGGGTTT Thi4_CHK80  GCGCCGCTGGCTGCAGGGTCTGCCCAAGGCAAGCTAACCCAGCTCCTCTCCCCGACAATA
Thi4_CHK22  GCGCCGCTGGCTGCAGGGTCTGCCCAAGGCAAGCTAACCCAGCTCCTCTCCCCGACAATA Thi4_CHK80  CTCTCGCAGGCAAAGCCGGTCACTTGCCTTCCAGATTGCCAATAAACTCAATTATGGCCT
Thi4_CHK22  CTCTCGCAGGCAAAGCCGGTCACTTGCCTTCCAGATTGCCAATAAACTCAATTATGGCCT Thi4_CHK80  CTGTCATGCCATCCATGGGTCTGATGAATGGTCACGCTCGTGTCCTGACCGTTCCCCAGC
Thi4_CHK22  CTGTCATGCCATCCATGGGTCTGATGAATGGTCACGCTCGTGTCCTGACCGTTCCCCAGC
```

TABLE 12-continued

```
Thi4_CHK80  CTCTGGCGTCCCCTGCCCCGCCCACCAGCCCACGCCGCGCGGCAGTCGCTGCCAAGGCTG
Thi4_CHK22  CTCTGGCGTCCCCTGCCCCGCCCACCAGCCCACGCCGCGCGGCAGTCGCTGCCAAGGCTG

Thi4_CHK80  TCTCGGATGCCCAGCGCCATGCCACGCCCTTTGATGGCTTCAAGTACGATTACGGTGTTG
Thi4_CHK22  TCTCGGATGCCCAGCGCCATGCCACGCCCTTTGATGGCTTCAAGTACGATTACGGTGTTG

Thi4_CHK80  GATTGTGTGTTTGTTGCGTAGTGTGCATGGTTTAGAATAATACACTTGATTTCTTGCTCA
Thi4_CHK22  GATTGTGTGTTTGTTGCGTAGTGTGCATGGTTTAGAATAATACACTTGATTTCTTGCTCA

Thi4_CHK80  CGGCAATCTCGGCTTGTCCGCAGGTTCAACCCCATTTCGGAGTCTCAGGTCAGCCGCGCA
Thi4_CHK22  CGGCAATCTCGGCTTGTCCGCAGGTTCAACCCCATTTCGGAGTCTCAGGTCAGCCGCGCA

Thi4_CHK80  ATGACCAGCCGCTACTTCAAGGACTTGCACGACAACGCCGAGGTGAGCTATGTTTAGGAC
Thi4_CHK22  ATGACCAGCCGCTACTTCAAGGACTTGCACGACAACGCCGAGGTGAGCTATGTTTAGGAC

Thi4_CHK80  TTGATTGGAAATTGTCGTCGACGCATATTCGCGCTCCGCGACAGCACCCAAGCAAAATGT
Thi4_CHK22  TTGATTGGAAATTGTCGTCGACGCATATTCGCGCTCCGCGACAGCACCCAAGCAAAATGT

Thi4_CHK80  CAAGTGCGTTCCGATTTGCGTCCGCAGGTCGATGTTGTGATCGTCGGCGCCGGATCCGCC
Thi4_CHK22  CAAGTGCGTTCCGATTTGCGTCCGCAGGTCGATGTTGTGATCGTCGGCGCCGGATCCGCC

Thi4_CHK80  GGTCTGTCCTGCGCTTACGAGCTGACCAAGCACCCTGACGTCCGGGTACGCGAGCTGAGA
Thi4_CHK22  GGTCTGTCCTGCGCTTACGAGCTGACCAAGCACCCTGACGTCCGGGTACGCGAGCTGAGA

Thi4_CHK80  TTCGATTAGACATAAATTGAAGATTAAACCCGTAGAAAAATTTGATGGTCGCGAAACTGT
Thi4_CHK22  TTCGATTAGACATAAATTGAAGATTAAACCCGTAGAAAAATTTGATGGTCGCGAAACTGT

Thi4_CHK80  GCTCGATTGCAAGAAATTGATCGTCCTCCACTCCGCAGGTCGCCATCATCGAGCAGGGCG
Thi4_CHK22  GCTCGATTGCAAGAAATTGATCGTCCTCCACTCCGCAGGTCGCCATCATCGAGCAGGGCG

Thi4_CHK80  TTGCTCC-GGCGGCGGCGCCTGGCTGGGGGGACAGCTGTTCTCGGCCATGTGTGTACGTA
Thi4_CHK22  TTGCTCCCGGCGGCGGCGCCTGGCTGGGGGGACAGCTGTTCTCGGCCATGTGTGTACGTA

Thi4_CHK80  GAAGGATGAATTTCAGCTGGTTTTCGTTGCACAGCTGTTTGTGCATGATTTGTTTCAGAC
Thi4_CHK22  GAAGGATGAATTTCAGCTGGTTTTCGTTGCACAGCTGTTTGTGCATGATTTGTTTCAGAC

Thi4_CHK80  TATTGTTGAATGTTTTTAGATTTCTTAGGATGCATGATTTGTCTGCATGCGACTtttagc
Thi4_CHK22  TATTGTTGAATGTTTTTAGATTTCTTAGGATGCATGATTTGTCTGCATGCGACTtttagc Thi4_CHK80  tagcacccttacacaccatccaacatcttgctgccttgcctcccctgcgcagatccgcaa
Thi4_CHK22  tagcacccttacacaccatccaacatcttgctgccttgcctcccctgcgcagatccgcaa Thi4_CHK80  gccggcgcacaagctgatggacgagctcaacatcccttacgacgacgaggtgggtattgg
Thi4_CHK22  gccggcgcacaagctgatggacgagctcaacatcccttacgacgacgaggtgggtattgg Thi4_CHK80  gcagctagaacgcatgcgtgctgtgcgactgggtcgatccattgtgcgaaacgtgtggcg
Thi4_CHK22  gcagctagaacgcatgcgtgctgtgcgactgggtcgatccattgtgcgaaacgtgtggcg Thi4_CHK80  gaatacgtgcgcgtccccggccatgcaccgaccccccctcccaccacccccacaaatataa
Thi4_CHK22  gaatacgtgcgcgtccccggccatgcaccgaccccccctcccaccacccccacaaatataa Thi4_CHK80  cagggtgacatggtggtggtcaagcacgccgccctggtgacgtccacgctgctgtccaag
Thi4_CHK22  cagggtgacatggtggtggtcaagcacgccgccctggtgacgtccacgctgctgtccaag Thi4_CHK80  gtgctggcggcccccaacatcaagcttttcaacgccaccgcggcggaggacctgatcgtc
Thi4_CHK22  gtgctggcggcccccaacatcaagcttttcaacgccaccgcggcggaggacctgatcgtc Thi4_CHK80  aagtccaagccggccggcggggcggccgtcccgcacgtggccggggccgtgaccaactgg
Thi4_CHK22  aagtccaagccggccggcggggcggccgtcccgcacgtggccggggccgtgaccaactgg Thi4_CHK80  accctggtgtccctcaaccacgacacccagatgtgcatggaccccaacaccatcctgagc
Thi4_CHK22  accctggtgtccctcaaccacgacacccagatgtgcatggaccccaacaccatcctgagc Thi4_CHK80  aaggtcatggtctcctccaccggccacgacggccccatgggcgcctccggggtcaagcgc
Thi4_CHK22  aaggtcatggtctcctccaccggccacgacggccccatgggcgcctccggggtcaagcgc Thi4_CHK80  ctggccaagctgggcctgatcgagcgcgcgccgggcatgggcgcgctggacatgaacagc
Thi4_CHK22  ctggccaagctgggcctgatcgagcgcgcgccgggcatgggcgcgctggacatgaacagc Thi4_CHK80  gccgaggacgcggtggtcgaccggacgcgggagatcgtccctggcatggtcatctgcggc
Thi4_CHK22  gccgaggacgcggtggtcgaccggacgcgggagatcgtccctggcatggtcatctgcggc Thi4_CHK80  atggaggtcgccgagctggacgggtgcccgcgcatgggcccccacctttggcgccatgttt
Thi4_CHK22  atggaggtcgccgagctggacgggtgcccgcgcatgggcccccacctttggcgccatgttt Thi4_CHK80  gtgtccggggtcaaggccgcgcacgtggccctggcctcgctgcgccgccagcaggaggag
Thi4_CHK22  gtgtccggggtcaaggccgcgcacgtggccctggcctcgctgcgccgccagcaggaggag
```

TABLE 12-continued

```
Thi4_CHK80  gaggggctccgcgccaagaccgcagacaccctgcgcagcgcggcgccgtccatggccatg
Thi4_CHK22  gaggggctccgcgccaagaccgcagacaccctgcgcagcgcggcgccgtccatggccatg Thi4_CHK80  gcgtgacctggtgatccccaagagggcggacatgcgtcgcgtctccctccggtgcccaga
Thi4_CHK22  gcgtgacctggtgatccccaagagggcggacatgcgtcgcgtctccctccggtgcccaga Thi4_CHK80  gatctgttccacggttgtctgcgatgcttttcaaaactgttatttcactaaaatgactcga
Thi4_CHK22  gatctgttccacggttgtctgcgatgcttttcaaaactgttatttcactaaaatgactcga Thi4_CHK80  ttctcctctaaaaaaaacatgatgttgatagtatctccacaaaagcatggcgactcagat
Thi4_CHK22  ttctcctctaaaaaaaacatgatgttgatagtatctccacaaaagcatggcgactcagat Thi4_CHK80  gcctctactgcactgtactcaagaatacaactctggagacccgggtcccgttcccatttg
Thi4_CHK22  gcctctactgcactgtactcaagaatacaactctggagacccgggtcccgttcccatttg Thi4_CHK80  gcgccgaatgttgatgcgccacttttgctggccatgcctgaggtattctgtacaaaagaa
Thi4_CHK22  gcgccgaatgttgatgcgccacttttgctggccatgcctgaggtattctgtacaaaagaa Thi4_CHK80  ggagcggccaatgcgggttttcaagcagacggcgcgctggggcctggaaatcaaaaggcg
Thi4_CHK22  ggagcggccaatgcgggttttcaagcagacggcgcgctggggcctggaaatcaaaaggcg Thi4_CHK80  gtagtacacgggagagagtcggattgatgatgagggatttaaaaaaggccaggcagtgag
Thi4_CHK22  gtagtacacgggagagagtcggattgatgatgagggatttaaaaaaggccaggcagtgag Thi4_CHK80  gtgagagttgtacgattgttgccccaggattgccttttttaggggggacggccaggggcg
Thi4_CHK22  gtgagagttgtacgattgttgccccaggattgccttttttaggggggacggccaggggcg Thi4_CHK80  cagttattggggcaccgcacatatagatccgcgcaagcaaatggcctcgagagcaggcgc
Thi4_CHK22  cagttattggggcaccgcacatatagatccgcgcaagcaaatggcctcgagagcaggcgc Thi4_CHK80  gatggttaagaaaggaaggacgagtagcggatgacgtgatactgcatacgaagaacgtac
Thi4_CHK22  gatggttaagaaaggaaggacgagtagcggatgacgtgatactgcatacgaagaacgtac Thi4_CHK80  tagtgaggagagtgcttgaaacaacatatgatgctgcccccctctctgccaac
Thi4_CHK22  tagtgaggagagtgcttgaaacaacatatgatgctgcccccctctctgccaac
```

Key:
Background DNA flanking homology arm recognition site: lowercase, non-bold
Homology arm recognition site: CAPITALIZED, NON-BOLD
Genomic region of interest between recognition sites: CAPITAL, BOLD
SNP difference: underlined a c g t TABLE 13 shows genetic sequences of selectable markers that can be used to generate genetically modified microalgae. The classically improved microalgal strains provided herein do not comprises any of these exogenous sequences. *Saccharomyces cerevisiae* suc2 (ScSUC2) encodes for sucrose invertase, which allows for selection of strains that grow on sucrose media. *Saccharomyces carlbergenesis* MEL1 (ScarMEL) encodes for alpha-galactosidase (melibiase), which allows for selection of strains that grow on melibiose media. *Arabidopsis thaliana* ThiC (AtTHIC) encodes for phosphomethylpyrimidine synthase, an enzyme involved in pyrimidine synthesis in the thiamine biosynthesis pathway.

TABLE 13

| | |
|---|---|
| *S. cerevisiae* suc2 sucrose invertase (ScSUC2) (SEQ ID NO: 27) | ATGCTGCTGCAGGCCTTCCTGTTCCTGCTGGCCGGCTTCGCCGCCAAGATCAGCGC<br>CTCCATGACGAACGAGACGTCCGACCGCCCCCTGGTGCACTTCACCCCCAACAAGG<br>GCTGGATGAACGACCCCAACGGCCTGTGGTACGACGAGAAGGACGCCAAGTGGCAC<br>CTGTACTTCCAGTACAACCCGAACGACACCGTCTGGGGGACGCCCTTGTTCTGGGG<br>CCACGCCACGTCCGACGACCTGACCAACTGGGAGGACCAGCCCATCGCCATCGCCC<br>CGAAGCGCAACGACTCCGGCGCCTTCTCCGGCTCCATGGTGGTGGACTACAACAAC<br>ACCTCCGGCTTCTTCAACGACACCATCGACCCGCGCCAGCGCTGCGTGGCCATCTG<br>GACCTACAACACCCCGGAGTCCGAGGAGCAGTACATCTCCTACAGCCTGGACGGCG<br>GCTACACCTTCACCGAGTACCAGAAGAACCCCGTGCTGGCCGCCAACTCCACCCAG<br>TTCCGCGACCCGAAGGTCTTCTGGTACGAGCCCTCCCAGAAGTGGATCATGACCGC<br>GGCCAAGTCCCAGGACTACAAGATCGAGATCTACTCCTCCGACGACCTGAAGTCCT<br>GGAAGCTGGAGTCCGCGTTCGCCAACGAGGGCTTCCTCGGCTACCAGTACGAGTGC<br>CCCGGCCTGATCGAGGTCCCCACCGAGCAGGACCCCAGCAAGTCCTACTGGGTGAT<br>GTTCATCTCCATCAACCCCGGCGCCCCGGCCGGCGGCTCCTTCAACCAGTACTTCG<br>TCGGCAGCTTCAACGGCACCCACTTCGAGGCCTTCGACAACCAGTCCCGCGTGGTG<br>GACTTCGGCAAGGACTACTACGCCCTGCAGACCTTCTTCAACACCGACCCGACCTA<br>CGGGAGCGCCCTGGGCATCGCGTGGGCCTCCAACTGGGAGTACTCCGCCTTCGTGC<br>CCACCAACCCCTGGCGCTCCTCCATGTCCCTCGTGCGCAAGTTCTCCCTCAACACC<br>GAGTACCAGGCCAACCCGGAGACGGAGCTGATCAACCTGAAGGCCGAGCCGATCCT<br>GAACATCAGCAACGCCGGCCCCTGGAGCCGGTTCGCCACCAACACCACGTTGACGA<br>AGGCCAACAGCTACAACGTCGACCTGTCCAACAGCACCGGCACCCTGGAGTTCGAG<br>CTGGTGTACGCCGTCAACACCACCCAGACGATCTCCAAGTCCGTGTTCGCGGACCT<br>CTCCCTCTGGTTCAAGGGCCTGGAGGACCCCGAGGAGTACCTCCGCATGGGCTTCG<br>AGGTGTCCGCGTCCTCCTTCTTCCTGGACCGCGGGAACAGCAAGGTGAAGTTCGTG |

TABLE 13-continued

| | |
|---|---|
| | AAGGAGAACCCCTACTTCACCAACCGCATGAGCGTGAACAACCAGCCCTTCAAGAG<br>CGAGAACGACCTGTCCTACTACAAGGTGTACGGCTTGCTGGACCAGAACATCCTGG<br>AGCTGTACTTCAACGACGGCGACGTCGTGTCCACCAACACCTACTTCATGACCACC<br>GGGAACGCCCTGGGCTCCGTGAACATGACGACGGGGGTGGACAACCTGTTCTACAT<br>CGACAAGTTCCAGGTGCGCGAGGTCAAGTGA |
| S. carlbergenesis MEL 1 alpha galactosidase or melibiase (ScarMEL) (SEQ ID NO: 28) | ATGTTCGCGTTCTACTTCCTGACGGCCTGCATCTCCCTGAAGGGCGTGTTCGGCGT<br>CTCCCCCTCCTACAACGGCCTGGGCCTGACGCCCCAGATGGGCTGGGACAACTGGA<br>ACACGTTCGCCTGCGACGTCTCCGAGCAGCTGCTGCTGGACACGGCCGACCGCATC<br>TCCGACCTGGGCCTGAAGGACATGGGCTACAAGTACATCATCCTGGACGACTGCTG<br>GTCCTCCGGCCGCGACTCCGACGGCTTCCTGGTCGCCGACGAGCAGAAGTTCCCCA<br>ACGGCATGGGCCACGTCGCCGACCACCTGCACAACAACTCCTTCCTGTTCGGCATG<br>TACTCCTCCGCGGGCGAGTACACGTGCGCCGGCTACCCCGGCTCCCTGGGCCGCGA<br>GGAGGAGGACGCCCAGTTCTTCGCGAACAACCGCGTGGACTACCTGAAGTACGACA<br>ACTGCTACAACAAGGGCCAGTTCGGCACGCCCGAGATCTCCTACCACCGCTACAAG<br>GCCATGTCCGACGCCCTGAACAAGACGGGCCGCCCCATCTTCTACTCCCTGTGCAA<br>CTGGGGCCAGGACCTGACCTTCTACTGGGGCTCCGGCATCGCGAACTCCTGGCGCA<br>TGTCCGGCGACGTCACGGCGGAGTTCACGCGCCCCGACTCCCGCTGCCCCTGCGAC<br>GGCGACGAGTACGACTGCAAGTACGCCGGCTTCCACTGCTCCATCATGAACATCCT<br>GAACAAGGCCGCCCCCATGGGCCAGAACGCGGGCGTCGGCGGCTGGAACGACCTGG<br>ACAACCTGGAGGTCGGCGTCGGCAACCTGACGGACGACGAGGAGAAGGCGCACTTC<br>TCCATGTGGGCCATGGTGAAGTCCCCCCTGATCATCGGCGCGAACGTGAACAACCT<br>GAAGGCCTCCTCCTACTCCATCTACTCCCAGGCGTCCGTCATCGCCATCAACCAGG<br>ACTCCAACGGCATCCCCGCCACGCGCGTCTGGCGCTACTACGTGTCCGACACGGAC<br>GAGTACGGCCAGGGCGAGATCAGATGTGGTCCGGCCCCCTGGACAACGGCGACCA<br>GGTCGTGGCGCTGCTGAACGGCGGCTCCGTGTCCCGCCCCATGAACACGACCCTGG<br>AGGAGATCTTCTTCGACTCCAACCTGGGCTCCAAGAAGCTGACCTCCACCTGGGAC<br>ATCTACGACCTGTGGGCGAACCGCGTCGACAACTCCACGGCGTCCGCCATCCTGGG<br>CCGCAACAAGACCGCCACCGGCATCCTGTACAACGCCACCGAGCAGTCCTACAAGG<br>ACGGCCTGTCCAAGAACGACACCCGCCTGTTCGGCCAGAAGATCGGCTCCCTGTCC<br>CCCAACGCGATCCTGAACACGACCGTCCCCGCCCACGGCATCGCGTTCTACCGCCT<br>GCGCCCCTCCTCCTGA |
| A. thaliana ThiC (AtTHIC) (SEQ ID NO: 29) | ATGGCCGCGTCCGTCCACTGCACCCTGATGTCCGTGGTCTGCAACAACAAGAACCA<br>CTCCGCCCGCCCCAAGCTGCCCAACTCCTCCCTGCTGCCCGGCTTCGACGTGGTGG<br>TCCAGGCCGCGGCCACCCGCTTCAAGAAGGAGACGACGACCACCCGCGCCACGCTG<br>ACGTTCGACCCCCCCACGACCAACTCCGAGCGCGCCAAGCAGCGCAAGCACACCAT<br>CGACCCCTCCTCCCCCGACTTCCAGCCCATCCCCTCCTTCGAGGAGTGCTTCCCCA<br>AGTCCACGAAGGAGCACAAGGAGGTGGTGCACGAGGAGTCCGGCCACGTCCTGAAG<br>GTGCCCTTCCGCCGCGTGCACCTGTCCGGCGGCGAGCCCGCCTTCGACAACTACGA<br>CACGTCCGGCCCCCAGAACGTCAACGCCCACATCGGCCTGGCGAAGCTGCGCAAGG<br>AGTGGATCGACCGCCGCGAGAAGCTGGGCACGCCCCGCTACACGCAGATGTACTAC<br>GCGAAGCAGGGCATCATCACGGAGGAGATGCTGTACTGCGCGACGCGCGAGAAGCT<br>GGACCCCGAGTTCGTCCGCTCCGAGGTCGCGCGGGGCCGCGCCATCATCCCCTCCA<br>ACAAGAAGCACCTGGAGCTGGAGCCCATGATCGTGGGCCGCAAGTTCCTGGTGAAG<br>GTGAACGCGAACATCGGCAACTCCGCCGTGGCCTCCTCCATCGAGGAGGAGGTCTA<br>CAAGGTGCAGTGGGCCACCATGTGGGGCGCCGACACCATCATGGACCTGTCCACGG<br>GCCGCCACATCCACGAGACGCGCGAGTGGATCCTGCGCAACTCCGCGGTCCCCGTG<br>GGCACCGTCCCCATCTACCAGGCGCTGGAGAAGGTGGACGGCATCGCGGAGAACCT<br>GAACTGGGAGGTGTTCCGCGAGACGCTGATCGAGCAGGCCGAGCAGGGCGTGGACT<br>ACTTCACGATCCACGCGGGCGTGCTGCTGCGCTACATCCCCCTGACCGCCAAGCGC<br>CTGACGGGCATCGTGTCCCGCGGCGGCTCCATCCACGCGAAGTGGTGCCTGGCCTA<br>CCACAAGGAGAACTTCGCCTACGAGCACTGGGACGACATCCTGGACATCTGCAACC<br>AGTACGACGTCGCCCTGTCCATCGGCGACGGCCTGCGCCCCGGCTCCATCTACGAC<br>GCCAACGACACGGCCCAGTTCGCCGAGCTGCTGACCCAGGGCGAGCTGACGCGCCG<br>CGCGTGGGAGAAGGACGTGCAGGTGATGAACGAGGGCCCCGGCCACGTGCCCATGC<br>ACAAGATCCCCGAGAACATGCAGAAGCAGCTGGAGTGGTGCAACGAGGCGCCCTTC<br>TACACCCTGGGCCCCCTGACGACCGACATCGCGCCCGGCTACGACCACATCACCTC<br>CGCCATCGGCGCGGCCAACATCGGCGCCCTGGGCACCGCCCTGCTGTGCTACGTGA<br>CGCCCAAGGAGCACCTGGGCCTGCCCAACCGCGACGACGTGAAGGCGGGCGTCATC<br>GCCTACAAGATCGCCGCCCACGCGGCCGACCTGGCCAAGCAGCACCCCCACGCCCA<br>GGCGTGGGACGACGCGCTGTCCAAGGCGCGCTTCGAGTTCCGCTGGATGGACCAGT<br>TCGCGCTGTCCCTGGACCCCATGACGGCGATGTCCTTCCACGACGGACGCTGCCC<br>GCGGACGGCGCGAAGGTCGCCCACTTCTGCTCCATGTGCGGCCCCAAGTTCTGCTC<br>CATGAAGATCACGGAGGACATCCGCAAGTACGCCGAGGAGAACGGCTACGGCTCCG<br>CCGAGGAGGCCATCCGCCAGGGCATGGACGCCATGTCCGAGGAGTTCAACATGCC<br>AAGAAGACGATCTCCGGCGAGCAGCACGGCGAGGTCGGCGGCGAGATCTACCTGCC<br>CGAGTCCTACGTCAAGGCCGCGCAGAAGTGA |

Example 9. Characterization of High Oleic Acid Triglyceride Oils Produced by Classically Improved Microalgal Strains The sterol and triterpene alcohol compositions of high oleic refined, bleached, and deodorized (RBD) triglyceride oils of the disclosure were determined using gas chromatography combined with mass spectrometry and flame ionization detection. Samples were prepared using the technique described in the German standardized method F-III for sterols in fats and oils from Aitzetmüller, et al. (1998), *Analysis of sterol content and composition in fats and oils by capillary-gas liquid chromatography using an internal standard. Comments on the German sterol method*. Fett/Lipid, 100: 429-435, which is incorporated herein by reference in its entirety. After addition of an internal standard, the oils were saponified. The unsaponifiable fractions were isolated using solid-phase extraction. Trimethylsilyl (TMS) derivatives of the unsaponifiable fraction were injected on an Agilent 8890 gas chromatograph equipped with a 5977B single quadrupole EI-MS and FID detector. A capillary flow technology (CFT) splitter was used to split the sample between the MS and FID detectors following separation using a DB-5MS Ultra Inert column (60 m length×0.25 mm inner diameter X 0.25 µm film thickness). Mass spectra data, in conjunction with retention time comparison with analytical standards, if available, were used to identify each of the sterol species. Quantification was based on the FID response of the sterol TMS ethers compared to that of the internal standard.

The resulting sterol profiles are shown in TABLE 14. Amounts are shown as mg/100 g of the oil and as approximate percentages of total detected sterols. Minor unidentified peaks were not accounted for. Not all sterols were identifiable and are listed as unknown. Ergosterol was the main sterol present in both oils. Various other sterols were present in the high oleic oils in significant amounts, including ergosta-5,8-dien-3-ol, (3β)- and 5.xi.-ergost-7-en-3(3-ol, (3β). Campesterol, stigmasterol, and β-sitosterol were not detected in either oils.

TABLE 14

Sterol and triterpene alcohol composition (mg/100 g and %)

| RBD Oil Strain | CHK74 | CHK80 |
|---|---|---|
| Brassicasterol (Ergosta-5,22-dien-3β-ol) | ND (0%) | ND (0%) |
| Ergosta-5,7,9(11),22-tetraen-3-ol,(3β,22E) | ND (0%) | ND (0%) |
| Ergosta-7,22-dien-3-ol, (3β,22E) | ND (0%) | ND (0%) |
| Unknown | ND (0%) | ND (0%) |
| Ergosterol | 118.7 (48%) | 166.1 (60%) |
| Campesterol | ND (0%) | ND (0%) |
| Ergost-8(14)-en-3-ol, (3β) | ND (0%) | ND (0%) |
| Stigmasterol | ND (0%) | ND (0%) |
| Unknown (MS similar to Ergost-8(14)-en-3-ol, (3β)) | 6.9 (3%) | 7.2 (3%) |
| Ergosta-5,8-dien-3-ol, (3β) | 13.5 (5%) | 18.7 (7%) |
| 5.Xi.-Ergost-7-en-3β-ol | 30.4 (12%) | 32.0 (11%) |
| β-Sitosterol | ND (0%) | ND (0%) |
| 9,19-Cyclolanost-24-en-3-ol, (3β) | 60.6 (24%) | 36.1 (13%) |
| 9,19-Cyclolanostan-3-ol, 24-methylene-, (3β) | 11.4 (5%) | 10.9 (4%) |
| Unknown | 7.9 (3%) | 7.8 (3%) |
| TOTAL | 249.4 (100%) | 278.8 (100%) |

ND, not detectable.

TABLE 15 shows fatty acid profiles of a TAG oil produced by strains CHK74 and CHK80. Values are in percentages of total detected fatty acids.

TABLE 15

| Fatty Acid Species | CHK74 | CHK80 |
|---|---|---|
| Titer (g/L) | 143.7 | 148.5 |
| C12:0 | 0 | 0 |
| C14:0 | 0.2 | 0.18 |
| C14:1 | 0 | 0 |
| C15:0 | 0.01 | 0.01 |
| C16:0 | 3.83 | 3.9 |
| C16:1 | 0.17 | 0.14 |
| C17:0 | 0.02 | 0.02 |
| C17:1 | 0.02 | 0.02 |
| C18:0 | 2.11 | 2.51 |
| C18:1 | 85.91 | 86.35 |
| C18:2 | 6.14 | 5.09 |
| C18:3 alpha | 0.14 | 0.16 |

TABLE 15-continued

| Fatty Acid Species | CHK74 | CHK80 |
|---|---|---|
| C20:0 | 0.15 | 0.22 |
| C20:1 | 0.98 | 0.90 |
| C22:0 | 0.03 | 0.05 |
| 12-OH—C18:1 | 0.11 | 0.09 |
| C24:0 | 0.01 | 0.02 |
| TOTAL | 99.83 | 99.84 |

TAG analysis was carried out utilizing Liquid Chromatography/Time of Flight-Mass Spectrometry (LC/TOF-MS), where fractionation of TAG species is carried out on a C18 column followed by interrogation of individual peaks on a TOF LC-MS equipped with an Atmospheric Pressure Chemical Ionization (APCI) source. LC TAG standards from NuChek and samples were run on a Shimadzu Shimpack XR-ODS III 2.2 micron, 2.0×200 mm column and confirmed by MS on an Agilent TOF LC-MS equipped with an APCI ionization source utilizing a method from Neff, et al. (1995), *Soybean Oil Triacylglycerol Analysis by Reversed-Phase High-Performance Liquid Chromatography Coupled with Atmospheric Pressure Chemical Ionization Mass Spectrometry*, JAOCS, 72: 1185-1191, which is incorporated herein by reference in its entirety. TABLE 16 shows TAG profiles of a TAG oil produced by strains CHK74 and CHK80. Values are in percentages of total detected TAG species.

TABLE 16

| TAG Species | CHK74 | CHK80 |
|---|---|---|
| LOL | 1.54 | 1.26 |
| OOLn | 0.36 | 0.38 |
| LLP | 0.24 | 0.12 |
| OOL | 12.71 | 11.21 |
| POL | 1.67 | 1.28 |
| OOM | 0.66 | 0.45 |
| LOG | 0.14 | 0.14 |
| OOO | 60.73 | 63.19 |
| SOL | 0.90 | 0.50 |
| OOP | 10.59 | 9.15 |
| POP | 0.58 | 0.44 |
| OOG | 1.03 | 2.22 |
| OOS | 4.45 | 5.54 |
| POS | 0.34 | 0.28 |
| OOA | 0.42 | 0.45 |
| OOB | 0.07 | 0.06 |
| TOTAL | 96.43 | 96.67 |

EMBODIMENTS

Embodiment A1. A non-naturally occurring oil comprising a triacylglyceride (TAG) component and ergosterol, wherein the TAG component has a fatty acid content comprising 80% or more C18:1 fatty acids.

Embodiment A2. The non-naturally occurring oil of embodiment A1, wherein the C18:1 fatty acids comprise oleic acid.

Embodiment A3. The non-naturally occurring oil of embodiment A1 or A2, wherein the C18:1 fatty acids comprise at least 90% of oleic acid.

Embodiment A4. The non-naturally occurring oil of any one of embodiments A1-A3, wherein the fatty acid content of the TAG component comprises more than 85% of C18:1 fatty acids.

Embodiment A5. The non-naturally occurring oil of any one of embodiments A1-A4, wherein the fatty acid content of the TAG component comprises one or more of C14:0, C16:0, C18:2, C18:3, C20:0, or C20:1 fatty acids.

Embodiment A6. The non-naturally occurring oil of any one of embodiments A1-A5, wherein the fatty acid content of the TAG component comprises C16:0 and C18:2 fatty acids.

Embodiment A7. The non-naturally occurring oil of any one of embodiments A1-A6, wherein the fatty acid content of the TAG component comprises 2% or more of C16:0 fatty acids.

Embodiment A8. The non-naturally occurring oil of any one of embodiments A1-A7, wherein the fatty acid content of the TAG component comprises more than 2% of C16:0 fatty acids.

Embodiment A9. The non-naturally occurring oil of any one of embodiments A1-A8, wherein the fatty acid content of the TAG component comprises 1.5% or more of C18:0 fatty acids.

Embodiment A10. The non-naturally occurring oil of any one of embodiments A1-A9, wherein the fatty acid content of the TAG component comprises 2% or more of C18:0 fatty acids.

Embodiment A11. The non-naturally occurring oil of any one of embodiments A1-A10, wherein the fatty acid content of the TAG component comprises less than 3% of C18:0 fatty acids.

Embodiment A12. The non-naturally occurring oil of any one of embodiments A1-A11, wherein the fatty acid content of the TAG component comprises 2% or more of C18:2 fatty acids.

Embodiment A13. The non-naturally occurring oil of any one of embodiments A1-A12, wherein the fatty acid content of the TAG component comprises 5% or more of C18:2 fatty acids.

Embodiment A14. The non-naturally occurring oil of any one of embodiments A1-A13, wherein the fatty acid content of the TAG component comprises 6% or more of C18:2 fatty acids.

Embodiment A15. The non-naturally occurring oil of any one of embodiments A1-A14, wherein the fatty acid content of the TAG component comprises less than 1% of C20:1 fatty acids.

Embodiment A16. The non-naturally occurring oil of any one of embodiments A1-A15, wherein the non-naturally occurring oil comprises one or more of brassicasterol, campesterol, stigmasterol, β-sitosterol, delta-5-avenasterol, cycloartenol, or ergosterol.

Embodiment A17. The non-naturally occurring oil of any one of embodiments A1-A16, wherein the non-naturally occurring oil comprises brassicasterol, cycloartenol, and ergosterol.

Embodiment A18. The non-naturally occurring oil of any one of embodiments A1-A17, wherein the non-naturally occurring oil comprises more than 50 mg of ergosterol per 100 g of the non-naturally occurring oil.

Embodiment A19. The non-naturally occurring oil of any one of embodiments A1-A18, wherein the non-naturally occurring oil comprises more than 100 mg of ergosterol per 100 g of the non-naturally occurring oil.

Embodiment A20. The non-naturally occurring oil of any one of embodiments A1-A19, wherein the non-naturally occurring oil comprises more than 150 mg of ergosterol per 100 g of the non-naturally occurring oil.

Embodiment A21. The non-naturally occurring oil of any one of embodiments A1-A20, wherein the non-naturally occurring oil comprises less than 10 mg of cycloartenol per 100 g of the non-naturally occurring oil.

Embodiment A22. The non-naturally occurring oil of any one of embodiments A1-A21, wherein the non-naturally occurring oil comprises more than 5 mg of brassicasterol per 100 g of the non-naturally occurring oil.

Embodiment A23. The non-naturally occurring oil of any one of embodiments A1-A22, wherein the non-naturally occurring oil comprises more than 10 mg of brassicasterol per 100 g of the non-naturally occurring oil.

Embodiment A24. The non-naturally occurring oil of any one of embodiments A1-A23, wherein the non-naturally occurring oil comprises more than 10 mg of stigmasterol per 100 g of the non-naturally occurring oil.

Embodiment A25. The non-naturally occurring oil of any one of embodiments A1-A24, wherein the non-naturally occurring oil comprises less than 30 mg of β-sitosterol per 100 g of the non-naturally occurring oil.

Embodiment A26. A formulation comprising the non-naturally occurring oil of any one of embodiments A1-A25; and one or more excipients.

Embodiment A27. The formulation of embodiment A26, wherein the formulation is a polyol formulation.

Embodiment A28. The formulation of embodiment A26, wherein the formulation is a polyurethane formulation.

Embodiment A29. The formulation of embodiment A26, wherein the formulation is a polyurethane foam.

Embodiment A30. The formulation of embodiment A29, wherein the formulation is a polyurethane hard foam.

Embodiment A31. The formulation of embodiment A29, wherein the formulation is a polyurethane soft foam.

Embodiment A32. The formulation of embodiment A26, wherein the formulation is a cast polyurethane formulation.

Embodiment A33. The formulation of embodiment A26, wherein the formulation is a polyurethane dispersion.

Embodiment A34. The formulation of embodiment A26, wherein the formulation is a sporting goods equipment.

Embodiment A35. The formulation of embodiment A26, wherein the formulation is a personal care product.

Embodiment A36. The formulation of embodiment A35, wherein the personal care product is a cosmetic.

Embodiment A37. The formulation of embodiment A35, wherein the personal care product is a soap.

Embodiment A38. The formulation of embodiment A35, wherein the personal care product is an emollient.

Embodiment A39. The formulation of embodiment A35, wherein the personal care product is a hair care product.

Embodiment A40. The formulation of embodiment A35, wherein the personal care product is a skin care product.

Embodiment A41. The formulation of embodiment A26, wherein the formulation is a food product.

Embodiment A42. The formulation of embodiment A41, wherein the food product is a condiment.

Embodiment A43. The formulation of embodiment A41, wherein the food product is a nutritional supplement.

Embodiment A44. The formulation of embodiment A43, wherein the nutritional supplement is an infant formula.

Embodiment A45. The formulation of embodiment A41, wherein the food product is a food additive.

Embodiment A46. The formulation of embodiment A41, wherein the food additive is a flavoring agent.

Embodiment A47. The formulation of embodiment A41, wherein the food product is a beverage.

Embodiment A48. An oleaginous, non-naturally occurring microorganism that produces the non-naturally occurring oil of any one of embodiments A1-A25.

Embodiment A49. The oleaginous, non-naturally occurring microorganism of embodiment A48, wherein the microorganism is a microalgae.

Embodiment A50. The oleaginous, non-naturally occurring microorganism of embodiment A48 or A49, wherein the microalgae is of the genus Prototheca.

Embodiment A51. The oleaginous, non-naturally occurring microorganism of any one of embodiments A48-A50, wherein the microorganism does not comprise an exogenous gene.

Embodiment A52. The oleaginous, non-naturally occurring microorganism of any one of embodiments A48-A50, wherein the microorganism does not comprise an exogenous gene encoding an active ketoacyl-ACP synthase.

Embodiment A53. A bioreactor comprising the oleaginous, non-naturally occurring microorganism of any one of embodiments A48-A52.

Embodiment A54. A method for producing a non-naturally occurring oil, the method comprising: culturing in a bioreactor the oleaginous, non-naturally occurring microorganism of any one of embodiments A48-A52, thereby producing the non-naturally occurring oil.

Embodiment A55. The method of embodiment A54, wherein the non-naturally occurring oil is the non-naturally occurring oil of any one of embodiments A1-A25.

What is claimed is:

1. An oil comprising a triacylglyceride (TAG) component and at least 100 mg of ergosterol per 100 g of the oil, wherein the TAG component has a fatty acid content comprising 80% or more C18:1 fatty acids, wherein the TAG component further comprises at least 60% triolein (OOO), and wherein the oil is produced from classical strain improvement of a microalgal cell.

2. The oil of claim 1, wherein the C18:1 fatty acids comprise oleic acid.

3. The oil of claim 1, wherein the fatty acid content of the TAG component comprises more than 85% C18:1 fatty acids.

4. The oil of claim 1, wherein the fatty acid content of the TAG component further comprises 3% or more C16:0 fatty acids.

5. The oil of claim 1, wherein the fatty acid content of the TAG component further comprises 2% or more C18:0 fatty acids.

6. The oil of claim 1, wherein the fatty acid content of the TAG component further comprises 5% or more C18:2 fatty acids.

7. The oil of claim 1, wherein the oil comprises at least 150 mg of ergosterol per 100 g of the oil.

8. The oil of claim 1, wherein the oil comprises no more than 5 mg of campesterol per 100 g of the oil.

9. The oil of claim 1, wherein the oil does not comprise campesterol.

10. The oil of claim 1, wherein the oil comprises no more than 5 mg of stigmasterol per 100 g of the oil.

11. The oil of claim 1, wherein the oil does not comprise stigmasterol.

12. The oil of claim 1, wherein the oil comprises at least 1 mg of ergosta-5,8-dien-3-ol, (3β)-per 100 g of the oil.

13. The oil of claim 1, wherein the oil comprises at least 15 mg of 5.xi.-ergost-7-en-3β-ol, (3β) per 100 g of the oil.

14. The oil of claim 1, wherein the oil comprises no more than 5 mg of β-sitosterol per 100 g of the oil.

15. The oil of claim 1, wherein the oil does not comprise β-sitosterol.

16. The oil of claim 1, wherein the oil comprises at least 30 mg of 9,19-cyclolanost-24-en-3-ol, (3β) per 100 g of the oil.

17. The oil of claim 1, wherein the oil comprises at least 12 mg of 9,19-cyclolanostan-3-ol, 24-methylene-, (3β) per 100 g of the oil.

18. The oil of claim 1, wherein the microalgal cell is of the genus *Prototheca*.

19. A formulation comprising the oil of claim 1; and one or more excipients.

20. An oil comprising a triacylglyceride (TAG) component and at least 100 mg of ergosterol per 100 g of the oil, wherein the TAG component has a fatty acid content comprising 80% or more C18:1 fatty acids, and wherein the oil does not comprise campesterol.

21. The oil of claim 20, wherein the C18:1 fatty acids comprise oleic acid.

22. The oil of claim 20, wherein the fatty acid content of the TAG component comprises more than 85% C18:1 fatty acids.

23. The oil of claim 20, wherein the fatty acid content of the TAG component further comprises 3% or more C16:0 fatty acids.

24. The oil of claim 20, wherein the fatty acid content of the TAG component further comprises 2% or more C18:0 fatty acids.

25. The oil of claim 20, wherein the fatty acid content of the TAG component further comprises 5% or more C18:2 fatty acids.

26. The oil of claim 20, wherein the oil comprises at least 150 mg of ergosterol per 100 g of the oil.

27. The oil of claim 20, wherein the oil comprises no more than 5 mg of stigmasterol per 100 g of the oil.

28. The oil of claim 20, wherein the oil does not comprise stigmasterol.

29. The oil of claim 20, wherein the oil comprises at least 1 mg of ergosta-5,8-dien-3-ol, (3β)-per 100 g of the oil.

30. The oil of claim 20, wherein the oil comprises at least 15 mg of 5.xi.-ergost-7-en-3β-ol, (3β) per 100 g of the oil.

31. The oil of claim 20, wherein the oil comprises no more than 5 mg of β-sitosterol per 100 g of the oil.

32. The oil of claim 20, wherein the oil does not comprise β-sitosterol.

33. The oil of claim 20, wherein the oil comprises at least 30 mg of 9,19-cyclolanost-24-en-3-ol, (3β) per 100 g of the oil.

34. The oil of claim 20, wherein the oil comprises at least 12 mg of 9,19-cyclolanostan-3-ol, 24-methylene-, (3β) per 100 g of the oil.

35. The oil of claim 20, wherein the TAG component further comprises at least 60% triolein (OOO).

36. The oil of claim 20, wherein the oil is produced from classical strain improvement of a microalgal cell.

37. The oil of claim 36, wherein the microalgal cell is of the genus *Prototheca*.

38. The oil of claim 20, wherein the oil is a microbial oil.

39. A formulation comprising the oil of claim 20; and one or more excipients.

40. An oil comprising a triacylglyceride (TAG) component and at least 100 mg of ergosterol per 100 g of the oil, wherein the TAG component has a fatty acid content comprising 80% or more C18:1 fatty acids, and wherein the oil does not comprise stigmasterol.

41. The oil of claim 40, wherein the C18:1 fatty acids comprise oleic acid.

42. The oil of claim 40, wherein the fatty acid content of the TAG component comprises more than 85% C18:1 fatty acids.

43. The oil of claim 40, wherein the fatty acid content of the TAG component further comprises 3% or more C16:0 fatty acids.

44. The oil of claim 40, wherein the fatty acid content of the TAG component further comprises 2% or more C18:0 fatty acids.

45. The oil of claim 40, wherein the fatty acid content of the TAG component further comprises 5% or more C18:2 fatty acids.

46. The oil of claim 40, wherein the oil comprises at least 150 mg of ergosterol per 100 g of the oil.

47. The oil of claim 40, wherein the oil comprises no more than 5 mg of campesterol per 100 g of the oil.

48. The oil of claim 40, wherein the oil comprises at least 1 mg of ergosta-5,8-dien-3-ol, (3β)-per 100 g of the oil.

49. The oil of claim 40, wherein the oil comprises at least 15 mg of 5.xi.-ergost-7-en-3β-ol, (3β) per 100 g of the oil.

50. The oil of claim 40, wherein the oil comprises no more than 5 mg of β-sitosterol per 100 g of the oil.

51. The oil of claim 40, wherein the oil does not comprise β-sitosterol.

52. The oil of claim 40, wherein the oil comprises at least 30 mg of 9,19-cyclolanost-24-en-3-ol, (3β) per 100 g of the oil.

53. The oil of claim 40, wherein the oil comprises at least 12 mg of 9,19-cyclolanostan-3-ol, 24-methylene-, (3β) per 100 g of the oil.

54. The oil of claim 40, wherein the TAG component further comprises at least 60% triolein (OOO).

55. The oil of claim 40, wherein the oil is produced from classical strain improvement of a microalgal cell.

56. The oil of claim 55, wherein the microalgal cell is of the genus *Prototheca*.

57. The oil of claim 40, wherein the oil is a microbial oil.

58. A formulation comprising the oil of claim 40; and one or more excipients.

59. An oil comprising a triacylglyceride (TAG) component and at least 100 mg of ergosterol per 100 g of the oil, wherein the TAG component has a fatty acid content comprising 80% or more C18:1 fatty acids, and wherein the oil comprises at least 1 mg of ergosta-5,8-dien-3-ol, (3β)-per 100 g of the oil.

60. The oil of claim 59, wherein the C18:1 fatty acids comprise oleic acid.

61. The oil of claim 59, wherein the fatty acid content of the TAG component comprises more than 85% C18:1 fatty acids.

62. The oil of claim 59, wherein the fatty acid content of the TAG component further comprises 3% or more C16:0 fatty acids.

63. The oil of claim 59, wherein the fatty acid content of the TAG component further comprises 2% or more C18:0 fatty acids.

64. The oil of claim 59, wherein the fatty acid content of the TAG component further comprises 5% or more C18:2 fatty acids.

65. The oil of claim 59, wherein the oil comprises at least 150 mg of ergosterol per 100 g of the oil.

66. The oil of claim 59, wherein the oil comprises no more than 5 mg of campesterol per 100 g of the oil.

67. The oil of claim 59, wherein the oil comprises no more than 5 mg of stigmasterol per 100 g of the oil.

68. The oil of claim 59, wherein the oil comprises at least 15 mg of 5.xi.-ergost-7-en-3β-ol, (3β) per 100 g of the oil.

69. The oil of claim 59, wherein the oil comprises no more than 5 mg of β-sitosterol per 100 g of the oil.

70. The oil of claim 59, wherein the oil does not comprise β-sitosterol.

71. The oil of claim 59, wherein the oil comprises at least 30 mg of 9,19-cyclolanost-24-en-3-ol, (3β) per 100 g of the oil.

72. The oil of claim 59, wherein the oil comprises at least 12 mg of 9,19-cyclolanostan-3-ol, 24-methylene-, (3β) per 100 g of the oil.

73. The oil of claim 59, wherein the TAG component further comprises at least 60% triolein (OOO).

74. The oil of claim 59, wherein the oil is produced from classical strain improvement of a microalgal cell.

75. The oil of claim 74, wherein the microalgal cell is of the genus *Prototheca*.

76. The oil of claim 59, wherein the oil is a microbial oil.

77. A formulation comprising the oil of claim 59; and one or more excipients.

78. An oil comprising a triacylglyceride (TAG) component and at least 100 mg of ergosterol per 100 g of the oil, wherein the TAG component has a fatty acid content comprising 80% or more C18:1 fatty acids, and wherein the oil comprises at least 15 mg of 5.xi.-ergost-7-en-3β-ol, (3β) per 100 g of the oil.

79. The oil of claim 78, wherein the C18:1 fatty acids comprise oleic acid.

80. The oil of claim 78, wherein the fatty acid content of the TAG component comprises more than 85% C18:1 fatty acids.

81. The oil of claim 78, wherein the fatty acid content of the TAG component further comprises 3% or more C16:0 fatty acids.

82. The oil of claim 78, wherein the fatty acid content of the TAG component further comprises 2% or more C18:0 fatty acids.

83. The oil of claim 78, wherein the fatty acid content of the TAG component further comprises 5% or more C18:2 fatty acids.

84. The oil of claim 78, wherein the oil comprises at least 150 mg of ergosterol per 100 g of the oil.

85. The oil of claim 78, wherein the oil comprises no more than 5 mg of campesterol per 100 g of the oil.

86. The oil of claim 78, wherein the oil comprises no more than 5 mg of stigmasterol per 100 g of the oil.

87. The oil of claim 78, wherein the oil comprises no more than 5 mg of β-sitosterol per 100 g of the oil.

88. The oil of claim 78, wherein the oil does not comprise β-sitosterol.

89. The oil of claim 78, wherein the oil comprises at least 30 mg of 9,19-cyclolanost-24-en-3-ol, (3β) per 100 g of the oil.

90. The oil of claim 78, wherein the oil comprises at least 12 mg of 9,19-cyclolanostan-3-ol, 24-methylene-, (3β) per 100 g of the oil.

91. The oil of claim 78, wherein the TAG component further comprises at least 60% triolein (OOO).

92. The oil of claim 78, wherein the oil is produced from classical strain improvement of a microalgal cell.

93. The oil of claim 92, wherein the microalgal cell is of the genus *Prototheca*.

94. The oil of claim 78, wherein the oil is a microbial oil.

95. A formulation comprising the oil of claim 78; and one or more excipients.

96. An oil comprising a triacylglyceride (TAG) component and at least 100 mg of ergosterol per 100 g of the oil, wherein the TAG component has a fatty acid content comprising 80% or more C18:1 fatty acids, and wherein the oil does not comprise β-sitosterol.

97. The oil of claim 96, wherein the C18:1 fatty acids comprise oleic acid.

98. The oil of claim 96, wherein the fatty acid content of the TAG component comprises more than 85% C18:1 fatty acids.

99. The oil of claim 96, wherein the fatty acid content of the TAG component further comprises 3% or more C16:0 fatty acids.

100. The oil of claim 96, wherein the fatty acid content of the TAG component further comprises 2% or more C18:0 fatty acids.

101. The oil of claim 96, wherein the fatty acid content of the TAG component further comprises 5% or more C18:2 fatty acids.

102. The oil of claim 96, wherein the oil comprises at least 150 mg of ergosterol per 100 g of the oil.

103. The oil of claim 96, wherein the oil comprises no more than 5 mg of campesterol per 100 g of the oil.

104. The oil of claim 96, wherein the oil comprises no more than 5 mg of stigmasterol per 100 g of the oil.

105. The oil of claim 96, wherein the oil comprises at least 30 mg of 9,19-cyclolanost-24-en-3-ol, (3β) per 100 g of the oil.

106. The oil of claim 96, wherein the oil comprises at least 12 mg of 9,19-cyclolanostan-3-ol, 24-methylene-, (3β) per 100 g of the oil.

107. The oil of claim 96, wherein the TAG component further comprises at least 60% triolein (OOO).

108. The oil of claim 96, wherein the oil is produced from classical strain improvement of a microalgal cell.

109. The oil of claim 108, wherein the microalgal cell is of the genus *Prototheca*.

110. The oil of claim 96, wherein the oil is a microbial oil.

111. A formulation comprising the oil of claim 96; and one or more excipients.

* * * * *

SEQUENCE LISTING

```
Sequence total quantity: 31
SEQ ID NO: 1            moltype = DNA  length = 4218
FEATURE                 Location/Qualifiers
source                  1..4218
                        mol_type = other DNA
                        organism = synthetic construct
SEQUENCE: 1
cggcgcgctg cttcgcgtgc cgggtgcagc aatcagatcc aagtctgacg acttgcgcgc    60
acgcgccgga tccttcaatt ccaaagtgtc gtccgcgtgc gcttcttcgc cttcgtcctc   120
ttgaacatcc agcgacgcaa gcgcagggcg ctgggcggct ggcgtcccga accggcctcg   180
gcgcacgcgg ctgaaattgc cgatgtcggc aatgtagtgc cgctccgccc acctctcaat   240
taagtttttc agcgcgtggt tgggaatgat ctgcgctcat ggggcgaaag aagggttca    300
gaggtgcttt attgttactc gactgggcgt accagcaftc gtgcatgact gattatacat   360
acaaaagtac agctcgcttc aatgccctgc gattcctact cccgagcgag cactcctctc   420
accgtcgggt tgcttccac gaccacgccg gtaagaggt ctgtggcctc gcgcccctcg    480
cgagcgcatc tttccagcca cgtctgtatg attttgcgct catacgtctg gcccgtcgac   540
cccaaaatga cgggatcctg cataatatcg cccgaaatgg gatccaggca ttcgtcagga   600
ggcgtcagcc ccgcgggaga tgccggtccc gccgcattgg aaaggtgtag aggggttgaa   660
tccccattt catgaaatgc ttggtcaacg atggtgcgca ttcgtgcaaa gtgaatatgg   720
ggtcacgcgg tggacgaacg cggaggggc atgaccgaat ctaggctcgc attcctcaga   780
tcacttcatg ccggcggtcc ggggtttgcg cgtcgcgcaa ggctacgtct ccctagccgc   840
tgcgcaccac gcgtgcgacg cggaggccat cttccggagc aacgaccatg gattgtcta    900
gcgatcgcac gaatgagtgc tagtgagtcg tacgctcgac ccagtcgctc gcaggagaag   960
gcggcagctg ccgagcttcg gcttaccagt cgtgactcgt atgtgatcag gaatcattgg  1020
cattggtagc attataattc ggcttccgcg ctgcgtatgg gcatggcaat gtctcatgca  1080
gtcgatctta gtcaaccaat tttgggtggc caggtccggg cgaccggcct ccgtgtccgc  1140
gggcaccacc tcctgccagg agtagcaggg ccgccctctc gtcccgacgt tggcccactg  1200
aataccgtgg cttcgagccc tacatgatgg gctgcctagt cgggcgggac gcgcaactgc  1260
ccgcgcgatc tgggggctgg tctgaatcct tcaggcgggt gttacccgag aaagaaaggg  1320
tgccgatttc aaagcagacc catgtgccgg gccctgtggc ctgtgttggc gcctatgtag  1380
tcaccccccc tcacccaatt gtcgccagtt tgcgcactcc ataaactcaa aacagcagct  1440
tctgagctgc gctgttcaag aacacctctg gggtttgctc acccgcgagg tcgacgccca  1500
gcatggctat caagacgaac aggcagcctg tggagaagcc tccgttcacg atcgggacgc  1560
tgcgcaaggc catccccgcg cactgttccg agcgctcggc gcttcgtagc agcatgtacc  1620
tggcctttga catcgcggtc atgtccctgc tctacgtcgc gtcgacgtac atcgaccctg  1680
caccggtgcc tacgtgggtc aagtacggca tcatgtggcc gctctactgg ttcttccagg  1740
tgtgtttgag ggtttgggtt gcccgtattg aggtcctggt ggcgcgcatg gaggagaagg  1800
cgcctgtccc gctgaccccc ccgccgaccc tcccccacc ttccagggcg ccttcggcac   1860
gggtgtctgg gtgtgcgcgc acgagtgcgg tcaccaggcc ttttcctcca gccaggccat  1920
caacgacggc gtgggcctgg tgttccacag cctgctgctg gtgccctact actcctggaa  1980
gcactcgcac cgccgccacc actccaacac ggggtgcctg gacaaggacg aggtgttgt   2040
gccgccgcac cgtgcggtgg cgcacgaggg cctggagtgg gaggagtggc tgcccatccg  2100
catgggcaag gtgctggtca ccttgaccct gggctggccg ctgtacctca tgttcaacgt  2160
cgcctcccgc ccttacccgc gcttcgccaa ccactttgac ccgtggtcgc ccatcttcag  2220
caagcgcgag cgcatcgagg tggtcatctc cgacctcgcg ttggtggcgg tgctcagcgg  2280
gctcagcgtg ctgggccgca ccatgggctg ggcctggctg gtcaagacct acgtggtgcc  2340
ctacatgatc gtgaacatgt ggctggtgct catcacgctg ctccagcaca cgcaccggc   2400
cctgccgcac tacttcgaga aggactggga ctggctacgc ggcgcatgg ccaccgtcga    2460
ccgctccatg ggcccgccct tcatgacag catcctgcac cacatctccg acacccacgt  2520
gctgcaccac ctcttcagca ccatcccgca ctaccacgcc gaggaggcct ccgccgccat  2580
ccggcccatc ctgggcaagt actaccaatc cgacacgcgc tgggtgggcc gcgccctgtg  2640
ggaggactgg cgcgactgcc gctacgtcgt cccccgacgg cccgaggacg actccgcgct  2700
ctggttccac aagtgagcgc gcctgcgcga ggacgcagaa caacgctgcc gccgtgtctt  2760
ttgcacgcgc gactccggcg cttcgctggt ggcacccca taagaaaacc ctcaattctg  2820
tttgtggaag acacggtgta cccccaccca cccaactgca cctctattat tggtattatt  2880
gacgcgggag tgggcgttgt accctacaac gtagcttctc tagttttcag ctggctccca  2940
```

```
ccattgtaaa ttcatgctag aatagtgcgt ggttatgtga gaggtatagt gtgtctgagc   3000
agacggggcg ggatgcatgt cgtggtggtg atctttggct caaggcgtcg tcgacgtgac   3060
gtgcccgatc atgagagcaa taccgcgctc aaagccgacg catagcctt actccgcaat   3120
ccaaacgact gtcgctcgta ttttttggat atctatttta aagagcgagc acagcgccgg   3180
gcatgggcct gaaaggcctc gcggccgtgc tcgtggtggg ggccgcgagc gcgtggggca   3240
tcgcggcagt gcaccaggcg cagacggagg aacgcatggt gcgtgcgcaa tataagatac   3300
atgtattgtt gtctgtacta taatgctaga gcatcaccag gggcttagtc atcgcacctg   3360
cttttggtcat tacagaaatt gcacaagggc gtcctccggg atgaggagat gtaccagctc   3420
aagctggagc ggcttcgagc caagcaggag cgcggcggca gacgacctat ccacatgtga   3480
caaaggggtc tgggtcgtac gaatcgacaa accagtcagg agacagcggg gtccatgagt   3540
tggcccgctc gcagcttcag cgctttgagc atcgcggcat tgtccacgat ccaaggctcc   3600
cgcagcgcct ccttgggacc cctgtgcgga gaagcgtgtg ccgagagggc tgtgagggcg   3660
gaggctggag gagaggctgc gaatcattgc gctgcctagg cgtctgccga gtagtagcac   3720
accacgcgcc ggtgctttca tttcattgtg tccgttgctg taatgcatgc gagcaatcct   3780
gcactaaaag ctgcgatcac cacctcggcg ttgttggtct ctagtaccgc tcacctgacc   3840
acgcgcacgg aagtatggcg gtcggcgacg gcctgctgca cgtggcagtg cagatccacg   3900
tggcccagga gcaggtctcg cagctgcaac accgcgcct cgtgctcgcc ggggtccatc   3960
cagtccatac cccgcgccgg gccctcgagc cggacggccg aacgccaggg ccgggggtcc   4020
gcgccgacgc ccggcggccc cgccgcgcag ctggggtcgg ccaggaagag ccactggacg   4080
gccggcccgg gcgagccccg cgccggcgtg ggacccaccc gcagcaccac cgcctgctcc   4140
aggtccacgt cgctcggcgg caggcccgcg tgcggcgcct gcgccagcgt ccagggcagg   4200
cggggccggg cgtgcatg                                                 4218

SEQ ID NO: 2           moltype = DNA   length = 4217
FEATURE                Location/Qualifiers
source                 1..4217
                       mol_type = unassigned DNA
                       note = Prototheca wickerhamii
                       organism = unidentified
SEQUENCE: 2
cggcgcgctg cttcgcgtgc cgggtgcagc aatcagatcc aagtctgacg acttgcgcgc   60
acgcgccgga tccttcaatt ccaaagtgtc gtccgcgtgc gcttcttcgc cttcgtcctc   120
ttgaacatcc agcgacgcaa gcgcagggcg ctgggcggct ggcgtccgga accggcctcg   180
gcgcacgcgg ctgaaattgc cgatgtcggc aatgtagtgc cgctccgcc acctctcaat   240
taagttttc agcgcgtggt tgggaatgat ctgcgctcat ggggcgaaag aaggggttca   300
gaggtgcttt attgttactc gactgggcgt accagcattc gtgcatgact gattatacat   360
acaaaagtac agctcgcttc aatgccctgc gattcctact cccgagcgag cactcctctc   420
accgtcgggt tgcttcccac gaccacgccg gtaagagggt ctgtggcctc gcgccctcg   480
cgagcgcatc ttttccagcca cgtctgtatg attttgcgct catacgtctg cgccgtcgac   540
cccaaaatga cgggatcctg cataatatcg cccgaaatgg gatccaggca ttcgtcagga   600
ggcgtcagcc ccgcgggaga tgccggtccc gccgcattgg aaaggtgtag aggggggtgaa   660
tcccccattt catgaaatgc ttggtcaacg atggtgcgca ttcgtgcaaa gtgaatatgg   720
ggtcacgcgg tggacgaacg cggaggggc atgaccgaat ctaggctgcg attcctcaga   780
tcacttcatg ccggcggtcc gggtttgcg cgtcgcgcaa ggctacgtct ccctagccgc   840
tgcgcaccac gcgtgcgacg cggaggccat cttccggagc aacgaccatg gattgtctta   900
gcgatcgcac gaatgagtgc tagtgagtcg tacgctcgac ccagtcgctc gcaggagaag   960
gcggcacgcg ccgagcttcg gcttaccagt cgtgactcgt atgtgatcag gaatcattgc   1020
cattggtagc attataattc ggcttccgcg ctgcgtatgg gcatggcaat gtctcatgca   1080
gtcgatctta gtcaaccaat tttgggtggc caggtccggg cgaccgggct ccgtgtcgcc   1140
gggcaccacc tcctgccagg agtagcaggg ccgccctctc gtcccgacgt tggcccactg   1200
aataccgtgg cttcgagccc tacatgatgg gctgcctagt cgggcgggac gcgcaactgc   1260
ccgcgcgatc tggggggctgg tctgaatcct tcaggcgggt gttacccgag aaagaaaggg   1320
tgccgattc aaagcagacc catgtgccgg gccctgtggc ctgtgttggc gcctatgtag   1380
tcacccccccc tcacccaatt gtcgccagtt tgcgcactcc ataaactcaa acagcagct   1440
tctgagctgc gctgttcaag aacacctctg gggtttgctc acccgcgagg tcgacgccca   1500
gcatggctat caagacgaac aggcagcctg tggagaagcc tccgttcacg atcgggacgc   1560
tgcgcaaggc catccccgcg cactgtttcg agcgctcggc gcttcgtagc agcatgtacc   1620
tggcctttga catcgcggtc atgtccctgc tctacgtcgc gtcgacgtac atcgaccctg   1680
caccggtgcc tacgtgggtc aagtacggca tcatgtggcc gctctactgg ttcttccagg   1740
tgtgtttgag ggttttggtt gcccgtattg aggtcctggt ggcgcgcatg gaggagaagg   1800
cgcctgtccc gctgaccccc ccgccgaccc tcccccacct tccagggcgc cttcggcacg   1860
ggtgtctggg tgtgcgcgca cgagtgcggt caccaggcct tttcctccag ccaggccatc   1920
aacgacggcg tgggcctggt gttccacagc ctgctgctgg tgccctacta ctcctggaag   1980
cactcgcacc gccgccacca ctccaacacg gggtgcctgg acaaggacga ggtgtttgtg   2040
ccgccgcacc gtgcggtggc gcacgagggc ctggagtggg aggagtggct gcccatccgc   2100
atgggcaagg tgctggtcac cttgaccctg gctggccgc tgtacctcat gttcaacgtc   2160
gcctcccgcc cttacccgcg cttcgccaac cactttgacc cgtggtcgcc catcttcagc   2220
aagcgcgagc gcatcgaggt ggtcatctcc gacctggcgt tggtggcggt gctcagcggg   2280
ctcagcgtgc tgggccgcac catgggctgg ggctggctagt tcaagaccta cgtggtgcca   2340
tacatgatcg tgaacatgtg gctggtgctc atcacgctgc tccagcacac gcacccggcc   2400
ctgccgcact acttcgagaa ggactgggac tggctacgcg gcgccatggc caccgtcgac   2460
cgctccatgg gcccgccctt catggacagc atcctgcacc acatctccga cacccacgtg   2520
ctgcaccacc tcttcagcac catcccgcac taccacgccg aggaggcctc cgccgccatc   2580
cggcccatc tgggcaagta ctaccaatcc gacgaccgct gggtcggcgg ccgaggacga ctccgcgctc   2640
gaggactggc gcgactgccg ctacgtcgtc cccgacgcgc ccgaggacga ctccgcgctc   2700
tggttccaca gtgagcgcg cctgcgcgag gacgcagaac aacgctgccg ccgtgtcttt   2760
tgcacgcgcg actccggcgc ttcgctggtg cacccccat aaagaaaccc tcaattctgt   2820
ttgtggaaga cacggtgtac ccccacccac ccacctgcac ctctattatt ggtattattg   2880
acgcgggagt gggcgttgta ccctacaacg tagcttctct agttttcagc tggctcccac   2940
```

```
cattgtaaat tcatgctaga atagtgcgtg gttatgtgag aggtatagtg tgtctgagca   3000
gacgggcgg  gatgcatgtc gtggtggtga tctttggctc aaggcgtcgt cgacgtgacg   3060
tgcccgatca tgagagcaat accgcgctca aagccgacgc atagcccttta ctccgcaatc  3120
caaacgactg tcgctcgtat ttttttggata tctattttaa agagcgagca cagcgccggg  3180
catggccctg aaaggcctcg cggccgtgct cgtggtgggg gccgcgacgg cgtggggcat  3240
cgcggcagtg caccaggcgc agacggagga acgcatggtg cgtgcgcaat ataagataca  3300
tgtattgttg tctgtactat aatgctagag catcaccagg ggcttagtca tcgcacctgc  3360
tttggtcatt acagaaattg cacaagggcg tcctccggga tgaggagatg taccagctca  3420
agctggagcg gcttcgagcc aagcaggagc gcggcgcatg acgacctatc cacatgtgac  3480
aaagggggtct gggtcgtacg aatcgacaaa ccagtcagga gacagcgggg tccatgagtt  3540
ggcccgctcg cagcttcagc gctttgagca tcgcggcatt gtccacgatc caaggctccc  3600
gcagcgcctc cttgggaccc ctgtgcgagg aagcgtgtgc cgagagggct gtgagggcgg  3660
aggctggagg agaggctgcg aatcattgcg ctgcctaggc gtctgccgag tagtagcaca  3720
ccacgccgcg gtgctttcat ttcattgtgt ccgttgctgt aatgcatgcg agcaatcctg  3780
cactaaaagc tgcgatcacc acctcggcgt tgttggtctc tagtaccgct cacctgacca  3840
cgcgcacgga agtatggcgg tcggcgacgg cctgctgcac gtggcagtgc agatccacgt  3900
ggcccaggag caggtctcgc agctgcaaca ccgcgccctc gtgctcgccg ggtccatcc   3960
agtccatacc ccgcgccggg ccctcgagcc ggacggccag cagccagggc cggggtccgg  4020
cgccgacgcc cggcggcccc gccgcgcagc tgggtcggc caggaagagc cactggacgg   4080
ccggcccggg cgagcccgc  gccggcgtgg gacccacccg cagcaccacc gcctgctcca  4140
ggtccacgtc gctcggcggc aggcccgcgt gcggcgcctg cgccagcgtc cagggcaggc  4200
gggccgggc  gtgcatg                                                  4217
```

SEQ ID NO: 3       moltype = DNA  length = 4227
FEATURE           Location/Qualifiers
source            1..4227
                     mol_type = other DNA
                     organism = synthetic construct
SEQUENCE: 3

```
cggctcgctg ctttgcgtgc cgggtgcagc gatcagatcc aagtctgacg acttgtgctg   60
atgtactgtg tcctttgagt ccagagcgcc ggccgcacgc gcttcttccc cttcttcttc   120
ctctcgaaca tccagcgatg caagtgcagg gcgctgggcg gctggcgtcc gaaccggcc    180
tcggcgcacg cggctgaaat tgccaatgtc ggcaatgtag tgccgctcgg cccatccctc   240
gatcaagttt ttcagcgcgt ggttgggat  gatctcgct  catgggaaga taaaaggggt  300
tctgaggtgg ttgattggta ctttaccgga agtactcata ttcatacatg actgatccca  360
cacaaaaaca aagctcactt caaagaaccg cgcatgtcta ctccccagca atcacttcgc  420
tcaccgtcgg gttgcttccc acgacaacgc cggtgagagg gtcggtggcc tcgcgacctt  480
cgcgggcaca tctttccagc catgtctgta taatctcacg ctcatacgtc tggcccgtcg  540
accccaaaat gacgggatcc tgcatgatat cgcccgaagt ggggttccagg cattcctctg  600
gaggcgtcag ccctgcggga gatgccggtc ccaccgcatt ggaaaggcac aaagggggtg  660
aatcccccat ttcatgaaat tgttggtcag cgatggtgcg cactcgtgcg caatgaatat  720
ggggtcacgc ggtggacgaa cgcggagggg gcctggccga atctaggctt gcattcctca  780
gatcactttc tgccggcggt ccggggtttg cgcgtcgcga acgctccgt  ctccctagcc  840
gctgcgcacc gcgcgtgcga cgcgaaggtc attttccaga acaacgacca tggcttgtct  900
tagcgatcgc tcgaatgact gctagtgagt cgtacgctcg acccagtcgc tcgcaggaga  960
acgcggcaac tgccgagctt cggcttgcca gtcgtgactc gtatgtgatc aggaatcatt  1020
ggcattggta gcattataat tcggcttccg cgctgtttat gggcatggca atgtctcatg  1080
cagtcgacct tagtcaacca attctgggtg gccagctccg ggcgaccggg ctccgtgtcg  1140
ccgggcacca cctcctgcca tgagtaacag ggccgccctc tcctcccgac gttggccac   1200
tgaataccgt gtcttgggc  cctacatgat gggctgccta gtcgggcggg acgcgcaact  1260
gcccgccgaa tctgggacgt ggtctgaatc ctccaggcgg gtttccccga gaaagaaagg  1320
gtgccgattt caaagcagag ccatgtgccg ggccctgtgg cctgtgttgg cgcctatgta  1380
gtcaccccc  ctcacccaat tgtcgccagt ttgcgcaatc cataaactca aaactgcagc  1440
ttctgagctg cgctgttcaa gaacacctct ggggtttgct cacccgcgag gtcgacgccc  1500
agcatggcta tcaagacgaa caggcagcct gtggagaagc ctccgttcac gatcgggacg  1560
ctgcgcaagg ccatccccgc gcactgtttc gagcgctcgg cgcttcgtag cagcatgtac  1620
ctggcctttg acatcgcggt catgtccctg ctctacgtcg cgtcgacgta catcgaccct  1680
gcgccggtgc ctacgtgggt caagtatggc gtcatgtggc cgctctactg gttcttccag  1740
gtgtgtgtga gggttgtggt tgcccgtatc gaggtcctgg tggcgcgcat gggggagaag  1800
gcgcctgtcc cgctgacccc cccggctacc ctccccggca cttccagggc gccttcggca  1860
cgggtgtctg ggtgtgcgcg cacgagtgcg gccaccagge cttttcctcc agccaggcca  1920
tcaacgacgg cgtgggcctg gtgttccaca gcctgctgct ggtgccctac tactcctgga  1980
agcactcgca ccgccgccac cactccaaca cggggtgcct ggacaaggac gaggtgtttg  2040
tgccgccgca ccgcgcagtg gcgcacgagg gcctggagtg g ctgcccatcc             2100
gcatgggcaa ggtgctggtc accctgaccc tgggctggcc gctgtacctc atgttcaacg  2160
tcgcctcgcg gccgtacccg cgcttcgcca accactttga cccgtggtcg cccatcttca  2220
gcaagcgcga gcgcatcgag gtggtcatct ccgacctggc gctggtggcg gtgctcagcg  2280
ggctcagcgt gctgggccgc accatgggct gggcctggct ggtcaagacc tacgtggtgc  2340
cctacctgat cgtgaacatg tggctcgtgc tcatcacgct gtccagcac  acgcaccccgg  2400
cgctgccgca ctacttcgag aaggactggg actggctgcg cggccgccatg gccaccgtgg  2460
accgctccat ggggcccgcc ttcatggaca acatcctgca ccacatctcc gacacccacg  2520
tgctgcacca cctcttcagc accatcccgc actaccacgc cgaggaggcc tccgccgcca  2580
tcaggcccat cctgggcaag tactaccagt ccgacagccg ctgggtcggc cgcgccctgt  2640
gggaggactg cgcctacgtcg tcccgggcgg gccgaggac gactccggac                 2700
tctggttcca caagtgagtg agtgagtcgc tcactcagcg cgcctgcgcg gggatgcgga  2760
acgccgcgc  cgccttgtct tttgcacgcg cgactccgtc gcttcgcggg tggcaccccc  2820
attgaaaaaa acctcaattc tgtttgtgga agacacggtg tacccccaac cacccacctg  2880
cacctctatt attggtatta ttgacgcggg agcgggcgtt gtactctaca acgtagcgtc  2940
tctggttttc agctggctcc caccattgta aattcttgct aaaatagtgc gtggttatgt  3000
```

```
gagaggtatg gtgtaacagg gcgtcagtca tgttggtttt cgtgctgatc tcgggcacaa  3060
ggcgtcgtcg acgtgacgtg cccgtgatga gagcaatacc gcgctcaaag ccgacgcatg  3120
gcctttactc cgcactccaa acgactgtcg ctcgtatttt tcggatatct attttttaag  3180
agcgagcaca gcgccgggca tgggcctgaa aggcctcgcg gccgtgctcg tggtgggggc  3240
cgccagcgcg tggggcatcg cggcagtgca ccaggcgcag acggaggaac gcatggtgag  3300
tgcgcatcac aagatgcatg tcttgttgtc tgtactataa tgctagagca tcaccagggg  3360
cttagtcatc gcacctgctt tggtcattac agaaattgca caagggcgtc ctccgggatg  3420
aggagatgta ccagctcaag ctggagcggg ttcgagccaa gcaggagcgc ggcgcatgac  3480
gacctaccca catgcgacaa aggggtctgg gtcgtacgac aaaccagtca ggaggcggcg  3540
gggtccatga gctggccgc tcgcagcttc agcgcttcga gcatcgcggc gttgtccgcg  3600
atccaagcct cccgcagcgc ctccttgggg cccctgtgcg gagaggcggg tgccgagagg  3660
gctgtgaggg cggaggctgg aggacaggct gcgaatcgtc gcgctgccta ggcgtctgcc  3720
gaggagaagc acaccacgcg ccgccgcttt catttcattg tgcccgttgc tgtaatgcat  3780
gcgagcgatc ctgcactaaa gctgcgatcg ccacctcagc gttgttcgtc tctagcaccg  3840
ctcacctgac cacgcgcacg gaagagtggc ggtcggcgca ggcctgctgc acgtggcagt  3900
gcaggtccac gtgccgagg agcaggtctc cgagctgcag caccgcgccc tcgtgctcgc  3960
cggggtccat ccagtccatg ccccgcgccg ggccctcgag ccggacggcc agcagccagg  4020
gccgggggtc cgcgccgacc ccggccgccc ccgccgccga gctggggtcg gccaggaaga  4080
gccactgggc ggccggcccg ggcgagcccc gcgccggcgc gggacccacc cgcagcacca  4140
ccgcctggtc caggtcgacg tcgctcggcg gcaggcccgc gtgcggcgcc tgcgccagcg  4200
tccagggcag gcggggcgc gcgtgca                                       4227

SEQ ID NO: 4            moltype = DNA   length = 4227
FEATURE                 Location/Qualifiers
source                  1..4227
                        mol_type = unassigned DNA
                        note = Prototheca wickerhamii
                        organism = unidentified
SEQUENCE: 4
cggctcgctg ctttgcgtgc cgggtgcagc gatcagatcc aagtctgacg acttgtgctg   60
atgtactgtg tcctttgagt ccagagcgcc ggccgcacgc gcttcttccc cttcttcttc  120
ctctcgaaca tccagcgatg caagtgcagg gcgctgggcg gctggcgtcc cgaaccggcc  180
tcggcgcacg cggctgaaat tgccaatgtc ggcaatgtag tgccgctcgg cccatccctc  240
gatcaagttt ttcagcgcgt ggttgggat gatctcgct catgggaaga taaaaggggt  300
tctgaggtgg ttgattggta cttaccgga agtactcata ttcatacatg actgatccca  360
cacaaaaaca aagctcactt caaagaaccg cgcatgtcta ctcccagca atcacttcgc  420
tcaccgtcgg gttgcttccc acgacaacgc cggtgagagg gtcggtggcc tcgcgacctt  480
cgcgggcaca tctttccagc catgtctgta taatctcacg ctcatcgtc tggcccgtcg  540
accccaaaat gacgggatcc tgcatgatat cgcccgaagt ggggtccagg cattcctctg  600
gaggcgtcag ccctgcggga gatgccggtc ccaccgcatt ggaaaggcac aaagggggtg  660
aatccccat tcatgaaat tgttggtcag cgatggtgcg cactcgtgcg caatgaatat  720
ggggtcacgc ggtggacgaa cgcggagggg gcctggccga atctaggctt gcattcctca  780
gatcactttc tgccggcggt ccgggggttg cgcgtccggc aacgctccgt ctccctagcc  840
gctgcgcacc gcgcgtgcga cgcgaaggtc attttccaga acaacgacca tggcttgtct  900
tagcgatcgc tcgaatgact gctagtgagt cgtacgctcg acccagtcgc tcgcaggaga  960
acgcggcaac tgccgagctt cggcttgcca gtcgtgactc gtatgtgatc aggaatcatt 1020
ggcattggta gcattataat tcggcttccg cgctgtttat gggcatggca atgtctcatg 1080
cagtcgacct tagtcaacca attctgggtg gccagctccg ggcgaccggg ctccgtgtcg 1140
ccgggcacca cctcctgcca tgagtaacag ggccgccctc tcctcccgac gttggccac  1200
tgaataccgt gtcttgggc cctacatgat gggctgccta gtcgggcggg acgcgcaact 1260
gcccgccgaa tctgggacgt ggtctgaatc ctccaggcgg gtttccccga gaaagaaagg 1320
gtgccgattt caaagcagag ccatgtgccg ggccctgtgg cctgtgttgg cgcctatgta 1380
gtcaccccc ctcacccaat tgtcgccagt ttgcgcaatc cataaactca aaactgcagc 1440
ttctgagctg cgctgttcaa gaacacctct ggggtttgct cacccgcgag gtcgacgccc 1500
agcatggcta tcaagacgaa caggcagcct gtggagaagc ctccgttcac gatcgggacg 1560
ctgcgcaagg ccatccccgc gcactgtttc gagcgctcgg cgcttcgtag cagcatgtac 1620
ctggcctttg acatcgcggt catgtccctg ctctacgtcg cgtcgacgta catcgaccct 1680
gcgccggtgc ctacgtgggt caagtatggc gtcatgtggc cgctctactg gttcttccag 1740
gtgtgtgtga gggttgtggt tgcccgtatc gaggtcctgg tggcgcgcat gggggagaag 1800
gcgcctgtcc cgctgacccc cccggctacc ctccccggcac cttccagggc gccttcgcca 1860
cgggtgtctg ggtgtgcgcg cacgagtgcg gccaccagge cttttcctcc agccaggcca 1920
tcaacgacgg cgtgggcctg gtgttccaca gcctgctgct ggtgccctac tactcctgga 1980
agcactcgca ccgccgccac cactccaaca cggggtgcct ggacaaggac gaggtgtttg 2040
tgccgccgca ccgcgcagtg gcgcacgagg gcctggactg ggaggagtgg ctgcccatcc 2100
gcatgggcaa ggtgctggtc accctgaccc tgggcgtggcc gctgtacctc atgttcaacg 2160
tcgcctcgcg gccgtacccg cgcttcgcca accactttga cccgtggtcg cccatcttca 2220
gcaagcgcga gcgcatcgag gtggtcatct ccgacctggc gctggtggcg tgctcagcg  2280
ggctcagcgt gctgggccgc accatgggct gggcctggct ggtcaagaca tacgtggtgc 2340
cctacctgat cgtgaacatg tggctcgtgc tcatcacgct gtccagcac acgcaccgg  2400
cgctgccgca ctacttcgag aaggactggg actggctgcg cggcgccatg gccaccgtgg 2460
accgctccat gggcccgccc ttcatggaca acatcctgca ccacatctcc gacacccacg 2520
tgctgcacca cctcttcagc accatcccgc actaccacgc cgaggaggcc tccgccgcca 2580
tcaggcccat cctgggcaag tactaccagt ccgcagccgc ctgggtcggc cgcgcccctgt 2640
gggaggactg gcgcgactgc ctgcacgtcg tcccggacgc cccgaggac gactccggcg 2700
tctggtccca caagtgagtg agtgagtcgc tcactcagcg cgcctgcgcg gggatgcgga 2760
acgccgccgc cgccttgtct ttgcacgcg cgactccgtc gcttcgcggg tggcacccc  2820
attgaaaaaa acctcaattc tgtttgtgga agacacggtg taccccccaac cacccacctg 2880
cacctctatt attggtatta ttgacgcggg agcgggcgtt gtactctaca acgtagcgtc 2940
tctggttttc agctggctcc caccattgta aattcttgct aaaatagtgc gtggttatgt 3000
```

-continued

```
gagaggtatg gtgtaacagg gcgtcagtca tgttggtttt cgtgctgatc tcgggcacaa 3060
ggcgtcgtcg acgtgacgtg cccgtgatga gagcaatacc gcgctcaaag ccgacgcatg 3120
gcctttactc cgcactccaa acgactgtcg ctcgtatttt tcggatatct attttttaag 3180
agcgagcaca gcgccgggca tgggcctgaa aggcctcgcg gccgtgctcg tggtgggggc 3240
cgcgagcgcg tggggcatcg cggcagtgca ccaggcgcag acggaggaac gcatggtgag 3300
tgcgcatcac aagatgcatg tcttgttgtc tgtactataa tgctagagca tcaccagggg 3360
cttagtcatc gcacctgctt tggtcattac agaaattgca caagggcgtc ctccgggatg 3420
aggagatgta ccagctcaag ctggagcggg ttcgagccaa gcaggagcgc ggcgcatgac 3480
gacctaccca catgcgacaa aggggtctgg gtcgtacgac aaaccagtca ggaggcggcg 3540
gggtccatga gctggccgc tcgcagcttc agcgcttcga gcatcgcggc gttgtccgcg 3600
atccaagcct cccgcagcgc ctccttgggg ccctgtgcg gagaggcggg tgccgagagg 3660
gctgtgaggg cggaggctgg aggacaggct gcgaatcgtc gcgctgccta ggcgtctgcc 3720
gaggagaagc acaccacgcg ccgccgcttt catttcattg tgcccgttgc tgtaatgcat 3780
gcgagcgatc ctgcactaaa gctgcgatcg ccacctcgca gttgttcgtc tctagcaccg 3840
ctcacctgac cacgcgcacg gaagagtggc ggtcggcgca ggcctgctgc acgtggcagt 3900
gcaggtccac gtgccgagg agcaggtctc cgagctgcag caccgcgccc tcgtgctcgc 3960
cggggtccat ccagtccatg ccccgcgccg ggccctcgag ccggacggcc agcagccagg 4020
gccggggtc cgcgccgacc ccggccgcca gctggggtcg gccaggaaga 4080
gccactgggc ggccggcccg ggcgagcccc gcgccggcgc gggacccacc cgcagccacca 4140
ccgcctggtc caggtcgacg tcgctcggcg gcaggcccgc gtgcggcgcc tgcgccagcg 4200
tccagggcag gcggggggcgc gcgtgca                                    4227

SEQ ID NO: 5              moltype = DNA  length = 4067
FEATURE                   Location/Qualifiers
source                    1..4067
                          mol_type = other DNA
                          organism = synthetic construct
SEQUENCE: 5
gcaatggcgc tcggtacagg gtctgcgtcc gtgctgggct ccctctccta cgatgcacaa   60
gggagcgccc cggccagctc agcgcgtcca caacctcccc tcgtcacaca cacacctgcg  120
gaaccaggcc gcccatttgc tgcttgagca tgccttgcat catgtccggg tttcccatca  180
tatcgttgag gttcttgggc tccagcttct gctccagcac accatcctgt cgatcgaaga  240
gaaggagaca tgtgtacatt attggtgtga gggcgctgaa tcggccatt tttaaatgat  300
cacgctcatg ccaatagacg cggcacataa cgacgttcaa ccccccgcca aagccgcgga  360
caaccccatc cctccacacc ccccacacaa agaacccgcc accgcttacc ttgcccacga  420
ggtaggcctt tcgttgcgca aaaccggcct cggtgatgaa tgcatgcccg ttcctgacga  480
gcgctgcccg ggccaaacg ctcttttgct gcgtctcctc aggcttgggg gcctccttgg  540
gcttgggtgc cgccatgatc tgcgcgcatc agagaaacgt tgctggtaaa aggagcgccc  600
ggctgcgcaa tatatatata ggcatgccaa cacagcccaa cctcactcgg gagcccgtcc  660
caccacccc aagtcgcgtg ccttgacggc atactgctgc agaagcttca tgagaatgat  720
gccgaacaag aggggcacga ggacccaatc ccggacatcc ttgtcgataa tgatctcgtg  780
agtccccatc gtccgcccga cgctccgggg agcccgccga tgctcaagac gagagggccc  840
tcgaccagga ggggctggcc cgggcggca ctggcgtcga aggtgcgccc gtcgttcgcc  900
tgcagtccta tgccacaaaa caagtcttct gacggggtgc gttttgctccc gtgcgggcag  960
gcaacagagg tattcaccct ggtcatgggg agatcggcga tcgagctggg ataagagata 1020
cggtcccgcg caaggatcgc tcatcctggt ctgagccgga cagtcattct ggcaagcaat 1080
gacaacttgt caggaccgga ccgtgccata tattctctac ctagcgccgc aaaacctaac 1140
aatttgggag tcactgtgcc actgagttcg actggtagct gaatgagtc gctgctccac 1200
taaacgaatt gtcagcaccg ccagccgcc gaggacccga gtcatagcga gggtagtagc 1260
gcgccatggc accgaccagc ctgcttgcca gtactggcgt ctcttccgct tctctgtggt 1320
cctctgcgcg ctccagcgcg tgcgcttttc cggtggatca tgcggtccgt gcgcgcaccgc 1380
agcggccgct gcccatgcag cgccgctgct tccgaacagt ggcggtcagg gccgcacccg 1440
cggtagccgt ccgtccggaa cccgcccaag agttttggga gcagcttgag ctctgcaaga 1500
tggcggagga caagcgcatc ttcctggagg agcaccggtg cgtggaggtc cggggctgac 1560
cggccgtcgc attcaacgta atcaatcgca tgatgatcag aggacacgaa gtcttggtgg 1620
cggtggccag aaaacactgtc cattgcaagg gcatagggat gcgttccttc acctctcatt 1680
tctcatttct gaatccctcc ctgctcactc tttctcctcc tccttcccgt tcacgcagca 1740
ttcggggcaa cgaggtgggc ccctcgcagc ggctgacgat cacggcggtg gccaacatcc 1800
tgcaggaggc ggcgggcaac cacgcggtgg ccatgtgggg ccggagctcg gagggtttcg 1860
cgacggaccc ggagctgcag gaggcgggtc tcatctttgt gatgacgcgc atgcagatcc 1920
agatgtaccg ctacccgcgc tggggcgacc tgatgcaggt ggagacctgg ttccagacgc 1980
cgggcaagct gggcgcgcag cgcgagtggg tgctgcgcga caagctgacc ggcgaggcgc 2040
tgggcgcggc cacctcgagc tgggtcatga tcaaacatccg cacgcgccgg ccgtgccgca 2100
tgccggagct cgttccgcgtc aagtcggcct tcttcgccgg cgcccgcgct ggcgc 2160
tgccgcccgc ggtcacgcgt gccaagctgc ccaacatcgc gacgccgcg ccgctgcgcg 2220
ggcaccgcca ggtcgcgcgc cgcaccgaca tggacatgaa cgggcacgtg aacaacgtgg 2280
cctacctggc ctggtgcctg gaggccgtgc ccgagcacgc cttcagcgac taccacctct 2340
accagatgga gatcgacttc aaggccgagt gccacgcggg cgacgtcatc tcctcccagg 2400
ccgagcagat cccgccccag ggcggcctca acaacggcca aaccctcc 2460
gcttcgtcca tagcattctg cgcgccgaga ccgagctcgt ccgcgcgcga accacatggt 2520
cggccccat cgacgcgccc gccgccaagc cgcccaaggc gagccactga ggacagggtg 2580
gttggctgga tgggggaaacg ctggtcgcgg gattcgatcc tgctgcttat atcctccctg 2640
gaagcacacc cacgactctg aagaagaaaa cgtgcacaca caacccaa ccggccgaat 2700
atttgcttcc ttatcccggg tccaagagga actgccctga cagcatcctc 2760
ctccctgccg cttcaatctt ccctgcttgc ctgcgcccgc ggtgcgccgt ctgcccgccc 2820
agtcagtcac tcctgcacag gcccttgtg cgcagtgctc ctgtacccttt accgctcct 2880
tccattctgc gaggccccct attgaatgta ttcgttgcct gtgtgccaa gcgggctgct 2940
gggcgcgccg ccgtcgggca gtgctcggcg actttggcgg aagccgattg ttcttctgta 3000
agccacgcgc ttgctgcttt gggaagagaa ggggggggta ctgaatggat gaggaggaga 3060
```

```
aggaggggta ttggtattat ctgagttggg gaggcaggga gagttggaaa atgtaagtgg  3120
cacgacgggc aaggagaatg gtgagcatgt gcatggtgat gtcgttggtc gaggacgatc  3180
ctgcacgcgt gtatctgatg tagaatacgg caatcaccct agtctacatc tataccttct  3240
ccgtataacg ccctttccaa atgccctccc gtttctctcc tattcttgat ccacatgatg  3300
accctggcac tatttcaagg gctggacatt tcaagaaggt ttgcgtatct gaagaaggat  3360
tggtttggag aggtggccga tgaaagtggg gtcaagctgc gtggagccct ctgcacggat  3420
ttctatggta atctgcgtcc acgtcatcag tagccgtacg cctctgcggc gtcgccgtgc  3480
tcctcagccg ccgcttcacc accagccagg agcccatac gcacgcgctc ccagacggcg   3540
cgcgcgacgg ggacgatcat gagcagcgcg atctggggcg tgtcgtgcga gctgagccgc  3600
acaaccacgt tgccctggcc gcgcgtggtg tactggcagt tggtcgagac catggtgtcg  3660
gacttgaagt aggagccgtc aaagcgcggg aggcgcgtct cggccgagac gttgccgccg  3720
atgaccaggc tctggcgctt ctggcgcggg tcgcggccct gccactgcgc ggagccgccc  3780
aggagcaggc gcgactcgtc acggccgcgc agcttgacgt cggccgccag cgccgtgccc  3840
ggctcgtagg ccgaccccat cttgacgaag aggcggccga tcgctgcgcg gaccttgacc  3900
gcgtcggaca ggcgcaggcg ctcgtccagc ttgaccccga gcgccgcgtt gccgggcttg  3960
aacggcagcg agaactcctc gcccagcttg gagccgagca ggcccagcgc cagcttctgc  4020
cgcttgccgc gcgcgcgcag gcgcgagtcg acgcgcagcg tgtagag                4067

SEQ ID NO: 6              moltype = DNA   length = 4069
FEATURE                   Location/Qualifiers
source                    1..4069
                          mol_type = unassigned DNA
                          note = Prototheca wickerhamii
                          organism = unidentified
SEQUENCE: 6
gcaatggcgc tcggtacagg gtctgcgtcc gtgctgggct ccctctccta cgatgcacaa  60
gggagcgccc cggccagctc agcgcgtcca caacctcccc tcgtcacaca cacacctgcg  120
gaaccaggcc gcccatttgc tgcttgagca tgccttgcat catgtccggg tttcccatca  180
tatcgttgag gttcttgggc tccagcttct gctccagcac accatcctgt cgatcgaaga  240
gaaggagaca tgtgtacatt attggtgtga gggcgctgaa tcggccattt tttaaaatga  300
tcacgctcat gccaatagac gcggcacata acgacgttca aacccccgcc aaagccgcgg  360
acaaccccat ccctccacac ccccacaca  aagaacccgc caccgcttac cttgcccacg  420
aggtaggcct ttcgttgcgc aaaaccggcc tcggtgatga atgcatgccc gttcctgacg  480
agcgctgccc gggccaacac gctcttttgc tgcgtctcct caggcttggg ggcctccttg  540
ggcttggtgt ccgccatgat ctgcgcgcat cagagaaacg ttgctggtaa aaaggagcgc  600
ccggctcgcg aatatatata taggcatgcc aacacagccc aacctcactc gggagcccgt  660
cccaccaccc ccaagtcgcg tgccttgacg gcatactgct gcagaagctt catgagaatg  720
atgccgaaca agaggggcac gaggacccaa tcccggacat cccttgtcgat aatgatctcg  780
tgagtcccca tcgtccgccc gacgctccgg ggagcccgcc gatgctcaag acgagagggc  840
cctcgaccag gaggggctgg cccggcgggg cactggcgtc gaaggtgcgc ccgtcgttcg  900
cctgcagtcc tatgccacaa aacaagtctt ctgacgggt gcgtttgctc ccgtgcgggc   960
aggcaacaga ggtattcacc ctggtcatgg ggagatcggc gatcgagctg ggataagaga 1020
tacggtcccg cgcaaggatc gctcatcctg gtctgagccg gacagtcatt ctggcaagca 1080
atgacaactt gtcaggaccg gaccgtgcca tatattcctc acctagcgcc gcaaaaccta 1140
acaatttggg agtcactgtg ccactgagtt cgactggtag ctgaatggag tcgctgctcc 1200
actaaacgaa ttgtcagcac cgccagccgg ccgaggaccc gagtcatagc gagggtagta 1260
gcgcgccatg gcaccgacca gcctgcttgc cagtactggc gtctcttccg cttctctgtg 1320
gtcctctgcg cgctcagcg cgtgcgcttt tccggtggat catgcggtcc gtggcgcacc 1380
gcagcggccg ctgccatgc agcgccgctg cttccgaaca gtggcggtca gggccgcacc 1440
cgcggtagcg gtccgtccgg aacccgccca agagttttgg gagcagcttg agccctgcaa 1500
gatggcggag gacaagcgca tcttcctgga ggagcaccgg tgcgtggagg tccggggctg 1560
accggccgtc gcattcaacg taatcaatcg catgatgatc agaggacacg aagtcttggt 1620
ggcggtggcc agaaacactg tccattgcaa gggcataggg atgcgttcct tcacctctca 1680
tttctcattt ctgaatccct ccctgctcac tctttctcct cctccttccc gttcacgcag 1740
cattcggggc aacgaggtgg gcccctcgca gcggctgacg atcacggcgg tggccaacat 1800
cctgcaggag gcggcgggca accacgcggt ggccatgtgg ggccggagct cggaggggttt 1860
cgcgacggac ccggagctgc aggagcggg tctcatcttt gtgatgacgc gcatggagat 1920
ccagatgtac cgctacccgc gctggggcga cctgatgcag gtggagacct ggttccagac 1980
ggcgggcaag ctgggcgcgc agcgcgagtg ggtgctgcgc gacaagctga ccgcgaggc  2040
gctgggcgcg gccacctcga gctgggtcat gatcaacatc cgcacgcgcg gccgtgccg  2100
catgccggag ctcgtccgcg tcaagtcggc cttcttcgcg cgcgagcgc cgcgcctggc   2160
gctgccgccc gcggtcacgc gtgccaagct gcccaacatc gcgacgccgg cgccgctgcg  2220
cgggcaccgc caggtcgcgc gccgcaccga catggacatg aacgggcacg tgaacaacgt  2280
ggcctacctg gcctggtgcc tggaggccgt gcccgagcac tgcttcagcg actaccacct  2340
ctaccagatg gagatcgact caaggccga gtgccacgcg ggcgacgtca tctcctccca  2400
ggccgagcag atcccgcccc aggaggcgct cacgcacaac ggcgccggcc gcaaccctc   2460
ctgcttcgtc catagcattc tgcgcgccga accgagctc gtccgcgcgc gaaccacatg   2520
gtcggccctc atcgacgcgc ccgccgctca gccgcccaag gcgagccact gaggacaggg  2580
tggttggctc gatgggaaa cgctggtcgc gggattcgat cctgctgctt atatcctcca  2640
tggaagcaca cccacgactc tgaagaagaa aacgtgcaca cacacaaccc aaccggccga  2700
atatttgctt cctatcccg ggtcaagag agactgcgat gcccccctca atcagcatcc   2760
tcctccctgc cgcttcaatc ttccctgctt gcctgcgccc gcgttgcgcc gtctgcccgc  2820
ccagtcagtc actcctgcac aggccccttg tgcgcagtgc tcctgtaccc tttaccgtc   2880
cttccattct gcgaggcccc ctattgaatg tattcgttgc ctgtgtggcc aagcggggctg 2940
ctgggcgcgc cgccgtcggg cagtgctcgg cgactttgcg ggaagccgat tgttcttctg 3000
taagccacgc gcttgctgct ttgggaagag aagggggggg tactgaatgg atgaggagga  3060
gaaggagggg tattggtatt atctgagttg ggaggcagg gagagttgga aaatgtaagt   3120
ggcacgacgg gcaaggagaa tggtgagcat gtgcatggtg atgtcgttgg tcgaggacga  3180
tcctgcacgc gtgtatctga tgtagaatac ggcaatcacc ctagtctaca tctataccttt 3240
```

```
ctccgtataa cgcccttttcc aaatgccctc ccgtttctct cctattcttg atccacatga  3300
tgaccctggc actatttcaa gggctggaca tttcaagaag gtttgcgtat ctgaagaagg  3360
attggtttgg agaggtggcc gatgaaagtg gggtcaagct gcgtggagcc ctctgcacgg  3420
atttctatgg taatctgcgt ccacgtcatc agtagccgta cgcctctgcg gcgtcgccgt  3480
gctcctcagc cgccgcttca ccaccagcca ggagcccat acgcacgcgc tcccagacgg  3540
cgcgcgcgac ggggacgatc atgagcagcg cgatctgggg cgtgtcgtgc gagctgagcc  3600
gcacaaccac gttgccctgg ccgcgcgtgg tgtactggca gttggtcgag accatggtgt  3660
cggacttgaa gtaggagccg tcaaagcgcg ggaggcgcgt ctcggccgag acgttgccgc  3720
cgatgaccag gctctggcgc ttctggcgcg ggtcgcggcc ctgccactgc gcggagccgc  3780
ccaggagcag gcgcgactcg tcaccgccgc gcagcttgca gtccgccgcc agcgccgtgc  3840
ccggctcgta ggccgacccc atcttgacga agaggcggcc gatcgctgcg cggaccttga  3900
ccgcgtcgga caggcgcagg cgctcgtcca gcttgacccc gagcgccgcg ttgccgggct  3960
tgaacggcag cgagaactcc tcgcccagct tggagccgag caggcccagc gccagcttct  4020
gccgcttgcc gcgcgcgcgc aggcgcgagt cgacgcgcag cgtgtagag              4069

SEQ ID NO: 7          moltype = DNA  length = 4083
FEATURE               Location/Qualifiers
source                1..4083
                      mol_type = other DNA
                      organism = synthetic construct
SEQUENCE: 7
gcaatggcgc tctgtgcagg gtctgtgtcc ggtctccctc tcctacgatg cacaaggcaa  60
cgcctttgct gactcagcgc gtccacaacc tcccctcgtc acacacacct gcggaaccag  120
gccgcccatt tgctgcttga gcatgccttg catcatgtcc gggttgccca tcatatcgtt  180
gaggttcttg ggctccagtt tctgctccag cacgccatcc tgtcggtcga agaggaggag  240
acatgtaagc gttgttggga tgagggttgc taaattggcc attattttta atgatcacgc  300
tcgtgccaat agacgcggca cattgcgatg ttcaaactcc cgtcaaagcc gcggacaacc  360
acatccctcc acaccccaca cacaaagaac ccgccaccgc tcaccttgcc cacgaggtag  420
gcctttcgtt gcgcaaaccc ggcctcggtg atgaatgcgt gcccgttcct gacgagcgct  480
gcccggggcca acacgctctt ttgctgcgtc tcctcaggct tggggcccct cttgggcttg  540
ggggccgcca tgatctgcgc gcaccagaga gaagtcattg gtgaaaagga gcgcccggct  600
gcgctatata tatatatata tgctcaggcc aataaagtcc aacctcactg gggagccccg  660
tcccaccacc cccaagtcgc gtaccttgac ggcatactgc tgcagaagct tcatgaggat  720
gatgccgaac aagaggggca caaggaccca atcccgacca tccttgtcga taatgatctc  780
gtgagtcccc atcgtccgcc cgacgctgcg gggagcccgc cgatgctcaa gacgagaggg  840
cccctcgacca ggaggggctg gcccgggcgg gcactggcgt cgaaggtgcg cccgtcgttc  900
gcctgcagtc cgatgacaca aaacaagtct tctgacgggg tgcgtttgct cccgtgcggg  960
caggcaacag aggtattcaa cctggtcatg gcagatcgg cgatcgagct gggataaag  1020
atacgtccc gcgcgaggat cgctcatcct ggtctgagcc ggacagtcat tctggcaagc  1080
aatgacaact tgccaggacc ggaccgtgcc atatatttct cacctagcgc ggcaaaacct  1140
aacaatttgg aagtcactgt gccactgagc tcgactggta gctgaatgga gtcgctgctc  1200
cactaatcga attgtcagca ccgccagccg gccgaggacc cgagtcatag cgagggtagt  1260
agcgcgccat ggcaccgacc agcctgcttg cccgtactgg cgtctcttcc gcttctctgt  1320
gctcctctac gcgctccggc gcgtgcgctt ttcggtgga tcatgcggtc cgtggcgcac  1380
cgcagcggcc gctgcccatg cagcgccgct gcttccgaac agtggctgtc agggccgcac  1440
ccgcagtagc cgtccgtccg gaacccgccc aagagttttg ggagcagctt gagccctgca  1500
agatgcggga ggacaagcgc atcttcctgt aggagcaccg gtgcgcggag gtccggggct  1560
gaccggccgt cgcattcaac gtaatcaatc gcatgatgat cacaggacgc gacgtcttgg  1620
tggcggtggc cagggacact gcccattgca caggcatagg aatgcgttcc ttctcatttc  1680
tcagtttttct gagcccctcc ctcttcactc tttctcctcc tcctcccctc tcacgcagca  1740
ttcgtggcaa cgaggtgggc ccctcgcagc ggctgacgat cacggcggtg gccaacatcc  1800
tgcaggaggc ggcgggcaac cacgcggtgg ccatgtgggg tcggagctcg gagggttcg  1860
cgacggaccc ggagctgcag gaggcgggcc tcatctttgt gatgacgcgc atgcagatcc  1920
aaatgtaccg ctaccccgcgc tggggcgacc tgatgcaggt ggagacctgg ttccagacgg  1980
cgggcaagct aggcgcgcag cgcgagtggg tgctgcgcaa caagctgacc ggcgaggcgc  2040
tgggcgcggc cacctccagc tgggtcatga tcaacatccg cacgcgccgg ccgtgccgca  2100
tgcccgagct cgtccgcgtc aagtcggcct tcttcgcgcg cgagccgccc cgcctggcgc  2160
tgccgcccac ggtcacgcgc gccaagctgc caacatcgc gacgccggcg ccgctgcgcg  2220
ggcaccgcca ggtcgcgcgc cgcaccgaca tggacatgaa cggcacgtg aacaacgttg  2280
cctacctggc ctggtgcctg gaggccgtgc ccgagcacgt cttcagcgac taccacctct  2340
accagatgga gatcgacttc aaggccgagt gccacgcggg cgacgtcatc tcctcccagg  2400
ccgagcagat cccgccccag gaggcgctca cgcacaacgg cgccgccgc aaccccttcct  2460
gcttcgtcca cagcattctg cgcgccgaga ccgagctcgt ccgcgcgcgc accacctggt  2520
cggcccccgt cgacgcgccc gccgccaagc gcccaaggc cgcactga gcagaggaga  2580
gggtggctgg tagttgcggg atggctggtc gcccgtcgat cctgctgctg ctattgtctc  2640
ctcctgcaca agccacccca cgactccgaa gaagaagaag aaaacgcgca cacacacaac  2700
ccaaccggcc gaatatttgc ttccttatcc cgggtccaag agacacggcg atgccccct  2760
caatcagcct cctcctcct gccactccaa tcttcccgcg ttgcatgcgc ccgcgagagg  2820
ctgtctgcgc gccccgtcag tcactcccgg tgcagacgcc tcgtgctcgg tgctcctgta  2880
tcctttaccg ctcctttcat tctgcgaggc ccctgttga atgtattcgt tgcctgtgtg  2940
gccaagcgcg ctgctgggcg cgccgccgtc gggcggtgct cggcgactct ggcggaagcc  3000
ggttgttctt ctgtaagcca cgcgcttgct gcttttggaa aagaggggggg tttactgaat  3060
ggaggaggag caggataatt ggtagtatct gagttgttgg ggaggcagga agagttggga  3120
aatggaagtg gcacgatggg caaggagaat ggtgagcatg tgtcgttgga  3180
cgagaacgat cctgcactcc cgtaagtaga atacgcaat cacgttgatc tacatctcta  3240
acttctccat ttaaagccct ttccacatgc cctcgcgttt gcatcctaca cccttttgatc  3300
cacatgattg atgaccctgg cactatctta agggctggac atttcaagaa ggtttgcgta  3360
tctgaagaag ggctggtttg aagggggtcgc cgatgagagt gggaacaagc tgcgaggatg  3420
cctctgcgcg aattcctaaa ggagtaatct gcgtccacgt catcagtagc cgtaggcctc  3480
```

```
tgcgacgtcg ccgtgctcct cggccgccgc ttcgccgccg cccagcagcc ccagacgcac   3540
gcgctcccag acggcgcgcg cgacggggac gatcatgagc agcgcgatct ggggcgtgtc   3600
gtgcgagctg agccggacga ccacgttgcc ctggccgcgc gtggtgtact ggcagtttgc   3660
cgagaccatg gtgtctgact tgaagtagga gccgtcaaag cgcggggaggc gcgtctcggc   3720
cgagacgttg ccgccgacga ccaggctctg gcgcttctga cgcgggtgcg ggccctgcca   3780
ctgcgcggag cctcccagga gcaggcgcgc ctcgtcgcgg ctgcgcagct tgaggtcggc   3840
cgccagcgcc gtgcccggct cgtaggccga cccatcttg acgaagaggc ggccgaccgc   3900
cgcgcggagc ttgaccgcgt cggacaggcg caggcgctcg tccagcttga ccccgagcgc   3960
cgcgttgccg ggcttgaacg gcagcgagaa ctcctcgccc agcttggagc cgagcaggcc   4020
cagcgccagc ttctgccgct tgccgcgcgc gcgcaggcgc gagtcgacgc gcagcgtgta   4080
gag                                                                 4083

SEQ ID NO: 8         moltype = DNA   length = 4083
FEATURE              Location/Qualifiers
source               1..4083
                     mol_type = unassigned DNA
                     note = Prototheca wickerhamii
                     organism = unidentified
SEQUENCE: 8
gcaatggcgc tctgtgcagg gtctgtgtcc ggtctccctc tcctacgatg cacaaggcaa   60
cgcctttgct gactcagcgc gtccacaacc tcccctcgtc acacacacct gcggaaccag   120
gccgcccatt tgctgcttga gcatgccttg catcatgtcc gggttgccca tcatatcgtt   180
gaggttcttg ggctccagtt tctgctccag cacgccatcc tgtcggtcga agaggaggag   240
acatgtaagc gttgttggga tgagggttgc taaaattggcc attattttta atgatcacgc   300
tcgtgccaat agacgcggca cattgcgatg ttcaaactcc cgtcaaagcc gcggacaacc   360
acatccctcc acaccccaca cacaaagaac ccgccaaccc tcaccttgcc cacgaggtag   420
gccttttcgtt gcgcaaaccc ggcctcggtg atgaatgcgt gcccgttcct gacgagcgct   480
gcccgggcca acacgctctt ttgctgcgtc tcctcaggct tggggcctc cttgggcttg   540
ggggccgcca tgatctgcgc gcaccagaga gaagtcattg gtgaaaagga gcgcccggct   600
gcgctatata tatatatata tgctcaggcc aataaagtcc aacctcactg gggagccccg   660
tcccaccacc cccaagtcgc gtaccttgac ggcatactgc tgcagaagct tcatgaggat   720
gatgccgaac aagaggggca caaggaccca atcccggaca tccttgtcga taatgatctc   780
gtgagtcccc atcgtccgcc cgacgctgcg gggagcccgc cgatgctcaa gacgagaggg   840
ccctcgacca ggaggggctg gcccgggcgg gcactggcgt cgaaggtgcg cccgtcgttc   900
gcctgcagtc cgatgacaca aaacaagtct tctgacgggg tgcgtttgct cccgtgcggg   960
caggcaacag aggtattcaa cctggtcatg gcgagatcgg cgatcgagct gggataagag   1020
atacggtccc cgcgcgaggat cgctcatcct ggtctgagcc ggacagtcat tctggcaagc   1080
aatgacaact tgcaggacc ggaccgtgcc atatatttct cacctagcgc ggcaaaaacct   1140
aacaatttgg aagtcactgt gccactgagc tcgactggta gctgaatgga gtcgctgctc   1200
cactaatcga attgtcagca ccgccagccg gccgaggacc cgagtcatag cgagggtagt   1260
agcgcgccat ggcaccgacc agcctgcttg ccgtactgg cgtctcttcc gcttctctgt   1320
gctcctctac gcgctccggc gcgtgcgctt ttccggtgga tcatgcggtc cgtggcgcac   1380
cgcagcggcc gtgcccatg cagcgccgct gcttccgaac agtggctgc agggccgcaa   1440
ccgcagtagc cgtccgtccg gaacccgccc aagagttttg ggagcagctt gagccctgca   1500
agatggcgga ggacaagcgc atcttcctgg aggagcaccg gtgcgcggag gtccggggct   1560
gaccggccgt cgcattcaac gtaatcaatc gcatgatgat cacaggacgc gacgtcttgg   1620
tggcggtgcc cagggacact gcccattgca caggcatagg aatgcgttcc ttctcatttc   1680
tcagtttttct gagcccctcc ctcttcactc tttctcctcc tcctcccctc tcacgcagca   1740
ttcgtggcaa cgaggtgggc ccctcgcagc ggctgacgat cacggcggtg gccaacatcc   1800
tgcaggaggc ggcgggcaac cacgcggtgg ccatgtgggg tcggagctcg gagggttcg   1860
cgacggaccc ggagctgcag gagcgggcc tcatcttttgt gatgacggc atgcagatcc   1920
aaatgtaccg ctaccccgcgc tggggcgacc tgatgcaggt ggagacctgg ttccagacgg   1980
cgggcaagct aggcgcgcag cgcgagtggg tgctgcgcga caagctgacc ggcgaggcgc   2040
tgggcgcggc caccttccagc tgggtcatga tcaacatccg cacgcgccgg ccgtgccgca   2100
tgcccgagct cgtccgcgtc aagtcggcct tcttcgcgcg cgagccggcg cgcctggccg   2160
tgccgcccac ggtcacgcgc gccaagctgc ccaacatcgc gacgccgcg ccgctgcgcg   2220
ggcaccgcca ggtcgcgcgc gcaccgaca tggacatgaa cggccacgtg aacaacgttg   2280
cctacctggc ctggtgcctg gaggccgtgc ccgagcacgt cttcagcgac taccacctct   2340
accagatgga gatcgacttc aagggcgagt gccacgcggg cgacgtcatc tcctcccagg   2400
ccgagcagat cccgccccag ggggcgctca cgcacaacgg ccggccgcgc aacccctcct   2460
gcttcgtcca cagcattctg cgcgccgaga ccgagctcgt ccgcgcgcgc accacctggt   2520
cggccccgt cgacgcgccc gccgccaagc cgccaaggc gagccactga gcagaggaga   2580
gggtggctgg tagttgcggg atggctggtc gcccgtcgat cctgctgctg ctattgtctc   2640
ctcctgcaaca agcccaccca cgactccgaa gaagaagaag aaaacgcgca cacacacaac   2700
ccaaccggcc gaatatttgc ttccttatcc cgggtccaag agagacgcg atgcccccct   2760
caatcagcct cctcctccct gccgctcaaa tcttccctgc ttgcatgcgc ccgcgagagg   2820
ctgtctgcgc gccccgtcag tcactccccg tgcagacgcc tcgtgctcgg tgctcctgta   2880
tcctttaccg ctccttcat tctgcgaggc ccccgttga atgtattcgt tgcctgtgtg   2940
gccaagccg ctgctgggcg cgccgccgtc gggcggtgct ggccgactct ggccgaagcc   3000
ggttgttctt ctgtaagcca cgcgcttgct gcttttggaa aagagggggg tttactgaat   3060
ggaggaggag caggataatt ggtagtatct gagttgttgg ggaggcagga agagttggga   3120
aatgaagtg gcacgatggg caaggagaat ggtgagcatg cgcagggtga tgtcgttggc   3180
cgagaacgat cctgcactcc cgtaagtaga atacggcaat cacgttgatc tacatctcta   3240
acttctccat ttaaagccgt ttccacatgc cctcgcgttt gcatcctaca cccttgatc   3300
cacatgattg atgaccctgg cactatctta agggcgtgga atttcaagaa ggtttgcgta   3360
tctgaagaag ggctggtttg aagggggtcgc cgatgagagt gggaacaagc tgcgaggatg   3420
cctctgcgcg aattcctaaaa ggagtaatct gcgtccacgt catcagtagc cgtaggcctc   3480
tgcgacgtcg ccgtgctcct cggccgccgc ttcgccgccg cccagcagcc ccagacgcac   3540
gcgctcccag acggcgcgcg cgacggggac gatcatgagc agcgcgatct ggggcgtgtc   3600
```

```
gtgcgagctg agccggacga ccacgttgcc ctggccgcgc gtggtgtact ggcagtttgc   3660
cgagaccatg gtgtctgact tgaagtagga gccgtcaaag cgcggaggc gcgtctcggc    3720
cgagacgttg ccgccgacga ccaggctctg gcgcttctga cgcgggtcgc ggccctgcca   3780
ctgcgcggag cctcccagga gcaggcgcgc ctcgtcgcgg ctgcgcagct tgaggtcggc   3840
cgccagcgcc gtgcccggct cgtaggccga ccccatcttg acgaagaggc ggccgaccgc   3900
cgcgcggagc ttgaccgcgt cggacaggcg caggcgctcg tccagcttga ccccgagcgc   3960
cgcgttgccg ggcttgaacg gcagcgagaa ctccctcgcc agcttggagc cgagcaggcc   4020
cagcgccagc ttctgccgct tgccgcgcgc gcgcaggcgc gagtcgacgc gcagcgtgta   4080
gag                                                                 4083

SEQ ID NO: 9            moltype = DNA  length = 4768
FEATURE                 Location/Qualifiers
source                  1..4768
                        mol_type = other DNA
                        organism = synthetic construct
SEQUENCE: 9
gcctgcctcg ccaactgcga gttctgcgcg cgcggcgggc gcgagggccg cgacggcgcg   60
ccggggttca ccgcctcggt cgaggagctc tgggagcggc ggcgaacaga gtttgtgcac   120
ctcccggagc aggagtttgc cggcatcatg ctcgtcatca tgccctgccg ctctgacaag   180
tcgaaaaaag gcgtcgccaa gtacgcaagc gggggtgggg tgggttgggg gtggtggcga   240
tgcgatgaaa atggtggtgt tggtggttcc gattggcgtg tcggaatttt gtgaactgag   300
cggcactctg cggctctgcc ggcgcatgcc tagtccagtt ttcgatgtgc gctatcatgt   360
accacgccgc atgcgaatct cacccttcct tctcccgccc aggtatggtc acctgagcga   420
cggcctgttg cacctggtgc tcatcaggcg gtgcagccgc ctccagtacc tcaagtttct   480
gctcaggatg tcgcacatcg gccttgaggc gggcgggcag cacgggtcct acatccaggt   540
cttgcctgcc cacgcggttgc acatcgaagc ggtacgaagc tggatcggga ggcacttgac   600
agtcgcgtcg ccgaacaagg gacgggtacc ctgaggagct tgttggaccg ctgattcact   660
ccctgacctc ccttttctct ttccaaaaca ggttggccag gagagccact ggaacgtcga   720
tggggagctc attcaaagcc gcacgataaa cgcgcagctc caccgcggag tgatcgatgt   780
gtttgcccga ggcgtggagg gctgacgtgc gcgaaactag ctgggggccc ccattcccgc   840
cctttaaacg cctgcctcct ggtccccgac cggtgctggc ggccctgatc aattcgtcca   900
ttccgttta ttctttgaca atgagcgcct catcccagtg ccaccgccca tcccaaatt    960
gttcctctca aacctctcag atacctccct tcaaactgct cccaagagtg cacgagtact  1020
tgtaatgtta tgcgaccgct gttcacaatg tagtcggcac gcttgtgtga gcgcgttcga  1080
aactcgctca gcccgtcggc ctgcccatgg acgtccctg atcgctttat gcccaccgca   1140
tggaccgcga cacgccagtt ttcgattca atagcaacga atacgcatcg ataattctgt    1200
gacattgcat gcctcaccgc gtgaattgct gtcccaaacg taagcattat catggctcgg  1260
tcacgcgatc ctggatccgg ggatcctgga ccgctggtgg agagcgctgc cgtcggattg  1320
gtggcaagca agattgcgca ggttggcgaa gggagagaac aaaaccggag gctgaagcg   1380
ggcacaacat cgtattattg cgtatagtag agcagtggca gtcgcatttc gaggtccga    1440
acggatctcg caagctcgct acgctcacag taggagatag gggaccactg cccctgccag  1500
aatggtcgcg accctgtccc tcgccggccc cgcctgcaac acgcagtgcg tatccagcaa  1560
gcgggttgtc gccttcaacc gccccccatgt tggcgtcggg gctcgatcag gtgcgctgag  1620
ggggggtttgg tgggcccgcg cctctgggcc cgtgtcggcc gtgcggacgt ggggcccggg  1680
gtagtggatc agcaggggtt gcatgcaaat gcctataccg gcgattgaat agcgatgaac  1740
gggatacggt tgcgctcact ccatgcccat gcgacccgc ttctgtccgc cagccgtggt    1800
cgcccgagct gcgaagcggg acccccaccca gcgcattgtg atcaccggaa tgggcgtggc  1860
ctccgtgttt ggcaacgatg tcgagaccctt ttacgacaag cttctggaag aacgagcgg   1920
cgtggacctg atttccaggt gcgtaggtcc ttgatgaat gcgtctaggt tgcgaggtga    1980
ctggccagga agcagcaggc ttgggggttg tgttctgat ttctggtaat ttgagggttc     2040
attataagat tctgtacggt ctttgttcga aaacatgcaa caactccaca cacacacact   2100
cctctcaact gagtctgcag gtttgacatc tccgagttcc cgaccaagtt tgcggcgcag  2160
atcaccggct tctccgtgga ggactgcgtg gacaagaaga acgcgcggcg gtacgacgac  2220
gcgctgtcgt acgcgatggt ggcctccaag aaggccctgc gccaggcagg cctggagaag  2280
gacaagtgcc ccgagggcta cggggcgctg gacaagcgc gacgggcgt gctggtcggc    2340
tcgggcatgg gcgggctgac ggtcttccag gacggcgtca aggcgctggt ggagaagggc  2400
tacaagaaga tgagccccctt cttcatcccc tacgccatca ccaacatggg ctccgcgctg  2460
gtgggcatcg accagggctt catgggcccc aactactccg tctccacagc ctgcgcgacg  2520
tccaactacg catttgtgaa cgcggccaac cacatccgca agggcgacgc ggacgtcatg  2580
gtcgtcggcg gcaccgaggc ctccatcgtg cccgtgggcc tgggcggctt tgtggcctgc  2640
cgcgcgctgt ccacgcgcaa cgacgagccc aagcgcgca gccggccgtg ggacgagggc    2700
cgcgacggct tgtgatggg cgagggcgcg ccgtgctgg tcatgagtc gctgagcac       2760
gcgcagaagc gtggcgcgac catcctgggc gagtacctgg gcggcgccat gacctgcgac  2820
ggccaccaca tgacggaccc gcaccccgag ggcctgggcg tgacacctg catccgccatg  2880
gcgctcgagg acgccggcgt ctcgcccgac gaggtcaact acgtcaacgc gcacgccacc  2940
tccaccctgg tgggcacaa ggccgaggtg cgcgcggtca gtcggtctt tggcgacatg    3000
aagggtatca agatgaacgc caccaagagt atgatcgggc actgcctggg cgccgccggc  3060
ggcatggagg ccgtcgcgac gctcatggcc atccgccacg gctgggtgca cccaccatc   3120
aaccacgaca ccccatcgc gcaggtcgat ggcctgacgc tcgtcgccaa cgccaagcgc   3180
cagcacgaca tcaacgtcgc catctccaac tccttcggct ttgcgggca caactccgtc   3240
gtcgcctttg cgcccttccg cgagtaggtg aagcgagcgt gctttgctga ggagggaggc  3300
ggggtgcgag cgctctggcc gtgcgcgcga tactctcccc gcatgagcag actcctcgtg  3360
ccacgcccga atctacttgt caacgagcaa ctgtgtgttt tgtccgtggc caatcttatt  3420
atttctccga ctgtggcgct actctgtttg gctgtgcaag caccccagga actcttttgt  3480
tgagcggggg gttatccgtag agaggggttg cgaaatgggc accgatcgga aggccttgca  3540
aacgtggcgg tcattggccg acatgatttc cgtggattca ctgatgcggc attgcttacc  3600
attcatattg aaaagacagc cttgcaacct acaatttgat ggagcaaata catatatata  3660
cggggccgac gtgtcagatg gccgttgcgc tcttgagctc cacggcccga cacagctgct  3720
cgatagcttc ctccagcggc aggcagccgc gctgccgt agcgtacgtg cgcaccgcca    3780
```

```
gggtcgagct cccggcctct tccgggccga tgaccgccat gacgggact ttggccctct  3840
cggcgttgcg aacgagcttg cccatggagg cgccgccggg cgcgagctcc acgcgcaggc  3900
cgcgcgcgcg catggcggct gccaccgtct ccatgtacgg ccgcaccgcg tccgtcgtgg  3960
gcagcagtca cacctgctcc ggggccagcc agagcgggaa ggcgcccgcg tagtgctcga  4020
tcaggatgcc gaaaagcgc tccagcgagc cgagcaggcc gcggtgcacc atgatgggcc  4080
gctggcggct gccgtcggcc gccgcgtact cgagcccgaa ccgctcgggc aggttgaagt  4140
ccagctgcac cgtggagcac tgccacttgc gcccgagcgc gtcctggatc ttgacgtcga  4200
tcttcgggcc gtaaaaggcg ccgccgccga cgtccaccgt gaaggcccag ccctgtcgat  4260
gaatgattgt tgggaggggg ggtttcgagg ttggatgaca ccacaataat atagtcagcg  4320
acacgcgtgc tgcacgataa ttaccagtac agactcggcg atgataacac cacccttttc  4380
atcaaccgaa atgagccgtt ccctgttgac aaacacacac gcacacacac cttgtcgttg  4440
agcgcttcag cgagcgccgc ctcggccctg gccagtcct cgtcggaccc gaccgactcg  4500
tccggccgcg tggagaggtt gacctcgaac cggcacgcgt cgaagccaaa ggcgcggaag  4560
acgcgctccg tgaggtccag cacggcccgg atctcggccg cgatctgctc cggcaggcag  4620
aagatgtggg cgtcgtcctg cgtgaagccg cgcacgcgga agaggccgtg catggtgccg  4680
gagcgctcgt agcggtagac agtgcccagc tccgcccagc gcagcggcag gtcgcggtag  4740
ctgacgggcc tggccgcgta gacgctga                                      4768

SEQ ID NO: 10         moltype = DNA   length = 4768
FEATURE               Location/Qualifiers
source                1..4768
                      mol_type = unassigned DNA
                      note = Prototheca wickerhamii
                      organism = unidentified
SEQUENCE: 10
gcctgcctcg ccaactgcga gttctgcgcg cgcggcgggc gcgagggccg cgacggcgcg  60
ccggggttca ccgcctcggt cgaggagctc tgggagcggc ggcgaacaga gtttgtgcac  120
ctcccggagc aggagtttgc cggcatcatg ctcgtcatca tgcccctgcc ctctgacaag  180
tcgaaaaaag gcgtcgccaa gtacgcaagc ggggtgggg tgggttgggg gtggtggcga  240
tgcgatgaaa atggtggtgt tggtggttcc gattggcgtc gtgaactgag  300
cggcactctg cggctctgcc ggcgcatgcc tagtccagtt ttcgatgtgc gctatcatgt  360
accacgccgc atgcgaatct caccctttct tctccgcccc aggtatggtc acctgagcga  420
cggcctgttg cacctggtgc tcatcaggcg gtgcagccgc ctccagtacc tcaagtttct  480
gctcaggatg tcgcacatcg gccttgaggc ggggcgggca cacgggtcct acatccaggt  540
cttgcctgcc cacgcggtgc acatcgaagc ggtacgagcg tggatcggga ggcacttgac  600
agtcgcgtcg ccgaacaagg gacgggtacc ctgaggagct tgttggaccg ctgattcact  660
ccctgacctc ccttttctct ttccaaaaca ggttggccag gagagccact ggaacgtcga  720
tggggagctc attcaaagcc gcacgataaa cgcgcagctc caccgcggag tgatcgatgt  780
gtttgcccga ggcgtggagg gctgacgtgc gcgaaactag ctgggggccc ccattcccgc  840
cctttaaacg cctgcctcct ggtccccgac cggtgctggc ggccctgatc aattcgtcca  900
ttccgtttta ttctttgaca atgagcgcct catcccagtg ccaccgccca tcccaaatt  960
gttcctctca aacctctcag atacctccct tcaaactgct cccaagagtg cacgagtact  1020
tgtaatgtta tgcgaccgct gttcacaatg tagtcggcat gcttgtgtga gcgcgttcga  1080
aactcgctca gcccgtcggc ctgcccatgg acgtcccctg atcgctttat gcccaccgca  1140
tggaccgcga cacgccagtt ttcggattca atagcaacga atacgcatcg ataattctgt  1200
gacattgcat gcctcaccgc gtgaattgct gtccaaacg taagcattat catggctcgg  1260
tcacgcgatc ctggatccgg ggatcctgga ccgctggtgg agagcgctgc cgtcggattg  1320
gtggcaagca agattgcgca ggttggcgaa gggagagacc aaaaccggag gctgaagcg  1380
ggcacaacat cgtattattg cgtatagtag agcagtggca gtcgcatttc gaggtccgca  1440
acggatctcg caagctcgct acgctcacag taggagatag gggaccactg cccctgccag  1500
aatgtcgcgg accctgtccc tcgccggccc cgcctgcaac acgcagtgcg tatccagcaa  1560
gcgggttgtc gccttcaacc gccccatgt tggcgtccgg gctcgatcag gtgcgctgag  1620
gggggtttgg tgggccccg cctctgggcc cgtgtcggcc gtgcggacgt ggggcccggg  1680
gtagtggatc agcaggggtt gcatgcaaat gcctataccg gcgattgaat agcgatgaac  1740
gggatacggt tgcgctcact ccatgcccat gcgacccgt ttctgtccgc cagccgtggt  1800
cgcccgagct gcgaagcggg accccaccca gcgcattgtg atcaccggaa tgggcgtggc  1860
ctccgtgttt ggcaacgatg tcgagacctt ttacgacaag cttctggaag aacgagcgg  1920
cgtggacctg atttccaggt gcgtaggtcc ttggatgaat gcgtctaggt tgcgaggtga  1980
ctggccagga agcagcaggc ttgggggtttg gtgttctgat ttctggtaat ttgaggtttc  2040
attataagat tctgtacggt cttgtttcga aaacatgcaa caactccaca cacacacact  2100
cctctcaact gagtctgcag gtttgacatc tccgagttcc cgaccaagtt tgcggcgcag  2160
atcaccggct tctccgtgga ggactgcgtg acaagaaga acgcgcggcg gtacgacgac  2220
gcgctgtcgt acgcgatggt ggcctccaag aaggccctgc gccaggcagg cctggagaag  2280
gacaagtgcc ccgagggcta cggggcgctg gacaagacgc gtcggtgga gcacgccaca  2340
tcgggcatgg gcgggctgac ggtcttccag gacggcgtca aggcgctggt ggagaagggc  2400
tacaagaaga tgagcccctt cttcatcccc tacgccatca ccaacatggg ctccgcgctg  2460
gtgggcatcg accagggctt catgggcccc aactactccg tctccacagc ctgcgcgacg  2520
tccaactacg catttgtgaa cgcggccaac cacatccgca agggcgacgc ggacgtcatg  2580
gtcgtcggcg gcaccgagcc ctccatcgtg cccgcgcggt tgggcgggtt tgtggcctgc  2640
cgcgcgctgt ccacgcgcaa cgacgagccc aagcgcgcga gccggccgtg ggacgagggc  2700
cgcgacggct ttgtgatggg cgagggcgcg ccgtgctgg tcatggagtc gctggagcac  2760
gcgcagaagc gtgcgcgac catcctgggc gagtacctgg cggcgccat gacctgcgac  2820
gcgcaccaca tgacggaccc gcaccccgag ggccggggcg tgagcacctg catccgcctg  2880
gcgctcagga gcaccggcgt ctcgcccgac gaggtcaact acgtcaacgc gcacgccacc  2940
tccaccctgg tgggcgacaa ggccgaggtg cgcgcggtca agtcggtctt tggcgacatg  3000
aagggtatca agatgaacgc caccaagagt atgatcggc actgcctggg cgccgccggc  3060
ggcatggagg ccgtcgcgac gctcatggcc atccgcaccg gctgggtgca ccccaccatc  3120
aaccacgaca accccatcgc cgaggtcgat ggcctgacg tcgtcgccaa cgccaaggcc  3180
cagcacgaca tcaacgtcgc catctccaac tccttcggct ttggcgggca caactccgtc  3240
```

```
gtcgcctttg cgcccttccg cgagtaggtg aagcgagcgt gctttgctga ggagggaggc    3300
ggggtgcgag cgctctggcc gtgcgcgcga tactctcccc gcatgagcag actcctcgtg    3360
ccacgcccga atctacttgt caacgagcaa ctgtgtgttt tgtccgtggc caatcttatt    3420
atttctccga ctgtggccgt actctgtttg gctgtgcaag caccccagga actcttttgt    3480
tgagcgggga gttatcgtag agagggtttg cgaaatggcg accgatcgga aggccttgca    3540
aacgtggccg tcattggccg acatgatttc cgtggattca ctgatgcggc attgcttacc    3600
attcatattg aaaagacagc cttgcaacct acaatttgat ggagcaaata catatatata    3660
cggggccgac gtgtcagatg gccgttgcgc tcttgagctc cacggcccga cacagctgct    3720
cgatagcttc ctccagcggc aggcagccgc gctggccgtc agcgtacgtg cgcaccgcca    3780
gggtcgagct cccggcctct tccggccgca tgaccgccat gacggggact ttggccctct    3840
cggcgttgcg aacgagcttg cccatggagg cgccgccggg cgcgagctcc acgcgcaggc    3900
cgcgcgcgcg catggcggct gccaccgtct ccatgtacgg ccgcaccgcg tccgtcgtgg    3960
gcagcagtcg cacctgctcc ggggccagcc agagcgggaa ggcgcccgcg tagtgctcga    4020
tcaggatgcc gaagaagcgc tccagcgagc cgagcaggcg gcggtgcacc atgatgggcg    4080
gctggcgggt gccgtcggcc gccgcgtact cgagcccgaa ccgctcgggc aggttgaagt    4140
ccagctgcac cgtggagcac tgccacttgc gcccgagcgc gtcctggatc ttgacgtcga    4200
tcttcgggcc gtaaaaggcg ccgccgccga cgtccaccgt gaaggcccag ccctgtcgat    4260
gaatgattgt tgggagggggg ggtttcgagg ttggatgaca ccacaataat atagtcagcg    4320
acacgcgtgc tgcacgataa ttaccagtac agactcggcg atgataacac cacccttttc    4380
atcaaccgaa atgagccgtt ccctgttgac aaacacacac gcacacacac cttgtcgttg    4440
agcgcttcag cgagcgccgc ctcggccctg gcccagtcct cgtcggaccc gaccgactcg    4500
tccggccgcg tggagaggtt gacctcgaac cggcacgcgt cgaagccaaa gagcgcggaag    4560
acgcgctccg tgaggtccag cacgcccgg atctcggccg cgatctgctc cggcaggcag    4620
aagatgtggg cgtcgtcctg cgtgaagccg cgcacgcgga agaggccgtg catggtgccg    4680
gagcgctcgt agcggtagac agtgcccagc tccgcccagc gcagcggcag gtcgcggtag    4740
ctgacgggcc tggccgcgta gacgctga                                       4768

SEQ ID NO: 11          moltype = DNA   length = 4792
FEATURE                Location/Qualifiers
source                 1..4792
                       mol_type = other DNA
                       organism = synthetic construct
SEQUENCE: 11
gcctgcctcg ccaactgcga gttctgcgcg cgcggcgggc gcgagggccg cgacggcgcg      60
gcgggggttca ccgcctcggc cgaggagctc tgggagcggc ggcgcagcaga gtttgtgcac    120
ctcccggagc aggagtttgc aggcatcatg ctcgtcatca tgccctgccg ctctgacaag    180
tcgaaaaagg gcgtcgccaa gtacgcaagc acaggggggtg gggtggggtg ggggtggtgg    240
cggtgcgatg aaaatggtgg tgtttggtgg ttcacattgg cgtgtcggag ttttgtgaag    300
tgagcttcac tctgcggctc tcccggcgca tgcctagtcc agtttcgat gtgcgctatc    360
gtgtaccacg ccgcgtgcga atcccaccct ttcttctccg ccccaggtat ggtcacctga    420
gcgacggcct gctgcacctg gtgctcatca ggcggtgcag ccgcctccag tacctcaagt    480
ttctgctcag gatgtcgcac atcggcctcg aggcgggcgg gcagcacggg tcctacatcc    540
aggtcctgcc cgcccacgcg gtgcacatcg aagcggtacg agcgtggatc gggaggcact    600
tgacagtcgc gtcgcccgac aaggcacggg cgccctgagg agcttgttgg gccgctgatt    660
cacttccctg gcctcccctt tctctttcca aaccaggttg gccaggagag ccactggaac    720
gtcgatgggg agctcattca aagccgcacg atcaacgcgc agctccaccg cggagtgatc    780
gacgtgtttg ccagaggcgt ggagggctga cgagcgcgaa actagctggg agccccattc    840
ccgcccttga aacgcctgcc tcctgggccc tggccggtgc tggcggccct gaccgattgc    900
tccattccgt tttattcttt gacaatgagc gcctcatccc agtgcctcat cccagtgcca    960
ccgcccatcc ccaaattgtt cctctcaaac ctctcagata cccccttcaa actgctccca    1020
agagtgcacg agtatttgta atgttatacg accgctgttc acaatgtagt cggcatgctt    1080
gtatgagcct gttcgaaact cgctcagccc gtcggcctgc ccatggacct cccctgatcg    1140
cttcacgccc accgcatgga ctgcgacacg ccagttttgg gattcaatat caaaaaatac    1200
gcttcggtaa ttctgtaacg ttgcatgcct caccgcgtga attgctgtcc caaacgtaag    1260
catccgctg gctcggtcac gcgatcctgg atccgggat cctagaccgc tggtggagag    1320
cgctgccgtc ggattggtgg caagtaagat tgccgcaggtt ggcgaaggga gagaccaaaa    1380
ccggaggctg gaagcgggca caacatcgta ttattgcgta tagtagagca gtggcagtcg    1440
catttcgagg tccgcaacgg atccgcaag ctcgctacgc tcacagtagg agaaagggga    1500
ccactgcccc tgccagaatg gtcgcgaccc tctccctcgc cggcccgcc tgcaacacg    1560
agtgcgtatc cggcaagcgg gctgtcgcct tcaaccgccc ccatgttggc gtccggctc    1620
gatcaggtgc gctgagggg gtttggtgtg cccgcgcctc tgggcccgtg tcggccgtgc    1680
ggacgtgggg ccctgggcag tggatcagca gggtttgcgt gcaaatgcct ataccggcga    1740
ttgaatagcg atgaacggga tacggttgcg ctcactccat gcccatgcga cccgttcct    1800
gtccgccagc cgtggtcgcc cgggctgcga agcggcgca cacccagcgc attgtgatca    1860
ccggaatggg cgtggcctcc gtgtttggca acgatgtcga gacctttac aacaagcttc    1920
tggaaggaac gagcggcgtg gacctgattt ccaggtgcgt aggtccttgg atgcatgcgt    1980
ctaggttggg aggcggctgg cgaggaagca gcaggcttgg ggtttggtgt tccgatttct    2040
ggcaatttga ggtttcattg tgagattcta tgcggtcttg tttcgaaaac atgcaacaac    2100
tccacacaca cacactcctc tccaccaact ctgcaggttt gacatctccg agttcccgac    2160
caagttttgcg gcgcagatca ccggcttctc cgtggaggac tgcgtggaca agaagaacgc    2220
gcggcggtac gacgacgcgc tgtcgtacgc gatggtggcc tccaagaagg ccctgcgcca    2280
ggcgggactg gagaaggaca agtgcccga gggctacgga gcgctggata agacgcgcgc    2340
gggcgtgctg gtcggctcgg gcatgggcgg gctgacggtc ttccaggacg cgtcaaggc    2400
gggag aaggctaca agaagatgag cccttcttc atcccctacg ccatcaccaa    2460
catgggctc gcgctggtgg gcatcgacca gggcttcatg gggccaact actccgtctc    2520
cacgcctgc gcgacctcca actacgcctt tgtgaacgcg ccaaccaca tccgcaaggg    2580
cgacgcggac gtcatggtcg tgggcggcac cgaggcctcc atcgtgcccg tgggcctggg    2640
cggctttgtg gcctgccgcg cgctgtccac gcgcaacgca gagcccaagc gcgcgagccg    2700
gccgtgggac gagggccgcg acggcttcgt gatgggcgag ggcgcggccg tgctggtcat    2760
```

```
ggagtcgctg gagcacgcgc agaagcgcgg cgcgaccatc ctgggcgagt acctgggggg    2820
cgccatgacc tgcgacgcgc accacatgac ggaccgcac  cccgagggcc tgggcgtgag    2880
cacctgcatc cgcctggcgc tcgaggacgc cggcgtctcg cccgacgagg tcaactacgt    2940
caacgcgcac gccacctcca ccctggtggg cgacaaggcc gaggtgcgcg cggtcaagtc    3000
ggtctttggc gacatgaagg gcatcaagat gaacgccacc aagtccatga tcgggcactg    3060
cctgggcgcc gccggcggca tggaggccgt cgccacgctc atggccatcc gcaccggctg    3120
ggtgcacccc accatcaacc acgacaaccc catcgccgag gtcgacggcc tggacgtcgt    3180
cgccaacgcc aaggcccagc acaaaatcaa cgtcgccatc tccaactcct tcggcttcgg    3240
cgggcacaac tccgtcgtcg cctttgcgcc cttccgcgag taggcgggagc gagcgcgctt    3300
ggctgaggag ggaggcgggg tgcgagccct ttggctgcgc gcgatactct ccccgcacga    3360
gcagactcca cgcgcctgaa tctacttgtc aacgagcaac cgtgtgtttt gtccgtggcc    3420
attcttatta tttctccgac tgtggccgta ctctgtttgg ctgtgcaagc accccaggaa    3480
ctcttttgtc gagcggggg  tgtcgtagag agggtccgcg aaacaggcac cgatcgcgag    3540
cctcgtggtg gtcattgttc gacatgattc ccggagattc actgatgcgg cattgcttac    3600
cattcatttg aaaagacagc ttgcaaccta caattcgaag gagcgaatac atatatatac    3660
ggggccggcg tgtcagatcg ccgtttcgct cttgagctcc acggcccgac acagctgctc    3720
gatgacttcc tccagcggca ggcagccgcg ctggccgtcg gcgtacgtgc gcaccgccag    3780
ggtcgagctc ccggcctctt ccgggccgat gaccgccatg acggggacct tggccctctc    3840
ggcgttgcgg atgagcttgc ccatggaggc cccgccgggc gcgagctcca cgcgcaggcc    3900
gcgcgcgcgc atgcgtctg  ccaccgtctc catgtagggc cgcaccgcgt ccgtcgtggg    3960
cagcaggcgc acctgctccg gggccagcca gagcgggaag gcgcccgcgt agtgctcgat    4020
caggatgccg aagaagcgct ccagcgagcc gagcaggggcg cggtgaatca tgatgggccg    4080
ctggcggctg ccgtcggcgg ccgcgtactc gagcccaaac cgctcgggca aattgaagtc    4140
cagctgcacc gtggagcact gccacttgcg cccgagcgcg tcctggatct tgacgtcgat    4200
cttcgggccg taaaggcgc  cgccgccggc gtccaccgtg aagcccagc  cctgtcgatg    4260
aatgattcgt ggttgagagg gcggatttt  cgaggtcgtg atatgatgac ggtatgcgcc    4320
acaataatac tacactcgcg ccagtcagcg acacgcgtgc tgcacaatgc ctactactat    4380
agactcggtg atgatgatac caccctttc  atcgaacgag atgggccatt ccctactgac    4440
aaacacacac gcaccttgtc gttcagcgct tcggcgagcg ccgcctcggc cctggcccag    4500
tcctcgtcgg acccgaccga ctcgtccggc cgcgtggaga ggttgacctc gaaccggcgc    4560
gcgtcgaagc caaggcgcg  gaagacgcgc tccgtgaggt ccagcacggc ccggatctcg    4620
gccgcgatct gctccggcag gcagaagacg tgggcgtcgt cctgcgtgaa gccgcgcacg    4680
cggaagaggc cgtgcatggt gccggagcgc tcgtagcggt agaccgtgcc cagctccgcc    4740
cagcgcagcg gcaggtcgcg gtagctgacg ggccgggccc cgtagacgct ga            4792

SEQ ID NO: 12            moltype = DNA   length = 4793
FEATURE                  Location/Qualifiers
source                   1..4793
                         mol_type = unassigned DNA
                         note = Prototheca wickerhamii
                         organism = unidentified
SEQUENCE: 12
gcctgcctcg ccaactgcga gttctgcgcg cgcggcgggc gcgagggccg cgacggcgcg     60
gcggggttca ccgcctcggc cgaggagctc tgggagcggc ggcgagcaga gtttgtgcac    120
ctcccggagc aggagtttgc aggcatcatg ctcgtcatca tgccctgccg ctctgacaag    180
tcgaaaaagg gcgtcgccaa gtacgcaagc acagggggtg gggtggggtg gggtggtgg     240
cggtgcgatg aaaatggtgg tgtttggtgg ttcacattgg cgtgtcggag ttttgtgaag    300
tgagcttcac tctgcggctc tcccggcgca tgcctagtcc agttttcgat gtgcgctatc    360
gtgtaccacg ccgcgtgcga atcccaccct ttcttctccg ccccaggtat ggtcacctga    420
gcgacggcct gctgcacctg tgctcatca  ggcggtgcag ccgcctccag tacctcaagt    480
ttctgctcag gatgtcgcac atcggcctcg aggcgggcgg gcagcacggg tcctacatcc    540
aggtcctgcc cgcccacgcg gtgcacatcg aagcggtacg agcgtggatc gggaggcact    600
tgacagtcgc gtcgcccgac aaggcacggg cgccctgagg agcttgttgg gccgctgatt    660
cacttccctg gcctcccctt tctctttcca accaggttg  gccaggagag ccactggaac    720
gtcgatgggg agctcattca aagccgcacg atcaacgccg agctccaccg cggagtgatc    780
gacgtgtttg ccagaggcgt ggagggctga cgagcgcgaa actagctggg gccccattc    840
ccgcccttga aacgcctgcc tcctgggccc tggccggtgc tggcggccct gaccgattcg    900
tccattccgt tttattcttt gacaatgagc gcctcatccc agtgcctcat cccagtgcca    960
ccgccatcc  ccaaattgtt cctctcaaac ctctcagata ccccccttca aactgctccc   1020
aagagtgcac gagtatttgt aatgttatac gaccgctgtt cacaatgtag tcggcatgct   1080
tgtatgagcc tgttcgaaac tcgctcagcc cgtcggcctg cccatggacc tcccctgatc   1140
gcttcacgcc caccgcatgg actgcgacac gccagttttg ggattcaata tcaaaaaata   1200
cgcttcggta attctgtaac gttgcatgcc tcaccgcgtg aattgctgtc ccaaacgtaa   1260
gcatcatcgt ggctcggtca cgcgatcctg gatccggaga tcctagaccg ctggtggaga   1320
gcgctgccgt cggattggtg gcaagtaaga ttgcgcaggt tggcgaaggg agagaccaaa   1380
accggaggct ggaagcgggc acaacatcgt attattgcgt atagtagagc agtggcagtc   1440
gcatttcgag gtccgcaacg gatctcgcaa gctcgctacg ctcacagtag agaaaggggg   1500
accactgccc ctgccagaat ggtcgcgacc ctctccctcg ccggccccgc ctgcaacacg   1560
cagtgcgtat ccggcaagcg ggctgtcgcc ttcaaccgcc ccatgttgg  cgtccgggct   1620
cgatcaggtg cgctgagggg ggtttggtgt gcccgcgcct ctgggccgt  gtcggccgtg   1680
cggacgtggg gccctgggca gtggatcagc agggtttgcg tgcaaatgcc tataccggcg   1740
attgaatagc gatgaacggg atacggttgc gctcactcca tgcccatgcg accccgtttc   1800
tgtccgccag ccgtggtcgc ccgggctgcg aagcgggacc ccacccagcg cattgtgatc   1860
accggaatgg gcgtggcctc cgtgtttggc aacgatgtcg agaccttttta caacaagctt   1920
ctggaaggaa cgagcggcgt ggacctgatt tccaggtcgc taggtccttg gatgcatgcg   1980
tctaggttgg gaggcggctg gcgaggaagc agcaggcttg gggtttggtg ttccgatttc   2040
tggcaatttg aggtttcatt gtgagattct atgcggtctt gtttcgaaaa catgcaacaa   2100
ctccacacac acacactcct ctccaccaac tctgcaggtt tgacatctcc gagttccga    2160
ccaagtttgc ggcgcagatc accggcttct ccgtggagga ctgcgtggac aagaagaacg   2220
```

```
cgcggcggta cgacgacgcg ctgtcgtacg cgatggtggc ctccaagaag gccctgcgcc    2280
aggcgggact ggagaaggac aagtgccccg agggctacgg agcgctggat aagacgcgcg    2340
cgggcgtgct ggtcggctcg ggcatgggcg ggctgacggt cttccaggac ggcgtcaagg    2400
cgctggtgga aagggctac aagaagatga gccccttctt catcccctac gccatcacca    2460
acatgggctc cgcgctggtg ggcatcgacc agggcttcat ggggcccaac tactccgtct    2520
ccacggcctg cgcgacctcc aactacgcct tgtgaacgc ggccaaccac atccgcaagg    2580
gcgacgcgga cgtcatggtc gtgggcggca ccgaggcctc catcgtgccc gtgggcctgg    2640
gcggctttgt ggcctgccgc gcgctgtcca cgcgcaacga cgagcccaag cgcgcgagcc    2700
ggccgtggga cgagggccgc gacggcttcg tgatgggcga gggcgcggcc gtgctggtca    2760
tggagtcgct ggagcacgcg cagaagcgcg cgcgaccat cctgggcgag tacctggggg    2820
gcgccatgac ctgcgacgcg caccacatga cggacccgca ccccgagggc ctgggcgtga    2880
gcacctgcat ccgcctggcg ctcgaggacg ccggcgtctc gcccgacgag gtcaactacg    2940
tcaacgcgca cgccacctcc accctggtgg gcgacaaggc cgaggtgcgc gcggtcaagt    3000
cggtctttgg cgacatgaag ggcatcaaga tgaacgccac caagtccatg atcgggcact    3060
gcctgggcgc cgccggcggc atggaggccg tcgccacgct catggccatc cgcaccggct    3120
gggtgcaccc caccatcaac cacgacaacc ccatcgccga ggtcgacggc ctggacgtcg    3180
tcgccaacgc caaggcccag cacaaaatca acgtcgccat ctccaactcc ttcggcttcg    3240
gcgggcacaa ctccgtcgtc gcctttcgc ccttccgcga gtaggcggga cgagcgcgct    3300
tggctgagga gggaggcggg gtgcgagccc tttggctgcg cgcgatactc tccccgcacg    3360
agcagactcc acgcgcctga atctacttgt caacgagcaa ccgtgtgttt tgtccgtggc    3420
cattcttatt atttctccga ctgtggccgt actctgtttg gctgtgcaag cacccaggga    3480
actctttgt cgagcggggg gtgtcgtaga gagggtccgc gaaacaggca ccgatcgcga    3540
gcctcgtggt ggtcattgtt cgacatgatt cccggagatt cactgatgcg gcattgctta    3600
ccattcattt gaaaagacag cttgcaacct acaattcgaa ggagcgaata catatatata    3660
cggggccggc gtgtcagatc gccgtttcgc tcttgagctc cacggcccga cacagctgct    3720
cgatgacttc ctccagcggc aggcacgcgc gctggccgtc ggcgtacgtg cgcaccgcca    3780
gggtcgagct cccggcctct tccgggccga tgaccgccat gacggggacc ttggccctct    3840
cggcgttgcg gatgagcttg cccatggagg ccccgccggg cgcgagctcc acgcgcaggc    3900
cgcgcgcgcg catggcgtct gccaccgtct ccatgtaggg ccgcaccgcg tccgtcgtgg    3960
gcagcaggca cacctgctcc ggggccagcc agagcgggaa ggcgcccgcg tagtgctcga    4020
tcaggatgcc gaagaagcgc tccagcgagc cgagcaggcg gcggtgaatc atgatgggcc    4080
gctggcggct gccgtcggcg gccgcgtact cgagcccaaa ccgctcgggc aaattgaagt    4140
ccagctgcac cgtggagcac tgccacttgc gcccgagcgc gtcctggatc ttgacgtcga    4200
tcttcgggcc gtaaaaggcg ccgccgccgg cgtccaccgt gaaggcccag ccctgctgat    4260
gaatgattcg tggttgagag ggcggatttt tcgaggtctg gatgatgata cggtatgccg    4320
cacaataata ctacactcgc gccagtcagc gacacgcgtg ctgcacaatg cctactacta    4380
tagactcggt gatgatgata ccacccttttt catcgaacga gatgggccat tccctactga    4440
caaacacaca cgcaccttgt cgttcagcgc ttcggcgagc gccgcctcgg ccctggccca    4500
gtcctcgtcg gacccgaccg actcgtccgg ccgcgtggga aggttgacct cgaaccggcg    4560
cgcgtcgaag ccaaaggcgc ggaagacgcg ctccgtgagg tccagcacgg cccggatctc    4620
ggccgcgatc tgctccggca ggcagaagac gtgggcgtcg tcctgcgtga agccgcgcac    4680
gcggaagagg ccgtgcatgg tgccggagcg ctcgtagcgg tagaccgtgc ccagctccgc    4740
ccagcgcagc ggcaggtcgc ggtagctgac gggccgggcc gcgtagacgc tga           4793
```

| SEQ ID NO: 13 | moltype = DNA length = 4205 |
|---|---|
| FEATURE | Location/Qualifiers |
| source | 1..4205 |
| | mol_type = other DNA |
| | organism = synthetic construct |

SEQUENCE: 13

```
aaacccgatg atgcccagcg cggagctcag catgtcgccg agcatcgctg gataggacga      60
attggcaggg taccacctga agaatgggag gcaggtgctg ctgattacga gtgtggaaaa     120
gaaaggggc agagagccgt cctcagatcc gaccactatg caggtagccg ctcgcccgtg     180
cccgcctggc tgaatattga cacatgccca tcaaggcagg caggcatttc tgtgcatgca     240
ccaaacccat aatcttcgaa aacacacagc atgtaccaac gcacgcgtaa aagttgggt     300
gctgccagtg cgtcatgcca ggcatgatgt gctcctgcac atcggccatg atctcctcca     360
tcgtctcggg cgtctccggc gcctggtccg ggagccgttc cgccagatac ccagacgcca     420
cctccgacct cacggggtac ttttcgagcg actgtcggta gtcgacgatc gcgtccacca     480
tggagtagcc gaggcgccgg aactggcgtg acggagggag aacaggggg gttgatgatc     540
acacgccagt ctcacaacgc atgtaagacc cgttggatta tgagtataat catgcattac     600
tagttgggtg agcgccaggc ataaggcaca ccgacgtcga tggcacgagc aactcccgca     660
tcatatttcc tattgtccta acgccaagcc ggtcaccacc gcatgctcg tactacagcg     720
cacgcaccgc ttcgtgatcc accgggtgaa cgtagtcctc gacggaaaca tctgttccgg     780
gcctcctgct tgcactcccg ccatgccga caaccttttcc ttaccacgac ccgaccaacaa     840
tgcaacgcga cacgaccgtg tgggactgat cggttcactg cacctgcatg caattgtcac     900
aagcgcttac tccaattgta ttcgtttgtt ttctgggagc agttgctcga ccgcccgcgt     960
cccgcaggca gcgatgacgt gtgcgtggcc tgggtgtttc gtcgaaaggc cagcaaccct    1020
aaatcgcagg cgatccggag attgggatct gatccgagtt tggaccagat ccgccccgat    1080
gcggcacggg aactgcatcg actcggcgcg gaacccagct ttcgtaaatg ccagattggt    1140
gtccgatacc tggatttgcc atcagcgaaa caagacttca gcagcgagcg tatttggcgg    1200
gcgtgctacc agggttgcat acattgccca tttctgtctg gaccgcttta ctggcgcaga    1260
gggtgagtta atggggttgg caggcatcga acgcgcgtg catggtgtgc gtgtctgttt    1320
tcggctgcac gaattcaata gtcggatggg cgacggtaga attgggtgtg cgctcgcgt    1380
gcatgccgtg ccccgtcggg tgtcatgacc gggactgaaa tccccccgtcg cgaccatctt    1440
gctaacgctc ccgactctcc cgaccgcgcg caggatagac tcttgttcaa caatcgaca    1500
atggcgtctg ccgtcacctt tgcgtgcgcc cctcccgcg gcgcggtcgc cgcgccgggt    1560
cgccgcgctg cctcgcgtcc cctggtggtg gcgcggtcg ccagcgaggc ccgctgggc    1620
gttccgccct cggtgcagcg cccctccccc gtggtctact ccaagctgga caagcagcac    1680
cgcctgacgc ccgagcgcct ggagctggtg cagagcatgg gcagtttgc ggaggagagg    1740
```

-continued

```
gtgctgcccg tgctgcaccc cgtggacaag ctgtggcagc cgcaggactt tttgcccgac  1800
cccgagtcgc ccgacttcga ggatcaggtg gcggagctgc gcgcgcgcgc caaggacctg  1860
cccgacgagt actttgtggt gctggtgggg gacatgatca cggaggaggc gctgccgacc  1920
tacatggcca tgctcaacac gctggacggc gtgcgcgacg acacgggcgc ggccgaccac  1980
ccgtgggcgc gctggacgcg gcagtggggtg gccgaggaga accggcacgg cgacctgctg  2040
aacaagtact gctggctgac ggggcgcgtc aacatgcggg ccgtggaggt gaccatcaac  2100
aacctgatca agagcggcat gaacccgcag acggacaaca accctttattt ggggttcgtc  2160
tacacctcct tccaggagcg cgccaccaag tacagccacg caacaccgc gcgccttgcg  2220
gccgagcacg gcgacaagaa cctgacagaa atctgcgggc tgatcgccag cgacgagggc  2280
cggcacgaga tcgcctacac gcgcatcgtg gacgagttct tccgcctcga ccccgagggg  2340
gccgtcgccg cctacgccaa catgatgcgc aagcagatca ccatgcccgc gcacctcatg  2400
gacgacatgg gccacggcga ggccaacccg ggccgcaacc tcttcgccga cttctccgcg  2460
gtcgccgaga agatcgacgt ctacgacgcc gaggactact gccgcatcct ggagcacctc  2520
aacgcgcgct ggaaggtgga cgagcgccag gtcagcggcc aggccgccgc ggaccaggag  2580
tacgtcctgg gcctgcccca gcgcttccgg aaactcgccg agaagaccgc cgccaagcgc  2640
aagcgcgtcg cgcgcaggcc cgtcgccttc tcctggatct ccgggcgcga gatcatggtc  2700
tagggagcga cgagtgtgcg tgcggggctg gcgggagtgg gacgccctcc tcgctcctct  2760
ctgttctgaa cggaacaatc gccaccccg cgctacgcgc cacgcatcga gcaacgaaga  2820
aaaccccccg atgataggtt gcggtggctg ccgggatata gatccggccg cacatcaaag  2880
ggcccctccg ccagagaaga agctcctttc ccagcagact ccttctgctg ccaaaacact  2940
tctctgtcca cagcaacacc aaaggatgaa cagatcaact tgcgtctccg cgtagcttcc  3000
tcggctagcg tgcttgcaac aggtccctgc actattatct tcctgctttc ctctgaatta  3060
tgcggcaggc gagcgctcgc tctggcgagc gctccttcgc gccgccctcg ctgatcgagt  3120
gtacagtcaa tgaatggtcc tgggcgaaga acgagggaat ttgtgggtaa acaagcatc  3180
gtctctcagg ccccggcgca gtggccgtta aagtccaaga ccgtgaccag gcagcgcagc  3240
gcgtccgtgt gcgggccctg cctggcggct cggcgtgcca ggctcgagag cagctccctc  3300
aggtcgcctt ggacggcctc tgcgaggccg tgagggcct gcaggagcgc ctcgagcgtg  3360
gcagtggcgg tcgtatccgg gtcgccggtc accgcctgcg actcgccatc cgaagagcca  3420
tcgtcgtcgt ctcccagact ggacgcgctc gccatcggcc ccgccgatgc agaacacgcc  3480
tctgcgctcg ccgtgcgcag cgccggcgc agcgctgcgc gcagggc cgcgtccagc  3540
aggcccatcg ccagctcccg gccgcgaggg ccggccagcg cctcaaagcc gccggcgcgg  3600
gcggccgcca ccaccgaggc cagcgcggcg cgcgcgccct ccagggtcgg cgcccgggtc  3660
acgggcgtcgc gcgcccaggc ggccagcgcc gccccccgta gaacgcagtg cgcctccatc  3720
gaccgcacaa agtgggagac ccggtggctc gtggggtcgt agggccgcac gcggcggcgc  3780
gcgggcctcg tggttgcgcg cgtgctgctc cgcagccccg caatcgtcac gctccccttgc  3840
cgatccacgc tcgcggcggc cagcctggcc caggccagct ggaggccag gcgcatgctg  3900
gcgcggacct gctccagaaa gggcccgtcg cccagcatgc acagcggcca ggggagcgtc  3960
aggtcgaacc gcaggcgctc cagcgtgcg acgcgcggag gctcgcccgg gagcggcag  4020
ggacgacggg gcgattgggt ggccggcggc gaataaccag ggtgcactcc gtcagcagcc  4080
tcctccgacc tcacaccccc ctgcctcttg agctggcggc accgggccgc gatggccgca  4140
ccggcgcgtgt ccagcacgcc cgcttccaca gccacgtgca gctcgatgcc ggcgacgtcc  4200
gtctc                                                              4205
```

```
SEQ ID NO: 14          moltype = DNA   length = 4205
FEATURE                Location/Qualifiers
source                 1..4205
                       mol_type = unassigned DNA
                       note = Prototheca wickerhamii
                       organism = unidentified
SEQUENCE: 14
aaacccgatg atgcccagcg cggagctcag catgtcgccg agcatcgctg gataggacga  60
attggcaggg taccacctga agaatgggag gcaggtgctg ctgattacga gtgtggaaaa  120
gaaaggggc agagagccgt cctcagatcc gaccactatg caggtagccg ctcgcccgtg  180
cccgcctggc tgaatattga cacatgccca tcaaggcagg caggcatttc tgtgcatgca  240
ccaaacccat aatcttcgaa aacacacagc atgtaccaac gcacgcgtaa aagttgggggt  300
gctgccagtg cgtcatgcca ggcatgatgt gctcctgcac atcggccatg atctcctcca  360
tcgtctcggg cgtctccggc gcctggtccg ggagccgttc cgccagatac ccagacgcca  420
cctccgacct cacggggtac ttttcgagcg actgtcggta gtcgacgatc gcgtccacca  480
tggagtagcc gaggcgccgg aactggcgtg acggagggag aacaggggg gttgatgatc  540
acacgccagt ctcacaacgc atgtaagacc cgttggatta tgagtataat catgcattac  600
tagttggtg agcgccaggc ataaggcaca ccgacgtcga tggcacgagc aactcccgca  660
tcatatttcc tattgtccta acgccaagcc ggtcaccacc gcatgctcg tactacagcg  720
cacgcaccgc ttcgtgatcc accgggtgaa cgtagtcctc gacggaaaca tctgttcgg  780
gcctcctgct tgcactcccg ccatgccga caacctttct gctgttacca cgacccacaa  840
tgcaacgcga cacgaccgtg tgggactgat cggttcactg cacctgcatg caattgtcac  900
aagcgcttac tccaattgta ttcgtttgtt ttctgggagc agttgctcga ccgcccgcgt  960
cccgcaggca gcgatgacgt gtgcgtggcc tgggtgtttc gtcgaaaggc cagcaaccct  1020
aaatcgcagg cgatccggag attgggatct gatccggagtt tggaccagat ccgccccgat  1080
gcggcacggg aactgcatcg actcggcgcg gaacccagct ttcgtaaatg ccagattggt  1140
gtccgatacc tggatttgcc atcagcgaaa caagacttca gcagcgagcg tatttggcgg  1200
gcgtgctacc agggttgcat acattgccca tttctgtctg gaccgcttta ctggcgcaga  1260
gggtgagtta atggggttgg caggcatcga acgcgcgtg catggtgtgc gtgtctgttt  1320
tcggctgcac gaattcaata gtcggatggg cgacggtaga attgggtgtg cgctcgcgt  1380
gcatgcctgc ccctcgcggg tgtcatgacc gggactgaga tcccccctcg cgaccatctt  1440
gctaacgctc ccgactctcc cgaccgcgcg caggatagac tcttgttcaa ccaatcgaca  1500
atggcgtctg ccgtcacctt tgcgtgcgcc cctcccgcg gcgcgtcgc cgcgcgggt  1560
cgccgcgctg cctcgcgtcc cctggtggtg gcgcggtcg ccagcgaggc cccgctgggc  1620
gttccgcct cggtgcagcg ccctccccc gtggtcact ccaagctgga caagcagcac  1680
cgcctgacgc ccgagcgcct ggagctggtg cagagcatgg ggcagtttgc ggaggagagg  1740
```

```
gtgctgcccg tgctgcaccc cgtggacaag ctgtggcagc cgcaggactt tttgcccgac  1800
cccgagtcgc ccgacttcga ggatcaggtg gcggagctgc gcgcgcgcgc caaggacctg  1860
cccgacgagt actttgtggt gctggtgggg gacatgatca cggaggaggc gctgccgacc  1920
tacatggcca tgctcaacac gctggacggc gtgcgcgacg acacgggcgc ggccgaccac  1980
ccgtggcgc  gctggacgcg gcagtgggtg gccgaggaga accggcacgg cgacctgctg  2040
aacaagtact gctggctgac ggggcgcgtc aacatgcggg ccgtggaggt gaccatcaac  2100
aacctgatca gagcggcat  gaacccgcag acggacaaca accccttattt ggggttcgtc  2160
tacacctcct tccaggagcg cgccaccaag tacagccacg gcaacaccgc gcgccttgcg  2220
gccgagcacg gcgacaagaa cctgacgaag atctgcgggc tgatcgccag cgacgagggc  2280
cggcacgaga tcgcctacac gcgcatcgtg gacgagttct tccgcctcga ccccgagggc  2340
gccgtcgccg cctacgccaa catgatgcgc aagcagatca ccatgcccgc gcacctcatg  2400
gacgacatgg gccacggcga ggccaacccg gccgcaacc  tcttcgccga cttctccgcg  2460
gtcgccgaga agatcgacgt ctacgacgcc gaggactact gccgcatcct ggagcacctc  2520
aacgcgcgct ggaaggtgga cgagcgccag gtcagcggcc aggccgccgc ggaccaggag  2580
tacgtcctgg gcctgcccca cgcgcttccg aaactcgccg agaagaccgc cgccaagcgc  2640
aagcgcgtcg cgcgcaggcc cgtcgccttc tcctggatct ccgggcgcga gatcatggtc  2700
tagggagcga cgagtgtgcg tgcggggctg gcgggagtgg gacgccctcc tcgctcctct  2760
ctgttctgaa cggaacaatc gccaccccg  cgctacgcgc cacgcatcga gcaacgaaga  2820
aaaccccccg atgataggtt gcggtggctg ccgggatata gatccggccg cacatcaaag  2880
ggcccctccg ccagagaaga agctcctttc ccagcagact ccttctgctg ccaaaacact  2940
tctctgtcca cagcaacacc aaaggatgaa cagatcaact tgcgtctccg cgtagcttcc  3000
tcggctagcg tgcttgcaac aggtccctgc actattatct ttctgctttc ctctgaatta  3060
tgcggcaggc gagcgctcgc tctggcgagc gctccttcgc gccgcctcg  ctgatcgagt  3120
gtacagtcaa tgaatggtcc tgggcgaaga acgagggaat ttgtgggtaa acaagcatc   3180
gtctctcagg ccccggcgca gtggccgtta aagtccaaga ccgtgaccag gcagcgcagc  3240
gcgtccgtgt gcgggccctg cctggccgct cggcgtgcca ggctcggagg cagctccctc  3300
aggtcgcctt ggacggcctc tgcgaggccg tgagggcct  gcaggagcgc ctcgagcgtg  3360
gcagtggcgg tcgtatccgg gtcgccggtc accgctgcg  actcgccatc cgaagagcca  3420
tcgtcgtcgt ctcccagact ggacgcgctc gccatcggcc ccgccgatgc agaacacgcc  3480
tctgcgctcg ccgtgcgcag cgccgcgcgc agcgctgcgc ggccaggc  cgcgtccagc  3540
aggcccatcg ccagctcccg gccgcgaggg ccggccagcg cctcaaagcc gccggcgcgg  3600
gcggccgcca ccaccgaggc cagcgcggcg cgcgcgccct ccagggtcgg cgcccgggtc  3660
acgggtcgc  gcgcccaggc ggccagcgcc gccccccgta aacgcagtg  cgcctccatc  3720
gaccgcacaa agtgggagac ccggtggctc gtggggtcgt agggccgcac gcggcggcgc  3780
gcgggcctcg tggttgcgcg cgtgctgctc cgcagcccg  caatcgtcac gctccccttgc  3840
cgatccacgc tcgcggcggc cagcctggcc caggccagct ggaggccccag gcgcatgctg  3900
gcgcggacct gctccagaaa ggggccgtcg cccagcatgc acagcggcca ggggagcgtc  3960
aggtcgaacc gcaggcgctc cagcgtgcg  acgcgcggag gctcgcccgg gagcggcag   4020
ggacgacgcgg gcgattgggt ggccggcggc gaataaccag ggtgcactcc gtcagcagcc  4080
tcctccgacc tcacacccccc ctgcctcttg agctggcggc accgggccgc gatggccgca  4140
ccggcgctgt ccagcacgcc cgcttccaca gccacgtgca gctcgatgcc ggcgacgtcc  4200
gtctc                                                              4205
```

```
SEQ ID NO: 15          moltype = DNA   length = 4184
FEATURE                Location/Qualifiers
source                 1..4184
                       mol_type = other DNA
                       organism = synthetic construct
SEQUENCE: 15
ggagctcagc atgtcgccag catcgctgga taagacgaat tggcagggta ccacctgaag   60
aatgggaggc aggtgttgct gattacgagt gtgtaaaaga aaggggtaga gagccgtcct  120
cagatccgac cactatgcag gtagccgctc gcccatgccc gcctggctga atattgacac  180
atgcccatca aggcaggcag gcatttctgt gcatgcacca agcccacaat cttccacaac  240
acacagcatg taccaacgca cgcgtaaaag ttggggtgct gccagtgcgt catgccaggc  300
atgatgtgct cctgcacatc ggccatgatc tcctccatcg tctcgggtgt ctccggcgcc  360
tggtccggga gccgttccgc cagatacccc gacgccacct ccgacctcac ggggtactttt  420
tcgagcgact gtcggtagtc gacgatcgcg tccaccatgg agtagccgag gcgccggaac  480
tggcgtgacg gagggaggag agggaggaga gagggggggg ggatgatcac acgccagtct  540
cacaacgcat gtaagacccg tttgattatg agtacaatca tgcactacta gttggatgag  600
cgccaggcat aaggcacacc gacgtcgatg gcacgagcaa ctcccgcatc atatttccta  660
ttgtcctcac gccaagccgg tcaccatccg catgctcgta ttacagcgca cgcaccgctt  720
cgtgatccac cgggtgaacg tagtcctcga cggaaacatc tggttcgggc ctcgtgctgg  780
cactcccctc catgccgaca acctttctgc tgtcaccacg acccacgatg caacgcgaca  840
cgaccggtgg gactgatcgg ttcactgcac ctgcatgcaa ttgtcacaag cgcatactcg  900
aatcgtatcc gtttgatttc tgtgaaaact cgctcgaccg cccgcgtccc gcaggcagcg  960
atgacgtgtg cgtggcctgg gtgtttcgtc gaaaggccag caacccccaaa tcgcaggcga 1020
tccggagatt gggatctgat ccgagttgga ccagatcccc ccgatgcggc acgggaactg  1080
catcgactcg gcgcggaacc cagctttcgt aaatgccaga ttggtgtccg ataccttgat  1140
ttgccatcag cgaaacaaga cttcagcagc gagcgtattt gggggcgtg  ctaccagggt  1200
tgcatacatt gcccatttct gtctggaccg ctttactggc gcagagggtg agttgatggg  1260
gttggcaggc atcgaaacgc gcgtgcatgg tgtgtgtgtc tgttttcggc tgcacaattc  1320
aatagtcgga tgggcgacgg tagaattggg tgttgcgctc gcgtgcatgc ctcgcccgt   1380
cgggtgtcat gaccgggact ggaatccccc tcgcgaccc  tcttgctaac gctcccgact  1440
ctcccgcccg cgcgcaggat agactctagt tcaaccaatc gacaatggcg tctgccgtca  1500
cctttgcgtg cgccctccc  cgcggcgcgg tcgccgcgcg gggtcgccgc gctgcctcgc  1560
gtccctggt  ggtgcgcgcc gtcgccagcg aggcccgct  gggcgtgccg ccctcggtgc  1620
agcgcccctc ccccgtggtc tactccaagc tggacaagac acaccgcctg acgcccgagc  1680
gcctggagct ggtgcagagc atgggtcagt tgcggagga  gagggtgctc ccgtgctgc   1740
accccgtgga caagctgtgg cagccgcagg acttttttgcc cgaccccgag tcgcccgact  1800
```

```
tcgaggacca ggtggcggag ctgcgcgcgc gcgccaagga cctgcccgac gagtactttg   1860
tggtgctggt gggcgacatg atcacggagg aggcgctgcc gacctacatg gccatgctca   1920
acaccttgga cggtgtgcgc gacgacacgg gcgcggctga ccacccgtgg gcgcgctgga   1980
cgcggcagtg ggtggccgag gagaaccggc acggcgacct gctgaacaag tactgttggc   2040
tgaccgggcg cgtcaacatg cgggccgtgg aggtgaccat caacaacctg atcaagagcg   2100
gcatgaaccc gcagacggac aacaacccct acttgggctt cgtctacacc tccttccagg   2160
agcgcgcgac caagtacagc cacggcaaca ccgcgcgcct ggcggccgag cacggcgaca   2220
agggcctgag caagatctgc gggctgatcg ccagcgacga gggccggcac gagatcgcct   2280
acacgcgcat cgtggacgag ttcttccgcc tcgacccgca gggccggtc gccgcctacg   2340
ccaacatgat gcgcaagcag atcaccatgc ccgcgcacct catggacgac atgggccacg   2400
gcgaggccaa cccgggccgc aacctcttcg ccgacttctc cgccgtcgcc gagaagatcg   2460
acgtctacga cgccgaggac tactgccgca tcctggagca cctcaacgcg cgctggaagg   2520
tggacgagcg ccaggtcagc ggccaggccg ccgcggacca ggagtacgtt ctgggcctgc   2580
cccagcgctt ccggaaactc gccgagaaga ccgccgccaa ggtcgcgcgca   2640
ggcccgtcgc cttctcctgg atctccggac gcgagattat ggtctaggga ggtacgagcg   2700
cgcgcgaggg attggtggga gtgggacgcg ctcgtcgctc ctttctattc tgaagggaag   2760
attggccacc ccgctccacg cgccacgcat cgagcaacga agaaaacccc ccgatgatag   2820
gttgcagtgg ctgccgagat atagatccgg ctgcacgtca aagggcccct cggccagaga   2880
agaagctctt ttccagcgac cgcagactcc ttctgccaaa aacactcttc tctgtccaca   2940
gcaacaccaa tggatggaca gatcaacttg tgtcttcgcg tagcttcctc ggctagcgtg   3000
cttgcaacag gtccctgcac tattatcctc ctgctttcct ctgaattatg cggcaggcga   3060
gcgctcgctc ttgcgagcgc tccttcgcgc ccccctcgct gatcgagtgt acagtcaatg   3120
aatggtcctg ggcgaagaac gagggaattt gtgggcgaga gagcatcgtc tctcaggccc   3180
cagcgcagtg gccgttaaag tccaagaccg tgaccaggca gcgcatcgcg tccgtgtgcg   3240
ggccctgcct ggcggctcgg cgcgccaggc tcgagagcag ctccctcagg tcgccttgga   3300
cagcctctgc gaggccggtg agggtctgca ggagcgcctc cagctggca gtggcggttg   3360
tatccgggtc gccggtcatc gactgcgact cgccatccga agagccatcg tcgtcgtctc   3420
ccagactgga agcgctcgcc atcggcccg ccgatacaga aaacgcctct gcgctcgccg   3480
tgcgcagcgc ggcgcgcacc agggccgcgt ccagcagacc catcgccagc tcccggccgc   3540
gagggccggc cagcgcctca agccgccgg cgcgggccgc cgagccgcg gaggccagcg   3600
cggcgcgcgc gccctccagg gtcggcgccc gggtcacggc gtcgcgcgcc caggcggcca   3660
gcgccgcccc ccgcaggacg cagtgcgcct ccatcgaccg cacaaagtgg gagacccggt   3720
ggctcgtggg gtcgtagggc cgcacgcggc ggcgcgcggg cctcgtgaac gtgcgtttgc   3780
cattccgcag ccctgcggtc gtcacactcc cttgccgatc cacgctcgcg gcggccagcc   3840
tggccaggc cagctggagg cccaggagca tgccggcgcg gacctgctcc agaaaggggc   3900
cgttgcccag catgcacagt ggccagggga gcgtcaggtg gaaccgcagg cgctccagcg   3960
tggcgacgcg cggaggctcg cccggggcg gccaggacg cgtggacgat tgggtggcgg   4020
catcgaagtg ctggagcgca ctccgtcagc ggcctccgcc gacgccgcac ccccctgcct   4080
cttgagctgg cggcaccggg ccgcgatggc cgcaccggcg ctgtccagca cgcccgcttc   4140
cacacgcacg tgcagctcga tgccggcgac gtctgtctcc atca                    4184
SEQ ID NO: 16           moltype = DNA  length = 4202
FEATURE                 Location/Qualifiers
source                  1..4202
                        mol_type = unassigned DNA
                        note = Prototheca wickerhamii
                        organism = unidentified
SEQUENCE: 16
ggagctcagc atgtcgccca gcatcgccgg ataagacgaa ttggcagggt accacctgaa    60
gaatgggagg caggtgttgt tgattatgag tgtgtaaaag aaaggggtag agagccgtcc   120
tcagatccga ctactatgca ggtagccgct cgcccatgcc cgcctggctg aatattgatg   180
catgcccatc aaggcaggca ggcatttctg tgcacgcacc aagcccacaa tcttccacaa   240
cacacagcat gtaccaacgc acgcgtaaaa gttggggtgc tgccagtgcg tcatgccagg   300
catgatgtgc tcctgcacat ccgccatgat ctcctccatc gtctcgggtg tttccggcgc   360
ctggtccggg agccgttccg ccagatacccc agacgccacc tccgacctca cggggtactt   420
ttcgagcgtc tgccggtagt cgacgatcgc gtccaccatg gagtagccga ggcgccggaa   480
ctggcgtgac ggagggagga gagggaggag agagagggggg gggggggggg gggatgatt   540
acacgccagt ctcacaacgc atgcaagacc cgtttgatta tgagtacaat catgcactac   600
tagatggatg agcgccaggc ataaggcaca ccgacgttga tggcatgage aactcccgca   660
tcatatttcc tattgtcctc acgccaagcc ggtcaccatc cgcatgctca tattacagcg   720
cacgcaccgc ttcgtgatcc accgggtgaa cgtagtcctc gacggaaaca tctggctcgg   780
gcctcgtgct ggcactccct cccatgccga caacctttct gctgtcacca cgacccacga   840
tgcaacgcga cacgacccgg tgggactgat cggttcactg cacctgcatg caattgtcac   900
aagcgcatac tccaatcgta tccgtttgat ttctgtgaaa tactcctcga ctcgccccgcgt   960
cccgcaggca gcgatgacgt gtgcgtgacc tgggtgtttc gtcgaaaggc cagcaacccc  1020
aaatcgcagg cgatccggag attgggatct gatccgagct tggaccagat cccccacgat  1080
gcggcacggg aactgcatcg actcggcgcg gaacccagct ttcgtaaatg ccagattggt  1140
gtccgatacc ttgatttgcc atcagcgaaa caagacttca gcagcgagcg tatttggcgg  1200
gcgtgctacc aggggttgcat acattgccca tttctgtctg gaccgcttta ccggcgcaga  1260
gggtgagttg atggggttgg caggcatcga aacgcgcgtg catggtgtgt gtgtctgttt  1320
tcggctgcac aatttcaata gtcggatggg cgacggtaga attgggtgtt gcgctcgcgt  1380
gcatgcctcg ccccgtcggg tgtcatgacc gggactggaa tccccctcg cgaccctcct  1440
gctaacgctc ccgactctcc cgcccgcgcg caggatagac tctagttcaa ccaatcgaca  1500
atggcgtctg cgtcaccttt tgcgtgcgtg cctccccgcg ggcggtgcgc ccgcccgcgt  1560
cgccgcgctg cctcgcgtcc cctggtggtg cacgccgtcg ccagcgaggc ccgctgggc  1620
gtccgccct cggtgcagcg cccctccccc gtggtctact ccaagctgga caagcaacac  1680
cgcctgacgc ccgagcgcct ggagctggtg cagagcatgg gtcagtttgc ggaggagagg  1740
gtgctccccg tgctgcaccc cgtggacaag ctgtggcagc gcaggactt cctgcccgac  1800
cccgagtcgc ccgacttcga ggaccaggtg gcggagctgc gcgcgcgcgc caaggacctg  1860
```

```
cccgacgagt actttgtggt gctggtgggc gacatgatca cggaggaggc gctgccgacc      1920
tacatggcca tgctcaacac cttggacggt gtgcgcgacg acacgggcgc ggctgaccac      1980
ccgtgggcgc gctggacgcg gcagtgggtg gccgaggaga accggcacgg cgacctgctg      2040
aacaagtact gttggctgac ggggcgcgtc aacatgcggg ccgtggaggt gaccatcaac      2100
aacctgatca agagcggcat gaacccgcag acggacaaca acccttactt gggcttcgtc      2160
tacacctcct tccaggagcg cgcgaccaag tacagccacg gcaacaccgc gcgcctggcg      2220
gccgagcacg gcgacaaggg cctgagcaag atctgcgggc tgatcgccag cgacgagggc      2280
cggcacgaga tcgcctacac gcgcatcgtg gacgagttct tccgcctcga ccccgagggc      2340
gccgtcgccg cctacgccaa catgatgcgc aagcagatca ccatgcccgc gcacctcatg      2400
gacgacatgg gccacggcga ggccaacccg ggccgcaacc tcttcgccga cttctccgcc      2460
gtcgccgaga agatcgacgt ctacgacgcc gaggactact gccgcatcct ggagcacctc      2520
aacgcgcgct ggaaggtgga cgagcgcag gtcagcggcc aggccgccgc ggaccaggag       2580
tacgttctgg gcctgcccca cgcttccgg aaactcgccg agaagaccgc cgccaagcgc       2640
aagcgctcg cgcgcaggcc cgtcgccttc tcctggatcc ccggacgcga gattatggtc       2700
tagggaggta cgagcgcgcg cgagggattg tgggagtgg gacgcgctcg tcgctccttt       2760
ctattctgaa gggaagattg gccaccccgc tccacgcgcc acgcatcgag caacgaagaa      2820
aaccccccga tgataggttg cagtggctgc cgagatatag atccggctgc acgtcaaagg      2880
gcccctcggc cagagaagaa gctctttttcc cagcgaccgc agactccttc tgccaaaaac      2940
actcttctct gtccacagca acaccaatgg atggacagat caacatgtgt cttcgcgtag      3000
cttcctcggc tagcgtgctt gcaacaggtc cctgcactat tatcctcctg ctttcctctg       3060
aattatgcgg caggcgagcg ctcgctcttg cgagcgctcc ttcgcgccgc cctcgctgat      3120
cgagtgtaca gtcaatgaat ggtcctgggc gaagaacgag ggaatttgtg gcgagagag       3180
catcgtctct caggccccag cgcagtggcc gttaaagtcc aagaccgtga ccaggcagcg      3240
catcgcgtcc gtgtgcgggc cctgcctggc ggctcggcgc gccaggctcg agagcagctc      3300
cctcaggtcg ccttggacag cctctgcgag gccggtgagg gtctgcagga gcgcctcgag      3360
cgtggcagtg gcggttgtat ccgggtcgcc ggtcatcgac tgcgactcgc catccgaaga      3420
gccatcgtcg tcgtctccca gactggaagc gctcgccatc ggcccgccg atacagaaaa       3480
cgcctctgcg ctcgccgtgc gcagcgcggc gcgcaccagg gccgcgtcca gcagacccat      3540
cgccagctcc cggccgcgag ggccggccag cgcctcaaag ccgccggcgc gggcggccgc      3600
cgccgccgag ccagccgcgg cgcgcgccgcc ctccaggtc ggcgcccgg tcacggcgtc       3660
gcgcgcccag gcggccagcg ccgccccccg caggacgcag tgcgcctcca tcgaccgcac      3720
aaagtgggag acccggtggc tcgtgggtc gtagggccgc acggcggc gcgcgggcct        3780
cgtgaacgtg cgtttgccat tccgcagccc tgcggtcgtc acactccctt gccgatccac      3840
gctgcgggcg gccagcctgg cccaggccag ctggaggccc aggagcatgc cggcgcggac      3900
ctgctccaga aaggggccgt tgcccagcat gcacagtggc cagtgggacg tcaggtggaa      3960
ccgcaggcgc tccagcgtgg cgacgcgcgg aggctcgccc gggagcggcc agggacgcgt      4020
ggacgattgg gtgcgggca tcgaagtgct ggagcgcact ccgtcagcgg cctccgccga       4080
cgccgcaccc ccctgcctct tgagctggcg gcaccgggcc gcgatggccg caccggcgct      4140
gtccagcacg cccgcttcca cagccacgtg cagctcgatg ccggcgacgt ctgtctccat      4200
ca                                                                    4202

SEQ ID NO: 17         moltype = DNA   length = 4448
FEATURE               Location/Qualifiers
source                1..4448
                      mol_type = unassigned DNA
                      note = Prototheca wickerhamii
                      organism = unidentified
SEQUENCE: 17
acgaattgtt gctttgaagg gtgctgaatg gcaccagata ctgggtcggt ggcatttgct        60
caggcgtcat ttgtaggttc tgccaataat aattccatga ggacagcaag ccattgacaa      120
gcccactgac tcgaatttta gagcaaccta cgagaccaca ccatccgtgc acgcacctcg      180
aggctgtttt tggatacgtg cagccgagcg catggcccgt cgccgtcctc ggtagaggga      240
gggcagcaca gggccctctc tttcttttg actggccaag ctggcacgct ttcggctgcc        300
gggatcaggt gagctttcgt cggcggggc gagcagggcc accaggtcga ggacctcct        360
ctccaggcag ccaatggtgt ggagcaggcc tctatgctgg tgatgagccg cttgctgctc      420
ctggctgtcg gcaccggtcc tcctggatgg cggaggtggc gcaagaacac ccgtgtgtcg      480
cacgttcatc aacacgtctt gcgcagtgtc gcacaccgca aggacgcagg tactttaaaa      540
agacacaagc gtgacatgtg cgtgatcatt gcaacggctg ccgcagagga cttacccag      600
ctcagcaagc agtgttgaga cggccttggc caccccatcg agctcagcga gcagctttc      660
gtgctggaag gccaggacct cgtttcttg ctgggtctcc acggctcgcc gtcgggattc      720
ctggagggag gagggagccc aggggagagt ggtgttgtga tgacgacgcg tgtgcgcaga      780
ggcagtagga tgctcatgag tgcagcctct ttgcagccag gtttgcctgt cgcacagact      840
tgagaggcac cacccaaagt ctactatcca aataatgctc cagagcatca gcaatgttgg      900
ccaccttcag taccaacgct cccaccctcg tctgcgcacc tcgctgcccc ggcctcggcc      960
ggcctcggca gcgacggacg cgcccgccgc gccctcggcg gcctccgcct gcgcctcgag     1020
cgcctcacgt tcccttcca gcgccgcag cgaggcctgg acgtccacca ggtgcttgaa      1080
ccgagcaaag ttgcgctcct gcagcccggc caggttggcc accagctcct ccatgctgga     1140
gtagcctgtg gccgtggaga tcttctggaa agcgtcggtg atggcctgct cgcgctgcgc     1200
gtgcgacgca aagtggacgc ctggtgaggc cgcgccctgg ccgtcgagga aggacccccc     1260
gcccggcccg gcctcggcgg cgccgccgcc gccgcccagc gccctcgccc ccgccggcgc     1320
gccgccgtgc gcgtccagcc gcacgggcgc tgggtagtcc tgcgagaaga gctgggccat     1380
ctcctgctcg cgcgcggcac gctccgcgcg gcgatcggca tccggggtcg gcgcgctcctg    1440
ctggatgagc gccgccagcc gccgccactc ctgctcgagc gcgcccgact cgcgctccgc     1500
ctgcgccgc gtgtgccgcg cggccgcctt ggccttttcg ccgcgctcgt gcgcgtcgct     1560
gatgtccatc accaggtcca tgaggtctgc cttcgccgg ctgagccact gcttcgtccg     1620
ggcggccaag aggagcatga gggaggactc ctggtccagg gtcctgacgt ggtcgcggct     1680
ctgggagcgg gccagcatca tctggctctg ccgcaccgag gccgcctcca actggtcctc     1740
cagcagccgc agtcgccgcc gaccctgca gaggaagaca ggtgagggg gtatgaattg       1800
tacagaacaa ccacgagcct tgtctaggca gaatccctac cagtcatggc tttacctgga     1860
```

```
tgacggcctg cgaacagctg tccagcgacc ctcgctgccg ccgcttctcc cgcacgcttc  1920
tttccagcac cgtgatggcg cgagccagcc ccgcacgctg gcgctgcgct tcgccgatct  1980
gaggacagtc ggggaactct gatcagtcta aaccccttg cgcgttagtg ttgccatcct  2040
ttgcagaccg gtgagagccg acttgttgtg cgccaccccc cacaccacct cctcccagac  2100
caattctgtc accttttggg cgaaggcatc ggcctgctgc tgcagagagg acagcagtgc  2160
ccagccgctg ggggttggcg gatgcacgct cagcttgttt tccagaagga gttgctcctt  2220
gagcctttca ttctcagcct cgataaacctc caaagccgct ctaattgtgg aggggggttcg  2280
aatttaaaag cttggaatgt tggttcgtgc gtctggaaca agcccagact tgttgctcac  2340
tgggaaaagg accatcagct ccaaaaaact tgccgctcaa accgcgtacc tctgctttcg  2400
cgcaatctgc cctgttgaaa tcgccaccac attcatattg tgacgcttga gcagtctgta  2460
attgcctcag aatgtggaat catctgcccc ctgtgcgagc ccatgccagg catgtcgcgg  2520
gcgaggacac ccgccactcg tacagcagac cattatgcta cctcacaata gttcataaca  2580
gtgaccatat ttctcgaagc tccccaacga gcacctccat gctctgagtg gccacccccc  2640
ggccctggtg cttgcggagg gcaggtcaac cggcatgggg ctaccgaaat ccccgaccgg  2700
atcccaccac ccccgcgatg ggaagaatct ctccccggga tgtgggccca ccaccagcac  2760
aacctgctgg cccaggcgag cgtcaaacca taccacacaa atatccttgg catcggccct  2820
gaattccttc tgccgctctg ctaccccgtg cttctgtccg aagcagggggt tgctagggat  2880
cgctccgagt ccgcaaaccc ttgtcgcgtg gcggggcttg ttcgagctcg cagcatcgct  2940
tgcacggggg ctatcttcaa gtagtcggga agcatgggtc gcgacgtcga cacgggcgag  3000
cgggcctatg ggtgagtcgg ccgtgcatgg ggagggctag cgccagggct cgggtcgccc  3060
cgatggccgg ggtcttttgct cggggtgcac gcggccgtgg gtgcgagaca ggttgcgtga  3120
cgaatttctt ggcacccccc cacggatgcc tcacgcggca gcccccctcc ctcgcaggta  3180
cgtccgcaag gtgtccggcc cggtggtggt ggccagcagc atgagcgggt ctgccatgta  3240
cgagctggtc cgcgtgggcg cggacaagct gattggcgag atcattcgcc tcgagggaga  3300
cacggcgacc atccaggtga ggtggcgggg gaggctgctt gagtggaagt ggggcgcaca  3360
accctccatt ggttggcggc caaggatgca gggaagcgaa tgtcgagcat tgcgcgcttt  3420
tgcttgctga catatcgttg cttgcacccc atgtattctc caggtgtacg aggataacctc  3480
gggcctgacg gtgggcgaca cggtcgtccg ctccggcaag gtgtgagggg tgtgagagtt  3540
gatgtatatg ctttggttcgc cccttgctc tggcacgtca gaggcgcacc ttcagtgctc  3600
acaagtggtg ccgttagtga aactgaacaa gtgcttgact gtgtaggatt tccgctcgcc  3660
ccttttcttac cctctcccct ttctctcttt ctccaccccct caaaatctcc agccctgtc  3720
tgtggagctg ggcccccggca tcatgggcac catctttgac ggcatccagc gcccgctcaa  3780
gtcgatcgcg gtgacagcg attcgtgctt catcccgcgc ggcgtggacg tgccggccct  3840
ggaccgcaag gcctcgtggg agtttgaccc ggtgtcaagc ttcaaggtgg gcgaccgcat  3900
cacgggcggc gacatctacg gcgtggtgca cgagaacacg ctgatggagc acaaggtgct  3960
gcttccgccg ggcgcgcgcg gcaccatctc ctacatcgcg ccggcgggga gctacagcat  4020
cacggacaag atcatcgagg tcgagtttgg cggcgcgcgc aaggagtact ccatgctgca  4080
gctctggccc gtgcgcgcgc cgcgcccccgt ggcgcagaag ctgctggcca cacgccgct  4140
gctgacgggg cagcgcgtgc tggacgcgct cttcccggc gtgctggggcg ggacgtgcgc  4200
catcccgggc gcgtttggct gcggcaagac ggtcatctcg caggcgctgt caaagtacag  4260
taactcggag ggcatcatct acgtcggctg cggcgagcgc ggcaacgaga tggccgaggt  4320
gctcatggac ttccccgcgc tgaccatgac catgccggac gggcgcgagg agagcatcat  4380
gcagcgcacc acgtcgtgg ccaacacctc caacatgccc gtcgccgcgc gcgaggccag  4440
catctaca                                                            4448
SEQ ID NO: 18      moltype = DNA   length = 4448
FEATURE            Location/Qualifiers
source             1..4448
                   mol_type = other DNA
                   organism = synthetic construct
SEQUENCE: 18
acgaattgtt gctttgaagg gtgctgaatg gcaccagata ctgggtcggt ggcatttgct    60
caggcgtcat ttgtaggttc tgccaataat aattccatga ggacagcaag ccattgacaa   120
gcccactgac tcgaattta gagcaaccta cgagaccaca ccatccgtgc acgcacctcg   180
aggctgtttt tggatacgtg cagccgagcg catggccgt cgccgtcctc ggtagaggga   240
gggcagcaca gggccctctc tttcttttg actggccaag ctggcacgct ttcggctgcc   300
gggatcaggt gagctttcgt cggcgggggc gagcagggcc accaggtcga ggacctccct   360
ctccaggcag ccaatggtgt ggagcaggcc tctatgctgg tgatgagccg cttgctgctc   420
ctggctgtcg gcaccggtcc tcctggatgg cggaggtggc gcaagaacac ccgtgtgtcg   480
cacgttcatc aacacgtctt gcgcagtgtc gcacaccgca aggacgcagg tactttaaaa   540
agacacaagc gtgacatgtg cgtgatcatt gcaacggctg ccgcagagga cttacccccag  600
ctcagcaagc agtgttgaga cggccttggc cacccccatcg agctcagcga gcagcttttc   660
gtgctggaag gccaggacct cgttttcttg ctgggtctcc acggctcgcc gtcgggattc   720
ctggagggga gagggagccc agggagagt ggtgttgtga ttgacgacgg tgtgcgcgaa   780
ggcagtagga tgctcatgag tgcagcctct ttgcagccag gtttgcctgt cgcacagact   840
tgagaggcac cacccaaagt ctactatcca aataatgctc cagagcatca gcaatgttgg   900
ccaccttcag taccaacgct cccaccctcg tctgcgcacc tgcgctgccc gccccgcgc    960
ggcctcggca gcgacggacg cgcccgccgc gccctcggcc gcctccgcct gcgcctcgag  1020
cgcctcacgt tcccttttca ccaggccaag cgaggcctgc acgtccacca ggtgcttgaa  1080
ccgagcaaag ttgcgctcct gcagcccggc caggttggcc accagctcct ccatgctgga  1140
gtagcctgtg gccgtggaga tcttctggaa agcgtcggtg atggcctgct cgcgctgcgc  1200
gtgcgacgca aagtggacgc ctggtgaggc gcgccctgg ccgtcgaggg aggaccccccc  1260
gcccggcccg gcctcggcgg cgcccgccgc gccgccccagc ccctcgccc ccgccggcgc  1320
gcccggcgtg gcgtccagcc gcacgggccg tgggtagtcc tgcgagaaga gctgggcat   1380
ctcctgctcg cgcgcggcac gctccgcgcg gcgatcggca tcccgggtcg cgcgctcctg  1440
ctggatgagc ccgccagcc gccgccactc ctgctcgagc gcgcccgact cgcgctccgc  1500
ctgcgcccgc gcgtgcgccg ccagcgcctt ggccttttcg ccgcgctcgt gcgcgtcgct  1560
gatgtccatc accaggtcca tgaggtctgc cttgcgccgg ctgagccact gcttcgtccg  1620
ggcggccaag aggagcatga gggaggactc ctggtccagg gtcctgacgt ggtcgcgcct  1680
```

```
ctgggagcgg gccagcatca tctggctctg ccgcaccgag gccgcctcca actggtcctc  1740
cagcagccgc agtcgccgcc gaccctggca gaggaagaca ggtgagggg gtatgaattg   1800
tacagaacaa ccacgagcct tgtctaggca gaatccctac cagtcatggc tttacctgga  1860
tgacggcctg cgaacagctg tccagcgacc ctcgctgccg ccgcttctcc cgcacgcttc  1920
tttccagcac cgtgatggcg cgagccagcg ccgcacgctg gcgctgcgct tcgccgatct  1980
gaggacagtc ggggaactct gatcagtcta aaccccttg cgcgttagtg ttgccatcct  2040
ttgcagaccg gtgagagccg acttgttgtg cgccacccc cacaccacct cctcccagac  2100
caattctgtc acctttttgg cgaaggcatc ggcctcggcc tgcagagagg acagcagtgc  2160
ccagccgctg ggggttggcg gatgcacgct cagcttgttt tccagaagga gttgctcctt  2220
gagcctttca ttctcagcct cgataacctc caaagccgct ctaattgtgg aggggttcg   2280
aatttaaaag cttggaatgt tggttcgtgc gtctggaaca agcccagact tgttgctcac  2340
tgggaaaagg accatcagct ccaaaaaact tgccgctcaa accgcgtacc tctgctttcg  2400
cgcaatctgc cctgttgaaa tcgccaccac attcatattg tgacgcttga gcagtctgta  2460
attgcctcag aatgtggaat catctgcccc ctgtgcgagc ccatgccagg catgtcgcgg  2520
gcgaggacac ccgccactcg tacagcagac cattatgcta cctcacaata gttcataaca  2580
gtgaccatat ttctcgaagc tccccaacga gcacctccat gctctgagtg gccaccccc   2640
ggccctggtg cttgcggagg gcaggtcaac cggcatgggg ctaccgaaat ccccgaccgg  2700
atcccaccac ccccgcgatg ggaagaatct ctccccggga tgtgggccca ccaccagcac  2760
aacctgctgg cccaggcgag cgtcaaacca taccacacaa atatccttgg catcggccct  2820
gaattccttc tgccgctctg ctaccccggtg cttctgtccg aagcaggggt tgctagggat  2880
cgctccgagt ccgcaaaccc ttgtcgcgtg gcggggcttg ttcgagctcg cagcatcgct  2940
tgcacggggg ctatcttcaa gtagtcggga agcatgggtc gcgacgtcga gacgggcagg  3000
cgggcctatg ggtgagtcgg ccgtgcatgg ggagggctag cgccagggct cgggtcgccc  3060
cgatggccgg ggtctttgct cggggtgcac gcggccgtgg gtgcgagaca ggttgcgtga  3120
cgaatttctt ggcaccccc cacgcgatgcc tcacgcgggc gcccccctcc ctcgcaggta  3180
cgtccgcaag gtgtccggcc cggtggtggt ggccagcagc atgagcgggt ctgccatgta  3240
cgagctggtc cgcgtgggcg cggacaagct gattggcgag atcattcgcc tcgagggaga  3300
cacggcgacc atccaggtga ggtggcgggg gaggctgctt gagtggaagt ggggcgcaca  3360
accctccatt ggttggcggc caaggatgca gggaagcgaa tgtcgagcat tgcgcgcttt  3420
tgcttgctga catatcgttg cttgcacccc atgtattctc caggtgtacg aggataaccttc 3480
gggcctgacg gtgggcgaca cggtcgtccg ctccggcaag gtgtggagg tgtgagagtt   3540
gatgtatatg ctttggtcgc ccccttgctc tggcacgtca gaggcgcacc ttcagtgctc  3600
acaagtggtg ccgttagtga aactgaacaa gtgcttgact gtgtaggatt tccgctcgcc  3660
cctttcttac cctctcccct ttctctcttt ctccaccct caaaatctcc agccctgtc    3720
tgtggagctg ggcccggca tcatgggcac catctttgac ggcatccagc gcccgctcaa   3780
gtcgatcgcg gtggacagcg attcgtgctt catcccgcgc ggctggacg tgccggccct   3840
ggaccgcaag gcctcgtggg agtttgaccc ggtgtcaagc ttcaaggtgg gcgaccgcat  3900
cacgggcggc gacatctacg gcgtggtgca cgagaacacg ctgatggagc acaaggtgct  3960
gcttccgccg ggcgcgcgcg gcaccatctc ctacatccgc ccggcgggga gctacagcat  4020
cacggacaag atcatcgagg tcgagtttgg cggcgcgcgc aaggagtact ccatgctgca  4080
gctctgcccc gtgcgcgcgc gcgcgcccgt ggcgcagaag ctgctggcca cacgccgct   4140
gctgacgggg cagcgcgtgc tggacgcgct cttccccggc gtgctgggcg ggacgtgcgc  4200
catcccggc gcgtttcgcg gtgcaagac ggtcatctcg caggcgctgt caaagtacag    4260
taactcggag ggcatcatct acgtcggctg cggcgagcgc ggcaacgaga tggccgaggt  4320
gctcatggac ttccccgcgc tgaccatgac catgccggac gggcgcgagg agagcatcat  4380
gcagcgcacc acgctcgtgg ccaacacctc caacatgccc gtcgccgcgc gcgaggccag  4440
catctaca                                                           4448

SEQ ID NO: 19         moltype = DNA   length = 4318
FEATURE               Location/Qualifiers
source                1..4318
                      mol_type = other DNA
                      organism = synthetic construct
SEQUENCE: 19
gcaatctccc gcccaacctc caccagccgg cgcaggacct ggagcgcgaa agaggatttc    60
gggggtgtgg gggagagtga gcgcgatgga agacactgat ttgcataaac aaccctttggc  120
cgctttcaaa gcaccacctc accaccataa aaccctccct cccatgcata ccttgatgcc   180
tgccgagatg gcctgggctt ggtggaccat ggccatgtag tccggcgtgg tcgcgatgga   240
cgccgcacgt tgtgcgatga gcgccttgcc cccgtcctcg tgcccgagcc cgcctcccggg 300
cggctcggcc agccccggcca gcagcccggc gtccagctcg gcgttgaggg agcgctttgc  360
cagcgcacgg atggactcgt acggcagcgt gatgaggtgg agcaggctgt cgagcaggcc  420
cggctgcgac cagagcatgg tgaggatgcg cgccgccgcg ggcgtgccgg gctgcaccgc  480
cagcagcaac gcggcgaccg tctcggccgc aaacaccgcc aggaagcagc cctccgaggt  540
cggggcgggc tccagcaggg gaccgcaggc gtgcatatg tccaggcgct ccgtgatgat   600
gtgcatggcc agcggcagca gcgagcgcag cacgctgctg gccaggtgcg tgagcgtgct  660
cgtgccggcc gagtccgagg tctcgtccgt ggccaggtcc atgggcggca gcgtgcgctc  720
gctcgcctgg tgccgcgtcc agctgcgccg gtggcacagc agccgcagca ccgcgtgaa    780
gagcggcagg cagcccgcct ccacccgcgc ggccgcggcc ggggcgccgc cctcctgcag  840
gctggccggc aggatggcgc ccgactgccg cgccgccgac agctgctgcc tgtgtctcaa   900
aagctgcgac agcgtcggag agatgtcctg cggctccggc tccggatgt ctgcggatgcc  960
acgcacaccg gtcgcaatca cctgttggat aatgggtggc aggatggttg gtaggttct   1020
gatgcggtcg gggaggcgga taaggtcaca gccgcgtgat cttgctgacc aaacactgct  1080
ggccaccca caaaagtcga ttgccaccga tgcacacggt atggcgccca gacagaagct  1140
cagcataccc tcaggagggc cagggccagg gcaggccaca tgtcagctg gaagccggtg  1200
tgggctgaag catgggccag cacgctcagg gcatgttttt gaaaggcagg aacgtggctt  1260
gtcacgtcaa caaccaggga gaggcctgc gacatcaagg gcaaagttg gaatgttcag    1320
catcatcagc ctgggaccaa tactctgctc acgttcagg gcagaaaggt ggcatagtca  1380
gggcctcgtt cagaatttca agtcccagtt taaacttcgt acctccgcga ggctgatccc  1440
ctcgccctga gcggactggg gccggggagc cggggtggga ccgtggtca cctgcgccat   1500
```

```
ggctagcccg caccctcgtt gatctgggag ccctgcgcag ccccttaaat catctcagtc 1560
aggtttctgt gttcaactga gcctaaaggg ctttcgtcat gcgcacgagc acacgtatat 1620
cggccacgca gtttctcaaa agcggtagaa cagttcgcga gccctcgtag gtcgaaaact 1680
tgcgccagta ctattaaatt aaattaattg atcgaacgag acgcgaaact tttgcagaat 1740
gccaccgagt ttgcccagag aatgggagtg gcgccattca ccatccgcct gtgcccggct 1800
tgattcgccg agacgatgga cggcgagacc agggagcggc ttgcgagccc cgagccggta 1860
gcaggaacaa tgatcgacaa tcttcctgtc caattactgg caaccattag aaagagccgg 1920
agcgcgttga aagtctgcaa tcgagtaatt tttcgatacg tcgggcctgc tgaaccctaa 1980
ggctccggac tttgtttaag gcgatccaag atgcacgcgg ccccaggcac gtatctcaag 2040
cacaaacccc agccttagtt tcgagactt gggagatagc gaccgatatc tagtttggca 2100
ttttgtatat taattacctc aagcaatgga gcgctctgat gcggtgcagc gtcggctgca 2160
gcacctggca gtggcgctag ggtcgcccta tcgctcggaa cctggtcagc tggctcccgc 2220
ctcctgctca gcctcttcca gccgtagcgt ctgcgtgttg ggagctggag tcgtgggctt 2280
gacgacggcg ctgcagctgt tgcaggatgt gcctggcgtg ccgttcacg tcgtggctga 2340
gaaatatggc gacgaaacgt tgacggctgg ggcggcggg ctgtggatgc catacgcatt 2400
gggtacgcgg ccattggatg ggattgatag gcttatggag ggataataga gttttgccg 2460
gatccaacgc atgtggatgc ggtatcccgg tgggctgaaa gtgtggaagg atagtgcatt 2520
ggctattcac atgcactgcc cacccctttt ggcaggaaat gtgccggcat cgttggtgca 2580
ccgatgggga aaatcgacgt tcgaccacta catgaagatt tatacgtctg aagatgcagc 2640
gactgcgggt gcgaaacgga tgacggtttg gtcgtgtatg tcacagcatg tgctggatct 2700
tgcgggctaa ctcccctgc cacggcccat tgcaggtgtc atgttgactg gagggtacga 2760
cctttcgtcc gtcaaattcc cagaggagga cccgctcgtg gccgacattg tgcccacttt 2820
tcgccgcctg ggcaaggcag agctcctggc ctacgacccc agcggcaagt cgatcgacgg 2880
ctacggcttc accaccatca tcacgtacga tgctcaatga aagggagtt cattgccttc 2940
actagagaaa catacatggg tctatgtaaa cttgatcgat ctccgaattt cctcttgttg 3000
tgtctctggt tgtgcaggga aggtcgcctc tacctgcctg atgcga gcagattcaa 3060
ggcttggggg ggacctttga acggcgccgc atctccagcc tgtcggagct gaaggagtat 3120
gatgccatcg tcaattgcac aggtgggttg gagttagtcc aggagatgtc gatagaccaa 3180
tgcaaatcgt gtgcaacgca ttagacccaa tcactgcctc cctcgccgct ctcaggcctg 3240
gaggcgccaa agctggtgca ggacgagtcc atgtacccgg tgccgggca cgttctgcgc 3300
gtacgggcgc cctgggtccg ccactacatc aaccgcgacg ggggcaccta catcatcccc 3360
aacacgga cggtggtgct gggcggcatc acgcaaaagg gcaactggtc cctcgagccg 3420
accgaggagg atcggcgcgg gatcctggag cgctgctacg agatcctgcc cagcctgcgc 3480
aaggcgcgaa tcctgcgcga gtgggtcggg ctccggcccg gccgcccaga catccgcctg 3540
gagcgcgaag atgcgcagct cgacggcaag tccgtacccg tcatccacaa ctacgggcac 3600
ggcgggtccg ggctcaccct gggctgggc tgcgccgcag acgccgtcgc gctcgtgcgc 3660
agggcgctgg ccctctgacg gtgagagggc ctgttcagg ctgtgcggtc ccgctcatct 3720
caaaggcctt ggaattggct gggcgaatat tctgatgcat tgatgtgtat ctcttcgctt 3780
ttcttatgat gcaccacttt ggagcgagta ttctggtgcc aattgtgctt tgaaatcacg 3840
ctgcccacgg tggcaaatgc aatgagagcc gagtaagtgg actggtagtt cctaaggcga 3900
cgggcagctc aaggaaagcc agccccgat cccagctcgc cacatccttg ttgcacgcct 3960
gtatctggcg gtttgaatga gactcgcgtc caccaggcc ggcctcgcg ctgcggctcc 4020
gcccacaact cgagcagctt gtcctttgcc cctggcaacta tggtctcgat ggtgtcgtac 4080
acggggcag gaaccaggtg caggcctgga gaagagggat ggaagtgcgc acagattcga 4140
gaaggtgatg gccctcttgc cgaaatgcac accctctttc cccagcctct gcctccaccc 4200
accgtctgct cgggaaggga tgcggcagtc caggacaacg tccgggttgc gctggtgtcg 4260
gagctccata tcgcggcccc gttctgaatg gatgggtgg gacagttggt gtgaccgg 4318

SEQ ID NO: 20          moltype = DNA   length = 4317
FEATURE                Location/Qualifiers
source                 1..4317
                       mol_type = unassigned DNA
                       note = Prototheca wickerhamii
                       organism = unidentified
SEQUENCE: 20
gcaatctccc gcccaacctc caccagccgg cgcaggacct ggagcgcgaa agaggatttc 60
ggggtgtggg ggagagtgag cgcgatggaa gacactgatt tgcataaaca acctttggcc 120
gctttcaaag caccacctca ccaccataaa ccctccctc ccatgcatac cttgatgcct 180
gccgagatgg cctgggcttg gtggaccatg gccatgtagt ccggcgtggt cgcgatggac 240
gccgcacgtt gtgcgatgag cgccttgccc ccgtcctcgt gcccgagccc gcgtccgggc 300
ggctcggcca gccccgccag cagccccggg tccagctcgg cgttgaggga gcgctttgcc 360
agcgcacgga tggactcgta cggcagcgtg atgaggtgga gcaggctgtc gagcaggccc 420
ggctgcgacc agagcatggt gaggatgcgc gccgccgcgg gcgtgccggg ctgcaccgcc 480
agcagcaacg cggcgaccgt ctcggccgca aacaccgcca ggaagcagcc ctccgaggtc 540
gggccgggct ccagcagggg accgcaggcg tgcactatgt ccaggcgctc cgtgatgatg 600
tgcatggcca gcggcagcag cgagcgcagc acgctgctgg ccaggtgcgt gagcgtgctc 660
gtgccggccg agtccgaggt ctcgtccgtg gccaggtcca tgggcggcag cgtgcgctcg 720
ctcgcctggt gcgccgtcca gctgcgccgg tggcacagca gccgcagcac cgcgtggaag 780
agcggcaggc agcccgcctc caccgccgcg ggcgccgcc ctcctgcagg 840
ctggcgcgca ggatgccgc cgactccgc gccgccgaca gctgctgcct gtgtctcaaa 900
agctgcgaca gcgtcggaga gatgtcctgc ggctccggct ccgggatgtg ctggatgcca 960
cgcacaccgg tcgcaatcac ctgttggata atgggtggca ggatggttgg ttaggttctg 1020
atgcggtcgg ggaggcggat aaggtcacag ccgcgtgatc ttgctgacca aacactgctg 1080
gccacccaac aaaagtcgat tgccaccgat gcacacggca tggacaagctc 1140
agcatacccct caggagggcc agggccaggc caggccacat gtgcagctgg aagccgggct 1200
gggctgaagc atgggccagc acgctcaggg catggttttg aaaggcagga acgtggcttg 1260
tcacgtcaac aaccagggaa gaggcctgcg acatcaaggg gcaaagttgg aatgttcagc 1320
atcatcagcc tgggaccaat actctgctca cggttcaggg cagaaaggtg gcatagtcag 1380
ggcctcgttc agaattcaa gtcccagttt aaacttcgta cctccgcgag gctgatcccc 1440
```

```
tcgccctgag cggactgggg ccggggagcc ggggtgggac cggtggtcac ctgcgccatg 1500
gctagcccgc accctcgttg atctgggagc cctgcgcagc cccttaaatc atctcagtca 1560
ggtttctgtg ttcaactgag cctaaagggc tttcgtcatg cgcacgagca cacgtatatc 1620
ggccacgcag tttctcaaaa gcggtagaac agttcgcgag ccctcgtagg tcgaaaactt 1680
gcgccagtac tattaaatta aattaattga tcgaacgaga ccgcgaaactt ttgcagaatg 1740
ccaccgagtt tgcccagaga atgggagtgg cgccattcac catccgcctg tgcccggctt 1800
gattcgccga gacgatggac ggcgagacca gggagcggct tgcgagcccc gagccggtag 1860
caggaacaat gatcgacaat cttcctgtcc aattactggc aaccattaga aagagccgga 1920
gcgcgttgaa agtctgcaat cgagtaattt ttcgatacgt cgggcctgct gaaccctaag 1980
gctccggact ttgtttaagg cgatccaaga tgcacgcggc cccaggcacg tatctcaagc 2040
acaaacccca gccttagttt cgagactttg ggagatagcg accgatatct agtttggcat 2100
tttgtatatt aattacctca agcaatggag cgctctgatg cggtgcagcg tcggctgcag 2160
cacctggcag tggcgctagg gtcgccctat cgctcggaac ctggtcagct ggctcccgcc 2220
tcctgctcag cctcttccag ccgtagcgtc tgcgtgttgg gagctggagt cgtggggcttg 2280
acgacggcgc tgcagctgtt gcaggatgtg cctggcgtgc gcgttcacgt cgtggctgag 2340
aaaatatggcg acgaaacgtt gacggctggg gccggcgggc tgtggatgcc atacgcattg 2400
ggtacgcggc cattggatgg gattgatagg cttatggagg gataatagag ttttgccgg 2460
atccaacgca tgtggatgcg gtatcccggt gggctgaaga tgtggaagga tagtgcattg 2520
gctattcaca tgcactgccc acccccttttg gcaggaaatg tgccggcatc gttggtgcac 2580
cgatggggaa aatcgacgtt cgaccactac atgaagattt atacgtctga agatgcagcg 2640
actgcgggtg cgaaacggat gacggtttgg tcgtgtatgt cacagcatgt gctggatctt 2700
gcgggctaac tcccccctgcc acggcccatt gcaggtgtca tgttgactgg agggtacgac 2760
cttcgtccg tcaaattccc agaggaggac ccgctctggg ccgacattgt gcccactttt 2820
cgccgcctgg gcaaggcaga gctcctggcc tacgacccca gcggcaagtc gatcgacggc 2880
tacgcttca ccaccatcat cacgtacgat gctcaatgaa aggggagttc attgccttca 2940
ctagagaaac atacatgggt ctatgtaaac ttgatcgatc tccgaattc ctcttgttgt 3000
gtctctggtt gtgcagggaa ggtcgcctct acctgccctg gctgatgcag cagattcaag 3060
gcttgggggg gacctttgaa cggcgccgca tctccagcct gtcggagctg aaggagtatg 3120
atgccatcgt caattgcaca ggtgggttgg agttagtcca ggagatgtcg atagaccaat 3180
gcaaatcgtg tgcaacgcat tagacccaat cactgcctcc tcgccgctc tcaggcctgg 3240
aggcgccaaa gctggtgcag gacgagtcca tgtaccggt gcgcgggcac gttctgcgcg 3300
tacgggcgcc ctgggtccgc cactacatca accgcgacgg gggcacctac atcatccca 3360
acacggacac ggtggtgctg gcggcatca cgcaaaaggg caactggtcc ctcgagccga 3420
ccgaggagga tcgcgcggg atcctggagc gctgctacga gatcctgccc agcctgcgca 3480
aggcgccgat cctgcgcgag tgggtcgggc tccggcccga ccgcccagac atccgcctgg 3540
agcgcgaaga tgcgcagctc gacggcaagt ccgtacccgt catccacaac tacgggcacg 3600
gcgggtccgg gctcaccctg ggctggggct gcgccgcaga cgccgtcgcg ctcgtgcgca 3660
gggcgctggc cctctgacgg tgagagggcc tgttgcaggc tgtgcggtcc cgctcatctc 3720
aaaggccttg gaattgctg ggcgaatatt ctgatgcatt gatgtgtatc tcttcgcttt 3780
tcttatgatg caccactttg gagcgagtat tctggtgcca attgtgcttt gaaatcacgc 3840
tgcccacggt ggcaaatgca atgagagccg agtaagtgga ctggtagttc ctaaggcgac 3900
gggcagctca aggaaagcca gccccgatc ccagctcgcc acatccttgt tgcacgcctg 3960
tatctggcgg tttgaatgag actcgcgtcc acccaggccg ggcgccggg ctccgtgtcg 4020
cccacaactc gagcagcttg tcctttgccc ctgcaacat ggtctcgatg gtgtcgtaca 4080
cggggggcagg aaccaggtgc aggcctggag aagagggatg gaagtgcgca cagattcgag 4140
aaggtgatgg ccctcttgcc gaaatgcaca ccctctttcc ccagcctctg cctccaccca 4200
ccgtctgctc gggaagggat gcggcagtcc aggacaacgt ccgggttgcg ctggtgtcgg 4260
agctccatat cgcggccccg ttctgaatgg atggggtggg acagttggtg tgaccgg 4317
```

SEQ ID NO: 21   moltype = DNA length = 4227
FEATURE     Location/Qualifiers
source      1..4227
          mol_type = other DNA
          organism = synthetic construct
SEQUENCE: 21

```
cggctcgctg ctttgcgtgc cgggtgcagc gatcagatcc aagtctgacg acttgtgctg 60
atgtactgtg tcctttgagt ccagagcgcc ggccgcacgc gcttcttccc cttcttcttc 120
ctctcgaaca tccagcgatg caagtgcagg gcgctgggcg gctggcgtcc cgaaccggcc 180
tcggcgcacg cggctgaaat tgccaatgtc ggcaatgtag tgccgctcgg cccatccctc 240
gatcaagttt ttcagcgcgt ggttgggggat gatctgcgct catgggaaga taaaggggt 300
tctgaggtgg ttgattggta ctttaccgga agtactcata ttcatacatg actgatccca 360
cacaaaaaca aagctcactt caaagaaccg cgcatgtcta ctcccagca atcacttcgc 420
tcaccgtcgg gttgcttccc acgacaacgc cggtgagagg gtcggtggcc tcgcgacctt 480
cgcgggcaca tcttcccagc catgtctgta taatctcacg ctcatacgtc gggtgctacg 540
acccaaaat gacgggatcc tgcatgatat cgcccgagat ggggtccagg cattcctctg 600
gaggcgtcag ccctgcggga gatgccggtc ccaccgcatt ggaaaggcac aaaggggtg 660
aatccccat tcatgaaat tgttggtcag cgatggtgcg cactcgtgcg caatgaatat 720
ggggtcacgc ggtggacgaa cgcggagggg gcctggccga atctaggctt gcattcctca 780
gatcactttc tgccggcgt ccggggtttg gcgtcgcgac aacgctccgt ctccctagcc 840
gctgcgcacc gcgcgtgcga cgcgaaggtc attttccaga acaacgacca tggcttgtct 900
tagcgatcgc tcgaatgact gctagtgagt cgtacgctcg accagtcgc tcgcaggaga 960
acgcggcaac tgccgagctt cggcttgcca gtcgtgactc gtatgtgatc aggaatcatt 1020
ggcattggta gcattataat tcggcttccg cgctgtttat gggcatggca atgtctcatg 1080
cagtcgacct tagtcaacca atttctgggtg gccagctcgg ggcgaccggg ctccgtgtcg 1140
ccgggcacca cctcctgcca tgagtaacag ggccgccctc tcctcccgac gttgcccac 1200
tgaataccgt gtcttgggc cctacatgat gggctgccta gtcgggcggg acgcgcaact 1260
gccccgcgcaa tctgggacgt ggtctgaatc ctccaggcgg gtttcccga gaaagaaagg 1320
gtgccgattt caaagcagag ccatgtgccg ggccctgtgg cctgtgttgg cgcctatgta 1380
gtcaccccccc ctcacccaat tgtcgccagt ttgcgcaatc cataaactca aaactgcagc 1440
```

```
ttctgagctg cgctgttcaa gaacacctct ggggtttgct cacccgcgag gtcgacgccc   1500
agcatggcta tcaagacgaa caggcagcct gtggagaagc ctccgttcac gatcgggacg   1560
ctgcgcaagg ccatcccgc gcactgtttc gagcgctcgg cgcttcgtag cagcatgtac    1620
ctggcctttg acatcgcggt catgtccctg ctctacgtcg cgtcgacgta catcgaccct   1680
gcgccggtgc ctacgtgggc caagtatggc gtcatgtggc cgctctactg gttcttccag   1740
gtgtgtgtga gggttgtggt tgcccgtatc gaggtcctgg tggcgcgcat ggggagaag    1800
gcgcctgtcc cgctgacccc cccggctacc ctcccggcac cttccagggc gccttcggca   1860
cgggtgtctg ggtgtgcgcg cacgagtgcg gccaccaggc ctttcctcc agccaggcca    1920
tcaacgacgg cgtgggcctg gtgttccaca gcctgctgct ggtgccctac tactcctgga   1980
agcactcgca ccgccgccac cactccaaca cggggtgcct ggacaaggac gaggtgtttg   2040
tgccgccgca ccgcgcagtg gcgcacgagg gcctggagtg ggaggagtgg ctgcccatcc   2100
gcatgggcaa ggtgctggtc accctgaccc tgggctggcc gctgtacctc atgttcaacg   2160
tcgcctcgcg gccgtacccg cgcttcgcca accactttga cccgtggtcg cccatcttca   2220
gcaagcgcga gcgcatcgag gtggtcatct ccgacctggc gctggtggcg gtgctcagcg   2280
ggctcagcgt gctgggccgc accatgggct gggcctggct ggtcaagacc tacgtggtgc   2340
cctacctgat cgtgaacatg tggctcgtgc tcatcacgct gctccagcac acgcacccgg   2400
cgctgccgca ctacttcgag aaggactggg actggctgcg cggcgccatg gccaccgtgg   2460
accgctccat gggcccgccc ttcatggaca acatcctgca ccacatctcc gacacccacg   2520
tgctgcacca cctcttcagc accatcccgc actaccacgc cgaggaggcc tccgccgcca   2580
tcaggcccat cctgggcaag tactaccagt ccgacagccg ctgggtcggc cgcgccctgt   2640
gggaggactg cgcgcgactgc cgctacgtcg tcccggacgc gcccgaggac gactccgcgc   2700
tctggttcca caagtgagtg agtgagtcgc tcactcagcg cgcctgcgcg gggatgcgga   2760
acgccgccgc cgccttgtct tttgcacgcg cgactccgtc gcttcgcggg tggcaccccc   2820
attgaaaaaa acctcaattc tgtttgtgga agacacggtg tacccccaac cacccacctg   2880
cacctctatt attggtatta ttgacgcggg agcgggcgtt gtactctaca acgtagcgtc   2940
tctggtttc agctggctcc caccattgta aattcttgct aaaatagtgc gtggttatgt    3000
gagaggtatg gtgtaacagg gcgtcagtca tgttggtttt cgtgctgatc tcgggcacaa   3060
ggcgtcgtcg acgtgacgtg cccgtgatga gagcaatacc gcgctcaaag ccgacgcatg   3120
gccttactc cgcactccaa acgactgtcg ctcgtatttt tcggatatct attttttaag    3180
agcgagcaca gcgccgggca tgggcctgaa aggcctcgcg gccgtgctcg tggtggggc    3240
cgcgagcgcg tggggcatcg cggcagtgca ccaggcgcag acggaggaac gcatggtgag   3300
tgcgcatcac aagatgcatg tcttgttgtc tgtactataa tgctagagca tcaccagggg   3360
cttagtcatc gcacctgctt tggtcattac agaaattgca caaggcgtc ctccgggatg    3420
aggagatgta ccagctcaag ctggagcggg ttcgagccaa gcaggagcgc ggcgcatgac   3480
gacctaccca catgcgacaa aggggtctgg gtcgtacgac aaaccagtca ggaggcggcg   3540
gggtccatga gctggcccgc tcgcagcttc agcgcttcga gcatcgcggc gttgtccgcg   3600
atccaagcct cccgcagcgc ctccttgggg ccctgtgcg gagaggcggg tgccgagagg    3660
gctgtgaggg cggaggctgg aggacaggct gcgaatcgtc gcgctgccta ggcgtctgcc   3720
gaggagaagc acaccacgcg ccgccgcttt catttcattg tgcccgttgc tgtaatgcat   3780
gcgagcgatc ctgcactaaa gctgcgatcg ccacctcagc gttgttcgtc tctagcaccg   3840
ctcacctgac cacgcgcacg gaagagtggc ggtcggcgac ggctgctgc acgtggcagt    3900
gcaggtccac gtggccgagg agcaggtctc gcagctgcag caccgcgccc tcgtgctcgc   3960
cggggtccat ccagtccatg ccccgcgcg gccctcgag ccggacggcc agcagccagg     4020
gccgggggtc cgcgccgacg cccggcggcc ccgccgcgca gctggggtcg gccaggaaga   4080
gccactgggc ggccggcccg ggcgagcccc gcgccggcgc gggacccacc cgcagcacca   4140
ccgcctggtc caggtcgacg tcgctcggcg caggcccgc gtgcggcgcc tgcgccagcg    4200
tccagggcag gcgggggcgc gcgtgca                                       4227
```

SEQ ID NO: 22      moltype = DNA  length = 4227
FEATURE             Location/Qualifiers
source              1..4227
                      mol_type = unassigned DNA
                      note = Prototheca wickerhamii
                      organism = unidentified
SEQUENCE: 22

```
cggctcgctg ctttgcgtgc cgggtgcagc gatcagatcc aagtctgacg acttgtgctg     60
atgtactgtg tcctttgagt ccagagcgcg ggccgcacgc gcttcttccc cttcttcttc    120
ctctcgaaca tccagcgatg caagtgcagg gcgctgggcg gctggcgtcc cgaaccggcc    180
tcggcgcacg cggctgaaat tgccaatgtc ggcaatgtag tgccgctcgg cccatccctc    240
gatcaagttt ttcagcgcgt ggttgggat gatctgcgct catggaaga taaaggggt     300
tctgaggtgg ttgattggta ctttaccgga agtactcata ttcatacatg actgatccca    360
cacaaaaaca aagctcactt caaagaaccg cgcatgtcta ctcccagca atcacttcgc    420
tcaccgtcgg gttgcttccc acgacaacgc cggtgagagg gtcggtggcc tcgcgacctt    480
cgcgggtcaca tctttccagc catgtctgta taatctcacg ctcatacgtc gttgtctcg    540
accccaaaat gacgggatcc tgcatgatat cgcccgagat ggggtccagg cattcctctg    600
gaggcgtcag ccctgcggga gatgccggtc ccaccgcatt ggaaaggcac aaaggggtg    660
aatcccccat ttcatgaaat tgttggtcag cgatggtgcg cactcgtgcg caatgaatat    720
ggggtcacgc ggtggacgaa cgcggagggg gcctggccga atctaggctt gcattcctca    780
gatcactttc tgccggcgct ccggggttg cgcgtcgcga aacgctccgt ctccctagcc    840
gctgcgcacc gcgcgtgcga cgcgaaggtc attttccaga acaacgacca tggcttgtct    900
tagcgatcgc tcgaatgact gctagtgagt cgtacgctcg acccagtcgc tcgcaggaga    960
acgcggcaac tgccgagctt cggcttgcca gtcgtgactc gtatgtgatc aggaatcatt    1020
ggcattggta gcattataat tcggcttccg cgctgtttat gggcatggca atgtctcatg    1080
cagtcgacct tagtcaacca attctgggtg gccagctccg cgaccgggg ctccgtgtcg     1140
ccgggcacca cctcctgcca tgagtaacag ggccgccctc tcctcccgac gttggccac     1200
tgaataccgt gtcttgggc cctacatgat gggctgccta gtcgggcggg acgcgcaact    1260
gccccgcgcaa tctgggacgt ggtctgaatc ctccaggcgg gttcccga gaaagaaagg     1320
gtgccgattt caaagcagag ccatgtgccg ggccctgtgg cctgtgttgg cgcctatgta   1380
gtcaccccc ctcacccaat tgtcgccagt ttgcgcaatc cataaactca aaactgcagc     1440
```

```
ttctgagctg cgctgttcaa gaacacctct ggggtttgct cacccgcgag gtcgacgccc   1500
agcatggcta tcaagacgaa caggcagcct gtggagaagc ctccgttcac gatcgggacg   1560
ctgcgcaagg ccatcccgc gcactgtttc gagcgctcgg cgcttcgtag cagcatgtac    1620
ctggcctttg acatcgcggt catgtccctg ctctacgtcg cgtcgacgta catcgaccct   1680
gcgccggtgc ctacgtgggt caagtatggc gtcatgtggc cgctctactg gttcttccag   1740
gtgtgtgtga gggttgtggt tgcccgtatc gaggtcctgg tggcgcgcat ggggagaag    1800
gcgcctgtcc cgctgacccc cccggctacc ctcccggcac cttccagggc gccttcggca   1860
cgggtgtctg ggtgtgcgcg cacgagtgcg gccaccaggc cttttcctcc agccaggcca   1920
tcaacgacgg cgtgggcctg gtgttccaca gcctgctgct ggtgccctac tactcctgga   1980
agcactcgca ccgccgccac cactccaaca cggggtgcct ggacaaggac gaggtgtttg   2040
tgccgccgca ccgcgcagtg gcgcacgagg gcctggagtg ggaggagtgg ctgcccatcc   2100
gcatgggcaa ggtgctggtc accctgaccc tgggctggcc gctgtacctc atgttcaacg   2160
tcgcctcgcg gccgtacccg cgcttcgcca accactttga cccgtggtcg cccatcttca   2220
gcaagcgcga gcgcatcgag gtggtcatct ccgacctggc gctggtggcg gtgctcagcg   2280
ggctcagcgt gctgggccgc accatggcc gggcctggct ggtcaagacc tacgtggtgc    2340
cctacctgat cgtgaacatg tggctcgtgc tcatcacgct gctccagcac acgcacccgg   2400
cgctgccgca ctacttcgag aaggactggg actggctgcg cggcgccatg gccaccgtgg   2460
accgctccat gggcccgccc ttcatggaca acatcctgca ccacatctcc gacacccacg   2520
tgctgcacca cctcttcagc accatcccgc actaccacgc cgaggaggcc tccgccgcca   2580
tcaggcccat cctgggcaag tactaccagt ccgacagccg ctgggtcggc cgcgccctgt   2640
gggaggactg cgcgcgactgc cgctacgtcg tcccggacgc ccccgaggac gactccgcgc   2700
tctggttcca caagtgagtg agtgagctgc tcactcagcc gccgtcgcgg gggatgcgga   2760
acgccgccgc cgccttgtct tttgcacgcg cgactccgtc gcttcgcggg tggcacccc    2820
attgaaaaaa acctcaattc tgtttgtgga agacacggtg tacccccaac cacccacctg   2880
cacctctatt attggtatta ttgacgcggg agcgggcgtt gtactctaca acgtagcgtc   2940
tctggttttc agctggctcc caccattgta aattcttgct aaaatagtgc gtggttatgt   3000
gagaggtatg gtgtaacagg gcgtcagtca tgttggtttt cgtgctgatc tcgggcacaa   3060
ggcgtcgtcg acgtgacgtg cccgtgatga gagcaatacc gcgctcaaag ccgacgcatg   3120
gcctttactc cgcactccaa acgactgtcg ctcgtatttt tcggatatct atttttaag    3180
agcgagcaca gcgccgggca tgggcctgaa aggcctccgg gccgtgctcg tggtgggggc   3240
cgcgagcgcg tggggcatcg cggcagtgca ccaggcgcag acggaggaac gcatggtgag   3300
tgcgcatcac aagatgcatg tcttgttgtc tgtactataa tgctagagca tcaccagggg   3360
cttagtcatc gcacctgctt tggtcattac agaaattgca caaggcgtc ctcccgggatg    3420
aggagatgta ccagctcaag ctggagcggc ttcgagccaa gcaggagcgc ggcgcatgac   3480
gacctaccca catgcgacaa aggggtctgg gtcgtacgac aaaccagtca ggaggcggcg   3540
gggtccatga gctggcccgc tcgcagcttc agcgcttcga gcatcgcggc gttgtccgcg   3600
atccaagcct cccgcagcgc ctccttgggg cccctgtgcg gagaggcggg tgccgagagg   3660
gctgtgaggg cggaggctgg aggacaggct gcgaatcgtc gcgctgccta ggcgtctgcc   3720
gaggagaagc acaccacgcg ccgccgcttt catttcattg tgccgcttgc tgtaatgcat   3780
gcgagcgatc ctgcactaaa gctgcgatcc ccacctcagc gttgttcgtc tctagcaccg   3840
ctcacctgac cacgcgcacg gaagagtggc ggtcggcgac ggctgctgc acgtggcagt   3900
gcaggtccac gtggccgagg agcaggtctc gcagctgcag caccgcgccc tcgtgctcgc   3960
cggggtccat ccagtccatg ccccgcgcg ggccctcgag ccggacggcc agcagcagg    4020
gccggggtc cgcgccgacg cccggcggcc ccgccgcgca gctggggtcg gcaggaaga    4080
gccactgggc ggccggcccg ggcgagcccc cgccggcgc gggacccacc cgcagcacca   4140
ccgcctggtc caggtcgacg tcgctcggcg caggcccgc gtgcggcgcc tgcgccagcg   4200
tccagggcag gcgggggcgc gcgtgca                                      4227

SEQ ID NO: 23         moltype = DNA  length = 4067
FEATURE               Location/Qualifiers
source                1..4067
                      mol_type = other DNA
                      organism = synthetic construct
SEQUENCE: 23
gcaatggcgc tcggtacagg gtctgcgtcc gtgctgggct ccctctccta cgatgcacaa    60
gggagcgccc cggccagctc agcgcgtcca caacctcccc tcgtcacaca cacacctgcg   120
gaaccaggcc gcccatttgc tgcttgagca tgccttgcat catgtccggg tttcccatca   180
tatcgttgag gttcttgggc tccagcttct gctccagcac accatcctgt cgatcgaaga   240
gaaggagaca tgtgtacatt attggtgtga gggcgctgaa tcggccattt tttaaatgat   300
cacgctcatg ccaatagacg cggcacataa cgacgttcaa accccgcca agccgcgca    360
caaccccatc cctccacacc cccacacaa agaacccgcc accgcttacc ttgcccacga   420
ggtaggcctt tcgttgcgca aaaccggcct cggtgatgaa tgcatgcccg ttcctgacga   480
gcgctgcccg ggccaacacg ctcttttgct gcgtctcctc aggcttgggg gctccttgg    540
gcttggtgc cgccatgatc tgcgcgcatc agagaaacgt tgctggtaaa aggagcgccc   600
ggctgcgcaa tatatatata ggcatgccaa cacagcccaa cctcactcgg agcccgtcc    660
caccaccccc aagtcgcgtg ccttgacggg atactgctgc agaagcttca tgagaatgat   720
gccgaacaag aggggcacga ggaccccaat ccggacatcc ttgtcgataa tgatctcgtg   780
agtccccatc gtccgcccga cgctccgggg agccgccga tgctcaagac gagagggccc    840
tcgaccagga ggggctggcc cgggggcca ctggcgtgcgccc gtcgttcgtc              900
tgcagtccta tgccacaaaa caagtcttct gacggggtgc gtttgctccc gtgcgggcag    960
gcaacagagg tattcacccct ggtcatgggg agatcggcga tcgagctggg ataagagata  1020
cggtcccgcg caaggatcgc tcatcctggt ctgagccgga cagtcattct ggcaagcaat   1080
gacaacttgt caggaccgga ccgtgccata tatttctcac ctagccgcgc aaaacctaac   1140
aatttgggag tcactgtgcc actgagttcg actggtagct gaatggagtc gctgctccac   1200
taaacgaatt gtcagcaccg ccagccgcc gaggacccga gtcatagcga gggtagtagc    1260
gcgccatggc accgaccagc ctgcttgcca gtactgcgct ctcttccgct tctctgtggt   1320
cctctgcgcg ctccagcgcg tgcgcttttc cggtggatca tgcggtccgt ggcgcaccgc   1380
agcggccgct gcccatgcag cgccgctgct tccgaacagt ggcggtcagg gccgcaccg    1440
cggtagccgt ccgtccggaa cccgcccaag agttttggga gcagcttgag ctctgcaaga   1500
```

```
tggcggagga caagcgcatc ttcctggagg agcaccggtg cgtggaggtc cggggctgac  1560
cggccgtcgc attcaacgta atcaatcgca tgatgatcag aggacacgaa gtcttggtgg  1620
cggtggccag aaacactgtc cattgcaagg gcatagggat gcgttccttc acctctcatt  1680
tctcatttct gaatccctcc ctgctcactc tttctcctcc tccttcccgt tcacgcagca  1740
ttcggggcaa cgaggtgggc ccctcgcagc ggctgacgat cacggcggtg gccaacatcc  1800
tgcaggaggc ggcgggcaac cacgcggtgg ccatgtgggg ccggagctcg gagggtttcg  1860
cgacggaccc ggagctgcag gaggcgggtc tcatctttgt gatgacgcgc atgcagatcc  1920
agatgtaccg ctaccgcgc tggggcgacc tgatgcaggt ggagacctgg ttccagacgg  1980
cgggcaagct gggcgcgcag cgcgagtggg tgctgcgcga caagctgacc ggcgaggcgc  2040
tgggcgcggc cacctcgagc tgggtcatga tcaacatccg cacgcgccgg ccgtgccgca  2100
tgccggagct cgtccgcgtc aagtcggcct tcttcgcgcg cgagccgccg cgcctggcgc  2160
tgccgccgc ggtcacgcgt gccaagctgc ccaacatcgc gacgcggcg ccgctgcgcg  2220
ggcaccgcca ggtcgcgcgc cgcaccgaca tggacatgaa cgggcacgtg aacaacgtgg  2280
cctacctgcc ctggtgcctg gaggcgtgc ccgagcacgt cttcagcgac taccacctct  2340
accagatgga gatcgacttc aaggccgagt gccacgcgac cgacgtcatc tcctcccagg  2400
ccgagcagat cccgccccag gaggcgctca cgcacaacgg cgccggccgc aaccccctcct  2460
gcttcgtcca tagcattctg cgcgccgaga ccgagctcgt ccgcgcgcga accacatggt  2520
cggccccat cgacgcgccc gccgccaagc gcccaaggc gagccactga ggacagggtg  2580
gttggctgga tggggaaacg ctggtcgcgg gattcgatcc tgctgcttat atcctccctg  2640
gaagcacacc cacgactctg aagaagaaaa cgtgcacaca cacaacccaa ccggccgaat  2700
atttgcttcc ttatcccggg tccaagagag actgcgatgc ccccctcaat cagcatcctc  2760
ctccctgccg cttcaatctt ccctgcttgc ctgcgcgcgcg ggtgcgcgt ctgcccgccc  2820
agtcagtcac tcctgcacag gcccttgtg cgcagtgctc ctgtaccctt taccgctcct  2880
tccattctgc gaggcccct attgaatgta ttcgttgcct gtgtgccaa gcgggctgct  2940
gggcgcgccg ccgtcgggca gtgctcggcg actttggcgg aagccgattg ttcttctgta  3000
agccacgcgc ttgctgcttt gggaagagaa ggggggggga ctgaatggat gaggaggaga  3060
aggaggggta ttggtattat ctgagttggg gaggcaggga gagttggaaa atgtaagtga  3120
cacgacgggc aaggagaatg tgagcatgt gcatggtgat gtcgttggtc gaggacgatc  3180
ctgcacgcgt gtatctgatg tagaatacgg caatcaccct agtctacatc tatatcttct  3240
ccgtataacg cccttccaa atgccctccc gtttctctcc tattcttgat ccacatgatg  3300
accctggcac tatttcaagg gctggacatt tcaagaaggt ttgcgtatct gaagaaggat  3360
tggtttggag aggtggccga tgaaagtggg gtcaagctgc gtggagccct ctgcacggat  3420
ttctatggta atctgcgtcc acgtcatcag tagccgtacg cctctgcggc gtcgccgtgc  3480
tcctcagccg ccgccttcacc accagccagg agccccatac gcacgcgctc ccagacggcg  3540
cgcgcgacgg ggacgatcat gagcagcgcg atctggggcg tgtcgtgcga gctgagccgc  3600
acaaccacgt tgccctggcc gcgcgtggtg tactggcagt tggtcgagac catggtgtcg  3660
gacttgaagt aggagccgtc aaagcgcggg aggcgcgtct cggccgagac gttgccgccg  3720
atgaccaggc tctggcgctt ctggcgcggg tcgcggccct gccactgcgc ggagccgccc  3780
aggagcggcc gcgactcgtc acggccgcgc agcttgacgt cggccgccag cgccgtgccc  3840
ggctcgtagg ccgaccccat cttgacgaag aggcggccga tcgctgcgcg gaccttgacc  3900
gcgtcggaca ggcgcaggcg ctcgtccagc ttgaccccga gcgccgcgtt gccgggcttg  3960
aacgcagcgc agaactcctc gcccagcttg agccgagca ggcccagcgc cagcttctgc  4020
cgcttgccgc gcgcgcgcag gcgcgagtcg acgcgcagcg tgtagag     4067
```

SEQ ID NO: 24    moltype = DNA   length = 4069
FEATURE           Location/Qualifiers
source            1..4069
                  mol_type = unassigned DNA
                  note = Prototheca wickerhamii
                  organism = unidentified
SEQUENCE: 24
```
gcaatggcgc tcggtacagg gtctgcgtcc gtgctgggct ccctctccta cgatgcacaa    60
gggagcgccc cggccagctc agcgcgtcca caacctcccc tcgtcacaca cacacctgcg   120
gaaccaggcc gcccatttgc tgcttgagca tgccttgcat catgtccggg tttcccatca   180
tatcgttgag gttcttgggc tccagcttct gctccagcac accatcctgt cgatcgaaga   240
gaaggagaca tgtgtacatt attggtgtga gggcgctgaa tcggccatt tttaaaatga   300
tcacgctcat gccaatagac gcggcacata acgacgttca aaccccgcc aaagccgcgg   360
acaaccccat ccctccacac ccccccacaca agaacccgc caccgcttac cttgcccacg   420
aggtaggcct ttcgttgcgc aaaaccggcc tcggtgatga atgcatgccc gttcctgacg   480
agcgctgccc gggccaacac gctcttttgc tgcgtctcct caggcttgg ggcctccttg   540
ggcttgggtg ccgccatgat ctgcgcgcat cagagaaacg ttgctggtaa aaaggagcgc   600
ccggctgcgc aatatatata taggcatgcc aacacagccc aacctcactc gggagcccgt   660
cccaccaccc ccaagtcgcg tgccttgacg gcatactgct gcagaagctt catgagaatg   720
atgccgaaca agaggggcac gaggacccaa tcccggacat ccttgtcgat aatgatctca   780
tgagtcccca tcgtccgccc gacgctccgg ggagcccgcc gatgctcaag acgagagggc   840
cctcgaccag gaggggctgg cccgggcggg cactggcgtc gaaggtgcgc ccgtcgttcg   900
cctgcagtcc tatgccacaa aacaagtctt ctgacgggt gcgtttgctc ccgtgcgggc   960
aggcaacaga ggtattcacc ctggtcatgg ggagatcggg gatcgagctg ggataagaga  1020
tacggtcccg cgcaaggatc gctcatcctg gtctgagtca gacagtcatt ctggcaagca  1080
atgacaactt gtcaggaccg gaccgtgcca tatatttctc acctagcgcc gcaaaaccta  1140
acaatttggg agtcactgtg ccactgagtt cgactggtag ctgaatggag tcgctgctcc  1200
actaaaacgaa ttgtcagcac cgccagccgg ccgaggaccc gagtcatagc gagggtagta  1260
gcgcgccatg gcaccgacca gcctgcttgc cagtactggc gtctcttccg cttctctgtg  1320
gtcctctgcg cgctccacgg cgtgcgtttc tccggtggat catgcggtcc gtggcgcacc  1380
gcagcggcc ctgccatgc agcgccgctg cttccgaaca gtggcggtca gggccgcacc  1440
cgcggtagcc gtccgtccgg aacccgccca agagttttgg gagcagcttg agccctgcaa  1500
gatgcggag gacaagcgca tcttcctgga ggagcaccgg tgcgtggagg tccggggctg  1560
accggccgtc gcattcaacg taatcaatcg catgatgatc agaggacacg aagtcttggt  1620
ggcggtggcc agaaacactg tccattgcaa gggcataggg atgcgttcct tcacctctca  1680
```

-continued

```
tttctcattt ctgaatccct ccctgctcac tctttctcct cctccttccc gttcacgcag  1740
cattcggggc aacgaggtgg gcccctcgca gcggctgacg atcacggcgg tggccaacat  1800
cctgcaggag gcggcgggca accacgcggt ggccatgtgg ggccggagct cggagggttt  1860
cgcgacggac ccggagctgc aggaggcggg tctcatcttt gtgatgacgc gcatgcagat  1920
ccagatgtac cgctacccgc gctggggcga cctgatgcag gtggagacct ggttccagac  1980
ggcgggcaag ctgggcgcgc agcgcgagtg ggtgctgcgc gacaagctga ccggcgaggc  2040
gctgggcgcg gccacctcga gctgggtcat gatcaacatc cgcacgcgcc ggccgtgccg  2100
catgccggag ctcgtccgcg tcaagtcggc cttcttcgcg cgcgagccgc cgcgcctggc  2160
gctgccgccc gcggtcacgc gtgccaagct gcccaacatc gcgacgccgg cgcgcctggc  2220
cgggcaccgc caggtcgcgc gccgcaccga catggacatg aacgggcacg tgaacaacgt  2280
ggcctacctg gctggtgcc tggaggccgt gcccgagcac gtcttcagcg actaccacct  2340
ctaccagatg gagatcgact tcaaggccga gtgccacgcg ggcgacgtca tctcctccca  2400
ggccgagcag atcccgcccc aggaggcgct cacgcacaac ggcgccggcc gcaaccccctc  2460
ctgcttcgtc catagcattc tgcgcgccga gaccgagctc gtccgcgcgc gaaccacatg  2520
gtcggccccc atcgacgcgc ccgccgccaa gccgcccaag gcgagccact gaggacaggg  2580
tggttggctg gatggggaaa cgctggtcgc gggattcgat cctgctgctt atatcctccc  2640
tggaagcaca cccacgactc tgaagaagaa aacgtgcaca cacacaccc aaccggccga  2700
atatttgctt ccttatcccg ggtccaagag agactgcgat gcccccctca atcagcatcc  2760
tcctccctgc cgcttcaatc ttccctgctt gcctgcgccc gcggtgcgcc gtctgcccgc  2820
ccagtcagtc actcctgcac aggcccccttg tgccagtgc tcctgtaccc tttaccgctc  2880
cttccattct gcgaggcccc ctattgaatg tattcgttgc ctgtgtggcc aagcgggctg  2940
ctgggcgcgc cgccgtcggg cagtgctcgg cgactttgcc ggaagccgat tgttcttctg  3000
taagccacgc gcttgctgct ttgggaagag aaggggggg tactgaatgg atgaggagga  3060
gaaggagggg tattggtatt atctgagttg gggaggcagg gagagttgga aaatgtaagt  3120
ggcacgacgg gcaaggagaa tggtgagcat gtgcatggtg atgtcgttgg tcgaggacga  3180
tcctgcacgc gtgtatctga tgtagaatac ggcaatcacc ctagtctaca tctataccctt  3240
ctccgtataa cgccctttcc aaatgccctc ccgtttctct cctattcttg atccacatga  3300
tgaccctggc actatttcaa gggctggaca tttcaagaag gtttgcgtat ctgaagaagg  3360
attggtttgg agaggtggcc gatgaaagtg gggtcaagct gcgtggagcc ctctgcacgg  3420
atttctatgg taatctgcgt ccacgtcatc agtagccgta cgcctctgcg gcgtcgcgcg  3480
gctcctcagc cgccgcttca ccaccagcca ggagccccat acgcacgcgc tcccagacgg  3540
cgcgcgcgac ggggacgatc atgagcagcg cgatctgggg cgtgtcgtgc gagctgagcc  3600
gcacaaccac gttgccctgg ccgcgcgtgg tgtactggca gttggtcgag accatggtgt  3660
cggacttgaa gtaggagccg tcaaagcgcg ggaggcgcgt ctcggccgag acgttgccgc  3720
cgatgaccag gctctggcgc ttctggcgcg ggtcgccgcc ctgccactgc gcggagccgc  3780
ccaggagcag gcgcgactcg tcacggccgc gcagcttgac gtcggccgcc agcgccgtgc  3840
ccggctcgta ggccgacccc atcttgacga agagcggcc gatcgctgcg cggaccttga  3900
ccgcgtcgga caggcgcagg cgctcgtcca gcttgacccc gagcgccgcg ttgccgggct  3960
tgaacggcag cgagaactcc tcgcccagct tggaccgaga caggcccagc gccagcttct  4020
gccgcttgcc gcgcgcgcgc aggcgcgagt cgacgcggca cgtgtagag           4069
```

SEQ ID NO: 25  moltype = DNA  length = 4492
FEATURE        Location/Qualifiers
source         1..4492
               mol_type = other DNA
               organism = synthetic construct
SEQUENCE: 25

```
ttgcgattcc tcttgaccca gccacacgca taaattttaa cgcaagctgg cccaatatgg    60
tatccgctgt gctcagaaca gcaccctcgt gcaccctctg gctctgaatc tcaccgtcac   120
ggtcatcctc ctcctagcct gccagcgctt gggcgcagcc atcgggcctg catagagaaa   180
gggtacaaag caacatatat aaatacacgt ggtattcata atactcgcgc atgtttgtct   240
tgcgcacgca tgcccacgct cgtcgacgcg ctcacctctg gccaggcagc ccccttgcgg   300
ggtcgcccgc agcgggcacc gcgaggcctg aggcgccacc agcagcatgt ttgaattatt   360
tatacgcagt tgtttgaggt acagagaaac cccttgtcat tctcttcttg tgtggggtgt   420
cgagtgccat tgcagtggtc tggccaccgg catatcgcat aagattgcct gcggatgtcg   480
ttcgtgccag cgtcatcggg gcgagagttt ataacgcgtg cccacgccag aagccctcac   540
gctttgcact tggcgaggta caaaaaatac caaaccgcgt cctgaagcat tatgcgggcg   600
aggacgaggc tgttcaaggt gcggatcgcg accttgagtg agagacgctc cgatggtcgc   660
ggcagaacc ccagcgcccg tcaaaagccg gtcctcacgc cccagggctg agtgcgcgcc   720
cgcaaacccc ttttgcagga actcaaggag gtggctcgat ccaaggacaa caacggcatc   780
gagctcattc ccaatgactc caacatcttc tctctggcggg cggtgattga ggcaaggggg   840
tctgcttcat tgggtggagg gagatgagtt gtgtgcaggg cgctcaaagg aggttttggt   900
cgcctattgc ccaaggtcat gcatccgtgt gtatcccgtg cccctccct tcaacagggc   960
cccgcggact cgccctatca ggggggtcac tttgaactca gcatccaagt gcctgagcag  1020
tacccattgg tcccgccgca agtcaagttc aagaccaagc tcttccaccc gaacgtgcac  1080
ttcaaggtga gctgtttgga gacaaaggtg cagggagag tgctagcaag caggggttga  1140
cgggcgttgc tgttgagttt tgatgtatag actcggccgg gaacttgagt ggaagccgac  1200
agacctttca tctgcctctc tgcccatgca gacggagagg atctgcctcg acattctcaa  1260
gaacgcctgg agcccagctt ggacgctgca ggtacgattg tttggttttag gagaggcggg  1320
cccttggtcg tcccctggca ctcacgactc ttgggaaaat atgccgatct ccgcattcct  1380
gtctccagac gcctgctctg tgcgcgctgt ctcgatgaag cattcttttc ctccccaatg  1440
cccgcagtcg gtgtgccagg ccatcgtggc gctcttgaca gattctgcgc cagactcccc  1500
cctcaactgc gacgctggga accttctccg ggcaggcgat gtgcgtgggt ttgcctcctt  1560
ggcacggctc tacaccgtcg agtacgccat gaggcggtga tggctgtgtc ggttgccact  1620
tcgtccagag acggcaagtc gtccatcctc tgcgtgtgtg cgcgacgct gcagcagtcc  1680
ctctgcagca gatgagcgtg acttggcca tttcacgcac tcgagtgtac acaatccatt  1740
tttcttaaag caaatgactg ctgattgacc agatactgta acgctgattt cgctccgat   1800
cgcacagata gcgaccatgt tgctgcgtct gaaaatctgg attccgaatt cgaccctggc  1860
gctccatcca tgcaacagat ggcgacactt gttacaattc ctgtcaccca tcggcatgga  1920
```

```
gcaggtccac ttagattccc gatcacccac gcacatctcg ctaatagtca ttcgttcgtg   1980
tcttcgatca atctcaagtg agtgtgcatg gatcttggtt gacgatgcgg tatgggtttg   2040
cgccgctggc tgcagggtct gcccaaggca agctaaccca gctcctctcc ccgacaatac   2100
tctcgcaggc aaagccggtc acttgccttc cagattgcca ataaactcaa ttatggcctc   2160
tgtcatgcca tccatgggtc tgatgaatgg tcacgctcgt gtcctgaccg ttcccagcc   2220
tctggcgtcc cctgccccgc ccaccagccc acgccgcgcg gcagtcgctg ccaaggctgt   2280
ctcggatgcc cagcgccatg ccacgccctt tgatggcttc aagtacgatt acggtgttgg   2340
attgtgtgtt tgttgcgtag tgtgcatggt ttagaataat acacttgatt tcttgctcac   2400
ggcaatctcg gcttgtccgc aggttcaacc ccatttcgga gtctcaggtc agccgcgcaa   2460
tgaccagccg ctacttcaag gacttgcacg acaacgccga ggtgagctat gtttaggact   2520
tgattggaaa ttgtcgtcga cgcatattcg cgctccgcga cagcacccaa gcaaaatgtc   2580
aagtgcgttc cgatttgcgt ccgcaggtcg atgttgtgat cgtcggcgcc ggatccgccg   2640
gtctgtcctg cgcttacgag ctgaccaagc acctgacgt ccgggtacgc gagctgagat   2700
tcgattagac ataaattgaa gattaaaccc gtagaaaaat ttgatggtcg cgaaactgtg   2760
ctcgattgca agaaattgat cgtcctccac tccgcaggtc gccatcatcg agcagggcgt   2820
tgctccggcg gcggcgcctg gctgggggga cagctgttct cggccatgtg tgtacgtaga   2880
aggatgaatt tcagctggtt ttcgttgcac agctgtttgt gcatgatttg tttcagacta   2940
ttgttgaatg ttttttagatt tcttaggatg catgatttgt ctgcatgcga cttttagcta   3000
gcacccttac acaccatcca acatcttgct gccttgcctc ccctgcgcag atccgcaagc   3060
cggcgcacaa gctgatggac gagctcaaca tcccttacga cgacgaggtg ggtattgggc   3120
agctagaacg catgcgtgct gtgcgactgg gtcgatccat tgtgcgaaac gtgtggcgga   3180
atacgtgcgc gtccccgcc atgcaccgac cccccctccc accaccccac aaatataaca   3240
gggtgacatg gtggtggtca agcacgccgc cctggtgacg tccacgctgc tgtccaaggt   3300
gctggcggcc cccaacatca agcttttcaa cgccaccgcg gcggaggacc tgatcgtcaa   3360
gtccaagccg ccggcggggg cggccgtccc gcacgtggcc ggggccgtga ccaactggac   3420
cctggtgtcc ctcaaccacg acacccagat gtgcatggac cccaacacca tcctgagcaa   3480
ggtcatggtc tcctccaccg gccacgacgg cccatgggc gcctccgggg tcaagcgcct   3540
ggccaagctg ggcctgatcg agcgcgcgc gggcatgggc gcgctggaca tgaacagcgc   3600
cgaggacgcg gtggtcgacc ggacgcggga gatcgtccct ggcatggtca tctgcggcat   3660
ggaggtcgcc gagctggacg ggtgcccgcg catgggcccc acctttggcg ccatgttgt   3720
gtccggggtc aaggccgcgc acgtggccct ggcctcgctg cgccgccagc aggaggagga   3780
ggggctccgc gccaagaccg cagacaccct cgcgcagcgcg gcgccgtcca tggccatggc   3840
gtgacctggt gatccccaag aggggcggaca tgcgtcgcgt ctccctcccgg tgcccagaga   3900
tctgttccac ggttgtctgc gatgctttca aaactgttat ttcactaaaa tgactcgatt   3960
ctcctctaaa aaaacatga tgttgatagt atctccacaa aagcatggcg actcagatgc   4020
ctctactgca ctgtactcaa gaatacaact ctggagaccc gggtcccgtt cccatttggc   4080
gccgaatgtt gatgcgccac ttttgctggc catgcctgag gtattctgta caaaagaagg   4140
agcggccaat gcgggttttc aagcagacgg cgcgctgggg cctggaaatc aaaaggcggt   4200
agtacacggg agagagtcgg attgatgatg agggatttaa aaaaggccag gcagtgagtt   4260
gagagttgta cgattgttgc cccaggattg ccttttttagg gggggacggc caggggcgca   4320
gttattgggg caccgcacat atagatccgc gcaagcaaat ggcctcgaga gcaggcgcga   4380
tggttaagaa aggaaggacg agtagcggat gacgtgtatac tgcatacgaa gaacgtacta   4440
gtgaggagag tgcttgaaac aacatatgat gctgcccccc ctctctgcca ac           4492

SEQ ID NO: 26         moltype = DNA    length = 4494
FEATURE               Location/Qualifiers
source                1..4494
                      mol_type = unassigned DNA
                      note = Prototheca wickerhamii
                      organism = unidentified
SEQUENCE: 26
ttgcgattcc tcttgaccca gccacacgca taaattttaa cgcaagctgg cccaatatgg     60
tatccgctgt gctcagaaca gcaccctcgt gcaccctctg gctctgaatc tcaccgtcac    120
ggtcatcctc ctcctagcct gccagcgctt gggcgcagcc atcgggcctg catagagaaa    180
gggtacaaag caacatatat aaatacacgt ggtattcata ataactcgcac atgttttgtct   240
tgcgcacgca tgcccacgct cgtcgacgcg ctcacctctg gccaggcagc ccccttgcgg    300
ggtcgcccgc agcggggcacc gcgaggcctg aggcgccacc agcagcatgt ttgaattatt    360
tatacgcagt gtttgaggt acagagaaac cccttgtcat tctcttcttg tgtggggtgt    420
cgagtgccat tgcagtggtc tggccaccgg catatcggat aagattgcct gcggatgtcg    480
ttcgtgccag cgtcatcggg gcgagagttt ataacgcgtg cccacgccag aagccctcac    540
gctttgcact tggcgaggta caaaaaatac caaaccgcgt cctgaagcat tatggcggcg    600
aggacgaggc tgttcaaggt gcggatcgcg accttgagtg agacgctc cgatggtcgc     660
ggccagaacc ccagcgcccg tcaaaagccg gtcctcacgc cccagggctg agtgcgcgcc    720
cgcaaacccc ttttgcagga actcaaggag gtggctcgat ccaaggacaa caacgccatc    780
gagctcattc ccaatgactc caacatcttc tctctggcgg cggtgattga ggcaagggg    840
tctgcttcat tgggtggagg gagatgagtt gtgtgcaggg cgctcaaagg aggttttggt   900
cgcctattgc ccaaggtcat gcatccgtgt gtatcccgtg cccctccct tcaacagggc    960
cccgcggact cgccctatca ggggggtcac tttgaactca gcatccaagt gcctgagcag   1020
taccaattgg tcccgccgca agtcaagttc aagaccaagc tcttccaccc gaacgtgcac   1080
ttcaaggtga gctgtttgga gacaaaggtg gcagggagag tgctagcaag cagggggtga   1140
cgggcgttgc tgttgagttt tgatgtatag actcggccgg gaacttgagt ggaagccgac   1200
agaccttttca tctgcctctc tgcccatgca gacgggagag atctgcctcg acattctcaa   1260
gaacgcctgg agcccagctt ggacgctgca ggtacgattg tttggtttag gagaggcggc   1320
cccctttggtc gtccctggc actcacgact ctttgggaaaa tatgccgatc tccgcattcc   1380
tgtctccaga cgcctgctct gtgcgcgctg tctcgatgaa gcattctttt cctccccaat   1440
gccgcagtc ggtgtgccag gccatgctgg cgctcttgac agattctgcg ccagactccc   1500
ccctcaactg cgacgctggg aaccttctcc gggcaggcga tgtgcgtggg tttgcctcct   1560
tggcacggct ctacaccgtc gagtacgcca tgaggcggtg atggctgtgt cggttgccac   1620
ttcgtccaga gacggcaagt cgtccatcct ctgcgtgtgt ggcgcgacgc tgcagcagtc   1680
```

```
cctctgcagc agatgagcgt gactttggcc atttcacgca ctcgagtgta cacaatccat    1740
ttttcttaaa gcaaatgact gctgattgac cagatactgt aacgctgatt tcgctccaga    1800
tcgcacagat agcgaccatg ttgctgcgtc tgaaaatctg gattccgaat tcgaccctgg    1860
cgctccatcc atgcaacaga tggcgacact tgttacaatt cctgtcaccc atcggcatgg    1920
agcaggtcca cttagattcc cgatcaccca cgcacatgtc gctaatagtc attcgttcgt    1980
gtcttcgatc aatctcaagt gagtgtgcat ggatcttggt tgacgatgcg gtatgggttt    2040
gcgccgctgg ctgcagggtc tgcccaaggc aagctaaccc agctcctctc cccgacaata    2100
ctctcgcagg caaagccggt cacttgcctt ccagattgcc aataaactca attatggcct    2160
ctgtcatgcc atccatgggc tgatgaatg gtcacgctcg tgtcctgacc gttccccagc    2220
ctctggcgtc ccctgccccg cccaccagcc cacgccgcgc ggcagtcgct gccaaggctg    2280
tctcggatgc ccagcgccat gccacgcgcct ttgatggctt caagtacgat tacggtgttg    2340
gattgtgtgt ttgttgcgta gtgtgcatgg tttagaataa tacacttgat ttcttgctca    2400
cggcaatctc ggcttgtccg caggttcaac cccatttcgg agtctcaggt cagccgcgca    2460
atgaccagcc gctacttcaa ggacttgcac gacaacgccg aggtgagcta tgtttaggac    2520
ttgattggaa attgtcgtcg acgcatattc gcgctccgcg acagcaccca agcaaaatgt    2580
caagtgcgtt ccgatttgcg tccgcaggtc gatgttgtga tcgtcggcgc cggatccgcc    2640
ggtctgtcct gcgcttacga gctgaccaag caccctgacg tccgggtacg cgagctgaga    2700
ttcgattaga cataaattga agattaaacc cgtagaaaaa tttgatggtc gcgaaactgt    2760
gctcgattgc aagaaattga tcgtcctcca ctccgcaggt cgccatcatc gagcagggcg    2820
ttgctcccgg cggcggcgcc tggctggggg gacagctgtt ctcggccatg tgtgtacgta    2880
gaaggatgaa tttcagctgg ttttcgttgc acagctgttt gtgcatgatt tgtttcagac    2940
tattgttgaa tgttttttaga tttcttagga tgcatgattt gtctgcatgc gacttttagc    3000
tagcacccctt acacaccatc caacatcttg ctgccttgcc tccctgcgc agatccgcaa    3060
gccggcgcac aagctgatgg acgagctcaa catcccttac gacgacgagg tgggtattgg    3120
gcagctagaa cgcatgcgtg ctgtgcgact gggtcgatcc attgtgcgaa acgtgtggcg    3180
gaatacgtgc gcgtccccgg ccatgcaccg accccccctcc ccaccaccccc acaaatataa    3240
cagggtgaca tggtggtggt caagcacgcc gccctggtga cgtccacgct gctgtccaag    3300
gtgctggcgg cccccaacat caagcttttc aacgccaccg cggcggagga cctgatcgtc    3360
aagtccaagc cggccggcgg ggcggccgtc cgcacgtgg ccggggccgt gaccaactgg    3420
accctggtgt ccctcaacca cgacacccag atgtgcagta accccaacac catcctggc    3480
aaggtcatgg tctcctccac cggccacgac ggcccatgg cgcgcctccg gggtcaagcgc    3540
ctggccaagc tgggcctgat cgagcgcgcg ccgggcatgg gcgcgctgga catgaacagc    3600
gccgaggacg cggtggtcga ccggacgcgg gagatcgtcc ctggcatggt catctgcggc    3660
atggaggtcg ccgagctgga cgggtgcccg cgcatgggcc ccacctttgg cgccatgttt    3720
gtgtccgggg tcaaggccgc gcacgtggcc ctggcctcgc tgcgccgcca gcaggaggag    3780
gaggggctcc gcgccaagac cgcagacacc ctgcgcagcg cggcgccgtc catggccatg    3840
gcgtgacctg gtgatcccca agagggcgga catgcgtcgc gtctccctcc ggtgcccaga    3900
gatctgttcc acggttgtct gcgatgcttt caaaactgtt atttcactaa aatgactcga    3960
ttctcctcta aaaaaaacat gatgttgata gtatctccac aaaagcatgg cgactcagat    4020
gcctctactg cactgtactc aagaatacaa ctctggagac ccgggtcccg ttcccatttg    4080
gcgccgaatg ttgatgcgcc acttttgctg gccatgcctg aggtattctg tacaaaagaa    4140
ggagcggcca atgcgggttt tcaagcagac ggcgcgctgg ggcctggaaa tcaaaaggcg    4200
gtagtacacg ggagagagtc ggattgatga tgagggattt aaaaaaggcc aggcagtgag    4260
gtgagagttg tacgattgtt gccccaggat tgccttttta gggggggacg gccaggggcg    4320
cagttattgg ggcaccgcac atatagatcc gcgcaagcaa atggcctcga gagcaggcgc    4380
gatggttaag aaaggaagga cgagtagcgg atgacgtgat actgcatacg aagaacgtac    4440
tagtgaggag agtgcttgaa acaacatatg atgctgcccc cctctctgc caac            4494

SEQ ID NO: 27        moltype = DNA   length = 1599
FEATURE              Location/Qualifiers
source               1..1599
                     mol_type = genomic DNA
                     organism = Saccharomyces cerevisiae
SEQUENCE: 27
atgctgctgc aggccttcct gttcctgctg gccggcttcg ccgccaagat cagcgcctcc     60
atgacgaacg agacgtccga ccgcccctg gtgcacttca cccccaacaa gggctggatg    120
aacgacccca acgccctgtg gtacgacgag aaggacgcca gtggcacct gtacttccag    180
tacaaccccga acgacaccgt ctgggggacg cccttgttct ggggcacgc cacgtccgac    240
gacctgacca actgggagga ccagcccatc gccatcgcct cgaagcgcaa cgactccggc    300
gccttctccg gctccatggt ggtggactac aacaacacct ccggcttctt caacgacaca    360
atcgacccgc gccagcgctg cgtggccatc tggacctaca acacccccgga gtccgaggag    420
cagtacatct cctacagcct ggacggcggc tacaccttca ccgagtacca gaagaacccc    480
gtgctggccg ccaactccac ccagttccgc gacccgaagg tcttctggta cgagccctcc    540
cagaagtgga tcatgaccgc ggccaagtcc caggactaca agatcgagat ctactcctcc    600
gacgacctga gtcctggaa gctggagtcc gcgttcgcca acgagggctt cctcggctac    660
cagtacgagt gccccggcct gatcgaggtc cccaccgagc aggaccccag caagtcctac    720
tgggtgatgt tcatctccat caaccccggc gccccggccg cgggctcctt caaccagtac    780
ttcgtcggca gcttcaacgg cacccacttc gaggccttca caaccagtc ccgcgtggtg    840
gacttcggca aggactacta cgccctgcag accttcttca acaccgaccc gacctacggg    900
agcgccctgg gcatcgcgtg ggcctccaac tgggagtact ccgccttcgt gcccaccaac    960
ccctggcgct cctccatgtc cctcgtgcgc aagttctccc tcaacaccga gtaccaggcc   1020
aacccggaga cggagctgat caacctgaag gccgagccga tcctgaacat cagcaacgcc   1080
ggcccctga gccggttcgc caccaacacc acgttgacga aggccaacag ctacaacgtc   1140
gacctgtcca agcagccggg tcagtacgag ttcgagctgg tgtacgacat caacaccacc   1200
cagacgatct ccaagtccgt gttcgcggac ctctcccctc ggttcaaggg cctggaggac   1260
cccgaggagt acctccgcat gggcttcgag gtgtccgcgt cctccttctt cctgaccgc    1320
gggaacagca aggtgaagtt cgtgaaggag aaccccact tcaccaaccg catgagcgtg   1380
aacaaccagc ccttcaagag cgagaacgac ctgtcctact acaaggtgta cggcttgctg   1440
gaccagaaca tcctggagct gtacttcaac gacggcgacg tcgtgtccac caacacctac   1500
```

```
ttcatgacca ccgggaacgc cctgggctcc gtgaacatga cgacgggggt ggacaacctg  1560
ttctacatcg acaagttcca ggtgcgcgag gtcaagtga                          1599

SEQ ID NO: 28            moltype = DNA  length = 1416
FEATURE                  Location/Qualifiers
source                   1..1416
                         mol_type = genomic DNA
                         organism = Saccharomyces carlsbergensis
SEQUENCE: 28
atgttcgcgt tctacttcct gacggcctgc atctccctga agggcgtgtt cggcgtctcc   60
ccctcctaca acggcctggg cctgacgccc cagatgggct gggacaactg gaacacgttc  120
gcctgcgacg tctccgagca gctgctgctg gacacggccg accgcatctc cgacctgggc  180
ctgaaggaca tgggctacaa gtacatcatc ctggacgact gctggtcctc cggccgcgac  240
tccgacggct cctggtcgc cgacgagcag aagttcccca acggcatggg ccacgtcgcc  300
gaccacctgc acaacaactc cttcctgttc ggcatgtact cctccgcggg cgagtacacg  360
tgcgccggct accccggctc cctgggccgc gaggaggagg acgcccagtt cttcgcgaac  420
aaccgcgtgg actacctgaa gtacgacaac tgctacaaca agggccagtt cggcacgccc  480
gagatctcct accaccgcta caaggccatg tccgacgccc tgaacaagac gggccgcccc  540
atcttctact ccctgtgcaa ctggggccag gacctgacct tctactgggg ctccggcatc  600
gcgaactcct ggcgcatgtc cggcgacgtc acggcggagt tcacgcgccc cgactcccgc  660
tgcccctgcg acggcgacga gtacgactgc aagtacgccg gcttccactg ctccatcatg  720
aacatcctga caaggccgc cccatgggc cagaacgcg gcgtcggcgg ctggaacgac  780
ctggacaacc tggaggtcgg cgtcggcaac ctgacgacg acgaggagaa ggcgcacttc  840
tccatgtggg ccatggtgaa gtcccccctg atcatcggcg cgaacgtgaa caacctgaag  900
gcctcctcct actccatcta ctcccaggcg tccgtcatcg ccatcaacca ggactccaac  960
ggcatccccg ccacgcgcgt ctggcgctac tacgtgtccg acacggacga gtacggccag 1020
ggcgagatcc agatgtggtc cggccccctg gacaacggcg accaggtcgt ggcgctgctg 1080
aacggcgggct ccgtgtcccg ccccatgaac acgaccctgg aggagatctt cttcgactcc 1140
aacctgggct ccaagaagct gacctccacc tgggacatct acgacctgtg ggcgaaccgc 1200
gtcgacaact ccacggcgtc cgccatcctg ggccgcaaca gaccgccac cggcatcctg 1260
tacaacgcca ccgagcagtc ctacaaggac ggcctgtcca gaacgacac ccgcctgttc 1320
ggccagaaga tcggctcctc gtcccccaac gcgatcctga cacgaccgt ccccgcccac 1380
ggcatcgcgt tctaccgcct gcgcccctcc tcctga                            1416

SEQ ID NO: 29            moltype = DNA  length = 1935
FEATURE                  Location/Qualifiers
source                   1..1935
                         mol_type = genomic DNA
                         organism = Arabidopsis thaliana
SEQUENCE: 29
atggccgcgt ccgtccactg caccctgatg tccgtggtct gcaacaacaa gaaccactcc   60
gcccgcccca gctgcccaa ctcctccctg ctgcccggct cgacgtggt ggtccaggcc  120
gcggccaccc gcttcaagaa ggagacgacg accaccccgcg ccacgctgac gttcgacccc  180
cccacgacca actccgagcg cgccaagcag cgcaagcaca ccatcgaccc ctcctccccc  240
gacttccagc ccatcccctc cttcgaggag tgcttcccca agtccacgaa ggagcacaag  300
gaggtggtgc acgaggagtc cggccacgtc ctgaaggtgc ccttccgccg cgtcgcacctg  360
tccggcggcg agcccgcctt cgacaactac gacacgtccg gccccagaa cgtcaacgcc  420
cacatcggcc tggcgaagct gcgcaaggag tggatcgacc gccgcgagaa gctgggcacg  480
ccccgctaca cgcagatgta ctacgcgaag cagggcatca tcacggagga gatgctgtac  540
tgcgcgacgc gcgagaagct ggaccccgag ttcgtccgct ccgaggtcgc gcggggccgc  600
gccatcatcc cctccaacaa gaagcacctg gagctggagc ccatgatcgt gggccgcaag  660
ttcctggtga aggtgaacgc gaacatccgg aactccggcc tggcctcctc catcgaggag  720
gaggtctaca aggtcagtg ggccaccatg tggggcgccg acaccatcat ggacctgtcc  780
acgggccgcc acatccacga cgcgcgagg tggatcctgc gcaactccgc ggtccccgtg  840
ggcaccgtcc ccatctacca ggcgctggag aaggtggacg gcatcgcgga gaacctgaac  900
tgggaggtgt ccgcgagac gctgatcgag caggccgagc agggcgtgga ctacttcacg  960
atccacgcgg gcgtgctgct gcgctacatc ccctgaccg ccaagcgcct gacgggcatc 1020
gtgtcccgcg gcggctccat ccacgcgaag tggtgcctgg cctaccacaa ggagaacttc 1080
gcctacgagc actgggacga catcctggac atctgcaacc agtacgacgt cgccctgttc 1140
atcggcgacg gcctgcgccc cggctccatc tacgacgcca acgacacggc ccagttcgcc 1200
gagctgctga cccagggcga gctgacgcgc gcgcgcgggg agaaggacgt gcaggtgatg 1260
aacgagggcc ccggccacgt gcccatgcac aagatccccg agaacatgca gaagcagctg 1320
gagtggtgca acgaggcgcc cttctacacc ctgggccccc tgacgaccga catcgcgccc 1380
ggctacgacc acatcacctc cgccatcggc gcggccaaca tcgcgccct gggcaccgcc 1440
ctgctgtgct acgtgacgcc caaggagcac ctgggcctgc ccaaccgcga cgacgtgaag 1500
gcgggcgtca tcgcctacaa gatgccgcc cacgcggcca cctggccaa gcagcaccc 1560
cacgcccagg cgtgggacga cgcgctgtcc aaggcgcgct cgagttccg ctggatggca 1620
cagttcgcgc tgtccctgga ccccatgacg gcgatgtcct tccacgacga cgctgccc  1680
gcggacggcc cgaaggtcgc ccacttctgc tccatgtgcg gcccaagtt ctgctccatg 1740
aagatcacgg aggacatccg caagtacgcc gaggagaacg gctacggctc cgccgaggag 1800
gccatccgcc agggcatgga cgccatgtcc gaggagttca acatcgccaa gaagacgatc 1860
tccggcgagc agcacggcga ggtcggcgg ggagatctacc tgcccgagtc ctacgtcaag 1920
gccgcgcaga agtga                                                   1935
```

```
SEQ ID NO: 30          moltype = DNA  length = 573
FEATURE                Location/Qualifiers
source                 1..573
                       mol_type = unassigned DNA
                       note = Prototheca wickerhamii
                       organism = unidentified
SEQUENCE: 30
tgttgaagaa tgagccggcg acttaaaata aatggcaggc taagagaatt aataactcga 60
aacctaagcg aaagcaagtc ttaatagggc gctaatttaa caaaacatta aataaaatct 120
aaagtcattt attttagacc cgaacctgag tgatctaacc atggtcagga tgaaacttgg 180
gtgacaccaa gtggaagtcc gaaccgaccg atgttgaaaa atcggcggat gaactgtggt 240
tagtggtgaa ataccagtcg aactcagagc tagctggttc tccccgaaat gcgttgaggc 300
gcagcaatat atctcgtcta tctaggggta aagcactgtt tcggtgcggg ctatgaaaat 360
ggtaccaaat cgtggcaaac tctgaatact agaaatgacg atatattagt gagactatgg 420
gggataagct ccatagtcga gagggaaaca gcccagacca ccagttaagg ccccaaaatg 480
ataatgaagt ggtaaaggag gtgaaaatgc aaatacaacc aggaggttgg cttagaagca 540
gccatccttt aaagagtgcg taatagctca ctg                               573

SEQ ID NO: 31          moltype = DNA  length = 531
FEATURE                Location/Qualifiers
source                 1..531
                       mol_type = unassigned DNA
                       note = Prototheca moriformis
                       organism = unidentified
SEQUENCE: 31
ttaaaataaa tggcaggcta agagaattaa taactcgaaa cctaagcgaa agcaagtctt 60
aatagggcgc taatttaaca aaacattaaa taaatctaa agtcatttat tttagacccg 120
aacctgagtg atctaaccat ggtcaggatg aaacttgggt gacaccaagt ggaagtccga 180
accgaccgat gttgaaaaat cggcggatga actgtggtta gtggtgaaat accagtgcaa 240
ctcagagcta gctggttctc cccgaaatgc gttgaggcgc agcaatatat ctcgtcatc 300
tagggtaaa gcactgtttc ggtgcgggct atgaaaatgg taccaaatcg tgcaaactc 360
tgaatactag aaatgacgat atattagtga gactatgggg gataagctcc atagtcgaga 420
gggaaacagc ccagaccacc agttaaggcc caaaatgat aatgaagtgg taaaggaggt 480
gaaaatgcaa atacaaccag gaggttggct tagaagcagc catcctttaa a          531
```